(12) United States Patent
Fujita et al.

(10) Patent No.: US 6,562,849 B1
(45) Date of Patent: May 13, 2003

(54) AMINE DERIVATIVE COMPOUNDS

(75) Inventors: Takashi Fujita, Kashiwa (JP); Kunio Wada, Asaka (JP); Minoru Oguchi, Tokyo (JP); Hidehito Honma, Tokyo (JP); Toshihiko Fujiwara, Ebina (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/971,634

(22) Filed: Oct. 5, 2001

Related U.S. Application Data

(63) Continuation-in-part of application No. PCT/JP00/02216, filed on Apr. 6, 2000.

(30) Foreign Application Priority Data

Apr. 7, 1999 (JP) ............................................. 11-099981

(51) Int. Cl.[7] ..................... C07D 417/12; A61K 31/427
(52) U.S. Cl. ........................................ 514/370; 548/181
(58) Field of Search ............................ 518/181; 514/370

(56) References Cited

U.S. PATENT DOCUMENTS

| 5,624,935 A | 4/1997 | Fujita et al. |
|---|---|---|
| 5,739,345 A | 4/1998 | Fujita et al. |
| 5,834,501 A | 11/1998 | Fujita et al. |
| 5,886,014 A | 3/1999 | Fujita et al. |
| 5,965,470 A | 10/1999 | Bening |
| 5,977,365 A | 11/1999 | Fujita et al. |
| 5,985,884 A | 11/1999 | Lohray et al. |

FOREIGN PATENT DOCUMENTS

| JP | 5-213913 A | 8/1993 |
|---|---|---|
| JP | 06-107542 | 4/1994 |
| JP | 7-101945 A | 4/1995 |
| JP | 7-165735 A | 6/1995 |
| JP | 9-165371 A | 6/1997 |
| JP | 10-195057 A | 7/1998 |
| WO | WO 94/15901 | 4/1994 |
| WO | WO 96/20913 | 7/1996 |
| WO | WO 98/29120 | 7/1998 |
| WO | WO 99/18081 A | 4/1999 |

OTHER PUBLICATIONS

Thibonnet et al., "Stereoselective Synthesis of All–trans–, (13Z)–and (9–nor)–Retinoic Acids via Stille Reaction", Synlett 1, (1999), pp. 141–143.

*Primary Examiner*—Robert Gerstl
(74) *Attorney, Agent, or Firm*—Frishauf, Holtz, Goodman & Chick, P.C.

(57) ABSTRACT

An amine compound of the formula (I):

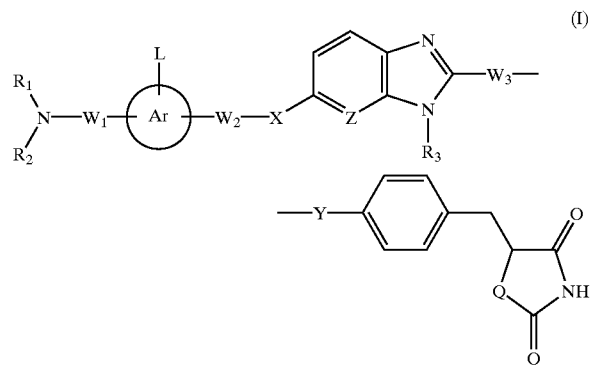

wherein $R_1$ represents an optionally substituted carbamoyl group, etc., $R_2$ represents a hydrogen atom, etc., $R_3$ represents a $C_1$–$C_{10}$ alkyl group etc., $W_1$, $W_2$ and $W_3$ are the same or different and each represent a single bond or a $C_1$–$C_8$ alkylene group, X, Y and Q represent a sulfur atom, etc., Z represents a =CH— group, etc., Ar represents a benzene ring, etc. and L represents a hydrogen atom, etc., or a pharmacologically acceptable salt thereof. These compounds are useful in the treatment and/or prophylaxis of diseases such as diabetes, hyperlipemia, arteriosclerosis, cancer, etc.

66 Claims, No Drawings

AMINE DERIVATIVE COMPOUNDS

This application is a continuation-in-part application of International Application PCT/JP00/02216 filed Apr. 6, 2000 (not published in English) which is incorporated herein by this reference.

TECHNICAL FIELD

The present invention relates to amine derivative compounds or their pharmacologically acceptable salts having superior insulin tolerance ameliorating effects, blood sugar lowering effects, anti-inflammatory effects, immunoregulatory effects, aldose reductase inhibitory effects, 5-lipoxygenase inhibitory effects, lipid peroxide formation inhibitory effects, PPAR activation effects, anti-osteoporosis effects, leukotriene antagonistic effects, fat cell promotion effects, cancer cell proliferation inhibitory effects and calcium antagonistic effects.

Moreover, the present invention relates to a preventing and/or therapeutic agent containing as an active ingredient the above-mentioned amine derivative compounds or their pharmacologically acceptable salts for diseases such as diabetes, hyperlipemia, obesity, glucose intolerance, hypertension, fatty liver, diabetic complications (including retinopathy, nephropathy, neuropathy, cataracts and coronary diseases), arteriosclerosis, pregnancy diabetes, polycystic ovary syndrome, cardiovascular diseases (such as ischemic heart disease), cell injury induced by atherosclerosis or ischemic heart disease (such as brain injury induced by apoplexy), gout, inflammatory diseases (including arthritis, pain, pyrexia, rheumatoid arthritis, inflammatory enteritis, acne, sunburn, psoriasis, eczema, allergic diseases, asthma, GI ulcer, cachexia, autoimmune diseases and pancreatitis), cancer, osteoporosis and cataracts.

Moreover, the present invention relates to pharmaceutical compositions comprising a combination of the above amine derivative compounds or their pharmacologically acceptable salts and at least one kind of RXR activator, sulfonylurea agent, α-glucosidase inhibitory agent, aldose reductase inhibitory agent, biguanide agent, statin compound, squalene synthesis inhibitory agent, fibrate compound, LDL disassimilation promoter, angiotensin II antagonist, angiotensin converting enzyme inhibitory agent, antitumor agent and FBPase inhibitory agent (and particularly preferably antitumor agents and preventing and/or therapeutic agents for diabetes or diabetic complications).

BACKGROUND ART

At present, thiazolidine compounds, oxazolidine compounds and the like are reported to be useful as preventing or therapeutic agents for various diseases such as diabetes and hyperlipemia.

For example, oxazolidinedione derivatives having blood sugar and blood lipid lowering effects are disclosed in (1) Japanese Patent Application (Kokai) No. Hei 7-101945 and (2) Japanese Patent Application (Kokai) No. Hei 7-165735. However, the compounds of the inventions as claimed in these publications have a structure that differs from the structure of the compounds of the present invention in that the oxazolidinedione has a comparatively long chain aliphatic hydrocarbon group (the compounds of the present invention have a thiazolidinedione- or oxazolidinedione-methyl group), and although it may have a benzimidazole or imidazopyridine group, each group only has comparatively small substituents such as hydrocarbon groups (the compounds of the present invention are required to have a benzimidazole or imidazopyridine structure, and its substituent is comparatively large and must include an amino group and an aryl group).

In addition, an azolidinedione derivative having antidiabetes effects is disclosed in (3) U.S. Pat. No. 5,985,884. However, the compound of the invention as claimed in this publication also has a different structure from the compounds of the present invention in that it is unable to have a benzimidazole or imidazopyridine structure having an amino group as its substituent.

Moreover, a thiazolidinedione compound capable of satisfactorily controlling blood sugar values is disclosed in (4) Japanese Patent Application (Kokai) No. Hei 5-213913. However, the compound of the invention as claimed in this publication also has a different structure from the compounds of the present invention in that it also requires a piperidine structure in the case of having a benzimidazole structure, and in that its substituent is comparatively small.

DISCLOSURE OF THE INVENTION

As a result of extensive studies on the synthesis of a series of amine derivative compounds and their pharmacological activity over the course of many years, the inventors of the present invention have found that amine derivative compounds having a novel structure have superior insulin tolerance ameliorating effects, blood sugar lowering effects, anti-inflammatory effects, immunoregulatory effects, aldose reductase inhibitory effects, 5-lipoxygenase inhibitory effects, lipid peroxide formation inhibitory effects, PPAR activation effects, anti-osteoporosis effects, leukotriene antagonistic effects, fat cell promotion effects, cancer cell proliferation inhibitory effects and calcium antagonistic effects, have less side effects, and have a high degree of antitumor activity, thereby leading to completion of the present invention.

It is another object of the present invention to provide a preventing and/or therapeutic agent containing as an active ingredient the above-mentioned amine derivative compounds or their pharmacologically acceptable salts for diseases such as diabetes, hyperlipemia, obesity, glucose intolerance, hypertension, fatty liver, diabetic complications (including retinopathy, nephropathy, neuropathy, cataracts and coronary diseases), arteriosclerosis, pregnancy diabetes, polycystic ovary syndrome, cardiovascular diseases (such as ischemic heart disease), cell injury induced by atherosclerosis or ischemic heart disease (such as brain injury induced by apoplexy), gout, inflammatory diseases (including arthritis, pain, pyrexia, rheumatoid arthritis, inflammatory enteritis, acne, sunburn, psoriasis, eczema, allergic diseases, asthma, GI ulcer, cachexia, autoimmune diseases and pancreatitis), cancer, osteoporosis and cataracts.

Further, it is another object of the present invention to provide pharmaceutical compositions comprising a combination of the above amine derivative compounds or their pharmacologically acceptable salts and at least one kind of RXR activator, sulfonylurea agent, α-glucosidase inhibitory agent, aldose reductase inhibitory agent, biguanide agent, statin compound, squalene synthesis inhibitory agent, fibrate compound, LDL disassimilation promoter, angiotensin II antagonist, angiotensin converting enzyme inhibitory agent, antitumor agent and FBPase inhibitory agent (and particularly preferably antitumor agents and agents for treating and/or preventing diabetes or diabetic complications).

The present invention relates to an amine derivative compound of the formula (I):

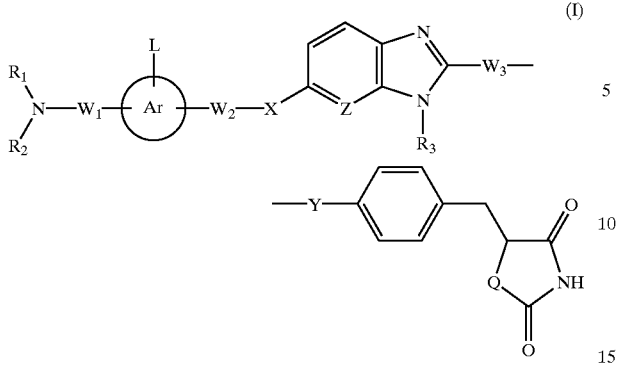
(I)

wherein:
- R₁ represents a carbamoyl group (which may have one or two substituents α described later), a thiocarbamoyl group (which may have one or two substituents α described later), a sulfonyl group (which has one substituent α described later) or a carbonyl group (which has one substituent α described later);
- R₂ and R₃ are the same or different and each represent a hydrogen atom, a $C_1$–$C_{10}$ alkyl group, a $C_6$–$C_{10}$ aryl group (which may have from 1 to 3 substituents β described later) or a $C_7$–$C_{16}$ aralkyl group (which may have from 1 to 3 substituents β described later on the aryl portion);
- $W_1$, $W_2$ and $W_3$ are the same or different and each represent a single bond or a $C_1$–$C_8$ alkylene group;
- X, Y and Q each represent an oxygen atom or a sulfur atom;
- Z represents a =CH— group or a nitrogen atom;
- Ar represents a benzene ring or a naphthalene ring;
- L represents from 1 to 4 substituents on the Ar ring and the or each substituent is a hydrogen atom, a $C_1$–$C_6$ alkyl group, a $C_6$–$C_{10}$ aryl group (which may have from 1 to 3 substituents β described later) or a $C_7$–$C_{16}$ aralkyl group (which may have from 1 to 3 substituents β described later on the aryl portion);
- the substituent α represents (i) a $C_1$–$C_{10}$ alkyl group, (ii) a $C_1$–$C_6$ halogenoalkyl group, (iii) a $C_3$–$C_{10}$ cycloalkyl group, (iv) a $C_6$–$C_{10}$ aryl group (which may have from 1 to 3 substituents γ described later), (v) a $C_7$–$C_{16}$ aralkyl group (which may have from 1 to 3 substituents γ described later on the aryl portion), (vi) a $C_4$–$C_{11}$ cycloalkylcarbonyl group, (vii) a $C_7$–$C_{11}$ arylcarbonyl group (which may have from 1 to 3 substituents γ described later on the aryl portion), (viii) a $C_8$–$C_{17}$ aralkylcarbonyl group (which may have from 1 to 3 substituents γ described later on the aryl portion), (ix) an aromatic heterocyclic group (which may have from 1 to 3 substituents γ described later), (x) an aromatic heterocyclic carbonyl group (which may have from 1 to 3 substituents γ described later), (xi) a $C_1$–$C_6$ alkylsulfonyl group, (xii) a $C_1$–$C_6$ halogenoalkylsulfonyl group, (xiii) a $C_6$–$C_{10}$ arylsulfonyl group (which may have from 1 to 3 substituents γ described later on the aryl portion), or (xiv) a $C_7$–$C_{16}$ aralkylsulfonyl group (which may have from 1 to 3 substituents γ described later on the aryl portion);
- the substituent, represents (i) a $C_1$–$C_6$ alkyl group, (ii) a $C_1$–$C_6$ halogenoalkyl group, (iii) a $C_1$–$C_6$ alkoxy group, (iv) a halogen atom, (v) a hydroxyl group, (vi) a $C_6$–$C_{10}$ aryl group (which may have from 1 to 3 substituents δ described later), (vii) a $C_7$–$C_{16}$ aralkyl group (which may have from 1 to 3 substituents δ described later on the aryl portion), (viii) a cyano group, (ix) a nitro group, or (x) an amino group (which may have one or two substituents δ described later);
- the substituent γ represents (i) a $C_1$–$C_6$ alkyl group, (ii) a $C_1$–$C_6$ halogenoalkyl group, (iii) a $C_1$–$C_6$ alkoxy group, (iv) a halogen atom, (v) a hydroxyl group, (vi) a cyano group, (vii) a nitro group, (viii) a $C_3$–$C_{10}$ cycloalkyl group, (ix) a $C_6$–$C_{10}$ aryl group (which may have from 1 to 3 $C_1$–$C_6$ alkyl groups, $C_1$–$C_6$ halogenoalkyl groups, $C_1$–$C_6$ alkoxy groups or halogen atoms as the substituents), (x) a $C_7$–$C_{16}$ aralkyl group (which may have from 1 to 3 $C_1$–$C_6$ alkyl groups, $C_1$–$C_6$ halogenoalkyl groups, $C_1$–$C_6$ alkoxy groups or halogen atoms as the substituents on the aryl portion), (xi) a $C_1$–$C_7$ aliphatic acyl group, (xii) a $C_1$–$C_7$ aliphatic acyloxy group, (xiii) an amino group, (xiv) a di-($C_1$–$C_6$ alkyl) amino group or (xv) a $C_1$–$C_4$ alkylenedioxy group;
- the substituent δ represents (i) a $C_1$–$C_{10}$ alkyl group, (ii) a $C_6$–$C_{10}$ aryl group (which may have from 1 to 3 $C_1$–$C_6$ alkyl groups, $C_1$–$C_6$ halogenoalkyl groups, $C_1$–$C_6$ alkoxy groups or halogen atoms as the substituents), (iii) a $C_7$–$C_{16}$ aralkyl group (which may have from 1 to 3 $C_1$–$C_6$ alkyl groups, $C_1$–$C_6$ halogenoalkyl groups, $C_1$–$C_6$ alkoxy groups or halogen atoms as the substituents on the aryl portion), (iv) a $C_1$–$C_7$ aliphatic acyl group, (v) a $C_4$–$C_{11}$ cycloalkylcarbonyl group, (vi) a $C_7$–$C_{11}$ arylcarbonyl group (which may have from 1 to 3 $C_1$–$C_6$ alkyl groups, $C_1$–$C_6$ halogenoalkyl groups, $C_1$–$C_6$ alkoxy groups or halogen atoms as the substituents), (vii) a $C_8$–$C_{17}$ aralkylcarbonyl group (which may have from 1 to 3 $C_1$–$C_6$ alkyl groups, $C_1$–$C_6$ halogenoalkyl groups, $C_1$–$C_6$ alkoxy groups or halogen atoms as the substituents on the aryl portion), (viii) an aromatic heterocyclic carbonyl group (which may have from 1 to 3 $C_1$–$C_6$ alkyl groups, $C_1$–$C_6$ halogenoalkyl groups, $C_1$–$C_6$ alkoxy groups or halogen atoms as the substituents);

or a pharmacologically acceptable salt thereof.

In the present specification,

The "carbamoyl group" means an $H_2N(C=O)$— group and in the case where the group has one or two substituents, one or two hydrogen atoms on the nitrogen atom are substituted by the substituents.

The "thiocarbamoyl group" means an $H_2N(C=S)$— group and in the case where the group has one or two substituents, one or two hydrogen atoms on the nitrogen atom are substituted by the substituents.

The "alkyl group" means a monovalent group formed by removing one hydrogen atom from a straight or branched chain aliphatic hydrocarbon.

The "aryl group" means a monovalent group formed by removing one hydrogen atom bonded to a ring of an aromatic hydrocarbon.

The "aralkyl group" means a monovalent group in which one hydrogen atom of the above alkyl group is substituted by the above aryl group.

The "alkylene group" means a divalent group generated by removing two hydrogen atoms from a carbon atom of a straight or branched chain aliphatic hydrocarbon.

The "halogenoalkyl group" means a monovalent group in which one or more hydrogen atoms of the alkyl group described above are substituted by a halogen atom.

The "cycloalkyl group" means a monovalent cyclic aliphatic hydrocarbon group which may be fused.

The "cycloalkylcarbonyl group" means a monovalent group in which the above cycloalkyl group is substituted by a carbonyl group.

The "arylcarbonyl group" means a monovalent group in which the above aryl group is substituted by a carbonyl group.

The "aralkylcarbonyl group" means a monovalent group in which the above aralkyl group is substituted by a carbonyl group.

The "aromatic heterocyclic group" means a monocyclic or polycyclic heterocyclic group with an aromatic property having from 1 to 3 heteroatoms selected from the group consisting of an oxygen atom, a nitrogen atom and a sulfur atom.

The "aromatic heterocyclic carbonyl group" means a monovalent group in which the above aromatic heterocyclic group is substituted by a carbonyl group.

The "alkylsulfonyl group" means a monovalent group in which the above alkyl group is substituted by a sulfonyl group.

The "arylsulfonyl group" means a monovalent group in which the above aryl group is substituted by a sulfonyl group.

The "aralkylsulfonyl group" means a monovalent group in which the above aralkyl group is substituted by a sulfonyl group.

The "alkoxy group" means a monovalent group generated by removing a hydrogen atom of a hydroxyl group from a straight or branched chain alcohol.

The "dialkylamino group" means a monovalent group in which two alkyl groups described above, which are the same or different, are bonded to a nitrogen atom.

The "alkylenedioxy group" means a divalent group in which both ends of a straight or branched chain alkylene group are substituted by oxygen atoms.

The "aliphatic acyl group" means a monovalent group in which the above alkyl group is substituted by a carbonyl group.

The "aliphatic acyloxy group" means a monovalent group in which an oxygen atom is bonded to the carbonyl group of the aliphatic acyl group described above. "$C_m$—$C_n$" means that a group has from m to n number of carbon atoms.

In the case where $R_2$, $R_3$ or substituent α or δ represents a "$C_1$–$C_{10}$ alkyl group", "$C_1$–$C_{10}$" and "alkyl" have the same meanings as defined above. The group may include methyl, ethyl, propyl, isopropyl, butyl, isobutyl, s-butyl, t-butyl, pentyl, s-pentyl, isopentyl, 2-methylbutyl, neopentyl, 1-ethylpropyl, hexyl, 4-methylpentyl (isohexyl), 3-methylpentyl, 2-methylpentyl, 1-methylpentyl (s-hexyl), 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl or 7,7-dimethyloctyl. $R_2$ and α are preferably a $C_1$–$C_8$ alkyl group, more preferably a $C_1$–$C_6$ alkyl group. $R_3$ and δ are preferably a $C_1$–$C_8$ alkyl group, more preferably a $C_1$–$C_6$ alkyl group, still more preferably a $C_1$–$C_4$ alkyl group, further more preferably a $C_1$–$C_2$ alkyl group, and most preferably a methyl group.

In the case where $R_2$, $R_3$ or L represents a "$C_6$–$C_{10}$ aryl group (which may have from 1 to 3 substituents β described later)", in the case where substituent α represents "a $C_6$–$C_{10}$ aryl group (which may have from 1 to 3 substituents γ described later)" and in the case where substituent β represents a "$C_6$–$C_{10}$ aryl group (which may have from 1 to 3 substituents δ)", "$C_6$–$C_{10}$" and "aryl" have the same meanings as defined above and the expressions "which may have from 1 to 3 substituents β", "which may have from 1 to 3 substituents γ" and "which may have from 1 to 3 substituents δ" mean that the group has no substituent β, γ or δ or that the group has from 1 to 3 substituents β, γ or δ which are the same or different. The aryl portion may include phenyl, indenyl or naphthyl.

In the case where $R_2$, $R_3$ or L represents a "$C_7$–$C_{16}$ aralkyl group (which may have from 1 to 3 substituents β described later on the aryl portion)", in the case where substituent α represents a "$C_7$–$C_{16}$ aralkyl group (which may have from 1 to 3 substituent γ described later on the aryl portion)" and in the case where substituent β represents a "$C_7$–$C_{16}$ aralkyl group (which may have from 1 to 3 substituents δ on the aryl portion)", "$C_7$–$C_{16}$", "aralkyl" and the expressions "which may have from 1 to 3 substituents β", "which may have from 1 to 3 substituents γ" and "which may have from 1 to 3 substituents δ" have the same meanings as defined above. The above aralkyl portion may include benzyl, naphthylmethyl, indenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 5-phenylpentyl, 5-naphthylpentyl, 6-phenylhexyl or 6-naphthylhexyl.

In the case where $W_1$, $W_2$ or $W_3$ represents a "$C_1$–$C_8$ alkylene group", "$C_1$–$C_8$" and "alkylene" have the same meanings as defined above. The group may include methylene, methylmethylene, ethylene, propylene, trimethylene, 1-methylethylene, tetramethylene, 1-methyltrimethylene, 2-methyltrimethylene, 3-methyltrimethylene, 1-methylpropylene, 1,1-dimethylethylene, pentamethylene, 1-methyltetramethylene, 2-methyltetramethylene, 3-methyltetramethylene, 4-methyltetramethylene, 1,1-dimethyltrimethylene, 2,2-dimethyltrimethylene, 3,3-dimethyltrimethylene, hexamethylene, 1-methylpentamethylene, 2-methylpentamethylene, 3-methylpentamethylene, 4-methylpentamethylene, 5-methylpentamethylene, 1,1-dimethyltetramethylene, 2,2-dimethyltetramethylene, 3,3-dimethyltetramethylene, 4,4-dimethyltetramethylene, heptamethylene, 1-methylhexamethylene, 2-methylhexamethylene, 5-methylhexamethylene, 3-ethylpentamethylene, octamethylene, 2-methylheptamethylene, 5-methylheptamethylene, 2-ethylhexamethylene, 2-ethyl-3-methylpentamethylene, or 3-ethyl-2-methylpentamethylene. It is preferably a straight chain $C_1$–$C_6$ alkylene group, more preferably a straight chain $C_1$–$C_4$ alkylene group, and still more preferably a straight chain $C_1$–$C_2$ alkylene group. With respect to $W_3$, the methylene group is most preferred.

In the case where L or substituent β or γ represents a "$C_1$–$C_6$ alkyl group", "$C_1$–$C_6$" and "alkyl" have the same meanings as defined above. The group may include methyl, ethyl, propyl, isopropyl, butyl, isobutyl, s-butyl, t-butyl, pentyl, s-pentyl, isopentyl, 2-methylbutyl, neopentyl, 1-ethylpropyl, hexyl, 4-methylpentyl (isohexyl), 3-methylpentyl, 2-methylpenthyl, 1-methylpentyl (s-hexyl), 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group. It is preferably a $C_1$–$C_4$ alkyl group, and more preferably a $C_1$–$C_2$ alkyl group.

In the case where substituent α, β or γ represents a "$C_1$–$C_6$ halogenoalkyl group", "$C_1$–$C_6$" and "halogenoalkyl group" have the same meanings as defined above. The group may include trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl or 2,2-dibromoethyl. It is preferably a $C_1$–$C_4$ halogenoalkyl group, and more preferably a $C_1$–$C_2$ halogenoalkyl group.

In the case where substituent α or γ represents a "$C_3$–$C_{10}$ cycloalkyl group", "$C_3$–$C_{10}$" and "cycloalkyl group" have the same meanings as defined above. The group may include cyclopropyl, cyclobutyl, cyclopentyl, cyclohexyl, cycloheptyl, norbornyl or adamantyl. It is preferably a cyclopropyl, cyclohexyl or adamantyl group, and more preferably a cyclohexyl or adamantyl group.

In the case where substituent α or δ represents a "$C_4$–$C_{11}$ cycloalkylcarbonyl group", "$C_4$–$C_{11}$" and "cycloalkylcarbonyl group" have the same meanings as defined above. The group may include cyclopropylcarbonyl, cyclobutylcarbonyl, cyclopentylcarbonyl, cyclohexylcarbonyl, cycloheptylcarbonyl, norbornylcarbonyl or adamantylcarbonyl, and is preferably $C_4$–$C_7$ cycloalkylcarbonyl.

In the case where substituent α represents a "$C_7$–$C_{11}$ arylcarbonyl group (which may have from 1 to 3 substituents γ to be described later on the aryl portion)", "$C_7$–$C_{11}$", "arylcarbonyl group" and "may have from 1 to 3 substituents γ" have the same meanings as defined above. The arylcarbonyl portion may include benzoyl, 1- or 2-indanecarbonyl, or 1- or 2-naphthoyl, and is preferably benzoyl.

In the case where substituent α represents "$C_8$–$C_{17}$ aralkylcarbonyl group (which may have from 1 to 3 substituents γ to be described later on the aryl portion)", "$C_8$–$C_{17}$", "aralkylcarbonyl group" and "may have from 1 to 3 substituents γ" have the same meanings as defined above. The aralkylcarbonyl portion may include phenylacetyl, 3-phenylpropionyl, 4-phenylbutyryl, 5-phenylpentanoyl, 6-phenylhexanoyl, naphthylacetyl, 4-naphthylbutyryl or 6-naphthylhexanoyl, is preferably phenyl-$C_2$–$C_7$ alkylcarbonyl, and is more preferably phenyl-$C_2$–$C_5$ alkylcarbonyl.

In the case where substituent α represents an "aromatic heterocyclic group (which may have from 1 to 3 substituents γ to be described later)", "aromatic heterocyclic group" and "may have from 1 to 3 substituents γ" have the same meanings as defined above. The aromatic heterocyclic portion may include a 5-membered aromatic heterocyclic group such as furyl, thienyl, pyrrolyl, pyrazolyl, imidazolyl, oxazolyl, isoxazolyl, thiazolyl, isothiazolyl, 1,2,3-oxadiazolyl, triazolyl, or thiadiazolyl; a 6-membered aromatic heterocyclic group such as pyranyl, pyridyl, pyridazinyl, pyrimidinyl, or pyrazinyl; or a 7-membered aromatic heterocyclic group such as azepinyl, preferably a 5- or 6-membered aromatic heterocyclic group.

In the case where substituent α represents an "aromatic heterocyclic carbonyl group (which may have from 1 to 3 substituents γ to be described later)", "aromatic heterocyclic carbonyl group" and "may have from 1 to 3 substituents γ" have the same meanings as defined above. The aromatic heterocyclic carbonyl portion may include a 5-membered aromatic heterocyclic carbonyl such as furylcarbonyl, thienylcarbonyl, pyrrolylcarbonyl, pyrazolylcarbonyl, imidazolylcarbonyl, oxazolylcarbonyl, isoxazolylcarbonyl, thiazolylcarbonyl, isothiazolylcarbonyl, 1,2,3-oxadiazolylcarbonyl, triazolylcarbonyl, or thiadiazolylcarbonyl; a 6-membered aromatic heterocyclic carbonyl such as pyranylcarbonyl, nicotinoyl, isonicotinoyl, pyridazinylcarbonyl, pyrimidinylcarbonyl, or pyrazinylcarbonyl; or a 7-membered aromatic heterocyclic carbonyl such as azepinylcarbonyl, and is preferably 5- or 6-membered aromatic heterocyclic carbonyl.

In the case where substituent α represents a "$C_1$–$C_6$ alkylsulfonyl group", "$C_1$–$C_6$" and "alkylsulfonyl group" have the same meanings as defined above. The alkylsulfonyl group may include methanesulfonyl, ethanesulfonyl, propanesulfonyl, isopropanesulfonyl, butanesulfonyl, isobutanesulfonyl, s-butanesulfonyl, t-butanesulfonyl, pentanesulfonyl, isopentanesulfonyl, 2-methylbutanesulfonyl, neopentanesulfonyl, 1-ethylpropanesulfonyl, hexanesulfonyl, 4-methylpentanesulfonyl, 3-methylpentansulfonyl, 2-methylpentanesulfonyl, 3,3-dimethylbutanesulfonyl, 2,2-dimethylbutanesulfonyl, 1,1-imethylbutanesulfonyl, 1,2-dimethylbutanesulfonyl, 1,3-dimethylbutanesulfonyl, 2,3-dimethylbutanesulfonyl or 2-ethylbutanesulfonyl, is preferably a $C_1$–$C_4$ alkylsulfonyl group, more preferably a $C_1$–$C_2$ alkylsulfonyl group, and most preferably the methanesulfonyl group.

In the case where substituent α represents a "$C_1$–$C_6$ halogenoalkylsulfonyl group", "$C_1$–$C_6$" and "halogenoalkylsulfonyl group" have the same meanings as defined above. The group may include trifluoromethanesulfonyl, trichloromethanesulfonyl, difluoromethanesulfonyl, dichloromethanesulfonyl, dibromomethanesulfonyl, fluoromethanesulfonyl, 2,2,2-trifluoroethanesulfonyl, 2,2,2-trichloroethanesulfonyl, 2-bromoethanesulfonyl, 2-chloroethanesulfonyl, 2-fluoroethanesulfonyl, 2-iodoethanesulfonyl, 3-chloropropanesulfonyl, 4-fluorobutanesulfonyl, 6-iodohexanesulfonyl or 2,2-dibromoethanesulfonyl, is preferably a $C_1$–$C_4$ halogenoalkylsulfonyl group, more preferably a $C_1$–$C_2$ halogenoalkylsulfonyl group and most preferably trifluoromethanesulfonyl.

In the case where substituent α represents a "$C_6$–$C_{10}$ arylsulfonyl group (which may have from 1 to 3 substituents γ to be described later on the aryl portion)", "$C_6$–$C_{10}$", "arylsulfonyl group" and "may have from 1 to 3 substituents γ" have the same meanings as defined above. The arylsulfonyl portion may include phenylsulfonyl, indenylsulfonyl or naphthylsulfonyl, and is preferably phenylsulfonyl.

In the case where substituent α represents a "$C_7$–$C_{16}$ aralkylsulfonyl group. (which may have from 1 to 3 substituents γ to be described later on the aryl portion)", "$C_7$–$C_{16}$", "aralkylsulfonyl group" and "may have, from 1 to 3 substituents γ" have the same meanings as defined above. The aralkylsulfonyl portion includes benzylsulfonyl, naphthylmethylsulfonyl, indenylmethylsulfonyl, 1-phenethylsulfonyl, 2-phenethylsulfonyl, 1-naphthylethylsulfonyl, 2-naphthylethylsulfonyl, 1-phenylpropylsulfonyl, 2-phenylpropylsulfonyl, 3-phenylpropylsulfonyl, 1-naphthylpropylsulfonyl, 2-naphthylpropylsulfonyl, 3-naphthylpropylsulfonyl, 1-phenylbutylsulfonyl, 2-phenylbutylsulfonyl, 3-phenylbutylsulfonyl, 4-phenylbutylsulfonyl, 1-naphthylbutylsulfonyl, 2-naphthylbutylsulfonyl, 3-naphthylbutylsulfonyl, 4-naphthylbutylsulfonyl, 5-phenylpentylsulfonyl, 5-naphthylpentylsulfonyl, 6-phenylhexylsulfonyl or 6-naphthylhexylsulfonyl, is preferably phenyl-$C_1$–$C_6$ alkylsulfonyl, and more preferably phenyl-$C_1$–$C_4$ alkylsulfonyl.

In the case where substituent β or γ represents a "$C_1$–$C_6$ alkoxy group", "$C_1$–$C_6$" and "alkoxy group" have the same meanings as defined above. The group may include methoxy, ethoxy, propoxy, isopropoxy, butoxy, isobutoxy, s-butoxy, t-butoxy, pentyloxy, isopentyloxy, 2-methylbutoxy, neopentyloxy, 1-ethylpropoxy, hexyloxy, 4-methylpentyloxy, 3-methylpentyloxy, 2-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy or 2-ethylbutoxy, is preferably a $C_1$–$C_4$ alkoxy group, and more preferably a $C_1$–$C_2$ alkoxy group.

In the case where substituent β or γ represents a "halogen atom", it may include a fluorine atom, a chlorine atom, a bromine atom or an iodine atom. It is preferably a fluorine atom, chlorine atom or bromine atom, and more preferably a fluorine atom or chlorine atom.

In the case where substituent γ or δ represents a "$C_6$–$C_{10}$ aryl group (which may have from 1 to 3 $C_1$–$C_6$ alkyl groups, $C_1$–$C_6$ halogenoalkyl groups, $C_1$–$C_6$ alkoxy groups and halogen atoms as the substituents)", the $C_1$–$C_6$ alkyl groups, $C_1$–$C_6$ halogenoalkyl groups, $C_1$–$C_6$ alkoxy groups and halogen atoms as the substituents include those described in the definition of each group described above. In addition to the nonsubstituted aryl group which is described as the aryl portion above, the group may include groups having substituents such as 4-methylphenyl, 4-methylnaphthyl, 3,4-dimethylphenyl, 2,3,4-trimethylphenyl, 4-propylphenyl, 4-propylnaphthyl, 2-, 3-, or 4-(trifluoromethyl)phenyl, 2-, 3-, or 4-(trifluoromethyl)naphthyl, 3,4-bis(trifluoromethyl), 2,3,4-tris(trifluoromethyl)phenyl, 4-(tetrafluoropropyl) phenyl, 4-(tetrafluoropropyl)naphthyl, 4-methoxyphenyl, 4-methoxynaphthyl, 3,4-dimethoxyphenyl, 2,3,4-trimethoxyphenyl, 4-propoxyphenyl, 4-propoxynaphthyl, 4-fluorophenyl, 4-fluoronaphthyl, 3,4-difluorophenyl or 2,3,4-trifluorophenyl, is preferably a phenyl group (which may have from 1 to 3 $C_1$–$C_6$ alkyl groups, $C_1$–$C_6$ halogenoalkyl groups, $C_1$–$C_6$ alkoxy groups and halogen atoms as the substituents), more preferably a phenyl group (which may have one group selected from $C_1$–$C_6$ alkyl groups, $C_1$–$C_6$ halogenoalkyl groups, $C_1$–$C_6$ alkoxy groups and halogen atoms as the substituent), and most preferably a phenyl group.

In the case where substituent γ or δ represents a $C_6$–$C_{10}$ aralkyl group (which may have from 1 to 3 $C_1$–$C_6$ alkyl groups, $C_1$–$C_6$ halogenoalkyl groups, $C_1$–$C_6$ alkoxy groups and halogen atoms as the substituents)", the $C_1$–$C_6$ alkyl groups, $C_1$–$C_6$ halogenoalkyl groups, $C_1$–$C_6$ alkoxy groups and halogen atoms as the substituents include those described in the definition of each group described above. In addition to the nonsubstituted aralkyl group which is described as the aralkyl portion above, the group may include groups having substituents such as 4-methylbenzyl, 2,3,4-trimethylbenzyl, 4-methylphenethyl, 2,3,4-trimethylphenethyl, 4-(4-methylphenyl)butyl, 2-, 3- or 4-(trifluoromethyl)benzyl, 3,4-bis(trifluoromethyl)benzyl, 2,3,4-tris(trifluoromethyl)benzyl, 4-(tetrafluoropropyl) benzyl, 4-(trifluoromethyl)phenethyl, 3,4-bis (trifluoromethyl)phenethyl, 2,3,4-tris(trifluoromethyl) phenethyl, 4-(tetrafluoropropyl)phenethyl, 4-[4-(trifluoromethyl)phenyl]butyl, 4-[4-(tetrafluoropropyl) phenyl]butyl, 6-[4-(trifluoromethyl)phenyl]hexyl, 6-[4-(tetrafluoropropyl)phenyl]hexyl, 2-, 3-, or 4-(trifluoromethyl)naphthylmethyl, 4-(tetrafluoropropyl) naphthylmethyl, 4-[4-(trifluoromethyl)naphthyl]butyl, 4-[4-(tetrafluoropropyl)naphthyl]butyl, 4-methoxybenzyl, 2,3,4-trimethoxybenzyl, 4-methoxyphenethyl, 2,3,4-trimethoxyphenethyl or 4-(4-methoxyphenyl)butyl, 4-fluorobenzyl, 2,3,4-trifluorobenzyl, 4-fluorophenethyl, 2,3,4-trifluorophenethyl or 4-(4-fluorophenyl)butyl, is preferably a phenyl-$C_1$–$C_6$ alkyl group (which may have from 1 to 3 $C_1$–$C_6$ alkyl groups, $C_1$–$C_6$ halogenoalkyl groups, $C_1$–$C_6$ alkoxy groups and halogen atoms as the substituents on the phenyl moiety), more preferably a phenyl-$C_1$–$C_4$ alkyl group (which may have from 1 to 3 $C_1$–$C_6$ alkyl groups, $C_1$–$C_6$ halogenoalkyl groups, $C_1$–$C_6$ alkoxy groups and halogen atoms as the substituents on the phenyl moiety), still more preferably a phenyl-$C_1$–$C_2$ alkyl group (which may have from 1 to 3 $C_1$–$C_6$ alkyl groups, $C_1$–$C_6$ halogenoalkyl groups, $C_1$–$C_6$ alkoxy groups and halogen atoms as the substituents on the phenyl moiety), further more preferably a phenyl-$C_1$–$C_2$ alkyl group (which may have one $C_1$–$C_6$ alkyl group, $C_1$–$C_6$ halogenoalkyl group, $C_1$–$C_6$ alkoxy groups or halogen atom as the substituent on the phenyl moiety), and most preferably a phenyl-$C_1$–$C_2$ alkyl group.

In the case where substituent γ or δ represents a "$C_1$–$C_7$ aliphatic acyl group", "$C_1$–$C_7$" and "aliphatic acyl group" have the same meanings as defined above. The group may include formyl, acetyl, propionyl, butyryl, isobutyryl, valeryl, isovaleryl, pivaloyl, hexanoyl, acryloyl, methacryloyl or crotonoyl, is preferably a $C_1$–$C_5$ aliphatic acyl group, more preferably a $C_1$–$C_3$ aliphatic acyl group, and most preferably acetyl.

In the case where substituent γ represents a "$C_1$–$C_7$ aliphatic acyloxy group", "$C_1$–$C_7$" and "aliphatic acyloxy group" have the same meanings as defined above. The group may include formyloxy, acetyloxy, propionyloxy, butyryloxy, isobutyryloxy, valeryloxy, isovaleryloxy, pivaloyloxy, hexanoyloxy, acryloyloxy, methacryloyloxy or crotonoyloxy, is preferably a $C_1$–$C_5$ aliphatic acyloxy group, more preferably a $C_1$–$C_3$ aliphatic acyloxy group, and most preferably acetyloxy.

In the case where substituent γ represents a "di-($C_1$–$C_6$ alkyl)amino group", "$C_1$–$C_6$" and "dialkylamino group" have the same meanings as defined above. The group may include dimethylamino, diethylamino, dipropylamino, diisopropylamino, dibutylamino, dipentylamino, dihexylamino, N-methyl-N-ethylamino or N-ethyl-N-isopropylamino, is preferably a di-($C_1$–$C_4$ alkyl)amino group and more preferably a di-($C_1$–$C_2$ alkyl)amino group.

In the case where substituent γ represents a "$C_1$–$C_4$ alkylenedioxy group", "$C_1$–$C_4$" and "alkylenedioxy group" have the same meanings as defined above. The group may include methylenedioxy, ethylenedioxy, trimethylenedioxy, tetramethylenedioxy or propylenedioxy, is preferably a $C_1$–$C_3$ alkylenedioxy group, and more preferably a $C_1$–$C_2$ alkylenedioxy group.

In the case where substituent δ represents a "$C_7$–$C_{11}$ arylcarbonyl group (which may have from 1 to 3 $C_1$–$C_6$ alkyl groups, $C_1$–$C_6$ halogenoalkyl groups, $C_1$–$C_6$ alkoxy groups and halogen atoms as the substituents)", the $C_1$–$C_6$ alkyl groups, $C_1$–$C_6$ halogenoalkyl groups, $C_1$–$C_6$ alkoxy groups and halogen atoms as the substituents include groups described in the definition of each group described above. In addition to the nonsubstituted $C_7$–$C_{11}$ aromatic acyl group which is described as the arylcarbonyl portion above, the group may include groups having substituents such as 4-methylbenzoyl, 4-methylnaphthoyl, 3,4-dimethylbenzoyl, 2,3,4-trimethylbenzoyl, 4-propylbenzoyl, 4-propylnaphthoyl, 2-, 3-, or 4-(trifluoromethyl)benzoyl, 2,3-, or 4-(trifluoromethyl)naphthoyl, 3,4-bis (trifluoromethyl)benzoyl, 2,3,4-tris(trifluoromethyl) benzoyl, 4-(tetrafluoropropyl)benzoyl, 4-(tetrafluoropropyl) naphthoyl, 4-methoxybenzoyl, 4-methoxynaphthoyl, 3,4- dimethoxybenzoyl, 2,3,4-trimethoxybenzoyl, 4-propoxybenzoyl, 4-propoxynaphthoyl, 4-fluorobenzoyl, 4-fluoronaphthoyl, 3,4-difluorobenzoyl, or 2,3,4-trifluorobenzoyl, is preferably a benzoyl group (which may have from 1 to 3 $C_1$–$C_6$ alkyl groups, $C_1$–$C_6$ halogenoalkyl groups, $C_1$–$C_6$ alkoxy groups and halogen atoms as the substituents), and more preferably a benzoyl group (which may have one $C_1$–$C_6$ alkyl group, $C_1$–$C_6$ halogenoalkyl group, $C_1$–$C_6$ alkoxy groups or halogen atom as the substituent).

In the case where substituent δ represents a "$C_8$–$C_{17}$ aralkylcarbonyl group (which may have from 1 to 3 $C_1$–$C_6$ alkyl groups, $C_1$–$C_6$ halogenoalkyl groups, $C_1$–$C_6$ alkoxy groups and halogen atoms as the substituents on the aryl portion)", the $C_1$–$C_6$ alkyl groups, $C_1$–$C_6$ halogenoalkyl groups, $C_1$–$C_6$ alkoxy groups and halogen atoms as the substituents include groups described in the definition of each group described above. In addition to the nonsubstituted $C_8$–$C_{12}$ aromatic aliphatic acyl group which is described as the aralkylcarbonyl portion in the definition for substituent α above, the group may include groups having substituents such as 4-methylphenylacetyl, 4-(4-methylphenyl)butyryl, 6-(4-methylnaphthyl)hexanoyl, 2-, 3- or 4-(trifluoromethyl)phenylacetyl, 4-(tetrafluoropropyl)phenylacetyl, 4-[4-(trifluoromethyl)phenyl]butyryl, 6-[4-(trifluoromethyl)phenyl]hexanoyl, 4-(trifluoromethyl)naphthylacetyl, 6-[4(trifluoromethyl)naphthyl]hexanoyl, 4-methoxyphenylacetyl, 4-(4-methoxyphenyl)butyryl, 6-(4-methoxynaphthyl)hexanoyl, 4-fluorophenylacetyl, 4-(4-fluorophenyl)butyryl or 6-(4-fluoronaphthyl)hexanoyl, is preferably a phenyl-$C_2$–$C_7$ alkylcarbonyl group (which may have from 1 to 3 $C_1$–$C_6$ alkyl groups, $C_1$–$C_6$ halogenoalkyl groups, $C_1$–$C_6$ alkoxy groups and halogen atoms as the substituents on the aryl portion), and most preferably a phenyl-$C_2$–$C_7$ alkylcarbonyl group (which may have one $C_1$–$C_6$ alkyl group, $C_1$–$C_6$ halogenoalkyl group, $C_1$–$C_6$ alkoxy group or halogen atom as the substituent).

In the case where substituent δ represents an "aromatic heterocyclic carbonyl group (which may have from 1 to 3 $C_1$–$C_6$ alkyl groups, $C_1$–$C_6$ halogenoalkyl groups, $C_1$–$C_6$ alkoxy groups and halogen atoms as the substituents)", the $C_1$–$C_6$ alkyl groups, $C_1$–$C_6$ halogenoalkyl groups, $C_1$–$C_6$ alkoxy groups and halogen atoms as the substituents include groups described in the definition of each group described above. In addition to the heterocyclic carbonyl group having a nonsubstituted aromatic heterocyclic portion described as the aromatic heterocyclic carbonyl group in the definition for substituent α above, the groups having substituents may include methylfurylcarbonyl, methylthienylcarbonyl, methylpyrrolylcarbonyl, methylnicotinoyl, (trifluoromethyl)furylcarbonyl, (trifluoromethyl)thienylcarbonyl, (trifluoromethyl)pyrrolylcarbonyl, (trifluoromethyl)oxazolylcarbonyl, (trifluoromethyl)thiazolylcarbonyl, (trifluoromethyl)nicotinoyl, (tetrafluoropropyl)furylcarbonyl, (tetrafluoropropyl)thienylcarbonyl, (tetrafluoropropyl)pyrrolylcarbonyl, methoxyfurylcarbonyl, methoxythienylcarbonyl, methoxypyrrolylcarbonyl, methoxynicotinoyl, fluorofurylcarbonyl, fluorothienylcarbonyl, fluoropyrrolylcarbonyl or fluoronicotinoyl, is preferably a 5- or 6-membered aromatic heterocyclic carbonyl group (which may have from 1 to 3 $C_1$–$C_6$ alkyl groups, $C_1$–$C_6$ halogenoalkyl groups, $C_1$–$C_6$ alkoxy groups and halogen atoms as the substituents), more preferably a 5- or 6-membered aromatic heterocyclic carbonyl group having one or two heteroatoms (which may be selected from 1 to 3 $C_1$–$C_6$ alkyl groups, $C_1$–$C_6$ halogenoalkyl groups, $C_1$–$C_6$ alkoxy groups and halogen atoms), and most preferably a 5- or 6-membered aromatic heterocyclic carbonyl group having one or two heteroatoms (which may have one $C_1$–$C_6$ alkyl group, $C_1$–$C_6$ halogenoalkyl group, $C_1$–$C_6$ alkoxy group or halogen atom as the substituent).

From the definition of the substituents γ and δ described above, in the case where substituent α represents a "$C_6$–$C_{10}$ aryl group (which may have from 1 to 3 substituents γ)," the groups having the substituents γ may include 2-, 3- or 4-methylphenyl, dimethylphenyl, trimethylphenyl, 2-, 3- or 4-isopropylphenyl, 2,3-, 2,4- or 3,4-diisopropylphenyl, 2,4,6- or 3,4,5-triisopropylphenyl, 2-, 3- or 4-(trifluoromethyl)phenyl, bis(trifluoromethyl)phenyl, tris(trifluoromethyl)phenyl, methoxyphenyl, dimethoxyphenyl, 2-, 3- or 4-fluorophenyl, 2,3-, 2,4- or 3,4-difluorophenyl, 2,4,6- or 3,4,5-trifluorophenyl, 2-, 3- or 4-chlorophenyl, dichlorophenyl, trichlorophenyl, hydroxyphenyl, 2-, 3- or 4-cyanophenyl, 2-, 3- or 4-nitrophenyl, cyclopropylphenyl, cyclohexylphenyl, adamantylphenyl, biphenyl, (methylphenyl)phenyl, [(trifluoromethyl)phenyl]phenyl, (methoxyphenyl)phenyl, (fluorophenyl)phenyl, (chlorophenyl)phenyl, benzylphenyl, (methylbenzyl)phenyl, [(trifluoromethyl)benzyl]phenyl, (methoxybenzyl)phenyl, (fluorobenzyl)phenyl, (chlorobenzyl)phenyl, acetylphenyl, acetyloxyphenyl, aminophenyl, dimethylaminophenyl, diethylaminophenyl, 3,4- or 2,3-methylenedioxyphenyl, 3,4- or 2,3-ethylenedioxyphenyl, methylnaphthyl, dimethylnaphthyl, trimethylnaphthyl, isopropylnaphthyl, diisopropylnaphthyl, triisopropylnaphthyl, (trifluoromethyl)naphthyl, bis(trifluoromethyl)naphthyl, tris(trifluoromethyl)naphthyl, methoxynaphthyl, dimethoxynaphthyl, fluoronaphthyl, difluoronaphthyl, trifluoronaphthyl, chloronaphthyl, dichloronaphthyl, trichloronaphthyl, cyanonaphthyl, nitronaphthyl, cyclopropylnaphthyl, cyclohexylnaphthyl, adamantylnaphthyl, phenylnaphthyl, (methylphenyl)naphthyl, (trifluoromethylphenyl)naphthyl, (methoxyphenyl)naphthyl, (fluorophenyl)naphthyl, (chlorophenyl)naphthyl, benzylnaphthyl, (methylbenzyl)naphthyl, [(trifluoromethyl)benzyl]naphthyl, (methoxybenzyl)naphthyl, (fluorobenzyl)naphthyl, (chlorobenzyl)naphthyl, acetylnaphthyl, acetyloxynaphthyl, aminonaphthyl, dimethylaminonaphthyl, diethylaminonaphthyl, methylenedioxynaphthyl or ethylenedioxynaphthyl, is preferably a phenyl group (which may have 1 to 3 substituents γ), more preferably a phenyl group (which may have one or two substituents γ), and most preferably a phenyl group (which may have one substituent γ).

In the case where substituent α represents a "$C_7$–$C_{16}$ aralkyl group (which may have from 1 to 3 substituents γ), the group having the substituents γ may include methylbenzyl, dimethylbenzyl, trimethylbenzyl, isopropylbenzyl, diisopropylbenzyl, triisopropylbenzyl, 2-, 3- or 4-(trifluoromethyl)benzyl, bis(trifluoromethyl)benzyl, tris(trifluoromethyl)benzyl, methoxybenzyl, dimethoxybenzyl, fluorobenzyl, difluorobenzyl, trifluorobenzyl, chlorobenzyl, dichlorobenzyl, trichlorobenzyl, hydroxybenzyl, cyanobenzyl, nitrobenzyl, cyclopropylbenzyl, cyclohexylbenzyl, adamantylbenzyl, phenylbenzyl, (methylphenyl)benzyl, [(trifluoromethyl)phenyl]benzyl, (methoxyphenyl)benzyl, (fluorophenyl)benzyl, (chlorophenyl)benzyl, benzylbenzyl, (methylbenzyl)benzyl, [(trifluoromethyl)benzyl]benzyl, (methoxybenzyl)benzyl, (fluorobenzyl)benzyl, (chlorobenzyl)benzyl, acetylbenzyl, acetyloxybenzyl, aminobenzyl, dimethylaminobenzyl, diethylaminobenzyl, methylenedioxybenzyl, ethylenedioxybenzyl, methylphenethyl, dimethylphenethyl, trimethylphenethyl, isopropylphenethyl, diisopropylphenethyl, triisopropylphenethyl, (trifluoromethyl)phenethyl, bis(trifluoromethyl)phenethyl, tris(trifluoromethyl)phenethyl, methoxyphenethyl, fluorophenethyl, difluorophenethyl, trifluorophenethyl, chlorophenethyl, hydroxyphenethyl, cyanophenethyl, nitrophenethyl, cyclopropylphenethyl, cyclohexylphenethyl, adamantylphenethyl, phenylphenethyl, benzylphenethyl, acetylphenethyl, acetyloxyphenethyl, aminophenethyl, dimethylaminophenethyl, diethylaminophenethyl, methylenedioxyphenethyl, ethylenedioxyphenethyl, methylnaphthylmethyl, dimethylnaphthylmethyl, trimethylnaphthylmethyl, isopropylnaphthylmethyl, diisopropylnaphthylmethyl, triisopropylnaphthylmethyl, (trifluoromethyl)naphthylmethyl, bis(trifluoromethyl)naphthylmethyl, tris(trifluoromethyl)naphthylmethyl, methoxynaphthylmethyl, fluoronaphthylmethyl, difluoronaphthylmethyl, trifluoronaphthylmethyl, chloronaphthylmethyl, hydroxynaphthylmethyl, cyanonaphthylmethyl, nitronaphthylmethyl, cyclopropylnaphthylmethyl, cyclohexylnaphthylmethyl, adamantylnaphthylmethyl, phenylnaphthylmethyl, benzylnaphthylmethyl, acetylnaphthylmethyl, acetyloxynaphthylmethyl, aminonaphthylmethyl, dimethylaminonaphthylmethyl, diethylaminonaphthylmethyl, methylenedioxynaphthylmethyl or ethylenedioxynaphthylmethyl, is preferably a phenyl-$C_1$–$C_6$ alkyl group (which may have from 1 to 3 substituents γ on the phenyl portion), more preferably a phenyl-$C_1$–$C_4$ alkyl group (which may have from 1 to 3 substituents γ on the phenyl portion), still more preferably a phenyl-$C_1$–$C_2$ alkyl group (which may have from 1 to 3 substituents γ on the phenyl portion), and most preferably a phenyl-$C_1$–$C_4$ alkyl group (which may have one substituent γ on the phenyl portion).

In the case where substituent α represents a "$C_7$–$C_{11}$ arylcarbonyl group (which may have from 1 to 3 substituents γ on the aryl portion)", the group having the substituents γ may include methylbenzoyl, dimethylbenzoyl, trimethylbenzoyl, isopropylbenzoyl, diisopropylbenzoyl, triisopropylbenzoyl, (trifliuoromethyl)benzoyl, methoxybenzoyl, fluorobenzoyl, difluorobenzoyl, trifluorobenzoyl, chlorobenzoyl, dichlorobenzoyl, hydroxybenzoyl, cyanobenzoyl, nitrobenzoyl, acetylbenzoyl, acetyloxybenzoyl, aminobenzoyl, dimethylaminobenzoyl, methylenedioxybenzoyl, methylnaphthoyl, isopropylnaphthoyl, diisopropylnaphthoyl, triisopropylnaphthoyl, (trifluoromethyl)naphthoyl, methoxynaphthoyl, fluoronaphthoyl, difluoronaphthoyl, trifluoronaphthoyl, chloronaphthoyl, dichloronaphthoyl, hydroxynaphthoyl, cyanonaphthoyl, nitronaphthoyl, acetylnaphthoyl, acetyloxynaphthoyl, aminonaphthoyl, dimethylaminonaphthoyl or methylenedioxynaphthoyl, is preferably a benzoyl group (which may have from 1 to 3 substituents γ), more preferably a benzoyl group (which may have one or two substituents γ) and most preferably a benzoyl group (which may have one substituent γ).

In the case where substituent α represents the "$C_8$–$C_{17}$ aralkylcarbonyl group (which may have from 1 to 3 substituents γ on the aryl portion)", the group having the substituents γ may include methylphenylacetyl, isopropylphenylacetyl, diisopropylphenylacetyl, triisopropylphenylacetyl, (trifluoromethyl)phenylacetyl, methoxyphenylacetyl, fluorophenylacetyl, difluorophenylacetyl, trifluorophenylacetyl, chlorophenylacetyl, dichlorophenylacetyl, hydroxyphenylacetyl, cyanophenylacetyl, nitrophenylacetyl, acetylphenylacetyl, acetyloxyphenylacetyl, aminophenylacetyl, dimethylaminophenylacetyl, methylenedioxyphenylacetyl, 4-(methylphenyl)butyryl, 4-(isopropylphenyl)butyryl, 4-(diisopropylphenyl)butyryl, 4-(triisopropylphenyl)butyryl, 4-[(trifluoromethyl)phenyl]butyryl, 4-(fluorophenyl)butyryl, 4-(difluorophenyl)butyryl, 4-(trifluorophenyl)butyryl, 4-(chlorophenyl)butyryl, 4-(hydroxyphenyl)butyryl, 4-(cyanophenyl)butyl, 4-(nitrophenyl)butyryl, 4-(acetylphenyl)butyryl, 4-(acetyloxyphenyl)butyryl, 4-(aminophenyl)butyryl, 4-(dimethylaminophenyl)butyryl or 4-(methylenedioxyphenyl)butyryl, is preferably a phenyl-$C_2$–$C_7$ alkylcarbonyl group (which may have from 1 to 3 substituents γ), more preferably a phenyl-$C_2$–$C_5$ alkylcarbonyl group (which may have from 1 to 3 substituents γ), and most preferably a phenyl-$C_2$–$C_5$ alkylcarbonyl group (which may have one substituent γ).

In the case where substituent α represents an "aromatic heterocyclic group (which may have from 1 to 3 substituents γ)", the group having the substituents γ may include methylfuryl, isopropylfuryl, (trifluoromethyl)furyl, cyanofuryl, nitrofuryl, fluorofuryl, chlorofuryl, methylthienyl, isopropylthienyl, (trifluoromethyl)thienyl, cyanothienyl, nitrothienyl, fluorothienyl, chlorothienyl, methylpyrrolyl, isopropylpyrrolyl, (trifluoromethyl)pyrrolyl, cyanopyrrolyl, nitropyrrolyl, fluoropyrrolyl, chloropyrrolyl, methylpyridyl, isopropylpyridyl, (trifluoromethyl)pyridyl, cyanopyridyl, nitropyridyl, fluoropyridyl or chloropyridyl, is preferably a 5- or 6-membered aromatic heterocyclic group (which may have from 1 to 3 substituents γ), more preferably a 5- or 6-membered aromatic heterocyclic group (which may have one or two substituents γ), and most preferably a 5- or 6-membered aromatic heterocyclic group (which may have one substituent γ).

In the case where substituent α represents an "aromatic heterocyclic carbonyl group (which may have from 1 to 3 substituents γ)", the group having the substituents γ may include methylfurylcarbonyl, isopropylfurylcarbonyl, (trifluoromethyl)furylcarbonyl, cyanofurylcarbonyl, nitrofurylcarbonyl, fluorofurylcarbonyl, chlorofurylcarbonyl, methylthienylcarbonyl, isopropylthienylcarbonyl, (trifluoromethyl)thienylcarbonyl, cyanothienylcarbonyl, nitrothienylcarbonyl, fluorothienylcarbonyl, chlorothienylcarbonyl, methylpyrrolylcarbonyl, isopropylpyrrolylcarbonyl, (trifluoromethyl)pyrrolylcarbonyl, cyanopyrrolylcarbonyl, nitropyrrolylcarbonyl, fluoropyrrolylcarbonyl, chloropyrrolylcarbonyl, methylnicotinoyl, isopropylnicotinoyl, (trifluoromethyl)nicotinoyl, cyanonicotinoyl, nitronicotinoyl, fluoronicotinoyl or chloronicotinoyl, is preferably a 5- or 6-membered aromatic heterocyclic carbonyl group (which may have from 1 to 3 substituents γ), more preferably a 5- or 6-membered aromatic heterocyclic carbonyl group (which may have one or two substituents γ), and most preferably a 5- or 6-membered aromatic heterocyclic carbonyl group (which may have one substituent γ).

In the case where substituent α represents a "$C_6$–$C_{11}$ arylsulfonyl group (which may have from 1 to 3 substituents γ on the aryl portion)", the group having the substituents γ may include methylphenylsulfonyl, isopropylphenylsulfonyl, (trifluoromethyl)phenylsulfonyl, methoxyphenylsulfonyl, fluorophenylsulfonyl, chlorophenylsulfonyl, hydroxyphenylsulfonyl, cyanophenylsulfonyl, nitrophenylsulfonyl, cyclohexylphenylsulfonyl, adamantylphenylsulfonyl, biphenylsulfonyl, benzylphenylsulfonyl, acetylphenylsulfonyl, acetyloxyphenylsulfonyl, aminophenylsulfonyl, dimethylaminophenylsulfonyl, methylenedioxyphenylsulfonyl, methylnaphthylsulfonyl, dimethylnaphthylsulfonyl, trimethylnaphthylsulfonyl, isopropylnaphthylsulfonyl, (trifluoromethyl) naphthylsulfonyl, methoxynaphthylsulfonyl, fluoronaphthylsulfonyl, chloronaphthylsulfonyl, cyanonaphthylsulfonyl, nitronaphthylsulfonyl, cyclohexylnaphthylsulfonyl, adamantylnaphthylsulfonyl, phenylnaphthylsulfonyl, benzylnaphthylsulfonyl, acetylnaphthylsulfonyl, acetyloxynaphthylsulfonyl, aminonaphthylsulfonyl, dimethylaminonaphthylsulfonyl or methylenedioxynaphthylsulfonyl, is preferably a phenylsulfonyl group (which may have from 1 to 3 substituents γ), more preferably a phenylsulfonyl group (which may have one or two substituents γ), and most preferably a phenyl-sulfonyl group (which may have one substituent γ).

In the case where substituent α represents a "$C_7$–$C_{16}$ aralkylsulfonyl group (which may have from 1 to 3 substituents γ on the aryl portion)", the group having the substituents γ may include methylbenzylsulfonyl, isopropylbenzylsulfonyl, (trifluoromethyl)benzylsulfonyl, methoxybenzylsulfonyl, fluorobenzylsulfonyl, chlorobenzylsulfonyl, hydroxybenzylsulfonyl, cyanobenzylsulfonyl, nitrobenzylsulfonyl, cyclohexylbenzylsulfonyl, adamantylbenzylsulfonyl, phenylbenzylsulfonyl, benzylbenzylsulfonyl, acetylbenzylsulfonyl, acetyloxybenzylsulfonyl, aminobenzylsulfonyl, dimethylaminobenzylsulfonyl, methylenedioxybenzylsulfonyl, methylphenethylsulfonyl, isopropylphenethylsulfonyl, (trifluoromethyl) phenethylsulfonyl, methoxyphenethylsulfonyl, fluorophenethylsulfonyl, chlorophenethylsulfonyl, hydroxyphenethylsulfonyl, cyanophenethylsulfonyl, nitrophenethylsulfonyl, cyclohexylphenethylsulfonyl, adamantylphenethylsulfonyl, phenylphenethylsulfonyl, benzylphenethylsulfonyl, acetylphenethylsulfonyl, acetyloxyphenethylsulfonyl, aminophenethylsulfonyl, dimethylaminophenethylsulfonyl, methylenedioxyphenethylsulfonyl, methylnaphthylmethylsulfonyl, isopropylnaphthylmethylsulfonyl, (trifluoromethyl) naphthylmethylsulfonyl, methoxynaphthylmethylsulfonyl, fluoronaphthylmethylsulfonyl, chloronaphthylmethylsulfonyl, hydroxynaphthylmethylsulfonyl, cyanonaphthylmethylsulfonyl, nitronaphthylmethylsulfonyl, cyclohexylnaphthylmethylsulfonyl, adamantylnaphthylmethylsulfonyl, phenylnaphthylmethylsulfonyl, benzylnaphthylmethylsulfonyl, acetylnaphthylmethylsulfonyl, acetyloxynaphthylmethylsulfonyl, aminonaphthylmethylsulfonyl, dimethylaminonaphthylmethylsulfonyl or methylenedioxynaphthylmethylsulfonyl, is preferably a phenyl-$C_1$–$C_6$ alkylsulfonyl group (which may have from 1 to 3 substituents γ), more preferably a phenyl-$C_1$–$C_4$ alkylsulfonyl group (which may have from 1 to 3 substituents γ), still more preferably a phenyl-$C_1$–$C_2$ alkylsulfonyl group (which may have from 1 to 3 substituents γ), and most preferably a phenyl-$C_1$–$C_2$ alkylsulfonyl group (which may have one substituent γ).

In the case where substituent β represents a "$C_6$–$C_{10}$ aryl group (which may have from 1 to 3 substituents δ)", the group having the substituents δ may include methylphenyl, isopropylphenyl, biphenyl, benzylphenyl, acetylphenyl, cyclohexylphenyl, adamantylphenyl, benzoylphenyl, phenylacetylphenyl, nicotinoylphenyl, methylnaphthyl, isopropylnaphthyl, phenylnaphthyl, benzylnaphthyl, acetylnaphthyl, cyclohexylnaphthyl, adamantylnaphthyl, benzoylnaphthyl, phenylacetylnaphthyl or nicotinoylnaphthyl, is preferably a phenyl group (which may have from 1 to 3 substituents δ), more preferably a phenyl group (which may have one or two substituents δ), and most preferably a phenyl group (which may have one substituent δ).

In the case where substituent β represents a "$C_7$–$C_{16}$ aralkyl group (which may have from 1 to 3 substituents δ on the aryl portion)," the group having the substituents δ may include methylbenzyl, isopropylbenzyl, phenylbenzyl, benzylbenzyl, acetylbenzyl, cyclohexylbenzyl, adamantylbenzyl, benzoylbenzyl, phenylacetylbenzyl, nicotinoylbenzyl, methylphenethyl, isopropylphenethyl, phenylphenethyl, benzylphenethyl, acetylphenethyl, cyclohexylphenethyl, adamantylphenethyl, benzoylphenethyl, phenylacetylphenethyl, nicotinoylphenethyl, methylnaphthylmethyl, isopropylnaphthylmethyl, phenylnaphthylmethyl, benzylnaphthylmethyl, acetylnaphthylmethyl, cyclohexylnaphthylmethyl, adamantylnaphthylmethyl, benzoylnaphthylmethyl, phenylacetylnaphthylmethyl or nicotinoylnaphthylmethyl, is preferably a phenyl-$C_1$–$C_6$ alkyl group (which may have from 1 to 3 substituents δ on the phenyl portion), more preferably a phenyl-$C_1$–$C_4$ alkyl group (which may have from 1 to 3 substituents δ on the phenyl portion), still more preferably a phenyl-$C_1$–$C_2$ alkyl group (which may have from 1 to 3 substituents δ on the phenyl portion), and most preferably a phenyl-$C_1$–$C_2$ alkyl group (which may have one substituent δ on the phenyl portion).

In the case where substituent β represents an "amino group which may have one or two substituents δ", the group may include amino, methylamino, ethylamino, propylamino, isopropylamino, butylamino, s-butylamino, t-butylamino, pentylamino, hexylamino, dimethylamino, diethylamino, N-ethyl-N-methylamino, dipropylamino, dibutylamino, dipentylamino, dihexylamino, phenylaamino, 1- or 2-indenylamino, 1- or 2-naphthylamino, benzylamino, 1- or 2-naphthylmethylanio, 1-indenylmethylamino, 1- or 2-phenethylamino, 1-, 2- or 3-phenylpropylamino, 4-phenylbutylamino, 1-phenylbutylamino, 5-phenylpentylamino, 6-phenylhexylamino, dibenzylamino, formylamino, acetylamino, propionylamino, butyrylamino, isobutyrylamino, valerylamino, isovalerylamino, pivaloylamino, hexanoylamino, acryloylamino, methacryloylamino, crotonylamino, cyclopropylcarbonylamino, cyclohexylcarbonylamino, adamantylcarbonylamino, benzoylamino, 1- or 2-naphthoylamino, 1-indenecarbonylamino, phenylacetylamino, 3-phenylpropionylamino, 4-phenylbutyrylamino, 5-phenylpentanoylamino, 6-phenylhexanoylamino, pyrrolylcarbonylamino, imidazolylcarbonylamino, pyrazolylcarbonylamino, triazolylcarbonylamino, tetrazolylcarbonylamino, nicotinoylamino, isonicotinoylamino, pyrazinylcarbonylamino, pyrimidinylcarbonylamino, pyridazinylcarbonylamino, thiazolylcarbonylamino, oxazolylcarbonylamino, oxadiazolylcarbonylamino, thiadiazolylcarbonylamino, N,N-diacetylamino, N-formyl- N-hexylamino, N-acetyl-N-methylamino, N-acetyl-N-ethylamino, N-acetyl-N-propylamino, N-acetyl-N-butylamino, N-acetyl-N-pentylamino, N-acetyl-N-hexylamino, N-benzoyl-N-methylamino, N-benzoyl-N-ethylamino, N-benzoyl-N-propylamino, N-benzoyl-N-butylamino, N-benzoyl-N-pentylamino, N-benzoyl-N-hexylamino, N-benzoyl-N-phenylamino, N-benzyl-N-benzoylamino, N-hexyl-N-1-naphthoylamino, N-hexyl-N-2-naphthoylamino, N-hexyl-N-phenylacetylamino, N-butyl-N-nicotinoylamino, N-hexyl-N-nicotinoylamino, N-isonicotinoyl-N-hexylamino or 4-trifluoromethylphenylcarbamoylamino, is preferably an amino group (which may be substituted one or two $C_1$–$C_{10}$ alkyl or $C_1$–$C_7$ aliphatic acyl groups), more preferably an amino group (which may be substituted with one or two $C_1$–$C_6$ alkyl groups or $C_1$–$C_2$ aliphatic acyl groups).

From the above-mentioned definition for the substituents α and β, in the case where $R_1$ represents a "carbamoyl group (which may have one or two substituents α)", the group having the substituent may include methylcarbamoyl, ethylcarbamoyl, propylcarbamoyl, isopropylcarbamoyl, butylcarbamoyl, s-butylcarbamoyl, t-butylcarbamoyl, pentylcarbamoyl, hexylcarbamoyl, decylcarbamoyl, (trifluoromethyl)carbamoyl, (tetrafluoropropyl)carbamoyl, cyclopropylcarbamoyl, cyclopentylcarbamoyl, cyclohexylcarbamoyl, adamantylcarbamoyl, phenylcarbamoyl, methylphenylcarbamoyl, isopropylphenylcarbamoyl, diisopropylphenylcarbamoyl, triisopropylphenylcarbamoyl, 2-, 3- or 4-(trifluoromethyl)phenylcarbamoyl, 2-, 3- or 4-methoxyphenylcarbamoyl, fluorophenylcarbamoyl, difluorophenylcarbamoyl, trifluorophenylcarbarnoyl, 2-, 3- or 4-chlorophenylcarbamoyl, difluorophenylcarbamoyl, hydroxyphenylcarbamoyl, 2,5dimethyl-4-hydroxyphenylcarbamoyl, 2,5-t-butyl-4-hydroxyphenylcarbamoyl, cyanophenylcarbamoyl, nitrophenylcarbamoyl, cyclopropylphenylcarbamoyl, cyclohexylphenylcarbamoyl, adamantylphenylcarbamoyl, biphenylcarbamoyl, benzylphenylcarbamoyl, acetylphenylcarbamoyl, acetyloxyphenylcarbamoyl, aminophenylcarbamoyl, dimethylaminophenylcarbamoyl, diethylaminophenylcarbamoyl, methylenedioxyphenylcarbamoyl, ethylenedioxyphenylcarbamoyl, 1- or 2-naphthylcarbamoyl, benzylcarbamoyl, methylbenzylcarbamoyl, isopropylbenzylcarbamoyl, diisopropylbenzylcarbamoyl, triisopropylbenzylcarbamoyl, (trifluoromethyl)benzylcarbamoyl, methoxybenzylcarbamoyl, fluorobenzylcarbamoyl, difluorobenzylcarbamoyl, trifluorobenzylcarbamoyl, 2-, 3- or 4-chlorobenzylcarbamoyl, dichlorobenzylcarbamoyl, hydroxybenzylcarbamoyl, cyanobenzylcarbamoyl, nitrobenzylcarbamoyl, cyclopropylbenzylcarbamoyl, cyclohexylbenzylcarbamoyl, adamantylbenzylcarbamoyl, phenylbenzylcarbamoyl, benzylbenzylcarbamoyl, acetylbenzylcarbamoyl, acetyloxybenzylcarbamoyl, aminobenzylcarbamoyl, dimethylaminobenzylcarbamoyl, methylenedioxybenzylcarbamoyl, phenethylcarbamoyl, (trifluoromethyl)phenethylcarbamoyl, fluorophenethylcarbamoyl, cyclopropylcarbonylcarbamoyl, cyclohexylcarbonylcarbamoyl, adamantylcarbonylcarbamoyl, benzoylcarbamoyl, phenylacetylcarbamoyl, 4-phenylbutylcarbamoyl, pyrrolylcarbamoyl, furylcarbamoyl, thienylcarbamoyl, 2-, 3- or 4-pyridylcarbamoyl, pyrrolylcarbonylcarbamoyl, furylcarbonylcarbamoyl, thienylcarbonylcarbamoyl, nicotinoylcarbamoyl, methanesulfonylcarbamoyl, trifluoromethylcarbamoyl, benzenesulfonylcarbamoyl, toluenesulfonylcarbamoyl or benzylsulfonylcarbamoyl, is preferably a carbamoyl group which may have one substituent α, more preferably a carbamoyl group which may be substituted with one group selected from a $C_1$–$C_{10}$ alkyl group, a $C_3$–$C_{10}$ cycloalkyl group, a $C_6$–$C_{10}$ aryl group which may have from 1 to 3 substituents γ, or an aralkyl group consisting of a $C_1$–$C_6$ alkyl group which is substituted by a $C_6$–$C_{10}$ aryl group, which itself may have from 1 to 3 substituents γ.

In the case where $R_1$ represents a "thiocarbamoyl group (which may have one or two substituents α)", the group having the substituent may include methylthiocarbamoyl, ethylthiocarbamoyl, propylthiocarbamoyl, isopropylthiocarbamoyl, butylthiocarbamoyl, s-butylthiocarbamoyl, t-butylthiocarbamoyl, pentylthiocarbamoyl, hexylthiocarbamoyl, decylthiocarbamoyl, cyclopropylthiocarbamoyl, cyclopentylthiocarbamoyl, cyclohexylthiocarbamoyl, adamantylthiocarbamoyl, phenylthiocarbamoyl, methylphenylthiocarbamoyl, isopropylphenylthiocarbamoyl, diisopropylphenylthiocarbamoyl, triisopropylphenylthiocarbamoyl, 2-, 3- or 4-(trifluoromethyl)phenylthiocarbamoyl, 2- 3- or 4-methoxyphenylthiocarbamoyl, fluorophenylthiocarbamoyl, difluorophenylthiocarbamoyl, trifluorophenylthiocarbamoyl, 2-, 3- or 4-chlorophenylthiocarbamoyl, dichlorophenylthiocarbamoyl, 2,5-dimethyl-4-hydroxyphenylthiocarbamoyl, 2,5-t-butyl-4-hydroxyphenylthiocarbamoyl, hydroxyphenylthiocarbamoyl, cyanophenylthiocarbamoyl, nitrophenylthiocarbamoyl, cyclohexylphenylthiocarbamoyl, adamantylphenylthiocarbamoyl, biphenylthiocarbamoyl, benzylphenylthiocarbamoyl, acetylphenylthiocarbamoyl, acetyloxyphenylthiocarbamoyl, aminophenylthiocarbamoyl, dimethylaminophenylthiocarbamoyl, methylenedioxyphenylthiocarbamoyl, 1- or 2-naphthylthiocarbamoyl, benzylthiocarbamoyl, methylbenzylthiocarbamoyl, isopropylbenzylthiocarbamoyl, diisopropylbenzylthiocarbamoyl, triisopropylbenzylthiocarbamoyl, (trifluoromethylbenzyl)thiocarbamoyl, fluorobenzylthiocarbamoyl, difluorobenzylthiocarbamoyl, trifluorobenzylthiocarbamoyl, 2-, 3- or 4-chlorobenzylthiocarbamoyl, dichlorobenzylthiocarbamoyl, hydroxybenzylthiocarbamoyl, cyanobenzylthiocarbamoyl, nitrobenzylthiocarbamoyl, cyclopropylbenzylthiocarbamoyl, cyclohexylbenzylthiocarbamoyl, adamantylbenzylthiocarbamoyl, acetylbenzylthiocarbamoyl, acetyloxybenzylthiocarbamoyl, aminobenzylthiocarbamoyl, dimethylaminobenzylthiocarbamoyl, methylenedioxybenzylthiocarbamoyl, cyclopropylcarbonylthiocarbamoyl, cyclohexylcarbonylthiocarbamoyl, adamantylcarbonylthiocarbamoyl, benzoylthiocarbamoyl, phenylacetylthiocarbamoyl, 2-, 3- or 4-pyridylthiocarbamoyl, nicotinoylthiocarbamoyl, methanesulfonylthiocarbamoyl, trifluoromethylthiocarbamoyl, benzenesulfonylthiocarbamoyl, toluenesulfonylthiocarbamoyl or benzylsulfonylthiocarbamoyl, is preferably a thiocarbamoyl group which may have one substituent α, and more preferably a thiocarbamoyl group which may be substituted with one group selected from a $C_1$–$C_{10}$ alkyl group, a $C_3$–$C_{10}$ cycloalkyl group, a $C_6$–$C_{10}$ aryl group (which may have from 1 to 3 substituents γ) and a $C_7$–$C_{16}$ aralkyl group (which may have from 1 to 3 substituents γ on the aryl portion).

In the case where $R_1$ represents a "sulfonyl group having one substituent α", the group may include methanesulfonyl, ethanesulfonyl, propanesulfonyl, isopropanesulfonyl, butanesulfonyl, s-butanesulfonyl, t-butanesulfonyl, pentanesulfonyl, hexanesulfonyl, cyclopropanesulfonyl, cyclopentanesulfonyl, cyclohexanesulfonyl, adamantanesulfonyl, benzenesulfonyl, toluenesulfonyl, isopropylbenzenesulfonyl, diisopropylbenzenesulfonyl, triisopropylbenzenesulfonyl, (trifluoromethyl)benzenesulfonyl, fluorobenzenesulfonyl, chlorobenzenesulfonyl, hydroxybenzenesulfonyl, cyanobenzenesulfonyl, nitrobenzenesulfonyl, cyclohexylbenzenesulfonyl, adamantylbenzensulfonyl, acetylbenzenesulfonyl, acetyloxybenzenesulfonyl, aminobenzenesulfonyl, dimethylaminobenzenesulfonyl, methylenedioxybenzenesulfonyl, 1- or 2-naphthalenesulfonyl, phenylmethylsulfonyl or pyridinesulfonyl, and is preferably a sulfonyl group which is substituted with one group selected from a $C_1$–$C_{10}$ alkyl group, a $C_3$–$C_{10}$ cycloalkyl group, a $C_6$–$C_{10}$ aryl group (which may have from 1 to 3 substituents γ), or with a $C_7$–$C_{16}$ aralkyl group (which may have from 1 to 3 substituents γ on the aryl portion).

In the case where $R_1$ represents a "carbonyl group which has one substituent α", the group having the substituent may include acetyl, propionyl, butyryl, isopropylcarbonyl, butylcarbonyl, s-butylcarbonyl, t-butylcarbonyl, pentylcarbonyl, hexylcarbonyl, decylcarbonyl, cyclopropylcarbonyl, cyclopentylcarbonyl, cyclohexylcarbonyl, adamantylcarbonyl, phenylcarbonyl, methylphenylcarbonyl, isopropylphenylcarbonyl, diisopropylphenylcarbonyl, triisopropylphenylcarbonyl, 2-, 3- or 4-(trifluoromethylphenyl)carbonyl, 2-, 3- or 4-methoxyphenylcarbonyl, fluorophenylcarbonyl, difluorophenylcarbonyl, trifluorophenylcarbonyl, 2-, 3- or 4-chlorophenylcarbonyl, dichlorophenylcarbonyl, 2,5-dimethyl-4-hydroxyphenylcarbonyl, 2,5-t-butyl4-hydroxyphenylcarbonyl, hydroxyphenylcarbonyl, cyanophenylcarbonyl, nitrophenylcarbonyl, cyclohexylphenylcarbonyl, adamantylphenylcarbonyl, biphenylcarbonyl, benzylphenylcarbonyl, acetylphenylcarbonyl, acetyloxyphenylcarbonyl, aminophenylcarbonyl, dimethylaminophenylcarbonyl, methylenedioxyphenylcarbonyl, 1- or 2-naphthylcarbonyl, benzylcarbonyl, methylbenzylcarbonyl, isopropylbenzylcarbonyl, diisopropylbenzylcarbonyl, triisopropylbenzylcarbonyl, (trifluoromethyl)benzylcarbonyl, fluorobenzylcarbonyl, difluorobenzylcarbonyl, trifluorobenzylcarbonyl, 2-, 3- or 4-chlorobenzylcarbonyl, dichlorobenzylcarbonyl, hydroxybenzylcarbonyl, cyanobenzylcarbonyl, nitrobenzylcarbonyl, cyclopropylbenzylcarbonyl, cyclohexylbenzylcarbonyl, adamantylbenzylcarbonyl, acetylbenzylcarbonyl, acetyloxybenzylcarbonyl, aminobenzylcarbonyl, dimethylaminobenzylcarbonyl, methylenedioxybenzylcarbonyl, cyclopropylcarbonylcarbonyl, cyclohexylcarbonylcarbonyl, adamantylcarbonylcarbonyl, benzoylcarbonyl, phenylacetylcarbonyl, 2-, 3- or 4-pyridylcarbonyl, nicotinoylcarbonyl, methanesulfonylcarbonyl, trifluoromethylcarbonyl, benzenesulfonylcarbonyl, toluenesulfonylcarbonyl or benzylsulfonylcarbonyl, and is preferably a carbonyl group which, may be substituted with one group selected from a $C_1$–$C_{10}$ alkyl group, a $C_3$–$C_{10}$ cycloalkyl group, a $C_6$–$C_{10}$ aryl group (which may have from 1 to 3 substituents γ) and a $C_7$–$C_{16}$ aralkyl group (which may have from 1 to 3 substituents γ on the aryl portion).

In the case where $R_2$, $R_3$ or L represents a "$C_6$–$C_{10}$ aryl group (which may have from 1 to 3 substituents β)", the group having the substituents may include methylphenyl, isopropylphenyl, (trifluoromethyl)phenyl, methoxyphenyl, fluorophenyl, chlorophenyl, hydroxyphenyl, biphenyl, benzylphenyl, cyanophenyl, nitrophenyl, aminophenyl, dimethylaminophenyl, diethylaminophenyl or 1- or 2-naphthyl, is preferably a phenyl group (which may have from 1 to 3 substituents β), more preferably a phenyl group (which may have one or two substituents β), and most preferably a phenyl group (which may be substituted by one substituent β).

In the case where $R_2$, $R_3$ or L represents a "$C_7$–$C_{16}$ aralkyl group (which may have from 1 to 3 substituents β on the aryl portion)", the group having the substituents may include methylbenzyl, isopropylbenzyl, (trifluoromethyl)benzyl, methoxybenzyl, fluorobenzyl, chlorobenzyl, hydroxybenzyl, phenylbenzyl, cyanobenzyl, nitrobenzyl, aminobenzyl, dimethylaminobenzyl, methylphenethyl, isopropylphenethyl, (trifluoromethyl)phenethyl, methoxyphenethyl, fluorophenethyl, chlorophenethyl, hydroxyphenethyl, phenylphenethyl, cyanophenethyl, nitrophenethyl, aminophenethyl, dimethylaminophenethyl, methylnaphthylmethyl, isopropylnaphthylmethyl, (trifluoromethyl)naphthylmethyl, methoxynaphthylmethyl, fluoronaphthylmethyl, chloronaphthylmethyl, hydroxynaphthylmethyl, cyanonaphthylmethyl, nitronaphthylmethyl, aminonaphthylmethyl or dimethylaminonaphthylmethyl, is preferably a phenyl-$C_1$–$C_6$ alkyl group (which may have from 1 to 3 substituents β on the phenyl portion), more preferably a phenyl-$C_1$–$C_4$ alkyl group (which may have from 1 to 3 substituents β on the phenyl portion), still more preferably a phenyl-$C_1$–$C_2$ alkyl group (which may have from 1 to 3 substituents β on the phenyl portion), and most preferably a phenyl-$C_1$–$C_2$ alkyl group (which may have one substituent β on the phenyl portion).

The amine derivative compound of the present compound of formula (I) can be converted to a salt according to a conventional method. Such salt may include inorganic salts, for example alkali metal salts such as a sodium salt a potassium salt and a lithium salt; alkaline earth metals such as a calcium salt and a magnesium salt; metal salts such as an aluminum salt, an iron salt, a zinc salt, a copper salt, a nickel salt and a cobalt salt; an ammonium salt; amine salts such as organic salts, e.g., a t-octylamine salt, a dibenzylamine salt, a morpholine salt, a glucosamine salt, a phenylglycine alkyl ester salt, an ethylenediamine salt, a N-methylglucamine salt, a guanidine salt, a diethylamine salt, a triethylamine salt, a dicyclohexylamine salt, a N,N'-dibenzylethylenediamine salt, a chloroprocaine salt, a procaine salt, a diethanolamine salt, a N-benzyl-N-phenethylamine salt, a piperazine salt, a tetramethylammonium salt and a tris(hydroxymethyl)aminomethane salt; an inorganic acid salt, for example a hydrohalogenic acid salt such as a hydrofluoride, a hydrochloride, a hydrobromide and a hydroiodide; a nitrite, a perchlorate, a sulfate and a phosphate; a salt of an organic acid, for example a lower alkanesulfonate such as a methanesulfonate, trifluoromethanesulfonate and ethanesulfonate salt; an arylsulfonate such as a benzenesulfonate and p-toluenesulfonate salt; a salt of an amino acid such as a glutamate and an aspartate; a carboxylate such as fumarate, succinate, citrate, tartrate, oxalate and maleate; and amino acid salts such as ornithinate, glutamate and aspartate, more preferably a hydrohalogenic acid salt and an organic acid salt.

Various isomers are included in the compound of the present invention. For example, a thiazolidine ring and an oxazolidine ring of the amine derivative compound of the above formula (I) include an asymmetric carbon, and since an asymmetric carbon sometimes exists on a substituent group, such compounds have optical isomers.

That is, stereoisomers of R-configuration and S-configuration exist in the amine derivative compound of the above formula (I). Each of the respective stereoisomers or compounds containing such stereoisomers in an arbitrary proportion are all included in the present invention. Such stereoisomers can be obtained by synthesizing the amine derivative compound of the compound (I) by using an optically active starting material or by subjecting the synthesized amine derivative compound of the compound (I) to optical resolution, as necessary, using a conventional optical resolution or separation method.

The amine derivative compound of the compound (I) of the present invention absorbs moisture when it is left to stand in the atmosphere or recrystallized to carry adsorbed water or to be hydrated. Such compounds are also included in the present invention in the case they form hydrates.

The amine derivative compound of the compound (I) of the present invention sometimes absorbs other certain kinds of solvents to form a solvate and such a solvate is also included in the present invention.

Moreover, the present invention also includes all so-called prodrugs which are compounds that are metabolized in the living body and converted to the amine derivative compounds or their pharmacologically acceptable salts of the compound of formula (I) of the present invention.

The amine derivative compounds or their pharmacologically acceptable salts of the compound of formula (I) of the present invention may be used together with another drug (i.e., active agent), and particularly with sulfonylurea agents, α-glucosidase inhibitory agents, aldose reductase inhibitory agents, biguanide agents, statin type compounds, squalene synthesis inhibitory agents, fibrate type compounds, LDL disassimilation promoters, angiotensin II antagonists, angiotensin converting enzyme inhibitory agents, antitumor agents and FBPase inhibitory agents.

Among the above, sulfonylurea agents refer to drugs that promote the secretion of insulin, examples of which include tolbutamide, acetohexamide, tolazamide and chlorpropamide.

Among the above, α-glucosidase inhibitory agents refer to drugs that inhibit digestive enzymes such as amylase, maltase, α-dextrinase and squalase and have the effect of delaying digestion of starch and sucrose, examples of which include acarbose, N-(1,3-dihydroxy-2-propyl)valiolamine (generic name: voglibose) and migritol.

Among the above, aldose reductase inhibitory agents refer to drugs that inhibit diabetic complications by inhibiting the rate-determining enzyme of the first step of the polyol route, examples of which include tolrestat, epalrestat, 2,7-difluoro-spiro(9H-fluorene-9,4'-imidazolidine)-2',5'-dione (generic name: imirestat), 3-[(4-bromo-2-fluorophenyl)methyl]-7-chloro-3,4-dihydro-2,4-dioxo-1(2H)-quinazoline acetate (generic name: zenarestat), 6-fluoro-2,3-dihydro-2',5'-dioxo-spiro[4H-1-benzopyran-4,4'-imidazolidine]-2-carboxamide (SNK-860), zopolurestat, sorbinil and 1-[(3-bromo-2-benzofuranyl)sulfonyl]-2,4-imidazolidinedione (M-16209).

Among the above, biguanide agents refer to drugs having, effects such as anaerobic glycolysis promoting effects, enhancement of peripheral insulin effects, suppression of absorption of glucose from the intestinal tract, suppression of liver glyconeogenesis and inhibition of fatty acid oxidation, examples of which include fenformin, metformin and buformine.

Among the above, statin type compounds refer to drugs that lower blood cholesterol by inhibiting hydroxymethylglutaryl CoA (HMG-CoA) reductase, examples of which include pravastatin and its sodium salt, simvastatin, lovastatin, atorvastatin, cerivastatin and fluvastatin.

Among the above, squalene synthesis inhibitory agents refer to drugs that lower blood cholesterol by inhibiting squalene synthesis, examples of which include (S)-α-[bis(2, 2-dimethyl-1-oxopropoxy)methoxy]phosphinyl-3-phenoxybenzene butanesulfonate monopotassium salt (BMS-188494).

Among the above, fibrate type compounds refer to drugs that lower blood triglycerides by inhibiting triglyceride synthesis and secretion in the liver and activating lipoprotein lipase, examples of which include bezafibrate, beclobrate, vinifibrate, ciprofibrate, clinofibrate, clofibrate, clofibrinic acid, etofibrate, fenofibrate, gemfibrozil, nicofibrate, pyrifibrate, lonifibrate, simfibrate and theofibrate.

Among the above, LDL disassimilation promoters refer to drugs that lower blood cholesterol by increasing LDL (low-density lipoprotein) receptors, examples of which include the compound described in Japanese Patent Application (Kokai) No. Hei 7-346144 or its salt, and more specifically, N-{2-[4-bis(4-fluorophenyl)methyl-1-piperazinyl]ethyl}-7, 7-diphenyl-2,4,6-heptatrienic acid amide.

The above-mentioned statin type compounds, squalene synthesis inhibitory agents, fibrate type compounds and LDL disassimilation promoters may be substituted with other drugs that have the effects of lowering blood cholesterol and triglycerides. Examples of such drugs include nicotinic acid derivative such as nicomol and niceritrol, antioxidants such as probucol, and ion exchange resins such as colestyramine.

Among the above, angiotensin II antagonists refer to drugs that lower blood pressure by strongly suppressing elevation of blood pressure caused by angiotensin II. Examples of such drugs include losartan potassium, candesartan, cilexetil, valsartan, termisartan and ormesartan.

Among the above, angiotensin converting enzyme inhibitory agents refer to drugs that partially lower blood sugar in diabetes patients while simultaneously lowering blood pressure by inhibiting angiotensin convertase, examples of which include captopril, enalapril, alacepril, delapril, lamipril, lisinopril, imidapril, benazepril, ceronapril, cilazapril, enalapril maleate, fosinopril, mobertopril, perindopril, quinapril, spirapril, temocapril and trandolapril.

Among the above, FBPase inhibitory agents refer to diabetes therapeutic and/or preventing agents that are drugs having an inhibitory effect on fructose-1,6-bisphosphatase (FBPase), which is a rate-determining enzyme of glyconeogenesis in the liver.

The amine derivative compound of the above formula (I) may preferably include (1) the amine derivative compound or pharmacologically acceptable salt thereof in which $R_1$ represents a carbamoyl group (which may have one substituent α), a thiocarbamoyl group (which may have one substituent α), a sulfonyl group (which has one substituent α) or a carbonyl group (which has one substituent α);

(2) the amine derivative compound or pharmacologically acceptable salt thereof in which $R_1$ represents a carbamoyl group (which has one substituent α), a thiocarbamoyl group (which has one substituent α), a sulfonyl group (which has one substituent α) or a carbonyl group (which has one substituent α);

(3) the amine derivative compound or pharmacologically acceptable salt thereof in which $R_1$ represents a carbamoyl group (which has one substituent α), a thiocarbamoyl group (which has one substituent α) or a carbonyl group (which has one substituent α);

(4) the amine derivative compound or pharmacologically acceptable salt thereof in which $R_1$ represents a carbamoyl group (which has one substituent α);

(5) the amine derivative compound or pharmacologically acceptable salt thereof in which $R_1$ represents a thiocarbamoyl group (which has one substituent α);

(6) the amine derivative compound or pharmacologically acceptable salt thereof in which $R_1$ represents a carbonyl group (which has one substituent α);

(7) the amine derivative compound or pharmacologically acceptable salt thereof in which $R_2$ represents a hydrogen atom, a $C_1$–$C_{10}$ alkyl group, a phenyl group (which may have from 1 to 3 substituents β) or a benzyl group (which may have from 1 to 3 substituents β on the phenyl portion);

(8) the amine derivative compound or pharmacologically acceptable salt thereof in which $R_2$ represents a hydrogen atom, a $C_1$–$C_{10}$ alkyl group, a phenyl group (which may have one substituent β) or a benzyl group (which may have one substituent β on the phenyl portion);

(9) the amine derivative compound or pharmacologically acceptable salt thereof in which $R_2$ represents a hydrogen atom or a $C_1$–$C_{10}$ alkyl group;

(10) the amine derivative compound or pharmacologically acceptable salt thereof in which $R_2$ represents a hydrogen atom or a $C_1$–$C_6$ alkyl group;

(11) the amine derivative compound or pharmacologically acceptable salt thereof in which $R_2$ represents a hydrogen atom;

(12) the amine derivative compound or pharmacologically acceptable salt thereof in which $R_2$ represents a $C_1$–$C_6$ alkyl group;

(13) the amine derivative compound or pharmacologically acceptable salt thereof in which $R_3$ represents a hydrogen atom, a $C_1$–$C_6$ alkyl group, a phenyl group (which may have from 1 to 3 substituents β) or a benzyl group (which may have from 1 to 3 substituents β on the phenyl portion);

(14) the amine derivative compound or pharmacologically acceptable salt thereof in which $R_3$ represents a hydrogen atom, a $C_1$–$C_6$ alkyl group, a phenyl group (which may have one substituent β) or a benzyl group (which may have one substituent β on the phenyl portion);

(15) the amine derivative compound or pharmacologically acceptable salt thereof in which $R_3$ represents a hydrogen atom or a $C_1$–$C_4$ alkyl group;

(16) the amine derivative compound or pharmacologically acceptable salt thereof in which $R_3$ represents a $C_1$–$C_2$ alkyl group;

(17) the amine derivative compound or pharmacologically acceptable salt thereof in which $R_3$ represents a methyl group;

(18) the amine derivative compound or pharmacologically acceptable salt thereof in which $W_1$, $W_2$ and $W_3$ each represent a single bond or a $C_1$–$C_6$ alkylene group;

(19) the amine derivative compound or pharmacologically acceptable salt thereof in which $W_1$, $W_2$ and $W_3$ each represent a single bond or a $C_1$–$C_4$ alkylene group;

(20) the amine derivative compound or pharmacologically acceptable salt thereof in which $W_1$ and $W_2$ each represent a single bond or a $C_1$–$C_4$ alkylene group, and $W_3$ represents a $C_1$–$C_2$ alkylene group;

(21) the amine derivative compound or pharmacologically acceptable salt thereof in which $W_1$ and $W_2$ each represent a single bond or a $C_1$–$C_2$ alkylene group, and $W_3$ represents a methylene group;

(22) the amine derivative compound or pharmacologically acceptable salt thereof in which $W_1$ and $W_2$ represent a single bond and $W_3$ represents a methylene group;

(23) the amine derivative compound or pharmacologically acceptable salt thereof in which X represents an oxygen atom or a sulfur atom, Y represents an oxygen atom and Q represents a sulfur atom;

(24) the amine derivative compound or pharmacologically acceptable salt thereof in which X represents an oxygen atom, Y represents an oxygen atom and Q represents a sulfur atom;

(25) the amine derivative compound or pharmacologically acceptable salt thereof in which Z represents a =CH— group;

(26) the amine derivative compound or pharmacologically acceptable salt thereof in which Z represents a nitrogen atom;

(27) the amine derivative compound or pharmacologically acceptable salt thereof in which Ar represents a naphthalene ring;

(28) the amine derivative compound or pharmacologically acceptable salt thereof in which Ar represents a benzene ring;

(29) the amine derivative compound or pharmacologically acceptable salt thereof in which L represents from 1 to 4 substituents on the Ar ring and the or each substituent is a hydrogen atom, a $C_1$–$C_6$ alkyl group, a phenyl group (which may have from 1 to 3 substituents β) or a benzyl group (which may have from 1 to 3 substituents β on the phenyl portion);

(30) the amine derivative compound or pharmacologically acceptable salt thereof in which L represents from 1 to 4 substituents on the Ar ring and the or each substituent is a hydrogen atom, a $C_1$–$C_6$ alkyl group, a phenyl group (which may have from 1 to 3 substituents β) or a benzyl group (which may have from 1 to 3 substituents β on the phenyl portion);

(31) the amine derivative compound or pharmacologically acceptable salt thereof in which L represents from 1 to 4 substituents on the Ar ring and the or each substituent is a hydrogen atom or a $C_1$–$C_6$ alkyl group;

(32) the amine derivative compound or pharmacologically acceptable salt thereof in which L represents from 1 to 4 substituents on the Ar ring and the or each substituent is a hydrogen atom or a $C_1$–$C_4$ alkyl group;

(33) the amine derivative compound or pharmacologically acceptable salt thereof in which each L represents a hydrogen atom;

(34) the amine derivative compound or pharmacologically acceptable salt thereof in which substituent α represents (i) a $C_1$–$C_{10}$ alkyl group, (ii) a $C_5$–$C_{10}$ cycloalkyl group, (iii) a $C_6$–$C_{10}$ aryl group (which may have from 1 to 3 substituents γ), (iv) a phenyl-$C_1$–$C_6$ alkyl group (which may have from 1 to 3 substituents γ on the phenyl portion), (v) a phenylcarbonyl group (which may have from 1 to 3 substituents γ on the phenyl portion), (vi) an aromatic heterocyclic group (which may have from 1 to 3 substituents γ), (vii) a $C_1$–$C_4$ alkylsulfonyl group, (viii) a $C_1$–$C_4$ halogenoalkylsulfonyl group or (ix) a phenylsulfonyl group (which may have from 1 to 3 substituents γ on the phenyl portion);

(35) the amine derivative compound or pharmacologically acceptable salt thereof in which substituent α represents (i) a $C_1$–$C_8$ alkyl group, (ii) a $C_5$–$C_{10}$ cycloalkyl group, (iii) a $C_6$–$C_{10}$ aryl group (which may have from 1 to 3 substituents γ), (iv) a phenyl-$C_1$–$C_4$ alkyl group (which may have from 1 to 3 substituents γ on the phenyl portion), (v) a pyridyl group, (vi) a methanesulfonyl group, (vii) a trifluoromethanesulfonyl group or (viii) a phenylsulfonyl group (which may have from 1 to 3 substituents γ on the phenyl portion);

(36) the amine derivative compound or pharmacologically acceptable salt thereof in which a substituent cc represents (i) a $C_1$–$C_8$ alkyl group, (ii) a $C_5$–$C_{10}$ cycloalkyl group, (iii) a $C_6$–$C_{10}$ aryl group (which may have from 1 to 3 substituents γ), (iv) a phenyl-$C_1$–$C_4$ alkyl group (which may have from 1 to 3 substituents γ on the phenyl portion), (v) a pyridyl group or (vi) a phenylsulfonyl group (which may have from 1 to 3 substituents γ on the phenyl portion);

(37) the amine derivative compound or pharmacologically acceptable salt thereof in which the substituent α represents (i) a $C_1$–$C_4$ alkyl group, (ii) a $C_5$–$C_{10}$ cycloalkyl group, (iii) a $C_6$–$C_{10}$ aryl group (which may have from 1 to 3 substituents γ), (iv) a benzyl group (which may have from 1 to 3 substituents γ on the phenyl portion) or (v) a pyridyl group;

(38) the amine derivative compound or pharmacologically acceptable salt thereof in which substituent α represents (i) a $C_1$–$C_4$ alkyl group, (ii) a $C_5$–$C_{10}$ cycloalkyl group, (iii) a $C_6$–$C_{10}$ aryl group (which may have from 1 to 3 substituents γ) or (iv) a pyridyl group;

(39) the amine derivative compound or pharmacologically acceptable salt thereof in which substituent α represents a $C_1$–$C_4$ alkyl group;

(40) the amine derivative compound or pharmacologically acceptable salt thereof in which substituent α represents a $C_5$–$C_{10}$ cycloalkyl group;

(41) the amine derivative compound or pharmacologically acceptable salt thereof in which substituent α represents a phenyl group (which may have from 1 to 3 substituents γ);

(42) the amine derivative compound or pharmacologically acceptable salt thereof in which substituent α represents a pyridyl group;

(43) the amine derivative compound or pharmacologically acceptable salt thereof in which substituent β represents (i) a $C_1$–$C_4$ alkyl group, (ii) a $C_1$–$C_2$ halogenoalkyl group, (iii) a $C_1$–$C_4$ alkoxy group, (iv) a halogen atom, (v) a hydroxyl group, (vi) a cyano group, (vii) a nitro group or (viii) an amino group (which may have one or two substituents δ);

(44) the amine derivative compound or pharmacologically acceptable salt thereof in which substituent β represents (i) a $C_1$–$C_4$ alkyl group, (ii) a trifluoromethyl group, (iii) a $C_1$–$C_2$ alkoxy group, (iv) a halogen atom, (v) a hydroxyl group or (vi) an amino group;

(45) the amine derivative compound or pharmacologically acceptable salt thereof in which substituent β represents (i) a $C_1$–$C_4$ alkyl group, (ii) a halogen atom or (iii) a hydroxyl group;

(46) the amine derivative compound or pharmacologically acceptable salt thereof in which substituent γ represents (i) a $C_1$–$C_6$ alkyl group, (ii) a $C_1$–$C_4$ halogenoalkyl group, (iii) a $C_1$–$C_6$ alkoxy group, (iv) a halogen atom, (v) a hydroxyl group, (vi) a cyano group, (vii) a nitro group, (viii) a phenyl group, (ix) a benzyl group, (x) a $C_1$–$C_5$ aliphatic acyl group, (xi) an amino group or (xii) a $C_1$–$C_4$ alkylenedioxy group;

(47) the amine derivative compound or pharmacologically acceptable salt thereof in which substituent γ represents (i) a $C_1$–$C_6$ alkyl group, (ii) a $C_1$–$C_2$ halogenoalkyl group, (iii) a $C_1$–$C_4$ alkoxy group, (iv) a halogen atom, (v) a hydroxyl group, (vi) a cyano group, (vii) a nitro group, (viii) a $C_1$–$C_2$ aliphatic acyl group or (ix) a $C_1$–$C_4$ alkylenedioxy group;

(48) the amine derivative compound or pharmacologically acceptable salt thereof in which substituent γ represents (i) a $C_1$–$C_6$ alkyl group, (ii) a trifluoromethyl group, (iii) a $C_1$–$C_4$ alkoxy group, (iv) a halogen atom, (v) a hydroxyl group, (vi) a cyano group, (vii) a nitro group, (viii) a $C_1$–$C_2$ aliphatic acyl group or (ix) a $C_1$–$C_4$ alkylenedioxy group;

(49) the amine derivative compound or pharmacologically acceptable salt thereof in which substituent γ represents (i) a $C_1$–$C_4$ alkyl group, (ii) a trifluoromethyl group, (iii) a halogen atom or (iv) a nitro group;

(50) the amine derivative compound or pharmacologically acceptable salt thereof in which substituent γ represents a $C_1$–$C_4$ alkyl group or a halogen atom;

(51) the amine derivative compound or pharmacologically acceptable salt thereof in which substituent δ represents (i) a $C_1$–$C_4$ alkyl group, (ii) a phenyl group, (iii) a benzyl group, (iv) a $C_1$–$C_5$ aliphatic acyl group or (v) a benzoyl group;

(52) the amine derivative compound or pharmacologically acceptable salt thereof in which substituent δ represents a $C_1$–$C_4$ alkyl group or a $C_1$–$C_2$ aliphatic acyl group.

In the amine derivative compound of the above formula (I), preferred are the compounds in which $R_1$ is selected from (1) to (6), $R_2$ is selected from (7) to (12), $R_3$ is selected from (13) to (17), $W_1$, $W_2$ and $W_3$ are selected from (18) to (22), X, Y and Q are selected from (23) and (24), Z is selected from (25) and (26), Ar is selected from (27) and (28), L is selected from (29) to (33), substituent α is selected from (34) to (42), substituent β is selected from (43) to (45), substituent γ is selected from (46) to (50) and substituent δ is selected from (51) and (52) and used in appropriate combination.

For example, in the amine derivative compound of the above formula (I), the following compounds are also preferred:

(53) the amine derivative compound or pharmacologically acceptable salt thereof in which $R_1$ represents a carbamoyl group (which may have one substituent α), a thiocarbamoyl group (which may have one substituent α), a sulfonyl group (which has one substituent α) or a carbonyl group (which has one substituent α);

$R_2$ represents a hydrogen atom, a $C_1$–$C_{10}$ alkyl group, a phenyl group (which may have one substituent β)

or a benzyl group (which may have one substituent β on the phenyl portion);

$R_3$ represents a hydrogen atom, a $C_1$–$C_6$ alkyl group, a phenyl group (which may have one substituent β) or a benzyl group (which may have one substituent β on the phenyl portion);

$W_1$, $W_2$ and $W_3$ each represent a single bond or a $C_1$–$C_4$ alkylene group;

X represents an oxygen atom or a sulfur atom, Y represents an oxygen atom and Q represents a sulfur atom;

Z represents a =CH— group;

Ar represents a benzene ring;

L represents from 1 to 4 substituents on the Ar ring and the or each substituent is a hydrogen atom, a $C_1$–$C_6$ alkyl group, a phenyl group (which may have from 1 to 3 substituents β) or a benzyl group (which may have from 1 to 3 substituents β on the phenyl portion);

substituent α represents (i) a $C_1$–$C_8$ alkyl group, (ii) a $C_5$–$C_{10}$ cycloalkyl group, (iii) a $C_6$–$C_{10}$ aryl group (which may have from 1 to 3 substituents γ), (iv) a phenyl $C_1$–$C_4$ alkyl group (which may have from 1 to 3 substituents γ on the phenyl portion), (v) a pyridyl group, (vi) a methanesulfonyl group, (vii) a trifluoromethanesulfonyl group or (viii) a phenylsulfonyl group (which may have from 1 to 3 substituents γ on the phenyl portion);

substituent β represents (i) a $C_1$–$C_4$ alkyl group, (ii) a trifluoromethyl group, (iii) a $C_1$–$C_2$ alkoxy group, (iv) a halogen atom, (v) a hydroxyl group or (vi) an amino group; and substituent γ represents (i) a $C_1$–$C_6$ alkyl group, (ii) a $C_1$–$C_4$ halogenoalkyl group, (iii) a $C_1$–$C_6$ alkoxy group, (iv) a halogen atom, (v) a hydroxyl group, (vi) a cyano group, (vii) a nitro group, (viii) a phenyl group, (ix) a benzyl group, (x) a $C_1$–$C_5$ aliphatic acyl group, (xi) an amino group or (xii) a $C_1$–$C_4$ alkylenedioxy group;

(54) the amine derivative compound or pharmacologically acceptable salt thereof in which $R_1$ represents a carbamoyl group (which has one substituent α), a thiocarbamoyl group (which has one substituent α), a sulfonyl group (which has one substituent α) or a carbonyl group (which has one substituent α);

$R_2$ represents a hydrogen atom or a $C_1$–$C_{10}$ alkyl group;

$R_3$ represents a hydrogen atom or a $C_1$–$C_4$ alkyl group;

$W_1$ and $W_2$ each represent a single bond or a $C_1$–$C_4$ alkylene group and $W_3$ represents a $C_1$–$C_2$ alkylene group;

X represents an oxygen atom or a sulfur atom, Y represents an oxygen atom and Q represents a sulfur atom;

Z represents a =CH— group;

Ar represents a benzene ring;

L represents from 1 to 4 substituents on the Ar ring and the or each substituent is a hydrogen atom or a $C_1$–$C_4$ alkyl group;

substituent α represents (i) a $C_1$–$C_8$ alkyl group, (ii) a $C_5$–$C_{10}$ cycloalkyl group, (iii) a $C_6$–$C_{10}$ aryl group (which may have from 1 to 3 substituents γ), (iv) a phenyl-$C_1$–$C_4$ alkyl group (which may have from 1 to 3 substituents γ on the phenyl portion), (v) a pyridyl group or (vi) a phenylsulfonyl group (which may have from 1 to 3 substituents γ on the phenyl portion); and substituent γ represents (i) a $C_1$–$C_6$ alkyl group, (ii) a trifluoromethyl group, (iii) a $C_1$–$C_4$ alkoxy group, (iv) a halogen atom, (v) a hydroxyl group, (vi) a cyano group, (vii) a nitro group, (viii) a $C_1$–$C_2$ aliphatic acyl group or (ix) a $C_1$–$C_4$ alkylenedioxy group;

(55) the amine derivative compound or pharmacologically acceptable salt thereof in which $R_1$ represents a carbamoyl group (which has one substituent α), a thiocarbamoyl group (which has one substituent α) or a carbonyl group (which has one substituent α);

$R_2$ represents a hydrogen atom;

$R_3$ represents a $C_1$–$C_2$ alkyl group;

$W_1$ and $W_2$ each represent a single bond or a $C_1$–$C_2$ alkylene group and $W_3$ represents a methylene group;

X represents an oxygen atom, Y represents an oxygen atom and Q represents a sulfur atom;

Z represents a =CH— group;

Ar represents a benzene ring;

L represents a hydrogen atom;

substituent α represents (i) a $C_1$–$C_4$ alkyl group, (ii) a $C_5$–$C_{10}$ cycloalkyl group, (iii) a $C_6$–$C_{10}$ aryl group (which may have from 1 to 3 substituents γ), (iv) a benzyl group (which may have from 1 to 3 substituents γ on the phenyl portion) or (v) a pyridyl group; and substituent γ represents (i) a $C_1$–$C_6$ alkyl group, (ii) a $C_1$–$C_2$ halogenoalkyl group, (iii) a $C_1$–$C_4$ alkoxy group, (iv) a halogen atom, (v) a hydroxyl group, (vi) a cyano group, (vii) a nitro group, (viii) a $C_1$–$C_2$ aliphatic acyl group or (ix) a $C_1$–$C_4$ alkylenedioxy group.

Further, in the amine derivative compound of the above formula (I), the following compounds are preferable:

(56) the amine derivative compound or pharmacologically acceptable salt thereof in which $R_1$ represents a carbamoyl group (which may have one or two substituents α), a thiocarbamoyl group (which may have one or two substituents α) or a sulfonyl group (which has one substituent α);

$R_2$ and $R_3$ represent a hydrogen atom, a $C_1$–$C_{10}$ alkyl group, a $C_6$–$C_{10}$ aryl group (which may have from 1 to 3 substituents β) or a $C_7$–$C_{16}$ aralkyl group (which may have from 1 to 3 substituents β on the aryl portion) respectively;

$W_1$, $W_2$ and $W_3$ each represent a single bond or a $C_1$–$C_8$ alkylene group;

X, Y and Q each represent an oxygen atom or a sulfur atom;

Z represents a =CH— group or a nitrogen atom;

Ar represents a benzene ring or a naphthalene ring;

L represents from 1 to 4 substituents on the Ar ring and the or each substituent is a hydrogen atom, a $C_1$–$C_6$ alkyl group, a $C_6$–$C_{10}$ aryl group (which may have from 1 to 3 substituents β) or a $C_7$–$C_{16}$ aralkyl group (which may have from 1 to 3 substituents β on the aryl portion);

substituent α represents (i) a $C_1$–$C_{10}$ alkyl group, (ii) a $C_1$–$C_6$ halogenoalkyl group, (iii) a $C_3$–$C_{10}$ cycloalkyl group, (iv) a $C_6$–$C_{10}$ aryl group (which may have from 1 to 3 substituents γ), (v) a $C_7$–$C_{16}$ aralkyl group (which may have from 1 to 3 substituents γ on the aryl portion), (vi) a $C_4$–$C_{11}$ cycloalkylcarbonyl group, (vii) a $C_7$–$C_{11}$ arylcarbonyl group (which may have from 1 to 3 substituents γ on the aryl portion), (viii) a $C_8$–$C_{17}$ aralkylcarbonyl group (which may have from 1 to 3 substituents γ on the aryl portion), (ix) an aromatic heterocyclic group (which may have from 1 to 3 substituents γ), (x) a aromatic heterocyclic carbonyl group (which may have from 1 to 3 substituents γ), (xi) a $C_1$–$C_6$ alkylsulfonyl group, (xii) a $C_1$–$C_6$ halogenoalkylsulfonyl group, (xiii) a $C_6$–$C_{10}$ arylsulfonyl group (which may have from 1 to 3 substituents γ on the aryl portion) or (xiv) a $C_7$–$C_{16}$ aralkylsulfonyl group (which may have from 1 to 3 substituents γ on the aryl portion);

substituent β represents (i) a $C_1$–$C_6$ alkyl group, (ii) a $C_1$–$C_6$ halogenoalkyl group, (iii) a $C_1$–$C_6$ alkoxy group, (iv) a halogen atom, (v) a hydroxyl group, (vi) a $C_6$–$C_{10}$ aryl group (which may have from 1 to 3 substituents δ), (vii) a $C_7C_{16}$ aralkyl group (which may have from 1 to 3 substituents δ on the aryl portion), (viii) a cyano group, (ix) a nitro group or (x) an amino group (which may have one or two substituents δ);

substituent γ represents (i) a $C_1$–$C_6$ alkyl group, (ii) a $C_1$–$C_6$ halogenoalkyl group, (iii) a $C_1$–$C_6$ alkoxy group, (iv) a halogen atom, (v) a hydroxyl group, (vi) a cyano group; (vii) a nitro group, (viii) a $C_3$–$C_{10}$ cycloalkyl group, (ix) a $C_6$–$C_{10}$ aryl group (which may have from 1 to 3 $C_1$–$C_6$ alkyl groups, $C_1$–$C_6$ halogenoalkyl groups, $C_1$–$C_6$ alkoxy groups or halogen atoms as the substituents), (x) a $C_7$–$C_{16}$ aralkyl group (which may have from 1 to 3 $C_1$–$C_6$ alkyl groups, $C_1$–$C_6$ halogenoalkyl groups, $C_1$–$C_6$ alkoxy groups or halogen atoms as the substituents on the aryl moiety), (xi) a $C_1$–$C_7$ aliphatic acyl group, (xii) a $C_1$–$C_7$ aliphatic acyloxy group, (xiii) an amino group, (xiv) a di-($C_1$–$C_6$ alkyl)amino group or (xv) a $C_1$–$C_4$ alkylenedioxy group; and substituent δ represents (i) a $C_1$–$C_{10}$ alkyl group, (ii) a $C_6$–$C_{10}$ aryl group (which may have from 1 to 3 $C_1$–$C_6$ alkyl groups, $C_1$–$C_6$ halogenoalkyl groups, $C_1$–$C_6$ alkoxy groups or halogen atoms as the substituents), (iii) a $C_7$–$C_{16}$ aralkyl group (which may have from 1 to 3 $C_1$–$C_6$ alkyl groups, $C_1$–$C_6$ halogenoalkyl groups, $C_1$–$C_6$ alkoxy groups or halogen atoms as the substituents on the aryl moiety), (iv) a $C_1$–$C_7$ aliphatic acyl group, (v) a $C_4$–$C_{11}$ cycloalkylcarbonyl group, (vi) a $C_7$–$C_{11}$ arylcarbonyl group (which may have from 1 to 3 $C_1$–$C_6$ alkyl groups, $C_1$–$C_6$ halogenoalkyl groups, $C_1$–$C_6$ alkoxy groups or halogen atoms as the substituents), (vii) a $C_8$–$C_{17}$ aralkylcarbonyl group (which may have from 1 to 3 $C_1$–$C_6$ alkyl groups, $C_1$–$C_6$ halogenoalkyl groups, $C_1$–$C_6$ alkoxy groups or halogen atoms as the substituents on the aryl moiety) or (viii) an aromatic heterocyclic carbonyl group (which may have from 1 to 3 $C_1$–$C_6$ alkyl groups, $C_1$–$C_6$ halogenoalkyl groups, $C_1$–$C_6$ alkoxy groups or halogen atoms as the substituents).

The compound of the present invention may include the compounds listed in Table 1 to Table 6 but the present invention is not limited to these compounds.

The compounds listed in Table 1 and Table 2 have the structural formula (I-1) and the compounds listed in Table 3 to Table 6 have the structural formulae (I-2) to (I-5) respectively. The abbreviations in the Tables mean the following: Ac: acetyl group, Ada(1): 1-adamantyl group, Ada(1)c: 1-adamantylcarbonyl group, Boz: benzoyl group, Bu: butyl group, tBu: t-butyl group, Bz: benzyl group, EdO: ethylenedioxy group, Et: ethyl group, Hx: hexyl group, cHx: cyclohexyl group, cHxc: cyclohexylcarbonyl group, MdO: methylenedioxy group, Me: methyl group, Nic: nicotinoyl group, iNic: isonicotinoyl group, Np: naphthyl group, Ph: phenyl group, cPn: cyclopentyl group, cPnc: cyclopentylcarbonyl group, Pr: propyl group, cPrc: cyclopropylcarbonyl group, iPr: isopropyl group, Pyr: pyridyl group, and E. C. N.: exemplification compound number.

TABLE 1

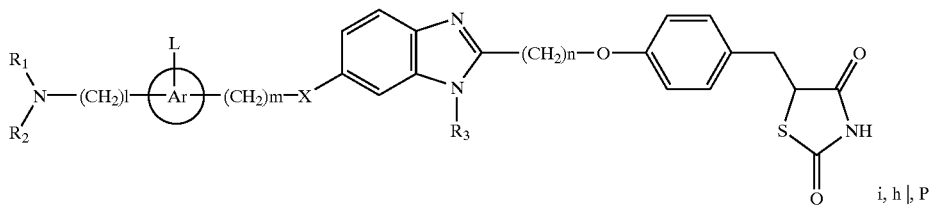

| E.C.N. | $R_1$ | $R_2$ | $R_3$ | Ar | L | X | l | m | n |
|---|---|---|---|---|---|---|---|---|---|
| 1-1 | MeNHCO | H | Me | 1,4-Ph | H | O | 0 | 0 | 1 |
| 1-2 | EtNHCO | H | Me | 1,4-Ph | H | O | 0 | 0 | 1 |
| 1-3 | BuNHCO | H | Me | 1,4-Ph | H | O | 0 | 0 | 1 |
| 1-4 | tBuNHCO | H | Me | 1,4-Ph | H | O | 0 | 0 | 1 |
| 1-5 | HxNHCO | H | Me | 1,4-Ph | H | O | 0 | 0 | 1 |
| 1-6 | CF$_3$NHCO | H | Me | 1,4-Ph | H | O | 0 | 0 | 1 |
| 1-7 | cHxNHCO | H | Me | 1,4-Ph | H | O | 0 | 0 | 1 |
| 1-8 | Ada(1)NHCO | H | Me | 1,4-Ph | H | O | 0 | 0 | 1 |
| 1-9 | PhNHCO | H | Me | 1,4-Ph | H | O | 0 | 0 | 1 |
| 1-10 | 2-MePhNHCO | H | Me | 1,4-Ph | H | O | 0 | 0 | 1 |
| 1-11 | 3-MePhNHCO | H | Me | 1,4-Ph | H | O | 0 | 0 | 1 |
| 1-12 | 4-MePhNHCO | H | Me | 1,4-Ph | H | O | 0 | 0 | 1 |
| 1-13 | 2,6-di-MePhNHCO | H | Me | 1,4-Ph | H | O | 0 | 0 | 1 |
| 1-14 | 3,4-di-MePhNHCO | H | Me | 1,4-Ph | H | O | 0 | 0 | 1 |
| 1-15 | 2,4,6-tri-MePhNHCO | H | Me | 1,4-Ph | H | O | 0 | 0 | 1 |
| 1-16 | 4-iPrPhNHCO | H | Me | 1,4-Ph | H | O | 0 | 0 | 1 |
| 1-17 | 2,6-di-iPrPhNHCO | H | Me | 1,4-Ph | H | O | 0 | 0 | 1 |
| 1-18 | 3,4-di-iPrPhNHCO | H | Me | 1,4-Ph | H | O | 0 | 0 | 1 |
| 1-19 | 2,4,6-tri-iPrPhNHCO | H | Me | 1,4-Ph | H | O | 0 | 0 | 1 |

TABLE 1-continued

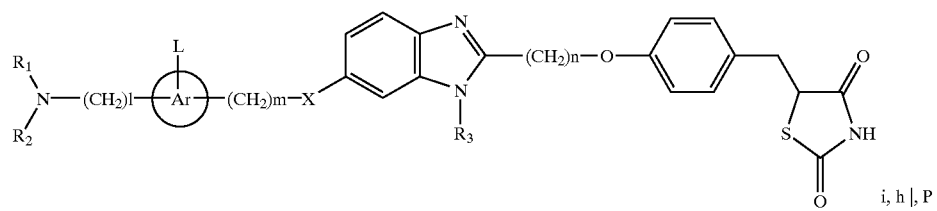

i, h |, P

| E.C.N. | R$_1$ | R$_2$ | R$_3$ | Ar | L | X | l | m | n |
|---|---|---|---|---|---|---|---|---|---|
| 1-20 | 4-tBuPhNHCO | H | Me | 1,4-Ph | H | O | 0 | 0 | 1 |
| 1-21 | 2,6-di-tBuPhNHCO | H | Me | 1,4-Ph | H | O | 0 | 0 | 1 |
| 1-22 | 3,4-di-tBuPhNHCO | H | Me | 1,4-Ph | H | O | 0 | 0 | 1 |
| 1-23 | 2,4,6-tri-tBuPhNHCO | H | Me | 1,4-Ph | H | O | 0 | 0 | 1 |
| 1-24 | 2-CF$_3$PhNHCO | H | Me | 1,4-Ph | H | O | 0 | 0 | 1 |
| 1-25 | 3-CF$_3$PhNHCO | H | Me | 1,4-Ph | H | O | 0 | 0 | 1 |
| 1-26 | 4-CF$_3$PhNHCO | H | Me | 1,4-Ph | H | O | 0 | 0 | 1 |
| 1-27 | 4-CF$_3$PhNHCO | H | Et | 1,4-Ph | H | O | 0 | 0 | 1 |
| 1-28 | 4-CF$_3$PhNHCO | H | Pr | 1,4-Ph | H | O | 0 | 0 | 1 |
| 1-29 | 4-CF$_3$PhNHCO | H | sBu | 1,4-Ph | H | O | 0 | 0 | 1 |
| 1-30 | 4-CF$_3$PhNHCO | H | Ph | 1,4-Ph | H | O | 0 | 0 | 1 |
| 1-31 | 4-CF$_3$PhNHCO | H | Bz | 1,4-Ph | H | O | 0 | 0 | 1 |
| 1-32 | 4-CF$_3$PhNHCO | H | Bz | 1,4-Ph | H | O | 1 | 0 | 1 |
| 1-33 | 4-CF$_3$PhNHCO | H | Bz | 1,4-Ph | H | O | 2 | 0 | 1 |
| 1-34 | 4-CF$_3$PhNHCO | H | Bz | 1,4-Ph | H | O | 3 | 0 | 1 |
| 1-35 | 4-CF$_3$PhNHCO | H | Bz | 1,4-Ph | H | O | 4 | 0 | 1 |
| 1-36 | 4-CF$_3$PhNHCO | H | Bz | 1,4-Ph | H | O | 5 | 0 | 1 |
| 1-37 | 4-CF$_3$PhNHCO | H | Bz | 1,4-Ph | H | O | 6 | 0 | 1 |
| 1-38 | 4-CF$_3$PhNHCO | H | Bz | 1,4-Ph | H | O | 7 | 0 | 1 |
| 1-39 | 4-CF$_3$PhNHCO | H | Bz | 1,4-Ph | H | O | 8 | 0 | 1 |
| 1-40 | 4-CF$_3$PhNHCO | H | Bz | 1,4-Ph | H | O | 0 | 1 | 1 |
| 1-41 | 4-CF$_3$PhNHCO | H | Bz | 1,4-Ph | H | O | 0 | 2 | 1 |
| 1-42 | 4-CF$_3$PhNHCO | H | Bz | 1,4-Ph | H | O | 0 | 3 | 1 |
| 1-43 | 4-CF$_3$PhNHCO | H | Bz | 1,4-Ph | H | O | 0 | 4 | 1 |
| 1-44 | 4-CF$_3$PhNHCO | H | Bz | 1,4-Ph | H | O | 0 | 5 | 1 |
| 1-45 | 4-CF$_3$PhNHCO | H | Bz | 1,4-Ph | H | O | 0 | 6 | 1 |
| 1-46 | 4-CF$_3$PhNHCO | H | Bz | 1,4-Ph | H | O | 0 | 7 | 1 |
| 1-47 | 4-CF$_3$PhNHCO | H | Bz | 1,4-Ph | H | O | 0 | 8 | 1 |
| 1-48 | 4-CF$_3$PhNHCO | H | Bz | 1,4-Ph | H | O | 0 | 0 | 0 |
| 1-49 | 4-CF$_3$PhNHCO | H | Bz | 1,4-Ph | H | O | 0 | 0 | 2 |
| 1-50 | 4-CF$_3$PhNHCO | H | Bz | 1,4-Ph | H | O | 0 | 0 | 3 |
| 1-51 | 4-CF$_3$PhNHCO | H | Bz | 1,4-Ph | H | O | 0 | 0 | 4 |
| 1-52 | 4-CF$_3$PhNHCO | H | Bz | 1,4-Ph | H | O | 0 | 0 | 5 |
| 1-53 | 4-CF$_3$PhNHCO | H | Bz | 1,4-Ph | H | O | 0 | 0 | 6 |
| 1-54 | 4-CF$_3$PhNHCO | H | Bz | 1,4-Ph | H | O | 0 | 0 | 7 |
| 1-55 | 4-CF$_3$PhNHCO | H | Bz | 1,4-Ph | H | O | 0 | 0 | 8 |
| 1-56 | 2-FPhNHCO | H | Me | 1,4-Ph | H | O | 0 | 0 | 1 |
| 1-57 | 3-FPhNHCO | H | Me | 1,4-Ph | H | O | 0 | 0 | 1 |
| 1-58 | 4-FPhNHCO | H | Me | 1,4-Ph | H | O | 0 | 0 | 1 |
| 1-59 | 2,4-di-FPhNHCO | H | Me | 1,4-Ph | H | O | 0 | 0 | 1 |
| 1-60 | 2,6-di-FPhNHCO | H | Me | 1,4-Ph | H | O | 0 | 0 | 1 |
| 1-61 | 3,4-di-FPhNHCO | H | Me | 1,4-Ph | H | O | 0 | 0 | 1 |
| 1-62 | 2,4,6-tri-FPhNHCO | H | Me | 1,4-Ph | H | O | 0 | 0 | 1 |
| 1-63 | 2-ClPhNHCO | H | Me | 1,4-Ph | H | O | 0 | 0 | 1 |
| 1-64 | 3-ClPhNHCO | H | Me | 1,4-Ph | H | O | 0 | 0 | 1 |
| 1-65 | 4-ClPhNHCO | H | Me | 1,4-Ph | H | O | 0 | 0 | 1 |
| 1-66 | 2-HOPhNHCO | H | Me | 1,4-Ph | H | O | 0 | 0 | 1 |
| 1-67 | 3-HOPhNHCO | H | Me | 1,4-Ph | H | O | 0 | 0 | 1 |
| 1-68 | 4-HOPhNHCO | H | Me | 1,4-Ph | H | O | 0 | 0 | 1 |
| 1-69 | 2-CNPhNHCO | H | Me | 1,4-Ph | H | O | 0 | 0 | 1 |
| 1-70 | 3-CNPhNHCO | H | Me | 1,4-Ph | H | O | 0 | 0 | 1 |
| 1-71 | 4-CNPhNHCO | H | Me | 1,4-Ph | H | O | 0 | 0 | 1 |
| 1-72 | 2-NO$_2$PhNHCO | H | Me | 1,4-Ph | H | O | 0 | 0 | 1 |
| 1-73 | 3-NO$_2$PhNHCO | H | Me | 1,4-Ph | H | O | 0 | 0 | 1 |
| 1-74 | 4-NO$_2$PhNHCO | H | Me | 1,4-Ph | H | O | 0 | 0 | 1 |
| 1-75 | 4-cHxPhNHCO | H | Me | 1,4-Ph | H | O | 0 | 0 | 1 |
| 1-76 | 4-Ada(1)PhNHCO | H | Me | 1,4-Ph | H | O | 0 | 0 | 1 |
| 1-77 | 4-PhPhNHCO | H | Me | 1,4-Ph | H | O | 0 | 0 | 1 |
| 1-78 | 4-(4-MePh)PhNHCO | H | Me | 1,4-Ph | H | O | 0 | 0 | 1 |
| 1-79 | 4-(4-CF$_3$Ph)PhNHCO | H | Me | 1,4-Ph | H | O | 0 | 0 | 1 |
| 1-80 | 4-(4-MeOPh)PhNHCO | H | Me | 1,4-Ph | H | O | 0 | 0 | 1 |
| 1-81 | 4-(4-FPh)PhNHCO | H | Me | 1,4-Ph | H | O | 0 | 0 | 1 |
| 1-82 | 4-(4-ClPh)PhNHCO | H | Me | 1,4-Ph | H | O | 0 | 0 | 1 |
| 1-83 | 4-(4-HOPh)PhNHCO | H | Me | 1,4-Ph | H | O | 0 | 0 | 1 |
| 1-84 | 4-(4-MeBz)PhNHCO | H | Me | 1,4-Ph | H | O | 0 | 0 | 1 |
| 1-85 | 4-(4-CF$_3$Bz)PhNHCO | H | Me | 1,4-Ph | H | O | 0 | 0 | 1 |

TABLE 1-continued

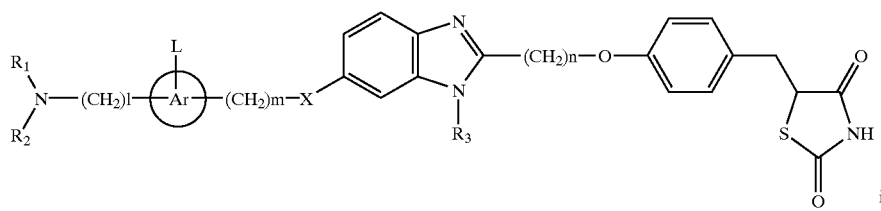

i, h |, P

| E.C.N. | R₁ | R₂ | R₃ | Ar | L | X | l | m | n |
|---|---|---|---|---|---|---|---|---|---|
| 1-86 | 4-(4-MeOBz)PhNHCO | H | Me | 1,4-Ph | H | O | 0 | 0 | 1 |
| 1-87 | 4-(4-FBz)PhNHCO | H | Me | 1,4-Ph | H | O | 0 | 0 | 1 |
| 1-88 | 4-(4-ClBz)PhNHCO | H | Me | 1,4-Ph | H | O | 0 | 0 | 1 |
| 1-89 | 4-(4-HOBz)PhNHCO | H | Me | 1,4-Ph | H | O | 0 | 0 | 1 |
| 1-90 | 2-AcPhNHCO | H | Me | 1,4-Ph | H | O | 0 | 0 | 1 |
| 1-91 | 3-AcPhNHCO | H | Me | 1,4-Ph | H | O | 0 | 0 | 1 |
| 1-92 | 4-AcPhNHCO | H | Me | 1,4-Ph | H | O | 0 | 0 | 1 |
| 1-93 | 2-AcOPhNHCO | H | Me | 1,4-Ph | H | O | 0 | 0 | 1 |
| 1-94 | 3-AcOPhNHCO | H | Me | 1,4-Ph | H | O | 0 | 0 | 1 |
| 1-95 | 4-AcOPhNHCO | H | Me | 1,4-Ph | H | O | 0 | 0 | 1 |
| 1-96 | 2-H₂NPhNHCO | H | Me | 1,4-Ph | H | O | 0 | 0 | 1 |
| 1-97 | 3-H₂NPhNHCO | H | Me | 1,4-Ph | H | O | 0 | 0 | 1 |
| 1-98 | 4-H₂NPhNHCO | H | Me | 1,4-Ph | H | O | 0 | 0 | 1 |
| 1-99 | 4-Me₂NPhNHCO | H | Me | 1,4-Ph | H | O | 0 | 0 | 1 |
| 1-100 | 4-iPr₂NPhNHCO | H | Me | 1,4-Ph | H | O | 0 | 0 | 1 |
| 1-101 | 3,4-MdOPhNHCO | H | Me | 1,4-Ph | H | O | 0 | 0 | 1 |
| 1-102 | 3,4-EdOPhNHCO | H | Me | 1,4-Ph | H | O | 0 | 0 | 1 |
| 1-103 | 1-NpNHCO | H | Me | 1,4-Ph | H | O | 0 | 0 | 1 |
| 1-104 | 2-NpNHCO | H | Me | 1,4-Ph | H | O | 0 | 0 | 1 |
| 1-105 | BzNHCO | H | Me | 1,4-Ph | H | O | 0 | 0 | 1 |
| 1-106 | Ph(CH₂)₂NHCO | H | Me | 1,4-Ph | H | O | 0 | 0 | 1 |
| 1-107 | Ph(CH₂)₃NHCO | H | Me | 1,4-Ph | H | O | 0 | 0 | 1 |
| 1-108 | 4-MeBzNHCO | H | Me | 1,4-Ph | H | O | 0 | 0 | 1 |
| 1-109 | 2-CF₃BzNHCO | H | Me | 1,4-Ph | H | O | 0 | 0 | 1 |
| 1-110 | 3-CF₃BzNHCO | H | Me | 1,4-Ph | H | O | 0 | 0 | 1 |
| 1-111 | 4-CF₃BzNHCO | H | Me | 1,4-Ph | H | O | 0 | 0 | 1 |
| 1-112 | 4-MeOBzNHCO | H | Me | 1,4-Ph | H | O | 0 | 0 | 1 |
| 1-113 | 4-FBzNHCO | H | Me | 1,4-Ph | H | O | 0 | 0 | 1 |
| 1-114 | 4-ClBzNHCO | H | Me | 1,4-Ph | H | O | 0 | 0 | 1 |
| 1-115 | 4-HOBzNHCO | H | Me | 1,4-Ph | H | O | 0 | 0 | 1 |
| 1-116 | 4-CNBzNHCO | H | Me | 1,4-Ph | H | O | 0 | 0 | 1 |
| 1-117 | 4-NO₂BzNHCO | H | Me | 1,4-Ph | H | O | 0 | 0 | 1 |
| 1-118 | 4-MePh(CH₂)₃NHCO | H | Me | 1,4-Ph | H | O | 0 | 0 | 1 |
| 1-119 | 2-CF₃Ph(CH₂)₃NHCO | H | Me | 1,4-Ph | H | O | 0 | 0 | 1 |
| 1-120 | 3-CF₃Ph(CH₂)₃NHCO | H | Me | 1,4-Ph | H | O | 0 | 0 | 1 |
| 1-121 | 4-CF₃Ph(CH₂)₃NHCO | H | Me | 1,4-Ph | H | O | 0 | 0 | 1 |
| 1-122 | 4-MeOPh(CH₂)₃NHCO | H | Me | 1,4-Ph | H | O | 0 | 0 | 1 |
| 1-123 | 4-FPh(CH₂)₃NHCO | H | Me | 1,4-Ph | H | O | 0 | 0 | 1 |
| 1-124 | 4-ClPh(CH₂)₃NHCO | H | Me | 1,4-Ph | H | O | 0 | 0 | 1 |
| 1-125 | 4-HOPh(CH₂)₃NHCO | H | Me | 1,4-Ph | H | O | 0 | 0 | 1 |
| 1-126 | 4-CNPh(CH₂)₃NHCO | H | Me | 1,4-Ph | H | O | 0 | 0 | 1 |
| 1-127 | 4-NO₂Ph(CH₂)₃NHCO | H | Me | 1,4-Ph | H | O | 0 | 0 | 1 |
| 1-128 | cPrcNHCO | H | Me | 1,4-Ph | H | O | 0 | 0 | 1 |
| 1-129 | cPncNHCO | H | Me | 1,4-Ph | H | O | 0 | 0 | 1 |
| 1-130 | cHxcNHCO | H | Me | 1,4-Ph | H | O | 0 | 0 | 1 |
| 1-131 | BozNHCO | H | Me | 1,4-Ph | H | O | 0 | 0 | 1 |
| 1-132 | 4-MeBozNHCO | H | Me | 1,4-Ph | H | O | 0 | 0 | 1 |
| 1-133 | 2-CF₃BozNHCO | H | Me | 1,4-Ph | H | O | 0 | 0 | 1 |
| 1-134 | 3-CF₃BozNHCO | H | Me | 1,4-Ph | H | O | 0 | 0 | 1 |
| 1-135 | 4-CF₃BozNHCO | H | Me | 1,4-Ph | H | O | 0 | 0 | 1 |
| 1-136 | 4-MeOBozNHCO | H | Me | 1,4-Ph | H | O | 0 | 0 | 1 |
| 1-137 | 4-FBozNHCO | H | Me | 1,4-Ph | H | O | 0 | 0 | 1 |
| 1-138 | 4-ClBozNHCO | H | Me | 1,4-Ph | H | O | 0 | 0 | 1 |
| 1-139 | 4-HOBozNHCO | H | Me | 1,4-Ph | H | O | 0 | 0 | 1 |
| 1-140 | 4-CNBozNHCO | H | Me | 1,4-Ph | H | O | 0 | 0 | 1 |
| 1-141 | 4-NO₂BozNHCO | H | Me | 1,4-Ph | H | O | 0 | 0 | 1 |
| 1-142 | Ph(CH₂)C=ONHCO | H | Me | 1,4-Ph | H | O | 0 | 0 | 1 |
| 1-143 | 4-MePh(CH₂)C=ONHCO | H | Me | 1,4-Ph | H | O | 0 | 0 | 1 |
| 1-144 | 2-CF₃Ph(CH₂)C=ONHCO | H | Me | 1,4-Ph | H | O | 0 | 0 | 1 |
| 1-145 | 3-CF₃Ph(CH₂)C=ONHCO | H | Me | 1,4-Ph | H | O | 0 | 0 | 1 |
| 1-146 | 4-CF₃Ph(CH₂)C=ONHCO | H | Me | 1,4-Ph | H | O | 0 | 0 | 1 |
| 1-147 | 4-MeOPh(CH₂)C=ONHCO | H | Me | 1,4-Ph | H | O | 0 | 0 | 1 |
| 1-148 | 4-FPh(CH₂)C=ONHCO | H | Me | 1,4-Ph | H | O | 0 | 0 | 1 |
| 1-149 | 4-ClPh(CH₂)C=ONHCO | H | Me | 1,4-Ph | H | O | 0 | 0 | 1 |
| 1-150 | 4-HOPh(CH₂)C=ONHCO | H | Me | 1,4-Ph | H | O | 0 | 0 | 1 |
| 1-151 | 4-CNPh(CH₂)C=ONHCO | H | Me | 1,4-Ph | H | O | 0 | 0 | 1 |

TABLE 1-continued

| E.C.N. | R₁ | R₂ | R₃ | Ar | L | X | l | m | n |
|---|---|---|---|---|---|---|---|---|---|
| 1-152 | 4-NO₂Ph(CH₂)C=ONHCO | H | Me | 1,4-Ph | H | O | 0 | 0 | 1 |
| 1-153 | 3-PyrNHCO | H | Me | 1,4-Ph | H | O | 0 | 0 | 1 |
| 1-154 | 6-Me(3-Pyr)NHCO | H | Me | 1,4-Ph | H | O | 0 | 0 | 1 |
| 1-155 | 6-CF₃(3-Pyr)NHCO | H | Me | 1,4-Ph | H | O | 0 | 0 | 1 |
| 1-156 | 6-MeO(3-Pyr)NHCO | H | Me | 1,4-Ph | H | O | 0 | 0 | 1 |
| 1-157 | 6-F(3-Pyr)NHCO | H | Me | 1,4-Ph | H | O | 0 | 0 | 1 |
| 1-158 | 6-Cl(3-Pyr)NHCO | H | Me | 1,4-Ph | H | O | 0 | 0 | 1 |
| 1-159 | 6-HO(3-Pyr)NHCO | H | Me | 1,4-Ph | H | O | 0 | 0 | 1 |
| 1-160 | 6-CN(3-Pyr)NHCO | H | Me | 1,4-Ph | H | O | 0 | 0 | 1 |
| 1-161 | 6-NO₂(3-Pyr)NHCO | H | Me | 1,4-Ph | H | O | 0 | 0 | 1 |
| 1-162 | NicNHCO | H | Me | 1,4-Ph | H | O | 0 | 0 | 1 |
| 1-163 | iNicNHCO | H | Me | 1,4-Ph | H | O | 0 | 0 | 1 |
| 1-164 | cHxNHCO | H | Me | 1,4-Ph | H | O | 2 | 0 | 1 |
| 1-165 | Ada(1)NHCO | H | Me | 1,4-Ph | H | O | 2 | 0 | 1 |
| 1-166 | PhNHCO | H | Me | 1,4-Ph | H | O | 2 | 0 | 1 |
| 1-167 | 4-MePhNHCO | H | Me | 1,4-Ph | H | O | 2 | 0 | 1 |
| 1-168 | 2,6-di-iPrPhNHCO | H | Me | 1,4-Ph | H | O | 2 | 0 | 1 |
| 1-169 | 2,4,6-tri-iPrPhNHCO | H | Me | 1,4-Ph | H | O | 2 | 0 | 1 |
| 1-170 | 2-CF₃PhNHCO | H | Me | 1,4-Ph | H | O | 2 | 0 | 1 |
| 1-171 | 3-CF₃PhNHCO | H | Me | 1,4-Ph | H | O | 2 | 0 | 1 |
| 1-172 | 4-CF₃PhNHCO | H | Me | 1,4-Ph | H | O | 2 | 0 | 1 |
| 1-173 | 4-FPhNHCO | H | Me | 1,4-Ph | H | O | 2 | 0 | 1 |
| 1-174 | 2,4-di-FPhNHCO | H | Me | 1,4-Ph | H | O | 2 | 0 | 1 |
| 1-175 | 4-ClPhNHCO | H | Me | 1,4-Ph | H | O | 2 | 0 | 1 |
| 1-176 | 3-CNPhNHCO | H | Me | 1,4-Ph | H | O | 2 | 0 | 1 |
| 1-177 | 4-NO₂PhNHCO | H | Me | 1,4-Ph | H | O | 2 | 0 | 1 |
| 1-178 | BzNHCO | H | Me | 1,4-Ph | H | O | 2 | 0 | 1 |
| 1-179 | cHxNHCO | H | Me | 1,4-Ph | 2,6-di-Me | O | 0 | 0 | 1 |
| 1-180 | Ada(1)NHCO | H | Me | 1,4-Ph | 2,6-di-Me | O | 0 | 0 | 1 |
| 1-181 | PhNHCO | H | Me | 1,4-Ph | 2,6-di-Me | O | 0 | 0 | 1 |
| 1-182 | 4-MePhNHCO | H | Me | 1,4-Ph | 2,6-di-Me | O | 0 | 0 | 1 |
| 1-183 | 2,6-di-iPrPhNHCO | H | Me | 1,4-Ph | 2,6-di-Me | O | 0 | 0 | 1 |
| 1-184 | 2,4,6-tri-iPrPhNHCO | H | Me | 1,4-Ph | 2,6-di-Me | O | 0 | 0 | 1 |
| 1-185 | 2-CF₃PhNHCO | H | Me | 1,4-Ph | 2,6-di-Me | O | 0 | 0 | 1 |
| 1-186 | 3-CF₃PhNHCO | H | Me | 1,4-Ph | 2,6-di-Me | O | 0 | 0 | 1 |
| 1-187 | 4-CF₃PhNHCO | H | Me | 1,4-Ph | 2,6-di-Me | O | 0 | 0 | 1 |
| 1-188 | 4-FPhNHCO | H | Me | 1,4-Ph | 2,6-di-Me | O | 0 | 0 | 1 |
| 1-189 | 4-MeOPhNHCO | H | Me | 1,4-Ph | 2,6-di-Me | O | 0 | 0 | 1 |
| 1-190 | 4-ClPhNHCO | H | Me | 1,4-Ph | 2,6-di-Me | O | 0 | 0 | 1 |
| 1-191 | 3-CNPhNHCO | H | Me | 1,4-Ph | 2,6-di-Me | O | 0 | 0 | 1 |
| 1-192 | 4-NO₂PhNHCO | H | Me | 1,4-Ph | 2,6-di-Me | O | 0 | 0 | 1 |
| 1-193 | BzNHCO | H | Me | 1,4-Ph | 2,6-di-Me | O | 0 | 0 | 1 |
| 1-194 | cHxNHCO | Hx | Me | 1,4-Ph | H | O | 0 | 0 | 1 |
| 1-195 | Ada(1)NHCO | Hx | Me | 1,4-Ph | H | O | 0 | 0 | 1 |
| 1-196 | PhNHCO | Hx | Me | 1,4-Ph | H | O | 0 | 0 | 1 |
| 1-197 | 4-MePhNHCO | Hx | Me | 1,4-Ph | H | O | 0 | 0 | 1 |
| 1-198 | 2,6-di-iPrPhNHCO | Hx | Me | 1,4-Ph | H | O | 0 | 0 | 1 |
| 1-199 | 2,4,6-tri-iPrPhNHCO | Hx | Me | 1,4-Ph | H | O | 0 | 0 | 1 |
| 1-200 | 2-CF₃PhNHCO | Hx | Me | 1,4-Ph | H | O | 0 | 0 | 1 |
| 1-201 | 3-CF₃PhNHCO | Hx | Me | 1,4-Ph | H | O | 0 | 0 | 1 |
| 1-202 | 4-CF₃PhNHCO | Hx | Me | 1,4-Ph | H | O | 0 | 0 | 1 |
| 1-203 | 4-FPhNHCO | Hx | Me | 1,4-Ph | H | O | 0 | 0 | 1 |
| 1-204 | 2,4-di-FPhNHCO | Hx | Me | 1,4-Ph | H | O | 0 | 0 | 1 |
| 1-205 | 4-ClPhNHCO | Hx | Me | 1,4-Ph | H | O | 0 | 0 | 1 |
| 1-206 | 3-CNPhNHCO | Hx | Me | 1,4-Ph | H | O | 0 | 0 | 1 |
| 1-207 | 4-NO₂PhNHCO | Hx | Me | 1,4-Ph | H | O | 0 | 0 | 1 |
| 1-208 | BzNHCO | Hx | Me | 1,4-Ph | H | O | 0 | 0 | 1 |
| 1-209 | cHxNHCO | H | Me | 1,7-Np | H | O | 0 | 0 | 1 |
| 1-210 | Ada(1)NHCO | H | Me | 1,7-Np | H | O | 0 | 0 | 1 |
| 1-211 | PhNHCO | H | Me | 1,7-Np | H | O | 0 | 0 | 1 |
| 1-212 | 4-MePhNHCO | H | Me | 1,7-Np | H | O | 0 | 0 | 1 |
| 1-213 | 2,6-di-iPrPhNHCO | H | Me | 1,7-Np | H | O | 0 | 0 | 1 |
| 1-214 | 2,4,6-tri-iPrPhNHCO | H | Me | 1,7-Np | H | O | 0 | 0 | 1 |
| 1-215 | 2-CF₃PhNHCO | H | Me | 1,7-Np | H | O | 0 | 0 | 1 |
| 1-216 | 3-CF₃PhNHCO | H | Me | 1,7-Np | H | O | 0 | 0 | 1 |
| 1-217 | 4-CF₃PhNHCO | H | Me | 1,7-Np | H | O | 0 | 0 | 1 |

TABLE 1-continued

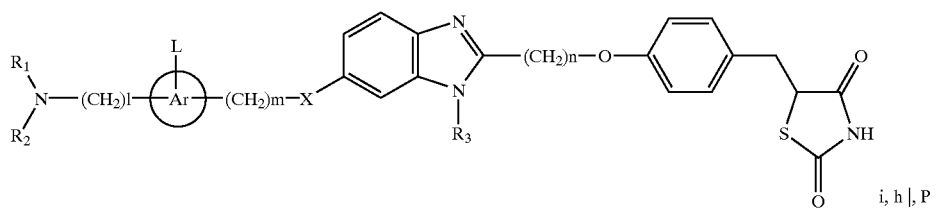

i, h |, P

| E.C.N. | R₁ | R₂ | R₃ | Ar | L | X | l | m | n |
|---|---|---|---|---|---|---|---|---|---|
| 1-218 | 4-FPhNHCO | H | Me | 1,7-Np | H | O | 0 | 0 | 1 |
| 1-219 | 2,4-di-FPhNHCO | H | Me | 1,7-Np | H | O | 0 | 0 | 1 |
| 1-220 | 4-ClPhNHCO | H | Me | 1,7-Np | H | O | 0 | 0 | 1 |
| 1-221 | 3-CNPhNHCO | H | Me | 1,7-Np | H | O | 0 | 0 | 1 |
| 1-222 | 4-NO₂PhNHCO | H | Me | 1,7-Np | H | O | 0 | 0 | 1 |
| 1-223 | BzNHCO | H | Me | 1,7-Np | H | O | 0 | 0 | 1 |
| 1-224 | cHxNHCO | H | Me | 1,4-Ph | H | O | 0 | 2 | 1 |
| 1-225 | Ada(1)NHCO | H | Me | 1,4-Ph | H | O | 0 | 2 | 1 |
| 1-226 | PhNHCO | H | Me | 1,4-Ph | H | O | 0 | 2 | 1 |
| 1-227 | 4-MePhNHCO | H | Me | 1,4-Ph | H | O | 0 | 2 | 1 |
| 1-228 | 2,6-di-iPrPhNHCO | H | Me | 1,4-Ph | H | O | 0 | 2 | 1 |
| 1-229 | 2,4,6-tri-iPrPhNHCO | H | Me | 1,4-Ph | H | O | 0 | 2 | 1 |
| 1-230 | 2-CF₃PhNHCO | H | Me | 1,4-Ph | H | O | 0 | 2 | 1 |
| 1-231 | 3-CF₃PhNHCO | H | Me | 1,4-Ph | H | O | 0 | 2 | 1 |
| 1-232 | 4-CF₃PhNHCO | H | Me | 1,4-Ph | H | O | 0 | 2 | 1 |
| 1-233 | 4-FPhNHCO | H | Me | 1,4-Ph | H | O | 0 | 2 | 1 |
| 1-234 | 2,4-di-FPhNHCO | H | Me | 1,4-Ph | H | O | 0 | 2 | 1 |
| 1-235 | 4-ClPhNHCO | H | Me | 1,4-Ph | H | O | 0 | 2 | 1 |
| 1-236 | 3-CNPhNHCO | H | Me | 1,4-Ph | H | O | 0 | 2 | 1 |
| 1-237 | 4-NO₂PhNHCO | H | Me | 1,4-Ph | H | O | 0 | 2 | 1 |
| 1-238 | BzNHCO | H | Me | 1,4-Ph | H | O | 0 | 2 | 1 |
| 1-239 | cHxNHCO | H | Me | 1,4-Ph | 2-tBu | O | 0 | 2 | 1 |
| 1-240 | Ada(1)NHCO | H | Me | 1,4-Ph | 2-tBu | O | 0 | 2 | 1 |
| 1-241 | PhNHCO | H | Me | 1,4-Ph | 2-tBu | O | 0 | 2 | 1 |
| 1-242 | 4-MePhNHCO | H | Me | 1,4-Ph | 2-tBu | O | 0 | 2 | 1 |
| 1-243 | 2,6-di-iPrPhNHCO | H | Me | 1,4-Ph | 2-tBu | O | 0 | 2 | 1 |
| 1-244 | 2,4,6-tri-iPrPhNHCO | H | Me | 1,4-Ph | 2-tBu | O | 0 | 2 | 1 |
| 1-245 | 2-CF₃PhNHCO | H | Me | 1,4-Ph | 2-tBu | O | 0 | 2 | 1 |
| 1-246 | 3-CF₃PhNHCO | H | Me | 1,4-Ph | 2-tBu | O | 0 | 2 | 1 |
| 1-247 | 4-CF₃PhNHCO | H | Me | 1,4-Ph | 2-tBu | O | 0 | 2 | 1 |
| 1-248 | 4-FPhNHCO | H | Me | 1,4-Ph | 2-tBu | O | 0 | 2 | 1 |
| 1-249 | 2,4-di-FPhNHCO | H | Me | 1,4-Ph | 2-tBu | O | 0 | 2 | 1 |
| 1-250 | 4-ClPhNHCO | H | Me | 1,4-Ph | 2-tBu | O | 0 | 2 | 1 |
| 1-251 | 3-CNPhNHCO | H | Me | 1,4-Ph | 2-tBu | O | 0 | 2 | 1 |
| 1-252 | 4-NO₂PhNHCO | H | Me | 1,4-Ph | 2-tBu | O | 0 | 2 | 1 |
| 1-253 | BzNHCO | H | Me | 1,4-Ph | 2-tBu | O | 0 | 2 | 1 |
| 1-254 | MeSO₂NHCO | H | Me | 1,7-Np | H | O | 0 | 0 | 1 |
| 1-255 | CF₃SO₂NHCO | H | Me | 1,7-Np | H | O | 0 | 0 | 1 |
| 1-256 | PhSO₂NHCO | H | Me | 1,7-Np | H | O | 0 | 0 | 1 |
| 1-257 | 4-MePhSO₂NHCO | H | Me | 1,7-Np | H | O | 0 | 0 | 1 |
| 1-258 | 2,6-di-iPrPhSO₂NHCO | H | Me | 1,7-Np | H | O | 0 | 0 | 1 |
| 1-259 | 2,4,6-tri-iPrPhSO₂NHCO | H | Me | 1,7-Np | H | O | 0 | 0 | 1 |
| 1-260 | 2-CF₃PhSO₂NHCO | H | Me | 1,7-Np | H | O | 0 | 0 | 1 |
| 1-261 | 3-CF₃PhSO₂NHCO | H | Me | 1,7-Np | H | O | 0 | 0 | 1 |
| 1-262 | 4-CF₃PhSO₂NHCO | H | Me | 1,7-Np | H | O | 0 | 0 | 1 |
| 1-263 | 4-FPhSO₂NHCO | H | Me | 1,7-Np | H | O | 0 | 0 | 1 |
| 1-264 | 2,4-di-FPhSO₂NHCO | H | Me | 1,7-Np | H | O | 0 | 0 | 1 |
| 1-265 | 4-ClPhSO₂NHCO | H | Me | 1,7-Np | H | O | 0 | 0 | 1 |
| 1-266 | 3-CNPhSO₂NHCO | H | Me | 1,7-Np | H | O | 0 | 0 | 1 |
| 1-267 | 4-NO₂PhSO₂NHCO | H | Me | 1,7-Np | H | O | 0 | 0 | 1 |
| 1-268 | BzSO₂NHCO | H | Me | 1,7-Np | H | O | 0 | 0 | 1 |
| 1-269 | cHxNHCO | H | Me | 1,4-Ph | 2-tBu | O | 0 | 1 | 1 |
| 1-270 | Ada(1)NHCO | H | Me | 1,4-Ph | 2-tBu | O | 0 | 1 | 1 |
| 1-271 | PhNHCO | H | Me | 1,4-Ph | 2-tBu | O | 0 | 1 | 1 |
| 1-272 | 4-MePhNHCO | H | Me | 1,4-Ph | 2-tBu | O | 0 | 1 | 1 |
| 1-273 | 2,6-di-iPrPhNHCO | H | Me | 1,4-Ph | 2-tBu | O | 0 | 1 | 1 |
| 1-274 | 2,4,6-tri-iPrPhNHCO | H | Me | 1,4-Ph | 2-tBu | O | 0 | 1 | 1 |
| 1-275 | 2-CF₃PhNHCO | H | Me | 1,4-Ph | 2-tBu | O | 0 | 1 | 1 |
| 1-276 | 3-CF₃PhNHCO | H | Me | 1,4-Ph | 2-tBu | O | 0 | 1 | 1 |
| 1-277 | 4-CF₃PhNHCO | H | Me | 1,4-Ph | 2-tBu | O | 0 | 1 | 1 |
| 1-278 | 4-FPhNHCO | H | Me | 1,4-Ph | 2-tBu | O | 0 | 1 | 1 |
| 1-279 | 2,4-di-FPhNHCO | H | Me | 1,4-Ph | 2-tBu | O | 0 | 1 | 1 |
| 1-280 | 4-ClPhNHCO | H | Me | 1,4-Ph | 2-tBu | O | 0 | 1 | 1 |
| 1-281 | 3-CNPhNHCO | H | Me | 1,4-Ph | 2-tBu | O | 0 | 1 | 1 |
| 1-282 | 4-NO₂PhNHCO | H | Me | 1,4-Ph | 2-tBu | O | 0 | 1 | 1 |
| 1-283 | BzNHCO | H | Me | 1,4-Ph | 2-tBu | O | 0 | 1 | 1 |

TABLE 1-continued

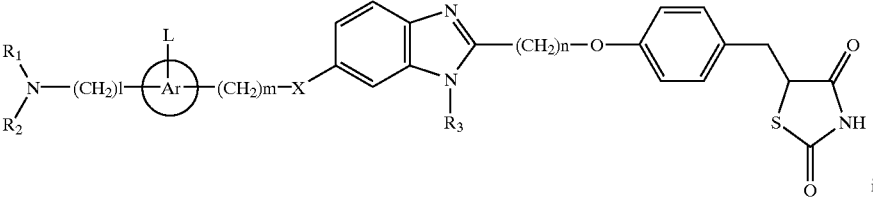

i, h |, P

| E.C.N. | $R_1$ | $R_2$ | $R_3$ | Ar | L | X | l | m | n |
|---|---|---|---|---|---|---|---|---|---|
| 1-284 | cHxNHCS | H | Me | 1,4-Ph | H | O | 0 | 0 | 1 |
| 1-285 | Ada(1)NHCS | H | Me | 1,4-Ph | H | O | 0 | 0 | 1 |
| 1-286 | PhNHCS | H | Me | 1,4-Ph | H | O | 0 | 0 | 1 |
| 1-287 | 4-MePhNHCS | H | Me | 1,4-Ph | H | O | 0 | 0 | 1 |
| 1-288 | 2,6-di-iPrPhNHCS | H | Me | 1,4-Ph | H | O | 0 | 0 | 1 |
| 1-289 | 2,4,6-tri-iPrPhNHCS | H | Me | 1,4-Ph | H | O | 0 | 0 | 1 |
| 1-290 | 2-CF$_3$PhNHCS | H | Me | 1,4-Ph | H | O | 0 | 0 | 1 |
| 1-291 | 3-CF$_3$PhNHCS | H | Me | 1,4-Ph | H | O | 0 | 0 | 1 |
| 1-292 | 4-CF$_3$PhNHCS | H | Me | 1,4-Ph | H | O | 0 | 0 | 1 |
| 1-293 | 4-FPhNHCS | H | Me | 1,4-Ph | H | O | 0 | 0 | 1 |
| 1-294 | 2,4-di-FPhNHCS | H | Me | 1,4-Ph | H | O | 0 | 0 | 1 |
| 1-295 | 4-ClPhNHCS | H | Me | 1,4-Ph | H | O | 0 | 0 | 1 |
| 1-296 | 3-CNPhNHCS | H | Me | 1,4-Ph | H | O | 0 | 0 | 1 |
| 1-297 | 4-NO$_2$PhNHCS | H | Me | 1,4-Ph | H | O | 0 | 0 | 1 |
| 1-298 | 1-NpNHCS | H | Me | 1,4-Ph | H | O | 0 | 0 | 1 |
| 1-299 | BzNHCS | H | Me | 1,4-Ph | H | O | 0 | 0 | 1 |
| 1-300 | BzNHCS | H | Me | 1,7-Np | H | O | 0 | 0 | 1 |
| 1-301 | cHxNHCS | H | Me | 1,4-Ph | 2,6-di-Me | O | 0 | 0 | 1 |
| 1-302 | Ada(1)NHCS | H | Me | 1,4-Ph | 2,6-di-Me | O | 0 | 0 | 1 |
| 1-303 | PhNHCS | H | Me | 1,4-Ph | 2,6-di-Me | O | 0 | 0 | 1 |
| 1-304 | 4-MePhNHCS | H | Me | 1,4-Ph | 2,6-di-Me | O | 0 | 0 | 1 |
| 1-305 | 2,6-di-iPrPhNHCS | H | Me | 1,4-Ph | 2,6-di-Me | O | 0 | 0 | 1 |
| 1-306 | 2,4,6-tri-iPrPhNHCS | H | Me | 1,4-Ph | 2,6-di-Me | O | 0 | 0 | 1 |
| 1-307 | 2-CF$_3$PhNHCS | H | Me | 1,4-Ph | 2,6-di-Me | O | 0 | 0 | 1 |
| 1-308 | 3-CF$_3$PhNHCS | H | Me | 1,4-Ph | 2,6-di-Me | O | 0 | 0 | 1 |
| 1-309 | 4-CF$_3$PhNHCS | H | Me | 1,4-Ph | 2,6-di-Me | O | 0 | 0 | 1 |
| 1-310 | 4-FPhNHCS | H | Me | 1,4-Ph | 2,6-di-Me | O | 0 | 0 | 1 |
| 1-311 | 2,4-di-FPhNHCS | H | Me | 1,4-Ph | 2,6-di-Me | O | 0 | 0 | 1 |
| 1-312 | 4-ClPhNHCS | H | Me | 1,4-Ph | 2,6-di-Me | O | 0 | 0 | 1 |
| 1-313 | 3-CNPhNHCS | H | Me | 1,4-Ph | 2,6-di-Me | O | 0 | 0 | 1 |
| 1-314 | 4-NO$_2$PhNHCS | H | Me | 1,4-Ph | 2,6-di-Me | O | 0 | 0 | 1 |
| 1-315 | BzNHCS | H | Me | 1,4-Ph | 2,6-di-Me | O | 0 | 0 | 1 |
| 1-316 | MeSO$_2$ | H | Me | 1,4-Ph | H | O | 0 | 0 | 1 |
| 1-317 | Ada(1)SO$_2$ | H | Me | 1,4-Ph | H | O | 0 | 0 | 1 |
| 1-318 | PhSO$_2$ | H | Me | 1,4-Ph | H | O | 0 | 0 | 1 |
| 1-319 | 4-MePhSO$_2$ | H | Me | 1,4-Ph | H | O | 0 | 0 | 1 |
| 1-320 | 2,6-di-iPrPhSO$_2$ | H | Me | 1,4-Ph | H | O | 0 | 0 | 1 |
| 1-321 | 2,4,6-tri-iPrPhSO$_2$ | H | Me | 1,4-Ph | H | O | 0 | 0 | 1 |
| 1-322 | 2-CF$_3$PhSO$_2$ | H | Me | 1,4-Ph | H | O | 0 | 0 | 1 |
| 1-323 | 3-CF$_3$PhSO$_2$ | H | Me | 1,4-Ph | H | O | 0 | 0 | 1 |
| 1-324 | 4-CF$_3$PhSO$_2$ | H | Me | 1,4-Ph | H | O | 0 | 0 | 1 |
| 1-325 | 4-FPhSO$_2$ | H | Me | 1,4-Ph | H | O | 0 | 0 | 1 |
| 1-326 | 2,4-di-FPhSO$_2$ | H | Me | 1,4-Ph | H | O | 0 | 0 | 1 |
| 1-327 | 4-ClPhSO$_2$ | H | Me | 1,4-Ph | H | O | 0 | 0 | 1 |
| 1-328 | 3-CNPhSO$_2$ | H | Me | 1,4-Ph | H | O | 0 | 0 | 1 |
| 1-329 | 4-NO$_2$PhSO$_2$ | H | Me | 1,4-Ph | H | O | 0 | 0 | 1 |
| 1-330 | BzSO$_2$ | H | Me | 1,4-Ph | H | O | 0 | 0 | 1 |
| 1-331 | cHxSO$_2$ | H | Me | 1,4-Ph | H | O | 2 | 0 | 1 |
| 1-332 | Ada(1)SO$_2$ | H | Me | 1,4-Ph | H | O | 2 | 0 | 1 |
| 1-333 | PhSO$_2$ | H | Me | 1,4-Ph | H | O | 2 | 0 | 1 |
| 1-334 | 4-MePhSO$_2$ | H | Me | 1,4-Ph | H | O | 2 | 0 | 1 |
| 1-335 | 2,6-di-iPrPhSO$_2$ | H | Me | 1,4-Ph | H | O | 2 | 0 | 1 |
| 1-336 | 2,4,6-tri-iPrPhSO$_2$ | H | Me | 1,4-Ph | H | O | 2 | 0 | 1 |
| 1-337 | 2-CF$_3$PhSO$_2$ | H | Me | 1,4-Ph | H | O | 2 | 0 | 1 |
| 1-338 | 3-CF$_3$PhSO$_2$ | H | Me | 1,4-Ph | H | O | 2 | 0 | 1 |
| 1-339 | 4-CF$_3$PhSO$_2$ | H | Me | 1,4-Ph | H | O | 2 | 0 | 1 |
| 1-340 | 4-FPhSO$_2$ | H | Me | 1,4-Ph | H | O | 2 | 0 | 1 |
| 1-341 | 2,4-di-FPhSO$_2$ | H | Me | 1,4-Ph | H | O | 2 | 0 | 1 |
| 1-342 | 4-ClPhSO$_2$ | H | Me | 1,4-Ph | H | O | 2 | 0 | 1 |
| 1-343 | 3-CNPhSO$_2$ | H | Me | 1,4-Ph | H | O | 2 | 0 | 1 |
| 1-344 | 4-NO$_2$PhSO$_2$ | H | Me | 1,4-Ph | H | O | 2 | 0 | 1 |
| 1-345 | BzSO$_2$ | H | Me | 1,4-Ph | H | O | 2 | 0 | 1 |
| 1-346 | MeSO$_2$ | H | Me | 1,7-Np | H | O | 0 | 0 | 1 |
| 1-347 | CF$_3$SO$_2$ | H | Me | 1,7-Np | H | O | 0 | 0 | 1 |
| 1-348 | PhSO$_2$ | H | Me | 1,7-Np | H | O | 0 | 0 | 1 |
| 1-349 | 4-MePhSO$_2$ | H | Me | 1,7-Np | H | O | 0 | 0 | 1 |

TABLE 1-continued

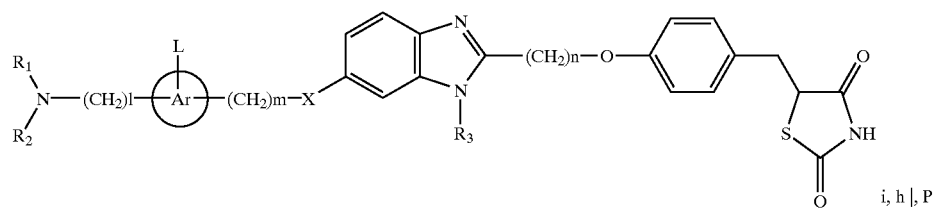

i, h |, P

| E.C.N. | R$_1$ | R$_2$ | R$_3$ | Ar | L | X | l | m | n |
|---|---|---|---|---|---|---|---|---|---|
| 1-350 | 2,6-di-iPrPhSO$_2$ | H | Me | 1,7-Np | H | O | 0 | 0 | 1 |
| 1-351 | 2,4,6-tri-iPrPhSO$_2$ | H | Me | 1,7-Np | H | O | 0 | 0 | 1 |
| 1-352 | 2-CF$_3$PhSO$_2$ | H | Me | 1,7-Np | H | O | 0 | 0 | 1 |
| 1-353 | 3-CF$_3$PhSO$_2$ | H | Me | 1,7-Np | H | O | 0 | 0 | 1 |
| 1-354 | 4-CF$_3$PhSO$_2$ | H | Me | 1,7-Np | H | O | 0 | 0 | 1 |
| 1-355 | 4-FPhSO$_2$ | H | Me | 1,7-Np | H | O | 0 | 0 | 1 |
| 1-356 | 2,4-di-FPhSO$_2$ | H | Me | 1,7-Np | H | O | 0 | 0 | 1 |
| 1-357 | 4-ClPhSO$_2$ | H | Me | 1,7-Np | H | O | 0 | 0 | 1 |
| 1-358 | 3-CNPhSO$_2$ | H | Me | 1,7-Np | H | O | 0 | 0 | 1 |
| 1-359 | 4-NO$_2$PhSO$_2$ | H | Me | 1,7-Np | H | O | 0 | 0 | 1 |
| 1-360 | BzSO$_2$ | H | Me | 1,7-Np | H | O | 0 | 0 | 1 |
| 1-361 | 4-MePhNHCO | iPr | Me | 1,4-Ph | H | O | 0 | 0 | 1 |
| 1-362 | 4-CF$_3$PhNHCO | iPr | Me | 1,4-Ph | H | O | 0 | 0 | 1 |
| 1-363 | 2,4-di-FPhNHCO | iPr | Me | 1,4-Ph | H | O | 0 | 0 | 1 |
| 1-364 | 2,6-di-FPhNHCO | iPr | Me | 1,4-Ph | H | O | 0 | 0 | 1 |
| 1-365 | 3,4-di-FPhNHCO | iPr | Me | 1,4-Ph | H | O | 0 | 0 | 1 |
| 1-366 | 2,4,6-tri-FPhNHCO | iPr | Me | 1,4-Ph | H | O | 0 | 0 | 1 |
| 1-367 | 4-ClPhNHCO | iPr | Me | 1,4-Ph | H | O | 0 | 0 | 1 |
| 1-368 | 4-HOPhNHCO | iPr | Me | 1,4-Ph | H | O | 0 | 0 | 1 |
| 1-369 | 4-CNPhNHCO | iPr | Me | 1,4-Ph | H | O | 0 | 0 | 1 |
| 1-370 | 4-NO$_2$PhNHCO | iPr | Me | 1,4-Ph | H | O | 0 | 0 | 1 |
| 1-371 | 4-cHxPhNHCO | iPr | Me | 1,4-Ph | H | O | 0 | 0 | 1 |
| 1-372 | 4-Ada(1)PhNHCO | iPr | Me | 1,4-Ph | H | O | 0 | 0 | 1 |
| 1-373 | 4-MeBzNHCO | iPr | Me | 1,4-Ph | H | O | 0 | 0 | 1 |
| 1-374 | 4-CF$_3$BzNHCO | iPr | Me | 1,4-Ph | H | O | 0 | 0 | 1 |
| 1-375 | 4-MeOBzNHCO | iPr | Me | 1,4-Ph | H | O | 0 | 0 | 1 |
| 1-376 | 4-FBzNHCO | iPr | Me | 1,4-Ph | H | O | 0 | 0 | 1 |
| 1-377 | 4-ClBzNHCO | iPr | Me | 1,4-Ph | H | O | 0 | 0 | 1 |
| 1-378 | 4-HOBzNHCO | iPr | Me | 1,4-Ph | H | O | 0 | 0 | 1 |
| 1-379 | 4-CNBzNHCO | iPr | Me | 1,4-Ph | H | O | 0 | 0 | 1 |
| 1-380 | 4-NO$_2$BzNHCO | iPr | Me | 1,4-Ph | H | O | 0 | 0 | 1 |
| 1-381 | 3-PyrNHCO | iPr | Me | 1,4-Ph | H | O | 0 | 0 | 1 |
| 1-382 | 2-CF$_3$PhNHCO | iPr | Me | 1,4-Ph | H | O | 2 | 0 | 1 |
| 1-383 | 4-FPhNHCO | iPr | Me | 1,4-Ph | H | O | 2 | 0 | 1 |
| 1-384 | 2,4-di-FPhNHCO | iPr | Me | 1,4-Ph | H | O | 2 | 0 | 1 |
| 1-385 | 4-ClPhNHCO | iPr | Me | 1,4-Ph | H | O | 2 | 0 | 1 |
| 1-386 | 3-CNPhNHCO | iPr | Me | 1,4-Ph | H | O | 2 | 0 | 1 |
| 1-387 | 4-NO$_2$PhNHCO | iPr | Me | 1,4-Ph | H | O | 2 | 0 | 1 |
| 1-388 | 4-MePhNHCS | iPr | Me | 1,4-Ph | H | O | 0 | 0 | 1 |
| 1-389 | 4-CF$_3$PhNHCS | iPr | Me | 1,4-Ph | H | O | 0 | 0 | 1 |
| 1-390 | 2,4-di-FPhNHCS | iPr | Me | 1,4-Ph | H | O | 0 | 0 | 1 |
| 1-391 | 2,6-di-FPhNHCS | iPr | Me | 1,4-Ph | H | O | 0 | 0 | 1 |
| 1-392 | 3,4-di-FPhNHCS | iPr | Me | 1,4-Ph | H | O | 0 | 0 | 1 |
| 1-393 | 2,4,6-tri-FPhNHCS | iPr | Me | 1,4-Ph | H | O | 0 | 0 | 1 |
| 1-394 | 4-ClPhNHCS | iPr | Me | 1,4-Ph | H | O | 0 | 0 | 1 |
| 1-395 | 4-HOPhNHCS | iPr | Me | 1,4-Ph | H | O | 0 | 0 | 1 |
| 1-396 | 4-CNPhNHCS | iPr | Me | 1,4-Ph | H | O | 0 | 0 | 1 |
| 1-397 | 4-NO$_2$PhNHCS | iPr | Me | 1,4-Ph | H | O | 0 | 0 | 1 |
| 1-398 | 4-cHxPhNHCS | iPr | Me | 1,4-Ph | H | O | 0 | 0 | 1 |
| 1-399 | 4-Ada(1)PhNHCS | iPr | Me | 1,4-Ph | H | O | 0 | 0 | 1 |
| 1-400 | 4-MeBzNHCS | iPr | Me | 1,4-Ph | H | O | 0 | 0 | 1 |
| 1-401 | 4-CF$_3$BzNHCS | iPr | Me | 1,4-Ph | H | O | 0 | 0 | 1 |
| 1-402 | 4-MeOBzNHCS | iPr | Me | 1,4-Ph | H | O | 0 | 0 | 1 |
| 1-403 | 4-FBzNHCS | iPr | Me | 1,4-Ph | H | O | 0 | 0 | 1 |
| 1-404 | 4-ClBzNHCS | iPr | Me | 1,4-Ph | H | O | 0 | 0 | 1 |
| 1-405 | 4-HOBzNHCS | iPr | Me | 1,4-Ph | H | O | 0 | 0 | 1 |
| 1-406 | 4-CNBzNHCS | iPr | Me | 1,4-Ph | H | O | 0 | 0 | 1 |
| 1-407 | 4-NO$_2$BzNHCS | iPr | Me | 1,4-Ph | H | O | 0 | 0 | 1 |
| 1-408 | 3-PyrNHCS | iPr | Me | 1,4-Ph | H | O | 0 | 0 | 1 |
| 1-409 | 4-MePhNHCS | iPr | Me | 1,4-Ph | H | O | 0 | 0 | 1 |
| 1-410 | 4-CF$_3$PhNHCS | iPr | Me | 1,4-Ph | H | O | 0 | 0 | 1 |
| 1-411 | 2,4-di-FPhNHCS | iPr | Me | 1,4-Ph | H | O | 0 | 0 | 1 |
| 1-412 | 4-ClPhNHCS | iPr | Me | 1,4-Ph | H | O | 0 | 0 | 1 |
| 1-413 | 4-HOPhNHCS | iPr | Me | 1,4-Ph | H | O | 0 | 0 | 1 |
| 1-414 | 4-CNPhNHCS | iPr | Me | 1,4-Ph | H | O | 0 | 0 | 1 |
| 1-415 | 4-NO$_2$PhNHCS | iPr | Me | 1,4-Ph | H | O | 0 | 0 | 1 |

TABLE 1-continued

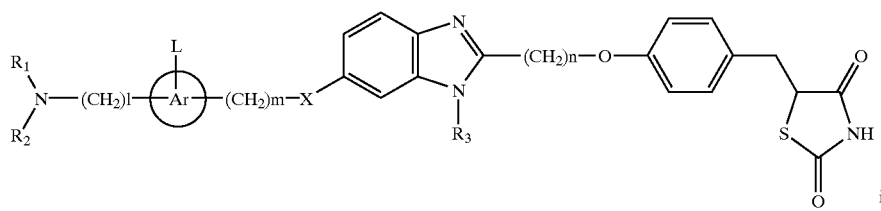

i, h |, P

| E.C.N. | R₁ | R₂ | R₃ | Ar | L | X | l | m | n |
|---|---|---|---|---|---|---|---|---|---|
| 1-416 | 4-cHxPhNHCS | iPr | Me | 1,4-Ph | H | O | 0 | 0 | 1 |
| 1-417 | 4-Ada(1)PhNHCS | iPr | Me | 1,4-Ph | H | O | 0 | 0 | 1 |
| 1-418 | 4-MeBzNHCS | iPr | Me | 1,4-Ph | H | O | 0 | 0 | 1 |
| 1-419 | 4-CF₃BzNHCS | iPr | Me | 1,4-Ph | H | O | 0 | 0 | 1 |
| 1-420 | 4-MeOBzNHCS | iPr | Me | 1,4-Ph | H | O | 0 | 0 | 1 |
| 1-421 | 4-FBzNHCS | iPr | Me | 1,4-Ph | H | O | 0 | 0 | 1 |
| 1-422 | 4-ClBzNHCS | iPr | Me | 1,4-Ph | H | O | 0 | 0 | 1 |
| 1-423 | 4-HOBzNHCS | iPr | Me | 1,4-Ph | H | O | 0 | 0 | 1 |
| 1-424 | 4-CNBzNHCS | iPr | Me | 1,4-Ph | H | O | 0 | 0 | 1 |
| 1-425 | 4-NO₂BzNHCS | iPr | Me | 1,4-Ph | H | O | 0 | 0 | 1 |
| 1-426 | 3-PyrNHCS | iPr | Me | 1,4-Ph | H | O | 0 | 0 | 1 |
| 1-427 | 4-MePhSO₂ | iPr | Me | 1,4-Ph | H | O | 0 | 0 | 1 |
| 1-428 | 4-CF₃PhSO₂ | iPr | Me | 1,4-Ph | H | O | 0 | 0 | 1 |
| 1-429 | 2,4-di-FPhSO₂ | iPr | Me | 1,4-Ph | H | O | 0 | 0 | 1 |
| 1-430 | 2,6-di-FPhSO₂ | iPr | Me | 1,4-Ph | H | O | 0 | 0 | 1 |
| 1-431 | 3,4-di-FPhSO₂ | iPr | Me | 1,4-Ph | H | O | 0 | 0 | 1 |
| 1-432 | 2,4,6-tri-FPhSO₂ | iPr | Me | 1,4-Ph | H | O | 0 | 0 | 1 |
| 1-433 | 4-ClPhSO₂ | iPr | Me | 1,4-Ph | H | O | 0 | 0 | 1 |
| 1-434 | 4-HOPhSO₂ | iPr | Me | 1,4-Ph | H | O | 0 | 0 | 1 |
| 1-435 | 4-CNPhSO₂ | iPr | Me | 1,4-Ph | H | O | 0 | 0 | 1 |
| 1-436 | 4-NO₂PhSO₂ | iPr | Me | 1,4-Ph | H | O | 0 | 0 | 1 |
| 1-437 | 4-cHxPhSO₂ | iPr | Me | 1,4-Ph | H | O | 0 | 0 | 1 |
| 1-438 | 4-Ada(1)PhSO₂ | iPr | Me | 1,4-Ph | H | O | 0 | 0 | 1 |
| 1-439 | 4-MeBzSO₂ | iPr | Me | 1,4-Ph | H | O | 0 | 0 | 1 |
| 1-440 | 4-CF₃BzSO₂ | iPr | Me | 1,4-Ph | H | O | 0 | 0 | 1 |
| 1-441 | 4-MeOBzSO₂ | iPr | Me | 1,4-Ph | H | O | 0 | 0 | 1 |
| 1-442 | 4-FBzSO₂ | iPr | Me | 1,4-Ph | H | O | 0 | 0 | 1 |
| 1-443 | 4-ClBzSO₂ | iPr | Me | 1,4-Ph | H | O | 0 | 0 | 1 |
| 1-444 | 4-HOBzSO₂ | iPr | Me | 1,4-Ph | H | O | 0 | 0 | 1 |
| 1-445 | 4-CNBzSO₂ | iPr | Me | 1,4-Ph | H | O | 0 | 0 | 1 |
| 1-446 | 4-NO₂BzSO₂ | iPr | Me | 1,4-Ph | H | O | 0 | 0 | 1 |
| 1-447 | 3-PyrSO₂ | iPr | Me | 1,4-Ph | H | O | 0 | 0 | 1 |
| 1-448 | 4-MePhSO₂ | iPr | Me | 1,4-Ph | H | O | 0 | 0 | 1 |
| 1-449 | 4-CF₃PhSO₂ | iPr | Me | 1,4-Ph | H | O | 0 | 0 | 1 |
| 1-450 | 2,4-di-FPhSO₂ | iPr | Me | 1,4-Ph | H | O | 0 | 0 | 1 |
| 1-451 | 4-ClPhSO₂ | iPr | Me | 1,4-Ph | H | O | 0 | 0 | 1 |
| 1-452 | 4-HOPhSO₂ | iPr | Me | 1,4-Ph | H | O | 0 | 0 | 1 |
| 1-453 | 4-CNPhSO₂ | iPr | Me | 1,4-Ph | H | O | 0 | 0 | 1 |
| 1-454 | 4-NO₂PhSO₂ | iPr | Me | 1,4-Ph | H | O | 0 | 0 | 1 |
| 1-455 | 4-cHxPhSO₂ | iPr | Me | 1,4-Ph | H | O | 0 | 0 | 1 |
| 1-456 | 4-Ada(1)PhSO₂ | iPr | Me | 1,4-Ph | H | O | 0 | 0 | 1 |
| 1-457 | 4-MeBzSO₂ | iPr | Me | 1,4-Ph | H | O | 0 | 0 | 1 |
| 1-458 | 4-CF₃BzSO₂ | iPr | Me | 1,4-Ph | H | O | 0 | 0 | 1 |
| 1-459 | 4-MeOBzSO₂ | iPr | Me | 1,4-Ph | H | O | 0 | 0 | 1 |
| 1-460 | 4-FBzSO₂ | iPr | Me | 1,4-Ph | H | O | 0 | 0 | 1 |
| 1-461 | 4-ClBzSO₂ | iPr | Me | 1,4-Ph | H | O | 0 | 0 | 1 |
| 1-462 | 4-HOBzSO₂ | iPr | Me | 1,4-Ph | H | O | 0 | 0 | 1 |
| 1-463 | 4-CNBzSO₂ | iPr | Me | 1,4-Ph | H | O | 0 | 0 | 1 |
| 1-464 | 4-NO₂BzSO₂ | iPr | Me | 1,4-Ph | H | O | 0 | 0 | 1 |
| 1-465 | 3-PyrSO₂ | iPr | Me | 1,4-Ph | H | O | 0 | 0 | 1 |
| 1-466 | 4-MePhNHCO | H | Me | 2,5-Np | H | O | 0 | 0 | 1 |
| 1-467 | 4-CF₃PhNHCO | H | Me | 2,5-Np | H | O | 0 | 0 | 1 |
| 1-468 | 2,4-di-FPhNHCO | H | Me | 2,5-Np | H | O | 0 | 0 | 1 |
| 1-469 | 2,6-di-FPhNHCO | H | Me | 2,5-Np | H | O | 0 | 0 | 1 |
| 1-470 | 3,4-di-FPhNHCO | H | Me | 2,5-Np | H | O | 0 | 0 | 1 |
| 1-471 | 2,4,6-tri-FPhNHCO | H | Me | 2,5-Np | H | O | 0 | 0 | 1 |
| 1-472 | 4-ClPhNHCO | H | Me | 2,5-Np | H | O | 0 | 0 | 1 |
| 1-473 | 4-HOPhNHCO | H | Me | 2,5-Np | H | O | 0 | 0 | 1 |
| 1-474 | 4-CNPhNHCO | H | Me | 2,5-Np | H | O | 0 | 0 | 1 |
| 1-475 | 4-NO₂PhNHCO | H | Me | 2,5-Np | H | O | 0 | 0 | 1 |
| 1-476 | 4-cHxPhNHCO | H | Me | 2,5-Np | H | O | 0 | 0 | 1 |
| 1-477 | 4-Ada(1)PhNHCO | H | Me | 2,5-Np | H | O | 0 | 0 | 1 |
| 1-478 | 4-MeBzNHCO | H | Me | 2,5-Np | H | O | 0 | 0 | 1 |
| 1-479 | 4-CF₃BzNHCO | H | Me | 2,5-Np | H | O | 0 | 0 | 1 |
| 1-480 | 4-MeOBzNHCO | H | Me | 2,5-Np | H | O | 0 | 0 | 1 |
| 1-481 | 4-FBzNHCO | H | Me | 2,5-Np | H | O | 0 | 0 | 1 |

TABLE 1-continued

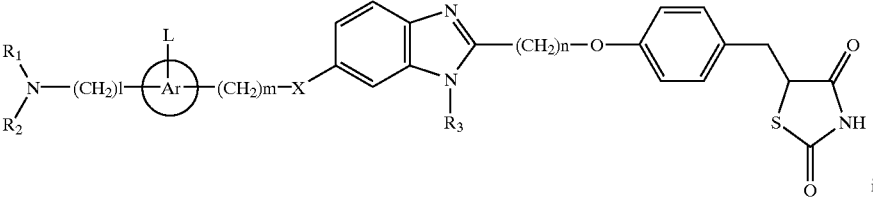

i, h |, P

| E.C.N. | R$_1$ | R$_2$ | R$_3$ | Ar | L | X | l | m | n |
|---|---|---|---|---|---|---|---|---|---|
| 1-482 | 4-ClBzNHCO | H | Me | 2,5-Np | H | O | 0 | 0 | 1 |
| 1-483 | 4-HOBzNHCO | H | Me | 2,5-Np | H | O | 0 | 0 | 1 |
| 1-484 | 4-CNBzNHCO | H | Me | 2,5-Np | H | O | 0 | 0 | 1 |
| 1-485 | 4-NO$_2$BzNHCO | H | Me | 2,5-Np | H | O | 0 | 0 | 1 |
| 1-486 | 3-PyrNHCO | H | Me | 2,5-Np | H | O | 0 | 0 | 1 |
| 1-487 | 2-CF$_3$PhNHCO | H | Me | 2,5-Np | H | O | 2 | 0 | 1 |
| 1-488 | 4-FPhNHCO | H | Me | 2,5-Np | H | O | 2 | 0 | 1 |
| 1-489 | 2,4-di-FPhNHCO | H | Me | 2,5-Np | H | O | 2 | 0 | 1 |
| 1-490 | 4-ClPhNHCO | H | Me | 2,5-Np | H | O | 2 | 0 | 1 |
| 1-491 | 3-CNPhNHCO | H | Me | 2,5-Np | H | O | 2 | 0 | 1 |
| 1-492 | 4-NO$_2$PhNHCO | H | Me | 2,5-Np | H | O | 2 | 0 | 1 |

TABLE 2

| E.C.N. | R$_1$ | R$_2$ | R$_3$ | Ar | L | X | l | m | n |
|---|---|---|---|---|---|---|---|---|---|
| 2-1 | MeNHCO | H | Me | 1,3-Ph | H | O | 0 | 0 | 1 |
| 2-2 | EtNHCO | H | Me | 1,3-Ph | H | O | 0 | 0 | 1 |
| 2-3 | BuNHCO | H | Me | 1,3-Ph | H | O | 0 | 0 | 1 |
| 2-4 | tBuNHCO | H | Me | 1,3-Ph | H | O | 0 | 0 | 1 |
| 2-5 | HxNHCO | H | Me | 1,3-Ph | H | O | 0 | 0 | 1 |
| 2-6 | CF$_3$NHCO | H | Me | 1,3-Ph | H | O | 0 | 0 | 1 |
| 2-7 | cHxNHCO | H | Me | 1,3-Ph | H | O | 0 | 0 | 1 |
| 2-8 | Ada(1)NHCO | H | Me | 1,3-Ph | H | O | 0 | 0 | 1 |
| 2-9 | PhNHCO | H | Me | 1,3-Ph | H | O | 0 | 0 | 1 |
| 2-10 | 2-MePhNHCO | H | Me | 1,3-Ph | H | O | 0 | 0 | 1 |
| 2-11 | 3-MePhNHCO | H | Me | 1,3-Ph | H | O | 0 | 0 | 1 |
| 2-12 | 4-MePhNHCO | H | Me | 1,3-Ph | H | O | 0 | 0 | 1 |
| 2-13 | 2,6-di-MePhNHCO | H | Me | 1,3-Ph | H | O | 0 | 0 | 1 |
| 2-14 | 3,4-di-MePhNHCO | H | Me | 1,3-Ph | H | O | 0 | 0 | 1 |
| 2-15 | 2,4,6-tri-MePhNHCO | H | Me | 1,3-Ph | H | O | 0 | 0 | 1 |
| 2-16 | 4-iPrPhNHCO | H | Me | 1,3-Ph | H | O | 0 | 0 | 1 |
| 2-17 | 2,6-di-iPrPhNHCO | H | Me | 1,3-Ph | H | O | 0 | 0 | 1 |
| 2-18 | 3,4-di-iPrPhNHCO | H | Me | 1,3-Ph | H | O | 0 | 0 | 1 |
| 2-19 | 2,4,6-tri-iPrPhNHCO | H | Me | 1,3-Ph | H | O | 0 | 0 | 1 |
| 2-20 | 4-tBuPhNHCO | H | Me | 1,3-Ph | H | O | 0 | 0 | 1 |
| 2-21 | 2,6-di-tBuPhNHCO | H | Me | 1,3-Ph | H | O | 0 | 0 | 1 |
| 2-22 | 3,4-di-tBuPhNHCO | H | Me | 1,3-Ph | H | O | 0 | 0 | 1 |
| 2-23 | 2,4,6-tri-tBuPhNHCO | H | Me | 1,3-Ph | H | O | 0 | 0 | 1 |
| 2-24 | 2-CF$_3$PhNHCO | H | Me | 1,3-Ph | H | O | 0 | 0 | 1 |
| 2-25 | 3-CF$_3$PhNHCO | H | Me | 1,3-Ph | H | O | 0 | 0 | 1 |
| 2-26 | 4-CF$_3$PhNHCO | H | Me | 1,3-Ph | H | O | 0 | 0 | 1 |
| 2-27 | 2-FPhNHCO | H | Me | 1,3-Ph | H | O | 0 | 0 | 1 |
| 2-28 | 3-FPhNHCO | H | Me | 1,3-Ph | H | O | 0 | 0 | 1 |
| 2-29 | 4-FPhNHCO | H | Me | 1,3-Ph | H | O | 0 | 0 | 1 |
| 2-30 | 2,4-di-FPhNHCO | H | Me | 1,3-Ph | H | O | 0 | 0 | 1 |
| 2-31 | 2,6-di-FPhNHCO | H | Me | 1,3-Ph | H | O | 0 | 0 | 1 |
| 2-32 | 3,4-di-FPhNHCO | H | Me | 1,3-Ph | H | O | 0 | 0 | 1 |
| 2-33 | 2,4,6-tri-FPhNHCO | H | Me | 1,3-Ph | H | O | 0 | 0 | 1 |
| 2-34 | 2-ClPhNHCO | H | Me | 1,3-Ph | H | O | 0 | 0 | 1 |
| 2-35 | 3-ClPhNHCO | H | Me | 1,3-Ph | H | O | 0 | 0 | 1 |
| 2-36 | 4-ClPhNHCO | H | Me | 1,3-Ph | H | O | 0 | 0 | 1 |
| 2-37 | 2-HOPhNHCO | H | Me | 1,3-Ph | H | O | 0 | 0 | 1 |
| 2-38 | 3-HOPhNHCO | H | Me | 1,3-Ph | H | O | 0 | 0 | 1 |
| 2-39 | 4-HOPhNHCO | H | Me | 1,3-Ph | H | O | 0 | 0 | 1 |
| 2-40 | 2-CNPhNHCO | H | Me | 1,3-Ph | H | O | 0 | 0 | 1 |
| 2-41 | 3-CNPhNHCO | H | Me | 1,3-Ph | H | O | 0 | 0 | 1 |
| 2-42 | 4-CNPhNHCO | H | Me | 1,3-Ph | H | O | 0 | 0 | 1 |
| 2-43 | 2-NO$_2$PhNHCO | H | Me | 1,3-Ph | H | O | 0 | 0 | 1 |
| 2-44 | 3-NO$_2$PhNHCO | H | Me | 1,3-Ph | H | O | 0 | 0 | 1 |
| 2-45 | 4-NO$_2$PhNHCO | H | Me | 1,3-Ph | H | O | 0 | 0 | 1 |
| 2-46 | 4-cHxPhNHCO | H | Me | 1,3-Ph | H | O | 0 | 0 | 1 |
| 2-47 | 4-Ada(1)PhNHCO | H | Me | 1,3-Ph | H | O | 0 | 0 | 1 |
| 2-48 | 4-PhPhNHCO | H | Me | 1,3-Ph | H | O | 0 | 0 | 1 |

TABLE 2-continued

| E.C.N. | R₁ | R₂ | R₃ | Ar | L | X | l | m | n |
|---|---|---|---|---|---|---|---|---|---|
| 2-49 | 4-(4-MePh)PhNHCO | H | Me | 1,3-Ph | H | O | 0 | 0 | 1 |
| 2-50 | 4-(4-CF₃Ph)PhNHCO | H | Me | 1,3-Ph | H | O | 0 | 0 | 1 |
| 2-51 | 4-(4-MeOPh)PhNHCO | H | Me | 1,3-Ph | H | O | 0 | 0 | 1 |
| 2-52 | 4-(4-FPh)PhNHCO | H | Me | 1,3-Ph | H | O | 0 | 0 | 1 |
| 2-53 | 4-(4-ClPh)PhNHCO | H | Me | 1,3-Ph | H | O | 0 | 0 | 1 |
| 2-54 | 4-(4-HOPh)PhNHCO | H | Me | 1,3-Ph | H | O | 0 | 0 | 1 |
| 2-55 | 4-(4-MeBz)PhNHCO | H | Me | 1,3-Ph | H | O | 0 | 0 | 1 |
| 2-56 | 4-(4-CF₃Bz)PhNHCO | H | Me | 1,3-Ph | H | O | 0 | 0 | 1 |
| 2-57 | 4-(4-MeOBz)PhNHCO | H | Me | 1,3-Ph | H | O | 0 | 0 | 1 |
| 2-58 | 4-(4-FBz)PhNHCO | H | Me | 1,3-Ph | H | O | 0 | 0 | 1 |
| 2-59 | 4-(4-ClBz)PhNHCO | H | Me | 1,3-Ph | H | O | 0 | 0 | 1 |
| 2-60 | 4-(4-HOBz)PhNHCO | H | Me | 1,3-Ph | H | O | 0 | 0 | 1 |
| 2-61 | 2-AcPhNHCO | H | Me | 1,3-Ph | H | O | 0 | 0 | 1 |
| 2-62 | 3-AcPhNHCO | H | Me | 1,3-Ph | H | O | 0 | 0 | 1 |
| 2-63 | 4-AcPhNHCO | H | Me | 1,3-Ph | H | O | 0 | 0 | 1 |
| 2-64 | 2-AcOPhNHCO | H | Me | 1,3-Ph | H | O | 0 | 0 | 1 |
| 2-65 | 3-AcOPhNHCO | H | Me | 1,3-Ph | H | O | 0 | 0 | 1 |
| 2-66 | 4-AcOPhNHCO | H | Me | 1,3-Ph | H | O | 0 | 0 | 1 |
| 2-67 | 2-H₂NPhNHCO | H | Me | 1,3-Ph | H | O | 0 | 0 | 1 |
| 2-68 | 3-H₂NPhNHCO | H | Me | 1,3-Ph | H | O | 0 | 0 | 1 |
| 2-69 | 4-H₂NPhNHCO | H | Me | 1,3-Ph | H | O | 0 | 0 | 1 |
| 2-70 | 4-Me₂NPhNHCO | H | Me | 1,3-Ph | H | O | 0 | 0 | 1 |
| 2-71 | 4-iPr₂NPhNHCO | H | Me | 1,3-Ph | H | O | 0 | 0 | 1 |
| 2-72 | 3,4-MdOPhNHCO | H | Me | 1,3-Ph | H | O | 0 | 0 | 1 |
| 2-73 | 3,4-EdOPhNHCO | H | Me | 1,3-Ph | H | O | 0 | 0 | 1 |
| 2-74 | 1-NpNHCO | H | Me | 1,3-Ph | H | O | 0 | 0 | 1 |
| 2-75 | 2-NpNHCO | H | Me | 1,3-Ph | H | O | 0 | 0 | 1 |
| 2-76 | BzNHCO | H | Me | 1,3-Ph | H | O | 0 | 0 | 1 |
| 2-77 | Ph(CH₂)₂NHCO | H | Me | 1,3-Ph | H | O | 0 | 0 | 1 |
| 2-78 | Ph(CH₂)₃NHCO | H | Me | 1,3-Ph | H | O | 0 | 0 | 1 |
| 2-79 | 4-MeBzNHCO | H | Me | 1,3-Ph | H | O | 0 | 0 | 1 |
| 2-80 | 2-CF₃BzNHCO | H | Me | 1,3-Ph | H | O | 0 | 0 | 1 |
| 2-81 | 3-CF₃BzNHCO | H | Me | 1,3-Ph | H | O | 0 | 0 | 1 |
| 2-82 | 4-CF₃BzNHCO | H | Me | 1,3-Ph | H | O | 0 | 0 | 1 |
| 2-83 | 4-MeOBzNHCO | H | Me | 1,3-Ph | H | O | 0 | 0 | 1 |
| 2-84 | 4-FBzNHCO | H | Me | 1,3-Ph | H | O | 0 | 0 | 1 |
| 2-85 | 4-ClBzNHCO | H | Me | 1,3-Ph | H | O | 0 | 0 | 1 |
| 2-86 | 4-HOBzNHCO | H | Me | 1,3-Ph | H | O | 0 | 0 | 1 |
| 2-87 | 4-CNBzNHCO | H | Me | 1,3-Ph | H | O | 0 | 0 | 1 |
| 2-88 | 4-NO₂BzNHCO | H | Me | 1,3-Ph | H | O | 0 | 0 | 1 |
| 2-89 | 4-MePh(CH₂)₃NHCO | H | Me | 1,3-Ph | H | O | 0 | 0 | 1 |
| 2-90 | 2-CF₃Ph(CH₂)₃NHCO | H | Me | 1,3-Ph | H | O | 0 | 0 | 1 |
| 2-91 | 3-CF₃Ph(CH₂)₃NHCO | H | Me | 1,3-Ph | H | O | 0 | 0 | 1 |
| 2-92 | 4-CF₃Ph(CH₂)₃NHCO | H | Me | 1,3-Ph | H | O | 0 | 0 | 1 |
| 2-93 | 4-MeOPh(CH₂)₃NHCO | H | Me | 1,3-Ph | H | O | 0 | 0 | 1 |
| 2-94 | 4-FPh(CH₂)₃NHCO | H | Me | 1,3-Ph | H | O | 0 | 0 | 1 |
| 2-95 | 4-ClPh(CH₂)₃NHCO | H | Me | 1,3-Ph | H | O | 0 | 0 | 1 |
| 2-96 | 4-HOPh(CH₂)₃NHCO | H | Me | 1,3-Ph | H | O | 0 | 0 | 1 |
| 2-97 | 4-CNPh(CH₂)₃NHCO | H | Me | 1,3-Ph | H | O | 0 | 0 | 1 |
| 2-98 | 4-NO₂Ph(CH₂)₃NHCO | H | Me | 1,3-Ph | H | O | 0 | 0 | 1 |
| 2-99 | cPrcNHCO | H | Me | 1,3-Ph | H | O | 0 | 0 | 1 |
| 2-100 | cPncNHCO | H | Me | 1,3-Ph | H | O | 0 | 0 | 1 |
| 2-101 | cHxcNHCO | H | Me | 1,3-Ph | H | O | 0 | 0 | 1 |
| 2-102 | BozNHCO | H | Me | 1,3-Ph | H | O | 0 | 0 | 1 |
| 2-103 | 4-MeBozNHCO | H | Me | 1,3-Ph | H | O | 0 | 0 | 1 |
| 2-104 | 2-CF₃BozNHCO | H | Me | 1,3-Ph | H | O | 0 | 0 | 1 |
| 2-105 | 3-CF₃BozNHCO | H | Me | 1,3-Ph | H | O | 0 | 0 | 1 |
| 2-106 | 4-CF₃BozNHCO | H | Me | 1,3-Ph | H | O | 0 | 0 | 1 |
| 2-107 | 4-MeOBozNHCO | H | Me | 1,3-Ph | H | O | 0 | 0 | 1 |
| 2-108 | 4-FBozNHCO | H | Me | 1,3-Ph | H | O | 0 | 0 | 1 |
| 2-109 | 4-ClBozNHCO | H | Me | 1,3-Ph | H | O | 0 | 0 | 1 |
| 2-110 | 4-HOBozNHCO | H | Me | 1,3-Ph | H | O | 0 | 0 | 1 |
| 2-111 | 4-CNBozNHCO | H | Me | 1,3-Ph | H | O | 0 | 0 | 1 |
| 2-112 | 4-NO₂BozNHCO | H | Me | 1,3-Ph | H | O | 0 | 0 | 1 |
| 2-113 | Ph(CH₂)C=ONHCO | H | Me | 1,3-Ph | H | O | 0 | 0 | 1 |
| 2-114 | 4-MePh(CH₂)C=ONHCO | H | Me | 1,3-Ph | H | O | 0 | 0 | 1 |
| 2-115 | 2-CF₃Ph(CH₂)C=ONHCO | H | Me | 1,3-Ph | H | O | 0 | 0 | 1 |
| 2-116 | 3-CF₃Ph(CH₂)C=ONHCO | H | Me | 1,3-Ph | H | O | 0 | 0 | 1 |
| 2-117 | 4-CF₃Ph(CH₂)C=ONHCO | H | Me | 1,3-Ph | H | O | 0 | 0 | 1 |
| 2-118 | 4-MeOPh(CH₂)C=ONHCO | H | Me | 1,3-Ph | H | O | 0 | 0 | 1 |
| 2-119 | 4-FPh(CH₂)C=ONHCO | H | Me | 1,3-Ph | H | O | 0 | 0 | 1 |
| 2-120 | 4-ClPh(CH₂)C=ONHCO | H | Me | 1,3-Ph | H | O | 0 | 0 | 1 |
| 2-121 | 4-HOPh(CH₂)C=ONHCO | H | Me | 1,3-Ph | H | O | 0 | 0 | 1 |
| 2-122 | 4-CNPh(CH₂)C=ONHCO | H | Me | 1,3-Ph | H | O | 0 | 0 | 1 |
| 2-123 | 4-NO₂Ph(CH₂)C=ONHCO | H | Me | 1,3-Ph | H | O | 0 | 0 | 1 |
| 2-124 | 3-PyrNHCO | H | Me | 1,3-Ph | H | O | 0 | 0 | 1 |
| 2-125 | 6-Me(3-Pyr)NHCO | H | Me | 1,3-Ph | H | O | 0 | 0 | 1 |

TABLE 2-continued

| E.C.N. | R₁ | R₂ | R₃ | Ar | L | X | l | m | n |
|---|---|---|---|---|---|---|---|---|---|
| 2-126 | 6-CF₃(3-Pyr)NHCO | H | Me | 1,3-Ph | H | O | 0 | 0 | 1 |
| 2-127 | 6-MeO(3-Pyr)NHCO | H | Me | 1,3-Ph | H | O | 0 | 0 | 1 |
| 2-128 | 6-F(3-Pyr)NHCO | H | Me | 1,3-Ph | H | O | 0 | 0 | 1 |
| 2-129 | 6-Cl(3-Pyr)NHCO | H | Me | 1,3-Ph | H | O | 0 | 0 | 1 |
| 2-130 | 6-HO(3-Pyr)NHCO | H | Me | 1,3-Ph | H | O | 0 | 0 | 1 |
| 2-131 | 6-CN(3-Pyr)NHCO | H | Me | 1,3-Ph | H | O | 0 | 0 | 1 |
| 2-132 | 6-NO₂(3-Pyr)NHCO | H | Me | 1,3-Ph | H | O | 0 | 0 | 1 |
| 2-133 | NicNHCO | H | Me | 1,3-Ph | H | O | 0 | 0 | 1 |
| 2-134 | iNicNHCO | H | Me | 1,3-Ph | H | O | 0 | 0 | 1 |
| 2-135 | cHxNHCS | H | Me | 1,3-Ph | H | O | 0 | 0 | 1 |
| 2-136 | Ada(1)NHCS | H | Me | 1,3-Ph | H | O | 0 | 0 | 1 |
| 2-137 | PhNHCS | H | Me | 1,3-Ph | H | O | 0 | 0 | 1 |
| 2-138 | 4-MePhNHCS | H | Me | 1,3-Ph | H | O | 0 | 0 | 1 |
| 2-139 | 2,6-di-iPrPhNHCS | H | Me | 1,3-Ph | H | O | 0 | 0 | 1 |
| 2-140 | 2,4,6-tri-iPrPhNHCS | H | Me | 1,3-Ph | H | O | 0 | 0 | 1 |
| 2-141 | 2-CF₃PhNHCS | H | Me | 1,3-Ph | H | O | 0 | 0 | 1 |
| 2-142 | 3-CF₃PhNHCS | H | Me | 1,3-Ph | H | O | 0 | 0 | 1 |
| 2-143 | 4-CF₃PhNHCS | H | Me | 1,3-Ph | H | O | 0 | 0 | 1 |
| 2-144 | 4-FPhNHCS | H | Me | 1,3-Ph | H | O | 0 | 0 | 1 |
| 2-145 | 2,4-di-FPhNHCS | H | Me | 1,3-Ph | H | O | 0 | 0 | 1 |
| 2-146 | 4-ClPhNHCS | H | Me | 1,3-Ph | H | O | 0 | 0 | 1 |
| 2-147 | 3-CNPhNHCS | H | Me | 1,3-Ph | H | O | 0 | 0 | 1 |
| 2-148 | 4-NO₂PhNHCS | H | Me | 1,3-Ph | H | O | 0 | 0 | 1 |
| 2-149 | 1-NpNHCS | H | Me | 1,3-Ph | H | O | 0 | 0 | 1 |
| 2-150 | BzNHCS | H | Me | 1,3-Ph | H | O | 0 | 0 | 1 |
| 2-151 | BzNHCS | H | Me | 1,7-Np | H | O | 0 | 0 | 1 |
| 2-152 | MeSO₂ | H | Me | 1,3-Ph | H | O | 0 | 0 | 1 |
| 2-153 | Ada(1)SO₂ | H | Me | 1,3-Ph | H | O | 0 | 0 | 1 |
| 2-154 | PhSO₂ | H | Me | 1,3-Ph | H | O | 0 | 0 | 1 |
| 2-155 | 4-MePhSO₂ | H | Me | 1,3-Ph | H | O | 0 | 0 | 1 |
| 2-156 | 2,6-di-iPrPhSO₂ | H | Me | 1,3-Ph | H | O | 0 | 0 | 1 |
| 2-157 | 2,4,6-tri-iPrPhSO₂ | H | Me | 1,3-Ph | H | O | 0 | 0 | 1 |
| 2-158 | 2-CF₃PhSO₂ | H | Me | 1,3-Ph | H | O | 0 | 0 | 1 |
| 2-159 | 3-CF₃PhSO₂ | H | Me | 1,3-Ph | H | O | 0 | 0 | 1 |
| 2-160 | 4-CF₃PhSO₂ | H | Me | 1,3-Ph | H | O | 0 | 0 | 1 |
| 2-161 | 4-FPhSO₂ | H | Me | 1,3-Ph | H | O | 0 | 0 | 1 |
| 2-162 | 2,4-di-FPhSO₂ | H | Me | 1,3-Ph | H | O | 0 | 0 | 1 |
| 2-163 | 4-ClPhSO₂ | H | Me | 1,3-Ph | H | O | 0 | 0 | 1 |
| 2-164 | 3-CNPhSO₂ | H | Me | 1,3-Ph | H | O | 0 | 0 | 1 |
| 2-165 | 4-NO₂PhSO₂ | H | Me | 1,3-Ph | H | O | 0 | 0 | 1 |
| 2-166 | BzSO₂ | H | Me | 1,3-Ph | H | O | 0 | 0 | 1 |
| 2-167 | cHxSO₂ | H | Me | 1,3-Ph | H | O | 2 | 0 | 1 |
| 2-168 | Ada(1)SO₂ | H | Me | 1,3-Ph | H | O | 2 | 0 | 1 |
| 2-169 | PhSO₂ | H | Me | 1,3-Ph | H | O | 2 | 0 | 1 |
| 2-170 | 4-MePhSO₂ | H | Me | 1,3-Ph | H | O | 2 | 0 | 1 |
| 2-171 | 2,6-di-iPrPhSO₂ | H | Me | 1,3-Ph | H | O | 2 | 0 | 1 |
| 2-172 | 2,4,6-tri-iPrPhSO₂ | H | Me | 1,3-Ph | H | O | 2 | 0 | 1 |
| 2-173 | 2-CF₃PhSO₂ | H | Me | 1,3-Ph | H | O | 2 | 0 | 1 |
| 2-174 | 3-CF₃PhSO₂ | H | Me | 1,3-Ph | H | O | 2 | 0 | 1 |
| 2-175 | 4-CF₃PhSO₂ | H | Me | 1,3-Ph | H | O | 2 | 0 | 1 |
| 2-176 | 4-FPhSO₂ | H | Me | 1,3-Ph | H | O | 2 | 0 | 1 |
| 2-177 | 2,4-di-FPhSO₂ | H | Me | 1,3-Ph | H | O | 2 | 0 | 1 |
| 2-178 | 4-ClPhSO₂ | H | Me | 1,3-Ph | H | O | 2 | 0 | 1 |
| 2-179 | 3-CNPhSO₂ | H | Me | 1,3-Ph | H | O | 2 | 0 | 1 |
| 2-180 | 4-NO₂PhSO₂ | H | Me | 1,3-Ph | H | O | 2 | 0 | 1 |
| 2-181 | BzSO₂ | H | Me | 1,3-Ph | H | O | 2 | 0 | 1 |
| 2-182 | cHxNHCO | H | Me | 1,3-Ph | 6-tBu | O | 0 | 1 | 1 |
| 2-183 | Ada(1)NHCO | H | Me | 1,3-Ph | 6-tBu | O | 0 | 1 | 1 |
| 2-184 | PhNHCO | H | Me | 1,3-Ph | 6-tBu | O | 0 | 1 | 1 |
| 2-185 | 4-MePhNHCO | H | Me | 1,3-Ph | 6-tBu | O | 0 | 1 | 1 |
| 2-186 | 2,6-di-iPrPhNHCO | H | Me | 1,3-Ph | 6-tBu | O | 0 | 1 | 1 |
| 2-187 | 2,4,6-tri-iPrPhNHCO | H | Me | 1,3-Ph | 6-tBu | O | 0 | 1 | 1 |
| 2-188 | 2-CF₃PhNHCO | H | Me | 1,3-Ph | 6-tBu | O | 0 | 1 | 1 |
| 2-189 | 3-CF₃PhNHCO | H | Me | 1,3-Ph | 6-tBu | O | 0 | 1 | 1 |
| 2-190 | 4-CF₃PhNHCO | H | Me | 1,3-Ph | 6-tBu | O | 0 | 1 | 1 |
| 2-191 | 4-FPhNHCO | H | Me | 1,3-Ph | 6-tBu | O | 0 | 1 | 1 |
| 2-192 | 2,4-di-FPhNHCO | H | Me | 1,3-Ph | 6-tBu | O | 0 | 1 | 1 |
| 2-193 | 4-ClPhNHCO | H | Me | 1,3-Ph | 6-tBu | O | 0 | 1 | 1 |
| 2-194 | 3-CNPhNHCO | H | Me | 1,3-Ph | 6-tBu | O | 0 | 1 | 1 |
| 2-195 | 4-NO₂PhNHCO | H | Me | 1,3-Ph | 6-tBu | O | 0 | 1 | 1 |
| 2-196 | BzNHCO | H | Me | 1,3-Ph | 6-tBu | O | 0 | 1 | 1 |
| 2-197 | cHxNHCO | H | Me | 1,3-Ph | 6-tBu | O | 0 | 2 | 1 |
| 2-198 | Ada(1)NHCO | H | Me | 1,3-Ph | 6-tBu | O | 0 | 2 | 1 |
| 2-199 | PhNHCO | H | Me | 1,3-Ph | 6-tBu | O | 0 | 2 | 1 |
| 2-200 | 4-MePhNHCO | H | Me | 1,3-Ph | 6-tBu | O | 0 | 2 | 1 |
| 2-201 | 2,6-di-iPrPhNHCO | H | Me | 1,3-Ph | 6-tBu | O | 0 | 2 | 1 |
| 2-202 | 2,4,6-tri-iPrPhNHCO | H | Me | 1,3-Ph | 6-tBu | O | 0 | 2 | 1 |

TABLE 2-continued

| E.C.N. | R₁ | R₂ | R₃ | Ar | L | X | l | m | n |
|---|---|---|---|---|---|---|---|---|---|
| 2-203 | 2-CF₃PhNHCO | H | Me | 1,3-Ph | 6-tBu | O | 0 | 2 | 1 |
| 2-204 | 3-CF₃PhNHCO | H | Me | 1,3-Ph | 6-tBu | O | 0 | 2 | 1 |
| 2-205 | 4-CF₃PhNHCO | H | Me | 1,3-Ph | 6-tBu | O | 0 | 2 | 1 |
| 2-206 | 4-FPhNHCO | H | Me | 1,3-Ph | 6-tBu | O | 0 | 2 | 1 |
| 2-207 | 2,4-di-FPhNHCO | H | Me | 1,3-Ph | 6-tBu | O | 0 | 2 | 1 |
| 2-208 | 4-ClPhNHCO | H | Me | 1,3-Ph | 6-tBu | O | 0 | 2 | 1 |
| 2-209 | 3-CNPhNHCO | H | Me | 1,3-Ph | 6-tBu | O | 0 | 2 | 1 |
| 2-210 | 4-NO₂PhNHCO | H | Me | 1,3-Ph | 6-tBu | O | 0 | 2 | 1 |
| 2-211 | BzNHCO | H | Me | 1,3-Ph | 6-tBu | O | 0 | 2 | 1 |

TABLE 3

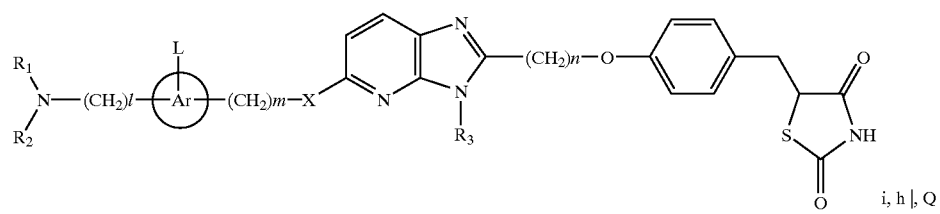

i, h|, Q

| E.C.N. | R₁ | R₂ | R₃ | Ar | L | X | l | m | n |
|---|---|---|---|---|---|---|---|---|---|
| 3-1 | MeNHCO | H | Me | 1,4-Ph | H | O | 0 | 0 | 1 |
| 3-2 | EtNHCO | H | Me | 1,4-Ph | H | O | 0 | 0 | 1 |
| 3-3 | BuNHCO | H | Me | 1,4-Ph | H | O | 0 | 0 | 1 |
| 3-4 | tBuNHCO | H | Me | 1,4-Ph | H | O | 0 | 0 | 1 |
| 3-5 | HxNHCO | H | Me | 1,4-Ph | H | O | 0 | 0 | 1 |
| 3-6 | CF₃NHCO | H | Me | 1,4-Ph | H | O | 0 | 0 | 1 |
| 3-7 | cHxNHCO | H | Me | 1,4-Ph | H | O | 0 | 0 | 1 |
| 3-8 | Ada(1)NHCO | H | Me | 1,4-Ph | H | O | 0 | 0 | 1 |
| 3-9 | PhNHCO | H | Me | 1,4-Ph | H | O | 0 | 0 | 1 |
| 3-10 | 4-MePhNHCO | H | Me | 1,4-Ph | H | O | 0 | 0 | 1 |
| 3-11 | 2,6-di-iPrPhNHCO | H | Me | 1,4-Ph | H | O | 0 | 0 | 1 |
| 3-12 | 2,4,6-tri-iPrPhNHCO | H | Me | 1,4-Ph | H | O | 0 | 0 | 1 |
| 3-13 | 2-CF₃PhNHCO | H | Me | 1,4-Ph | H | O | 0 | 0 | 1 |
| 3-14 | 3-CF₃PhNHCO | H | Me | 1,4-Ph | H | O | 0 | 0 | 1 |
| 3-15 | 4-CF₃PhNHCO | H | Me | 1,4-Ph | H | O | 0 | 0 | 1 |
| 3-16 | 4-FPhNHCO | H | Me | 1,4-Ph | H | O | 0 | 0 | 1 |
| 3-17 | 2,4-di-FPhNHCO | H | Me | 1,4-Ph | H | O | 0 | 0 | 1 |
| 3-18 | 4-ClPhNHCO | H | Me | 1,4-Ph | H | O | 0 | 0 | 1 |
| 3-19 | 3-CNPhNHCO | H | Me | 1,4-Ph | H | O | 0 | 0 | 1 |
| 3-20 | 4-NO₂PhNHCO | H | Me | 1,4-Ph | H | O | 0 | 0 | 1 |
| 3-21 | BzNHCO | H | Me | 1,4-Ph | H | O | 0 | 0 | 1 |
| 3-22 | NicNHCO | H | Me | 1,4-Ph | H | O | 0 | 0 | 1 |
| 3-23 | iNicNHCO | H | Me | 1,4-Ph | H | O | 0 | 0 | 1 |
| 3-24 | cHxNHCO | H | Me | 1,4-Ph | 2,6-di-Me | O | 0 | 0 | 1 |
| 3-25 | Ada(1)NHCO | H | Me | 1,4-Ph | 2,6-di-Me | O | 0 | 0 | 1 |
| 3-26 | PhNHCO | H | Me | 1,4-Ph | 2,6-di-Me | O | 0 | 0 | 1 |
| 3-27 | 4-MePhNHCO | H | Me | 1,4-Ph | 2,6-di-Me | O | 0 | 0 | 1 |
| 3-28 | 2,6-di-iPrPhNHCO | H | Me | 1,4-Ph | 2,6-di-Me | O | 0 | 0 | 1 |
| 3-29 | 2,4,6-tri-iPrPhNHCO | H | Me | 1,4-Ph | 2,6-di-Me | O | 0 | 0 | 1 |
| 3-30 | 2-CF₃PhNHCO | H | Me | 1,4-Ph | 2,6-di-Me | O | 0 | 0 | 1 |
| 3-31 | 3-CF₃PhNHCO | H | Me | 1,4-Ph | 2,6-di-Me | O | 0 | 0 | 1 |
| 3-32 | 4-CF₃PhNHCO | H | Me | 1,4-Ph | 2,6-di-Me | O | 0 | 0 | 1 |
| 3-33 | 4-FPhNHCO | H | Me | 1,4-Ph | 2,6-di-Me | O | 0 | 0 | 1 |
| 3-34 | 2,4-di-FPhNHCO | H | Me | 1,4-Ph | 2,6-di-Me | O | 0 | 0 | 1 |
| 3-35 | 4-ClPhNHCO | H | Me | 1,4-Ph | 2,6-di-Me | O | 0 | 0 | 1 |
| 3-36 | 3-CNPhNHCO | H | Me | 1,4-Ph | 2,6-di-Me | O | 0 | 0 | 1 |
| 3-37 | 4-NO₂PhNHCO | H | Me | 1,4-Ph | 2,6-di-Me | O | 0 | 0 | 1 |
| 3-38 | BzNHCO | H | Me | 1,4-Ph | 2,6-di-Me | O | 0 | 0 | 1 |
| 3-39 | MeNHCO | H | Me | 1,4-Ph | H | S | 0 | 0 | 1 |
| 3-40 | EtNHCO | H | Me | 1,4-Ph | H | S | 0 | 0 | 1 |
| 3-41 | BuNHCO | H | Me | 1,4-Ph | H | S | 0 | 0 | 1 |
| 3-42 | tBuNHCO | H | Me | 1,4-Ph | H | S | 0 | 0 | 1 |
| 3-43 | HxNHCO | H | Me | 1,4-Ph | H | S | 0 | 0 | 1 |
| 3-44 | CF₃NHCO | H | Me | 1,4-Ph | H | S | 0 | 0 | 1 |
| 3-45 | cHxNHCO | H | Me | 1,4-Ph | H | S | 0 | 0 | 1 |
| 3-46 | Ada(1)NHCO | H | Me | 1,4-Ph | H | S | 0 | 0 | 1 |
| 3-47 | PhNHCO | H | Me | 1,4-Ph | H | S | 0 | 0 | 1 |
| 3-48 | 4-MePhNHCO | H | Me | 1,4-Ph | H | S | 0 | 0 | 1 |
| 3-49 | 2,6-di-iPrPhNHCO | H | Me | 1,4-Ph | H | S | 0 | 0 | 1 |
| 3-50 | 2,4,6-tri-iPrPhNHCO | H | Me | 1,4-Ph | H | S | 0 | 0 | 1 |

TABLE 3-continued

[Structure: R1R2N-(CH2)l-Ar(L)-(CH2)m-X-[imidazo[4,5-b]pyridine with R3]-(CH2)n-O-C6H4-CH2-[thiazolidine-2,4-dione]  i, h|, Q]

| E.C.N. | R₁ | R₂ | R₃ | Ar | L | X | l | m | n |
|---|---|---|---|---|---|---|---|---|---|
| 3-51 | 2-CF₃PhNHCO | H | Me | 1,4-Ph | H | S | 0 | 0 | 1 |
| 3-52 | 3-CF₃PhNHCO | H | Me | 1,4-Ph | H | S | 0 | 0 | 1 |
| 3-53 | 4-CF₃PhNHCO | H | Me | 1,4-Ph | H | S | 0 | 0 | 1 |
| 3-54 | 4-FPhNHCO | H | Me | 1,4-Ph | H | S | 0 | 0 | 1 |
| 3-55 | 2,4-di-FPhNHCO | H | Me | 1,4-Ph | H | S | 0 | 0 | 1 |
| 3-56 | 4-ClPhNHCO | H | Me | 1,4-Ph | H | S | 0 | 0 | 1 |
| 3-57 | 3-CNPhNHCO | H | Me | 1,4-Ph | H | S | 0 | 0 | 1 |
| 3-58 | 4-NO₂PhNHCO | H | Me | 1,4-Ph | H | S | 0 | 0 | 1 |
| 3-59 | BzNHCO | H | Me | 1,4-Ph | H | S | 0 | 0 | 1 |
| 3-60 | NicNHCO | H | Me | 1,4-Ph | H | S | 0 | 0 | 1 |
| 3-61 | iNicNHCO | H | Me | 1,4-Ph | H | S | 0 | 0 | 1 |
| 3-62 | cHxNHCO | H | Me | 1,4-Ph | 2,6-di-Me | S | 0 | 0 | 1 |
| 3-63 | Ada(1)NHCO | H | Me | 1,4-Ph | 2,6-di-Me | S | 0 | 0 | 1 |
| 3-64 | PhNHCO | H | Me | 1,4-Ph | 2,6-di-Me | S | 0 | 0 | 1 |
| 3-65 | 4-MePhNHCO | H | Me | 1,4-Ph | 2,6-di-Me | S | 0 | 0 | 1 |
| 3-66 | 2,6-di-iPrPhNHCO | H | Me | 1,4-Ph | 2,6-di-Me | S | 0 | 0 | 1 |
| 3-67 | 2,4,6-tri-iPrPhNHCO | H | Me | 1,4-Ph | 2,6-di-Me | S | 0 | 0 | 1 |
| 3-68 | 2-CF₃PhNHCO | H | Me | 1,4-Ph | 2,6-di-Me | S | 0 | 0 | 1 |
| 3-69 | 3-CF₃PhNHCO | H | Me | 1,4-Ph | 2,6-di-Me | S | 0 | 0 | 1 |
| 3-70 | 4-CF₃PhNHCO | H | Me | 1,4-Ph | 2,6-di-Me | S | 0 | 0 | 1 |
| 3-71 | 4-FPhNHCO | H | Me | 1,4-Ph | 2,6-di-Me | S | 0 | 0 | 1 |
| 3-72 | 2,4-di-FPhNHCO | H | Me | 1,4-Ph | 2,6-di-Me | S | 0 | 0 | 1 |
| 3-73 | 4-ClPhNHCO | H | Me | 1,4-Ph | 2,6-di-Me | S | 0 | 0 | 1 |
| 3-74 | 3-CNPhNHCO | H | Me | 1,4-Ph | 2,6-di-Me | S | 0 | 0 | 1 |
| 3-75 | 4-NO₂PhNHCO | H | Me | 1,4-Ph | 2,6-di-Me | S | 0 | 0 | 1 |
| 3-76 | BzNHCO | H | Me | 1,4-Ph | 2,6-di-Me | S | 0 | 0 | 1 |

TABLE 4

[Structure: R1R2N-(CH2)l-Ar(L)-(CH2)m-X-[benzimidazole with R3]-(CH2)n-O-C6H4-CH2-[oxazolidine-2,4-dione]  i, h|, R]

| E.C.N. | R₁ | R₂ | R₃ | Ar | L | X | l | m | n |
|---|---|---|---|---|---|---|---|---|---|
| 4-1 | MeNHCO | H | Me | 1,4-Ph | H | O | 0 | 0 | 1 |
| 4-2 | EtNHCO | H | Me | 1,4-Ph | H | O | 0 | 0 | 1 |
| 4-3 | BuNHCO | H | Me | 1,4-Ph | H | O | 0 | 0 | 1 |
| 4-4 | tBuNHCO | H | Me | 1,4-Ph | H | O | 0 | 0 | 1 |
| 4-5 | HxNHCO | H | Me | 1,4-Ph | H | O | 0 | 0 | 1 |
| 4-6 | CF₃NHCO | H | Me | 1,4-Ph | H | O | 0 | 0 | 1 |
| 4-7 | cHxNHCO | H | Me | 1,4-Ph | H | O | 0 | 0 | 1 |
| 4-8 | Ada(1)NHCO | H | Me | 1,4-Ph | H | O | 0 | 0 | 1 |
| 4-9 | PhNHCO | H | Me | 1,4-Ph | H | O | 0 | 0 | 1 |
| 4-10 | 4-MePhNHCO | H | Me | 1,4-Ph | H | O | 0 | 0 | 1 |
| 4-11 | 2,6-di-iPrPhNHCO | H | Me | 1,4-Ph | H | O | 0 | 0 | 1 |
| 4-12 | 2,4,6-tri-iPrPhNHCO | H | Me | 1,4-Ph | H | O | 0 | 0 | 1 |
| 4-13 | 2-CF₃PhNHCO | H | Me | 1,4-Ph | H | O | 0 | 0 | 1 |
| 4-14 | 3-CF₃PhNHCO | H | Me | 1,4-Ph | H | O | 0 | 0 | 1 |
| 4-15 | 4-CF₃PhNHCO | H | Me | 1,4-Ph | H | O | 0 | 0 | 1 |
| 4-16 | 4-FPhNHCO | H | Me | 1,4-Ph | H | O | 0 | 0 | 1 |
| 4-17 | 2,4-di-FPhNHCO | H | Me | 1,4-Ph | H | O | 0 | 0 | 1 |
| 4-18 | 4-ClPhNHCO | H | Me | 1,4-Ph | H | O | 0 | 0 | 1 |
| 4-19 | 3-CNPhNHCO | H | Me | 1,4-Ph | H | O | 0 | 0 | 1 |
| 4-20 | 4-NO₂PhNHCO | H | Me | 1,4-Ph | H | O | 0 | 0 | 1 |
| 4-21 | BzNHCO | H | Me | 1,4-Ph | H | O | 0 | 0 | 1 |
| 4-22 | NicNHCO | H | Me | 1,4-Ph | H | O | 0 | 0 | 1 |

TABLE 4-continued

| E.C.N. | R₁ | R₂ | R₃ | Ar | L | X | l | m | n |
|---|---|---|---|---|---|---|---|---|---|
| 4-23 | iNicNHCO | H | Me | 1,4-Ph | H | O | 0 | 0 | 1 |
| 4-24 | cHxNHCO | H | Me | 1,4-Ph | H | O | 2 | 0 | 1 |
| 4-25 | Ada(1)NHCO | H | Me | 1,4-Ph | H | O | 2 | 0 | 1 |
| 4-26 | PhNHCO | H | Me | 1,4-Ph | H | O | 2 | 0 | 1 |
| 4-27 | 4-MePhNHCO | H | Me | 1,4-Ph | H | O | 2 | 0 | 1 |
| 4-28 | 2,6-di-iPrPhNHCO | H | Me | 1,4-Ph | H | O | 2 | 0 | 1 |
| 4-29 | 2,4,6-tri-iPrPhNHCO | H | Me | 1,4-Ph | H | O | 2 | 0 | 1 |
| 4-30 | 2-CF₃PhNHCO | H | Me | 1,4-Ph | H | O | 2 | 0 | 1 |
| 4-31 | 3-CF₃PhNHCO | H | Me | 1,4-Ph | H | O | 2 | 0 | 1 |
| 4-32 | 4-CF₃PhNHCO | H | Me | 1,4-Ph | H | O | 2 | 0 | 1 |
| 4-33 | 4-FPhNHCO | H | Me | 1,4-Ph | H | O | 2 | 0 | 1 |
| 4-34 | 2,4-di-FPhNHCO | H | Me | 1,4-Ph | H | O | 2 | 0 | 1 |
| 4-35 | 4-ClPhNHCO | H | Me | 1,4-Ph | H | O | 2 | 0 | 1 |
| 4-36 | 3-CNPhNHCO | H | Me | 1,4-Ph | H | O | 2 | 0 | 1 |
| 4-37 | 4-NO₂PhNHCO | H | Me | 1,4-Ph | H | O | 2 | 0 | 1 |
| 4-38 | BzNHCO | H | Me | 1,4-Ph | H | O | 2 | 0 | 1 |
| 4-39 | cHxNHCO | H | Me | 1,4-Ph | 2,6-di-Me | O | 0 | 0 | 1 |
| 4-40 | Ada(1)NHCO | H | Me | 1,4-Ph | 2,6-di-Me | O | 0 | 0 | 1 |
| 4-41 | PhNHCO | H | Me | 1,4-Ph | 2,6-di-Me | O | 0 | 0 | 1 |
| 4-42 | 4-MePhNHCO | H | Me | 1,4-Ph | 2,6-di-Me | O | 0 | 0 | 1 |
| 4-43 | 2,6-di-iPrPhNHCO | H | Me | 1,4-Ph | 2,6-di-Me | O | 0 | 0 | 1 |
| 4-44 | 2,4,6-tri-iPrPhNHCO | H | Me | 1,4-Ph | 2,6-di-Me | O | 0 | 0 | 1 |
| 4-45 | 2-CF₃PhNHCO | H | Me | 1,4-Ph | 2,6-di-Me | O | 0 | 0 | 1 |
| 4-46 | 3-CF₃PhNHCO | H | Me | 1,4-Ph | 2,6-di-Me | O | 0 | 0 | 1 |
| 4-47 | 4-CF₃PhNHCO | H | Me | 1,4-Ph | 2,6-di-Me | O | 0 | 0 | 1 |
| 4-48 | 4-FPhNHCO | H | Me | 1,4-Ph | 2,6-di-Me | O | 0 | 0 | 1 |
| 4-49 | 2,4-di-FPhNHCO | H | Me | 1,4-Ph | 2,6-di-Me | O | 0 | 0 | 1 |
| 4-50 | 4-ClPhNHCO | H | Me | 1,4-Ph | 2,6-di-Me | O | 0 | 0 | 1 |
| 4-51 | 3-CNPhNHCO | H | Me | 1,4-Ph | 2,6-di-Me | O | 0 | 0 | 1 |
| 4-52 | 4-NO₂PhNHCO | H | Me | 1,4-Ph | 2,6-di-Me | O | 0 | 0 | 1 |
| 4-53 | BzNHCO | H | Me | 1,4-Ph | 2,6-di-Me | O | 0 | 0 | 1 |
| 4-54 | cHxNHCO | H | Me | 1,7-Np | H | O | 0 | 0 | 1 |
| 4-55 | Ada(1)NHCO | H | Me | 1,7-Np | H | O | 0 | 0 | 1 |
| 4-56 | PhNHCO | H | Me | 1,7-Np | H | O | 0 | 0 | 1 |
| 4-57 | 4-MePhNHCO | H | Me | 1,7-Np | H | O | 0 | 0 | 1 |
| 4-58 | 2,6-di-iPrPhNHCO | H | Me | 1,7-Np | H | O | 0 | 0 | 1 |
| 4-59 | 2,4,6-tri-iPrPhNHCO | H | Me | 1,7-Np | H | O | 0 | 0 | 1 |
| 4-60 | 2-CF₃PhNHCO | H | Me | 1,7-Np | H | O | 0 | 0 | 1 |
| 4-61 | 3-CF₃PhNHCO | H | Me | 1,7-Np | H | O | 0 | 0 | 1 |
| 4-62 | 4-CF₃PhNHCO | H | Me | 1,7-Np | H | O | 0 | 0 | 1 |
| 4-63 | 4-FPhNHCO | H | Me | 1,7-Np | H | O | 0 | 0 | 1 |
| 4-64 | 2,4-di-FPhNHCO | H | Me | 1,7-Np | H | O | 0 | 0 | 1 |
| 4-65 | 4-ClPhNHCO | H | Me | 1,7-Np | H | O | 0 | 0 | 1 |
| 4-66 | 3-CNPhNHCO | H | Me | 1,7-Np | H | O | 0 | 0 | 1 |
| 4-67 | 4-NO₂PhNHCO | H | Me | 1,7-Np | H | O | 0 | 0 | 1 |
| 4-68 | BzNHCO | H | Me | 1,7-Np | H | O | 0 | 0 | 1 |
| 4-69 | cHxNHCO | H | Me | 1,4-Ph | 2-tBu | O | 0 | 1 | 1 |
| 4-70 | Ada(1)NHCO | H | Me | 1,4-Ph | 2-tBu | O | 0 | 1 | 1 |
| 4-71 | PhNHCO | H | Me | 1,4-Ph | 2-tBu | O | 0 | 1 | 1 |
| 4-72 | 4-MePhNHCO | H | Me | 1,4-Ph | 2-tBu | O | 0 | 1 | 1 |
| 4-73 | 2,6-di-iPrPhNHCO | H | Me | 1,4-Ph | 2-tBu | O | 0 | 1 | 1 |
| 4-74 | 2,4,6-tri-iPrPhNHCO | H | Me | 1,4-Ph | 2-tBu | O | 0 | 1 | 1 |
| 4-75 | 2-CF₃PhNHCO | H | Me | 1,4-Ph | 2-tBu | O | 0 | 1 | 1 |
| 4-76 | 3-CF₃PhNHCO | H | Me | 1,4-Ph | 2-tBu | O | 0 | 1 | 1 |
| 4-77 | 4-CF₃PhNHCO | H | Me | 1,4-Ph | 2-tBu | O | 0 | 1 | 1 |
| 4-78 | 4-FPhNHCO | H | Me | 1,4-Ph | 2-tBu | O | 0 | 1 | 1 |
| 4-79 | 2,4-di-FPhNHCO | H | Me | 1,4-Ph | 2-tBu | O | 0 | 1 | 1 |
| 4-80 | 4-ClPhNHCO | H | Me | 1,4-Ph | 2-tBu | O | 0 | 1 | 1 |
| 4-81 | 3-CNPhNHCO | H | Me | 1,4-Ph | 2-tBu | O | 0 | 1 | 1 |
| 4-82 | 4-NO₂PhNHCO | H | Me | 1,4-Ph | 2-tBu | O | 0 | 1 | 1 |
| 4-83 | BzNHCO | H | Me | 1,4-Ph | 2-tBu | O | 0 | 1 | 1 |
| 4-84 | cHxNHCS | H | Me | 1,4-Ph | 2,6-di-Me | O | 0 | 0 | 1 |
| 4-85 | Ada(1)NHCS | H | Me | 1,4-Ph | 2,6-di-Me | O | 0 | 0 | 1 |
| 4-86 | PhNHCS | H | Me | 1,4-Ph | 2,6-di-Me | O | 0 | 0 | 1 |
| 4-87 | 4-MePhNHCS | H | Me | 1,4-Ph | 2,6-di-Me | O | 0 | 0 | 1 |
| 4-88 | 2,6-di-iPrPhNHCS | H | Me | 1,4-Ph | 2,6-di-Me | O | 0 | 0 | 1 |

TABLE 4-continued

| E.C.N. | R₁ | R₂ | R₃ | Ar | L | X | l | m | n |
|---|---|---|---|---|---|---|---|---|---|
| 4-89 | 2,4,6-tri-iPrPhNHCS | H | Me | 1,4-Ph | 2,6-di-Me | O | 0 | 0 | 1 |
| 4-90 | 2-CF₃PhNHCS | H | Me | 1,4-Ph | 2,6-di-Me | O | 0 | 0 | 1 |
| 4-91 | 3-CF₃PhNHCS | H | Me | 1,4-Ph | 2,6-di-Me | O | 0 | 0 | 1 |
| 4-92 | 4-CF₃PhNHCS | H | Me | 1,4-Ph | 2,6-di-Me | O | 0 | 0 | 1 |
| 4-93 | 4-FPhNHCS | H | Me | 1,4-Ph | 2,6-di-Me | O | 0 | 0 | 1 |
| 4-94 | 2,4-di-FPhNHCS | H | Me | 1,4-Ph | 2,6-di-Me | O | 0 | 0 | 1 |
| 4-95 | 4-ClPhNHCS | H | Me | 1,4-Ph | 2,6-di-Me | O | 0 | 0 | 1 |
| 4-96 | 3-CNPhNHCS | H | Me | 1,4-Ph | 2,6-di-Me | O | 0 | 0 | 1 |
| 4-97 | 4-NO₂PhNHCS | H | Me | 1,4-Ph | 2,6-di-Me | O | 0 | 0 | 1 |
| 4-98 | BzNHCS | H | Me | 1,4-Ph | 2,6-di-Me | O | 0 | 0 | 1 |

TABLE 5

| E.C.N. | R₁ | R₂ | R₃ | Ar | L | X | l | m | n |
|---|---|---|---|---|---|---|---|---|---|
| 5-1 | MeNHCO | H | Me | 1,4-Ph | H | O | 0 | 0 | 1 |
| 5-2 | EtNHCO | H | Me | 1,4-Ph | H | O | 0 | 0 | 1 |
| 5-3 | BuNHCO | H | Me | 1,4-Ph | H | O | 0 | 0 | 1 |
| 5-4 | tBuNHCO | H | Me | 1,4-Ph | H | O | 0 | 0 | 1 |
| 5-5 | HxNHCO | H | Me | 1,4-Ph | H | O | 0 | 0 | 1 |
| 5-6 | CF₃NHCO | H | Me | 1,4-Ph | H | O | 0 | 0 | 1 |
| 5-7 | cHxNHCO | H | Me | 1,4-Ph | H | O | 0 | 0 | 1 |
| 5-8 | Ada(1)NHCO | H | Me | 1,4-Ph | H | O | 0 | 0 | 1 |
| 5-9 | PhNHCO | H | Me | 1,4-Ph | H | O | 0 | 0 | 1 |
| 5-10 | 4-MePhNHCO | H | Me | 1,4-Ph | H | O | 0 | 0 | 1 |
| 5-11 | 2,6-di-iPrPhNHCO | H | Me | 1,4-Ph | H | O | 0 | 0 | 1 |
| 5-12 | 2,4,6-tri-iPrPhNHCO | H | Me | 1,4-Ph | H | O | 0 | 0 | 1 |
| 5-13 | 2-CF₃PhNHCO | H | Me | 1,4-Ph | H | O | 0 | 0 | 1 |
| 5-14 | 3-CF₃PhNHCO | H | Me | 1,4-Ph | H | O | 0 | 0 | 1 |
| 5-15 | 4-CF₃PhNHCO | H | Me | 1,4-Ph | H | O | 0 | 0 | 1 |
| 5-16 | 4-FPhNHCO | H | Me | 1,4-Ph | H | O | 0 | 0 | 1 |
| 5-17 | 2,4-di-FPhNHCO | H | Me | 1,4-Ph | H | O | 0 | 0 | 1 |
| 5-18 | 4-ClPhNHCO | H | Me | 1,4-Ph | H | O | 0 | 0 | 1 |
| 5-19 | 3-CNPhNHCO | H | Me | 1,4-Ph | H | O | 0 | 0 | 1 |
| 5-20 | 4-NO₂PhNHCO | H | Me | 1,4-Ph | H | O | 0 | 0 | 1 |
| 5-21 | BzNHCO | H | Me | 1,4-Ph | H | O | 0 | 0 | 1 |
| 5-22 | NicNHCO | H | Me | 1,4-Ph | H | O | 0 | 0 | 1 |
| 5-23 | iNicNHCO | H | Me | 1,4-Ph | H | O | 0 | 0 | 1 |
| 5-24 | cHxNHCO | H | Me | 1,4-Ph | H | O | 2 | 0 | 1 |
| 5-25 | Ada(1)NHCO | H | Me | 1,4-Ph | H | O | 2 | 0 | 1 |
| 5-26 | PhNHCO | H | Me | 1,4-Ph | H | O | 2 | 0 | 1 |
| 5-27 | 4-MePhNHCO | H | Me | 1,4-Ph | H | O | 2 | 0 | 1 |
| 5-28 | 2,6-di-iPrPhNHCO | H | Me | 1,4-Ph | H | O | 2 | 0 | 1 |
| 5-29 | 2,4,6-tri-iPrPhNHCO | H | Me | 1,4-Ph | H | O | 2 | 0 | 1 |
| 5-30 | 2-CF₃PhNHCO | H | Me | 1,4-Ph | H | O | 2 | 0 | 1 |
| 5-31 | 3-CF₃PhNHCO | H | Me | 1,4-Ph | H | O | 2 | 0 | 1 |
| 5-32 | 4-CF₃PhNHCO | H | Me | 1,4-Ph | H | O | 2 | 0 | 1 |
| 5-33 | 4-FPhNHCO | H | Me | 1,4-Ph | H | O | 2 | 0 | 1 |
| 5-34 | 2,4-di-FPhNHCO | H | Me | 1,4-Ph | H | O | 2 | 0 | 1 |
| 5-35 | 4-ClPhNHCO | H | Me | 1,4-Ph | H | O | 2 | 0 | 1 |
| 5-36 | 3-CNPhNHCO | H | Me | 1,4-Ph | H | O | 2 | 0 | 1 |
| 5-37 | 4-NO₂PhNHCO | H | Me | 1,4-Ph | H | O | 2 | 0 | 1 |
| 5-38 | BzNHCO | H | Me | 1,4-Ph | H | O | 2 | 0 | 1 |

TABLE 5-continued

| E.C.N. | R₁ | R₂ | R₃ | Ar | L | X | l | m | n |
|---|---|---|---|---|---|---|---|---|---|
| 5-39 | cHxNHCO | H | Me | 1,4-Ph | 2,6-di-Me | O | 0 | 0 | 1 |
| 5-40 | Ada(1)NHCO | H | Me | 1,4-Ph | 2,6-di-Me | O | 0 | 0 | 1 |
| 5-41 | PhNHCO | H | Me | 1,4-Ph | 2,6-di-Me | O | 0 | 0 | 1 |
| 5-42 | 4-MePhNHCO | H | Me | 1,4-Ph | 2,6-di-Me | O | 0 | 0 | 1 |
| 5-43 | 2,6-di-iPrPhNHCO | H | Me | 1,4-Ph | 2,6-di-Me | O | 0 | 0 | 1 |
| 5-44 | 2,4,6-tri-iPrPhNHCO | H | Me | 1,4-Ph | 2,6-di-Me | O | 0 | 0 | 1 |
| 5-45 | 2-CF₃PhNHCO | H | Me | 1,4-Ph | 2,6-di-Me | O | 0 | 0 | 1 |
| 5-46 | 3-CF₃PhNHCO | H | Me | 1,4-Ph | 2,6-di-Me | O | 0 | 0 | 1 |
| 5-47 | 4-CF₃PhNHCO | H | Me | 1,4-Ph | 2,6-di-Me | O | 0 | 0 | 1 |
| 5-48 | 4-FPhNHCO | H | Me | 1,4-Ph | 2,6-di-Me | O | 0 | 0 | 1 |
| 5-49 | 2,4-di-FPhNHCO | H | Me | 1,4-Ph | 2,6-di-Me | O | 0 | 0 | 1 |
| 5-50 | 4-ClPhNHCO | H | Me | 1,4-Ph | 2,6-di-Me | O | 0 | 0 | 1 |
| 5-51 | 3-CNPhNHCO | H | Me | 1,4-Ph | 2,6-di-Me | O | 0 | 0 | 1 |
| 5-52 | 4-NO₂PhNHCO | H | Me | 1,4-Ph | 2,6-di-Me | O | 0 | 0 | 1 |
| 5-53 | BzNHCO | H | Me | 1,4-Ph | 2,6-di-Me | O | 0 | 0 | 1 |
| 5-54 | cHxNHCO | H | Me | 1,7-Np | H | O | 0 | 0 | 1 |
| 5-55 | Ada(1)NHCO | H | Me | 1,7-Np | H | O | 0 | 0 | 1 |
| 5-56 | PhNHCO | H | Me | 1,7-Np | H | O | 0 | 0 | 1 |
| 5-57 | 4-MePhNHCO | H | Me | 1,7-Np | H | O | 0 | 0 | 1 |
| 5-58 | 2,6-di-iPrPhNHCO | H | Me | 1,7-Np | H | O | 0 | 0 | 1 |
| 5-59 | 2,4,6-tri-iPrPhNHCO | H | Me | 1,7-Np | H | O | 0 | 0 | 1 |
| 5-60 | 2-CF₃PhNHCO | H | Me | 1,7-Np | H | O | 0 | 0 | 1 |
| 5-61 | 3-CF₃PhNHCO | H | Me | 1,7-Np | H | O | 0 | 0 | 1 |
| 5-62 | 4-CF₃PhNHCO | H | Me | 1,7-Np | H | O | 0 | 0 | 1 |
| 5-63 | 4-FPhNHCO | H | Me | 1,7-Np | H | O | 0 | 0 | 1 |
| 5-64 | 2,4-di-FPhNHCO | H | Me | 1,7-Np | H | O | 0 | 0 | 1 |
| 5-65 | 4-ClPhNHCO | H | Me | 1,7-Np | H | O | 0 | 0 | 1 |
| 5-66 | 3-CNPhNHCO | H | Me | 1,7-Np | H | O | 0 | 0 | 1 |
| 5-67 | 4-NO₂PhNHCO | H | Me | 1,7-Np | H | O | 0 | 0 | 1 |
| 5-68 | BzNHCO | H | Me | 1,7-Np | H | O | 0 | 0 | 1 |
| 5-69 | cHxNHCO | H | Me | 1,4-Ph | 2-tBu | O | 0 | 1 | 1 |
| 5-70 | Ada(1)NHCO | H | Me | 1,4-Ph | 2-tBu | O | 0 | 1 | 1 |
| 5-71 | PhNHCO | H | Me | 1,4-Ph | 2-tBu | O | 0 | 1 | 1 |
| 5-72 | 4-MePhNHCO | H | Me | 1,4-Ph | 2-tBu | O | 0 | 1 | 1 |
| 5-73 | 2,6-di-iPrPhNHCO | H | Me | 1,4-Ph | 2-tBu | O | 0 | 1 | 1 |
| 5-74 | 2,4,6-tri-iPrPhNHCO | H | Me | 1,4-Ph | 2-tBu | O | 0 | 1 | 1 |
| 5-75 | 2-CF₃PhNHCO | H | Me | 1,4-Ph | 2-tBu | O | 0 | 1 | 1 |
| 5-76 | 3-CF₃PhNHCO | H | Me | 1,4-Ph | 2-tBu | O | 0 | 1 | 1 |
| 5-77 | 4-CF₃PhNHCO | H | Me | 1,4-Ph | 2-tBu | O | 0 | 1 | 1 |
| 5-78 | 4-FPhNHCO | H | Me | 1,4-Ph | 2-tBu | O | 0 | 1 | 1 |
| 5-79 | 2,4-di-FPhNHCO | H | Me | 1,4-Ph | 2-tBu | O | 0 | 1 | 1 |
| 5-80 | 4-ClPhNHCO | H | Me | 1,4-Ph | 2-tBu | O | 0 | 1 | 1 |
| 5-81 | 3-CNPhNHCO | H | Me | 1,4-Ph | 2-tBu | O | 0 | 1 | 1 |
| 5-82 | 4-NO₂PhNHCO | H | Me | 1,4-Ph | 2-tBu | O | 0 | 1 | 1 |
| 5-83 | BzNHCO | H | Me | 1,4-Ph | 2-tBu | O | 0 | 1 | 1 |
| 5-84 | cHxNHCS | H | Me | 1,4-Ph | 2,6-di-Me | O | 0 | 0 | 1 |
| 5-85 | Ada(1)NHCS | H | Me | 1,4-Ph | 2,6-di-Me | O | 0 | 0 | 1 |
| 5-86 | PhNHCS | H | Me | 1,4-Ph | 2,6-di-Me | O | 0 | 0 | 1 |
| 5-87 | 4-MePhNHCS | H | Me | 1,4-Ph | 2,6-di-Me | O | 0 | 0 | 1 |
| 5-88 | 2,6-di-iPrPhNHCS | H | Me | 1,4-Ph | 2,6-di-Me | O | 0 | 0 | 1 |
| 5-89 | 2,4,6-tri-iPrPhNHCS | H | Me | 1,4-Ph | 2,6-di-Me | O | 0 | 0 | 1 |
| 5-90 | 2-CF₃PhNHCS | H | Me | 1,4-Ph | 2,6-di-Me | O | 0 | 0 | 1 |
| 5-91 | 3-CF₃PhNHCS | H | Me | 1,4-Ph | 2,6-di-Me | O | 0 | 0 | 1 |
| 5-92 | 4-CF₃PhNHCS | H | Me | 1,4-Ph | 2,6-di-Me | O | 0 | 0 | 1 |
| 5-93 | 4-FPhNHCS | H | Me | 1,4-Ph | 2,6-di-Me | O | 0 | 0 | 1 |
| 5-94 | 2,4-di-FPhNHCS | H | Me | 1,4-Ph | 2,6-di-Me | O | 0 | 0 | 1 |
| 5-95 | 4-ClPhNHCS | H | Me | 1,4-Ph | 2,6-di-Me | O | 0 | 0 | 1 |
| 5-96 | 3-CNPhNHCS | H | Me | 1,4-Ph | 2,6-di-Me | O | 0 | 0 | 1 |
| 5-97 | 4-NO₂PhNHCS | H | Me | 1,4-Ph | 2,6-di-Me | O | 0 | 0 | 1 |
| 5-98 | BzNHCS | H | Me | 1,4-Ph | 2,6-di-Me | O | 0 | 0 | 1 |

TABLE 6

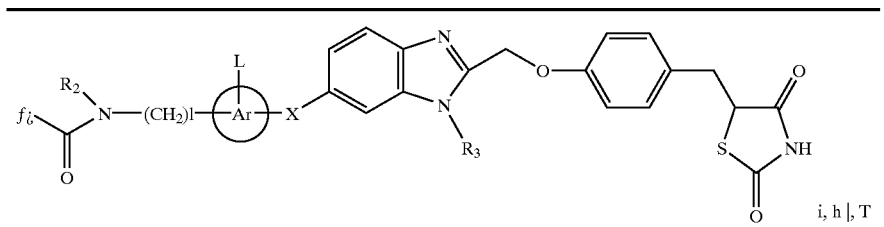

i, h |, T

| E.C.N. | α | $R_2$ | $R_3$ | Ar | L | X | l |
|---|---|---|---|---|---|---|---|
| 6-1 | Me | H | Me | 1,4-Ph | H | O | 0 |
| 6-2 | Me | Me | Me | 1,4-Ph | H | O | 0 |
| 6-3 | Me | H | tBu | 1,4-Ph | H | O | 0 |
| 6-4 | Me | H | Hx | 1,4-Ph | H | O | 0 |
| 6-5 | Et | H | Me | 1,4-Ph | H | O | 0 |
| 6-6 | $CF_3$ | H | Me | 1,4-Ph | H | O | 0 |
| 6-7 | cPn | H | Me | 1,4-Ph | H | O | 0 |
| 6-8 | cHx | H | Me | 1,4-Ph | H | O | 0 |
| 6-9 | Ada(1) | H | Me | 1,4-Ph | H | O | 0 |
| 6-10 | Ph | H | Me | 1,4-Ph | H | O | 0 |
| 6-11 | 2-Np | H | Me | 1,4-Ph | H | O | 0 |
| 6-12 | 4-MePh | H | Me | 1,4-Ph | H | O | 0 |
| 6-13 | 2,6-di-iPrPh | H | Me | 1,4-Ph | H | O | 0 |
| 6-14 | 2,4,6-tri-iPrPh | H | Me | 1,4-Ph | H | O | 0 |
| 6-15 | 2-$CF_3$Ph | H | Me | 1,4-Ph | H | O | 0 |
| 6-16 | 3-$CF_3$Ph | H | Me | 1,4-Ph | H | O | 0 |
| 6-17 | 4-$CF_3$Ph | H | Me | 1,4-Ph | H | O | 0 |
| 6-18 | 4-FPh | H | Me | 1,4-Ph | H | O | 0 |
| 6-19 | 2,4-di-FPh | H | Me | 1,4-Ph | H | O | 0 |
| 6-20 | 2-ClPh | H | Me | 1,4-Ph | H | O | 0 |
| 6-21 | 3-ClPh | H | Me | 1,4-Ph | H | O | 0 |
| 6-22 | 4-ClPh | H | Me | 1,4-Ph | H | O | 0 |
| 6-23 | 4-HOPh | H | Me | 1,4-Ph | H | O | 0 |
| 6-24 | 4-HO-3,5-diMePh | H | Me | 1,4-Ph | H | O | 0 |
| 6-25 | 4-HO-3,5-ditBuPh | H | Me | 1,4-Ph | H | O | 0 |
| 6-26 | 3-CNPh | H | Me | 1,4-Ph | H | O | 0 |
| 6-27 | 4-$NO_2$Ph | H | Me | 1,4-Ph | H | O | 0 |
| 6-28 | Bz | H | Me | 1,4-Ph | H | O | 0 |
| 6-29 | 2-ClBz | H | Me | 1,4-Ph | H | O | 0 |
| 6-30 | 3-ClBz | H | Me | 1,4-Ph | H | O | 0 |
| 6-31 | 4-ClBz | H | Me | 1,4-Ph | H | O | 0 |
| 6-32 | Boz | H | Me | 1,4-Ph | H | O | 0 |
| 6-33 | Nic | H | Me | 1,4-Ph | H | O | 0 |
| 6-34 | iNic | H | Me | 1,4-Ph | H | O | 0 |
| 6-35 | 2-Pyr | H | Me | 1,4-Ph | H | O | 0 |
| 6-36 | 3-Pyr | H | Me | 1,4-Ph | H | O | 0 |
| 6-37 | 4-Pyr | H | Me | 1,4-Ph | H | O | 0 |
| 6-38 | CHx | H | Me | 1,4-Ph | H | O | 2 |
| 6-39 | Ada(1) | H | Me | 1,4-Ph | H | O | 2 |
| 6-40 | Ph | H | Me | 1,4-Ph | H | O | 2 |
| 6-41 | 4-MePh | H | Me | 1,4-Ph | H | O | 2 |
| 6-42 | 2,6-di-iPrPh | H | Me | 1,4-Ph | H | O | 2 |
| 6-43 | 2,4,6-tri-iPrPh | H | Me | 1,4-Ph | H | O | 2 |
| 6-44 | 2-$CF_3$Ph | H | Me | 1,4-Ph | H | O | 2 |
| 6-45 | 3-$CF_3$Ph | H | Me | 1,4-Ph | H | O | 2 |
| 6-46 | 4-$CF_3$Ph | H | Me | 1,4-Ph | H | O | 2 |
| 6-47 | 4-FPh | H | Me | 1,4-Ph | H | O | 2 |
| 6-48 | 2,4-di-FPh | H | Me | 1,4-Ph | H | O | 2 |
| 6-49 | 4-ClPh | H | Me | 1,4-Ph | H | O | 2 |
| 6-50 | 4-HOPh | H | Me | 1,4-Ph | H | O | 2 |
| 6-51 | 4-HO-3,5-ditBuPh | H | Me | 1,4-Ph | H | O | 2 |
| 6-52 | 3-CNPh | H | Me | 1,4-Ph | H | O | 2 |
| 6-53 | 4-$NO_2$Ph | H | Me | 1,4-Ph | H | O | 2 |
| 6-54 | Bz | H | Me | 1,4-Ph | H | O | 2 |
| 6-55 | 2-ClBz | H | Me | 1,4-Ph | H | O | 2 |
| 6-56 | 3-ClBz | H | Me | 1,4-Ph | H | O | 2 |
| 6-57 | 4-ClBz | H | Me | 1,4-Ph | H | O | 2 |
| 6-58 | 2-Pyr | H | Me | 1,4-Ph | H | O | 2 |
| 6-59 | 3-Pyr | H | Me | 1,4-Ph | H | O | 2 |
| 6-60 | 4-Pyr | H | Me | 1,4-Ph | H | O | 2 |
| 6-61 | Me | iPr | Me | 1,4-Ph | H | O | 0 |
| 6-62 | Me | iPr | Me | 1,4-Ph | H | O | 0 |
| 6-63 | Me | iPr | tBu | 1,4-Ph | H | O | 0 |
| 6-64 | Me | iPr | Hx | 1,4-Ph | H | O | 0 |
| 6-65 | Et | iPr | Me | 1,4-Ph | H | O | 0 |
| 6-66 | $CF_3$ | iPr | Me | 1,4-Ph | H | O | 0 |

TABLE 6-continued

| E.C.N. | α | R$_2$ | R$_3$ | Ar | L | X | l |
|---|---|---|---|---|---|---|---|
| 6-67 | cPn | iPr | Me | 1,4-Ph | H | O | 0 |
| 6-68 | cHx | iPr | Me | 1,4-Ph | H | O | 0 |
| 6-69 | Ada(1) | iPr | Me | 1,4-Ph | H | O | 0 |
| 6-70 | Ph | iPr | Me | 1,4-Ph | H | O | 0 |
| 6-71 | Np | iPr | Me | 1,4-Ph | H | O | 0 |
| 6-72 | 4-MePh | iPr | Me | 1,4-Ph | H | O | 0 |
| 6-73 | 2,6-di-iPrPh | iPr | Me | 1,4-Ph | H | O | 0 |
| 6-74 | 2,4,6-tri-iPrPh | iPr | Me | 1,4-Ph | H | O | 0 |
| 6-75 | 2-CF$_3$Ph | iPr | Me | 1,4-Ph | H | O | 0 |
| 6-76 | 3-CF$_3$Ph | iPr | Me | 1,4-Ph | H | O | 0 |
| 6-77 | 4-CF$_3$Ph | iPr | Me | 1,4-Ph | H | O | 0 |
| 6-78 | 4-FPh | iPr | Me | 1,4-Ph | H | O | 0 |
| 6-79 | 2,4-di-FPh | iPr | Me | 1,4-Ph | H | O | 0 |
| 6-80 | 2-ClPh | iPr | Me | 1,4-Ph | H | O | 0 |
| 6-81 | 3-ClPh | iPr | Me | 1,4-Ph | H | O | 0 |
| 6-82 | 4-ClPh | iPr | Me | 1,4-Ph | H | O | 0 |
| 6-83 | 4-HOPh | iPr | Me | 1,4-Ph | H | O | 0 |
| 6-84 | 4-HO-3,5-diMePh | iPr | Me | 1,4-Ph | H | O | 0 |
| 6-85 | 4-HO-3,5-ditBuPh | iPr | Me | 1,4-Ph | H | O | 0 |
| 6-86 | 3-CNPh | iPr | Me | 1,4-Ph | H | O | 0 |
| 6-87 | 4-NO$_2$Ph | iPr | Me | 1,4-Ph | H | O | 0 |
| 6-88 | Bz | iPr | Me | 1,4-Ph | H | O | 0 |
| 6-89 | 2-ClBz | iPr | Me | 1,4-Ph | H | O | 0 |
| 6-90 | 3-ClBz | iPr | Me | 1,4-Ph | H | O | 0 |
| 6-91 | 4-ClBz | iPr | Me | 1,4-Ph | H | O | 0 |
| 6-92 | Boz | iPr | Me | 1,4-Ph | H | O | 0 |
| 6-93 | Nic | iPr | Me | 1,4-Ph | H | O | 0 |
| 6-94 | iNic | iPr | Me | 1,4-Ph | H | O | 0 |
| 6-95 | 2-Pyr | iPr | Me | 1,4-Ph | H | O | 0 |
| 6-96 | 3-Pyr | iPr | Me | 1,4-Ph | H | O | 0 |
| 6-97 | 4-Pyr | iPr | Me | 1,4-Ph | H | O | 0 |
| 6-98 | Me | iPr | Me | 1,3-Ph | H | O | 0 |
| 6-99 | Me | iPr | Me | 1,3-Ph | H | O | 0 |
| 6-100 | Me | iPr | tBu | 1,3-Ph | H | O | 0 |
| 6-101 | Me | iPr | Hx | 1,3-Ph | H | O | 0 |
| 6-102 | Et | iPr | Me | 1,3-Ph | H | O | 0 |
| 6-103 | CF$_3$ | iPr | Me | 1,3-Ph | H | O | 0 |
| 6-104 | cPn | iPr | Me | 1,3-Ph | H | O | 0 |
| 6-105 | cHx | iPr | Me | 1,3-Ph | H | O | 0 |
| 6-106 | Ada(1) | iPr | Me | 1,3-Ph | H | O | 0 |
| 6-107 | Ph | iPr | Me | 1,3-Ph | H | O | 0 |
| 6-108 | Np | iPr | Me | 1,3-Ph | H | O | 0 |
| 6-109 | 4-MePh | iPr | Me | 1,3-Ph | H | O | 0 |
| 6-110 | 2,6-di-iPrPh | iPr | Me | 1,3-Ph | H | O | 0 |
| 6-111 | 2,4,6-tri-iPrPh | iPr | Me | 1,3-Ph | H | O | 0 |
| 6-112 | 2-CF$_3$Ph | iPr | Me | 1,3-Ph | H | O | 0 |
| 6-113 | 3-CF$_3$Ph | iPr | Me | 1,3-Ph | H | O | 0 |
| 6-114 | 4-CF$_3$Ph | iPr | Me | 1,3-Ph | H | O | 0 |
| 6-115 | 4-FPh | iPr | Me | 1,3-Ph | H | O | 0 |
| 6-116 | 2,4-di-FPh | iPr | Me | 1,3-Ph | H | O | 0 |
| 6-117 | 2-ClPh | iPr | Me | 1,3-Ph | H | O | 0 |
| 6-118 | 3-ClPh | iPr | Me | 1,3-Ph | H | O | 0 |
| 6-119 | 4-ClPh | iPr | Me | 1,3-Ph | H | O | 0 |
| 6-120 | 4-HOPh | iPr | Me | 1,3-Ph | H | O | 0 |
| 6-121 | 4-HO-3,5-diMePh | iPr | Me | 1,3-Ph | H | O | 0 |
| 6-122 | 4-HO-3,5-ditBuPh | iPr | Me | 1,3-Ph | H | O | 0 |
| 6-123 | 3-CNPh | iPr | Me | 1,3-Ph | H | O | 0 |
| 6-124 | 4-NO$_2$Ph | iPr | Me | 1,3-Ph | H | O | 0 |
| 6-125 | Bz | iPr | Me | 1,3-Ph | H | O | 0 |
| 6-126 | 2-ClBz | iPr | Me | 1,3-Ph | H | O | 0 |
| 6-127 | 3-ClBz | iPr | Me | 1,3-Ph | H | O | 0 |
| 6-128 | 4-ClBz | iPr | Me | 1,3-Ph | H | O | 0 |
| 6-129 | Boz | iPr | Me | 1,3-Ph | H | O | 0 |
| 6-130 | Nic | iPr | Me | 1,3-Ph | H | O | 0 |
| 6-131 | iNic | iPr | Me | 1,3-Ph | H | O | 0 |
| 6-132 | 2-Pyr | iPr | Me | 1,3-Ph | H | O | 0 |

TABLE 6-continued

| E.C.N. | α | R₂ | R₃ | Ar | L | X | l |
|---|---|---|---|---|---|---|---|
| 6-133 | 3-Pyr | iPr | Me | 1,3-Ph | H | O | 0 |
| 6-134 | 4-Pyr | iPr | Me | 1,3-Ph | H | O | 0 |
| 6-135 | Me | iPr | Me | 2,5-Np | H | O | 0 |
| 6-136 | Me | iPr | Me | 2,5-Np | H | O | 0 |
| 6-137 | Me | iPr | tBu | 2,5-Np | H | O | 0 |
| 6-138 | Me | iPr | Hx | 2,5-Np | H | O | 0 |
| 6-139 | Et | iPr | Me | 2,5-Np | H | O | 0 |
| 6-140 | CF₃ | iPr | Me | 2,5-Np | H | O | 0 |
| 6-141 | CPn | iPr | Me | 2,5-Np | H | O | 0 |
| 6-142 | CHx | iPr | Me | 2,5-Np | H | O | 0 |
| 6-143 | Ada(1) | iPr | Me | 2,5-Np | H | O | 0 |
| 6-144 | Ph | iPr | Me | 2,5-Np | H | O | 0 |
| 6-145 | Np | iPr | Me | 2,5-Np | H | O | 0 |
| 6-146 | 4-MePh | iPr | Me | 2,5-Np | H | O | 0 |
| 6-147 | 2,6-di-iPrPh | iPr | Me | 2,5-Np | H | O | 0 |
| 6-148 | 2,4,6-tri-iPrPh | iPr | Me | 2,5-Np | H | O | 0 |
| 6-149 | 2-CF₃Ph | iPr | Me | 2,5-Np | H | O | 0 |
| 6-150 | 3-CF₃Ph | iPr | Me | 2,5-Np | H | O | 0 |
| 6-151 | 4-CF₃Ph | iPr | Me | 2,5-Np | H | O | 0 |
| 6-52 | 4-FPh | iPr | Me | 2,5-Np | H | O | 0 |
| 6-153 | 2,4-di-FPh | iPr | Me | 2,5-Np | H | O | 0 |
| 6-154 | 2-ClPh | iPr | Me | 2,5-Np | H | O | 0 |
| 6-155 | 3-ClPh | iPr | Me | 2,5-Np | H | O | 0 |
| 6-156 | 4-ClPh | iPr | Me | 2,5-Np | H | O | 0 |
| 6-157 | 4-HOPh | iPr | Me | 2,5-Np | H | O | 0 |
| 6-158 | 4-HO-3,5-diMePh | iPr | Me | 2,5-Np | H | O | 0 |
| 6-159 | 4-HO-3,5-ditBuPh | iPr | Me | 2,5-Np | H | O | 0 |
| 6-160 | 3-CNPh | iPr | Me | 2,5-Np | H | O | 0 |
| 6-161 | 4-NO₂Ph | iPr | Me | 2,5-Np | H | O | 0 |
| 6-162 | Bz | iPr | Me | 2,5-Np | H | O | 0 |
| 6-163 | 2-ClBz | iPr | Me | 2,5-Np | H | O | 0 |
| 6-164 | 3-ClBz | iPr | Me | 2,5-Np | H | O | 0 |
| 6-165 | 4-ClBz | iPr | Me | 2,5-Np | H | O | 0 |
| 6-166 | Boz | iPr | Me | 2,5-Np | H | O | 0 |
| 6-167 | Nic | iPr | Me | 2,5-Np | H | O | 0 |
| 6-168 | Inic | iPr | Me | 2,5-Np | H | O | 0 |
| 6-169 | 2-Pyr | iPr | Me | 2,5-Np | H | O | 0 |
| 6-170 | 3-Pyr | iPr | Me | 2,5-Np | H | O | 0 |
| 6-171 | 4-Pyr | iPr | Me | 2,5-Np | H | O | 0 |

In the above Tables, the present compounds preferably include those of exemplification compound Nos.:

(1-2) 1-(4-[2-[4-(2,4-dioxothiazolidin-5-ylmethyl) phenoxymethyl]-1-methyl-1H-benzimidazol-6-yloxy] phenyl)-3-ethylurea, (1-8) 1-(adamant-1-yl)-3-(4-[2-[4-(2,4-dioxothiazolidin-5-ylmethyl)phenoxymethyl]-1-methyl-1H-benzimidazol-6-yloxy]phenyl)urea, (1-9) 1-(4-[2-[4-(2,4-dioxothiazolidin-5-ylmethyl) phenoxymethyl]-1-methyl-1H-benzimidazol-6-yloxy] phenyl)-3-phenylurea, (1-59) 1-(2,4-difluorophenyl)-3-(4-[2-[4-(2,4-dioxothiazolidin-5-ylmethyl)phenoxymethyl]-1-methyl-1H-benzimidazol-6-yloxy]phenyl)urea, (1-165) 1-(adamant-1-yl)-3-[2-(4-[2-[4-(2,4-dioxothiazolidin-5-ylmethyl)phenoxymethyl]-1-methyl-1H-benzimidazol-6-yloxy]phenyl)ethyl]urea, (1-172) 1-[2-(4-[2-[4-(2,4-dioxothiazolidin-5-ylmethyl) phenoxymethyl]-1-methyl-1H-benzimidazol-6-yloxy] phenyl)ethyl]-3-[4-(trifluoromethyl)phenyl]urea, (1-174) 1-(2,4-difluorophenyl)-3-[2-(4-[2-[4-(2,4-dioxothiazolidin-5-ylmethyl)phenoxymethyl]-1-methyl-1H-benzimidazol-6-yloxy]phenyl]ethyl]urea, (1-192) 1-(4-[2-[4-(2,4-dioxothiazolidin-5-ylmethyl) phenoxymethyl]-1-methyl-1H-benzimidazol-6-yloxy]-2, 6-dimethylphenyl)-3-(4-nitrophenyl)urea, (1-196) 1-(4-[2-[4-(2,4-dioxothiazolidin-5-ylmethyl) phenoxymethyl]-1-methyl-1H-benzimidazol-6-yloxy] phenyl)-1-n-hexyl-3-phenylurea, (1-202) 1-(4-[2-[4-(2,4-dioxothiazolidin-5-ylmethyl) phenoxymethyl]-1-methyl-1H-benzimidazol-6-yloxy] phenyl-1-n-hexyl-3-[4-(trifluoromethyl)phenyl]urea, (1-203) 1-(4-[2-[4-(2,4-dioxothiazolidin-5-ylmethyl) phenoxymethyl]-1-methyl-1H-benzimidazol-6-yloxy] phenyl-1-n-hexyl-3-(4-fluorophenyl)urea, (1-210) 1-(adamant-1-yl)-3-(7-[2-[4-(2,4dioxothiazolidin-5-ylmethyl)phenoxymethyl]-1-methyl-1H-benzimidazol-6-yloxy]naphthalen-1-yl)urea, (1-213) 1-(2,6-diisopropylphenyl)-3-(7-[2-[4-(2,4-dioxothiazolidin-5-ylmethyl)phenoxymethyl]-1-methyl-1H-benzimidazol-6-yloxy]naphthalen-1-yl)urea, (1-217) 1-(7-[2-[4-(2,4-dioxothiazolidin-5-ylmethyl) phenoxymethyl]-1-methyl-1H-benzimidazol-6-yloxy] naphthalen-1-yl)-3-[4-(trifluoromethyl)phenyl]urea, (1-223) 1-benzyl-3-(7-[2-[4-(2,4-dioxothiazolidin-5-ylmethyl)phenoxymethyl]-1-methyl-1H-benzimidazol-6-yloxy]naphthalen-1-yl)urea, (1-232) 1-[4-(2-[2-[4-(2,4-dioxothiazolidin-5-ylmethyl) phenoxymethyl]-1-methyl-1H-benzimidazol-6-yloxy] ethyl)phenyl]-3-[4-(trifluoromethyl)phenyl]urea, (1-284) 1-(4-[2-[4-(2,4-dioxothiazolidin-5-ylmethyl) phenoxymethyl]-1-methyl-1H-benzimidazol-6-yloxy] phenyl)-3-(cyclohexyl)thiourea, (1-299) 1-benzyl-3-(4-[2-[4-(2,4-dioxothiazolidin-5-ylmethyl)phenoxymethyl]-1-methyl-1H-benzimidazol-6-yloxy]phenyl)thiourea, (1-300) 1-benzyl-3-(7-[2-[4-(2,4-dioxothiazolidin-5-ylmethyl)phenoxymethyl]-1-methyl-1H-benzimidazol-6-yloxy]naphthalen-1-yl)thiourea, (1-312) 1-(4-chlorophenyl)-3-(4-[2-[4-(2,4-dioxothiazolidin-5-ylmethyl)phenoxymethyl]-1-methyl-1H-benzimidazol-6-yloxy]-2,6-dimethylphenyl)thiourea, (1-316) N-(4-[2-[4-(2,4-dioxothiazolidin-5-ylmethyl) phenoxymethyl]-1-methyl-1H-benzimidazol-6-yloxy] phenyl)methanesulfonamide, (2-5) 1-(3-[2-[4-(2,4-dioxothiazolidin-5-ylmethyl) phenoxymethyl]-1-methyl-1H-benzimidazol-6-yloxy] phenyl)-3-n-hexylurea, (2-9) 1-(3-[2-[4-(2,4-dioxothiazolidin-5-ylmethyl) phenoxymethyl]-1-methyl-1H-benzimidazol-6-yloxy] phenyl)-3-phenylurea, (2-24) 1-(3-[2-[4-(2,4-dioxothiazolidin-5-ylmethyl) phenoxymethyl]-1-methyl-1H-benzimidazol-6-yloxy] phenyl)-3-[2-(trifluoromethyl)phenyl]urea, (2-26) 1-(3-[2-[4-(2,4-dioxothiazolidin-5-ylmethyl) phenoxymethyl]-1-methyl-1H-benzimidazol-6-yloxy] phenyl)-3-[4-(trifluoromethyl)phenyl]urea, (2-29) 1-(3-[2-[4-(2,4-dioxothiazolidin-5-ylmethyl) phenoxymethyl]-1-methyl-1H-benzimidazol-6-yloxy] phenyl)-3-(4-fluorophenyl)urea, (2-41) 1-(3-cyanophenyl)-3-(3-[2-[4-(2,4-dioxothiazolidin-5-ylmethyl)phenoxymethyl]-1-methyl-1H-benzimidazol-6-yloxy]phenyl)urea, (2-82) 1-(3-[2-[4-(2,4-dioxothiazolidin-5-ylmethyl) phenoxymethyl]-1-methyl-1H-benzimidazol-6-yloxy] phenyl)-3-(4-trifluoromethyl)benzylurea, (2-190) 1-(2-t-butyl-5-[2-[4-(2,4-dioxothiazolidin-5-ylmethyl)phenoxymethyl]-1-methyl-1H-benzimidazol-6-yloxymethyl]phenyl)-3-[4-(trifluoromethyl)phenyl]urea, (3-70) 1-(4-[2-[4-(2,4-dioxothiazolidin-5-ylmethyl) phenoxymethyl]-3-methyl-3H-imidazo[4,5-b]pyridin-5-ylthio]-2,6-dimethylphenyl)-3-[4-(trifluoromethyl) phenyl]urea, (6-1) N-[4-[2-[4-(2,4-dioxothiazolidin-5-ylmethyl) phenoxymethyl]-1-methyl-1H-benzimidazol-6-yloxy] phenyl]acetamide, (6-4) N-[4-[2-[4-(2,4-dioxothiazolidin-5-ylmethyl) phenoxymethyl]-1-methyl-1H-benzimidazol-6-yloxy] phenyl]-N-n-hexylacetamide, (6-7) N-[4-[2-[4-(2,4-dioxothiazolidin-5-ylmethyl) phenoxymethyl]-1-methyl-1H-benzimidazol-6-yloxy] phenyl]cyclopentanecarboxylic acid amide, (6-8) N-[4-[2-[4-(2,4-dioxothiazolidin-5-ylmethyl) phenoxymethyl]-1-methyl-1H-benzimidazol-6-yloxy] phenyl]cyclohexanecarboxylic acid amide, (6-10) N-[4-[2-[4-(2,4-dioxothiazolidin-5-ylmethyl) phenoxymethyl]-1-methyl-1H-benzimidazol-6-yloxy] phenyl]benzamide, (6-11) N-[4-[2-[4-(2,4-dioxothiazolidin-5-ylmethyl) phenoxymethyl]-1-methyl-1H-benzimidazol-6-yloxy] phenyl]naphthalene-2-carboxylic acid amide, (6-19) 2,4difluoro-N-[4-[2-[4-(2,4-dioxothiazolidin-5-ylmethyl)phenoxymethyl]-1-methyl-1H-benzimidazol-6-yloxy]phenyl]benzamide, (6-21) 3-chloro-N-[4-[2-[4-(2,4-dioxothiazolidin-5-ylmethyl)phenoxymethyl]-1-methyl-1H-benzimidazol-6-yloxy]phenyl]benzamide, (6-36) N-[4-[2-[4-(2,4-dioxothiazolidin-5-ylmethyl) phenoxyethyl]-1-methyl-1H-benzimidazol-6-yloxy] phenyl]nicotinamide, (6-37) N-[4-[2-[4-(2,4-dioxothiazolidin-5-ylmethyl) phenoxymethyl]-1-methyl-1H-benzimidazol-6-yloxy] phenyl]isonicotinamide, (6-51) 3,5-di-t-butyl-N-[2-(4-[2-[4-(2,4-dioxothiazolidin-5-ylmethyl)phenoxymethyl]-1-methyl-1H-benzimidazol-6-yloxy]phenyl)ethyl]-4-hydroxybenzamide, (6-56) 2-(3-chlorophenyl)-N-[2-[4-[2-[4-(2,4-dioxothiazolidin-5-ylmethyl)phenoxymethyl]-1-methyl-1H-benzimidazol-6-yloxy]phenyl]ethyl]acetamide, and (6-59) N-[2-[4-[2-[4-(2,4-dioxothiazolidin-5-ylmethyl) phenoxymethyl]-1-methyl-1H-benzimidazol-6-yloxy] phenyl]ethyl]nicotinamide, or pharmacologically acceptable salts thereof.

More preferably, they include those of exemplification compound Nos.:

(1-2) 1-(4-[2-[4-(2,4-dioxothiazolidin-5-ylmethyl) phenoxymethyl]-1-methyl-1H-benzimidazol-6-yloxy] phenyl)-3-ethylurea, (1-8) 1-(adamant-1-yl)-3-(4-[2-[4-(2,4-dioxothiazolidin-5-ylmethyl)phenoxymethyl]-1-methyl-1H-benzimidazol-6-yloxy]phenyl)urea, (1-9) 1-(4-[2-[4-(2,4-dioxothiazolidin-5-ylmethyl) phenoxymethyl]-1-methyl-1H-benzimidazol-6-yloxy] phenyl)-3-phenylurea, (1-174) 1-(2,4-difluorophenyl)-3-[2-[4-[2-[4-(2,4-dioxothiazolidin-5-ylmethyl)phenoxymethyl]-1-methyl-1H-benzimidazol-6-yloxy]phenyl]ethyl]urea, (1-192) 1-(4-[2-[4-(2,4-dioxothiazolidin-5-ylmethyl) phenoxymethyl]-1-methyl-1H-benzimidazol-6-yloxy]-2,6-dimethylphenyl)-3-(4-nitrophenyl)urea, (1-203) 1-(4-[2-[4-(2,4-dioxothiazolidin-5-ylmethyl) phenoxymethyl]-1-methyl-1H-benzimidazol-6-yloxy] phenyl-1-n-hexyl-3-(4-fluorophenyl)urea, (1-213) 1-(2,6-diisopropylphenyl)-3-(7-[2-[4-(2,4-dioxothiazolidin-5-ylmethyl)phenoxymethyl]-1-methyl-1H-benzimidazol-6-yloxy]naphthalen-1-yl)urea, (1-223) 1-benzyl-3-(7-[2-[4-(2,4-dioxothiazolidin-5-ylmethyl)phenoxymethyl]-1-methyl-1H-benzimidazol-6-yloxy]naphthalen-1-yl)urea, (1-284) 1-(4-[2-[4-(2,4-dioxothiazolidin-5-ylmethyl) phenoxymethyl]-1-methyl-1H-benzimidazol-6-yloxy] phenyl)-3-(cyclohexyl)thiourea, (1-300) 1-benzyl-3-(7-[2-[4-(2,4-dioxothiazolidin-5-ylmethyl)phenoxymethyl]-1-methyl-1H-benzimidazol-6-yloxy]naphthalen-1-yl)thiourea, (1-312) 1-(4-chlorophenyl)-3-(4-[2-[4-(2,4-dioxothiazolidin-5-ylmethyl)phenoxymethyl]-1-methyl-1H-benzimidazol-6-yloxy]-2,6-dimethylphenyl)thiourea, (1-316) N-(4-[2-[4-(2,4-dioxothiazolidin-5-ylmethyl) phenoxymethyl]-1-methyl-1H-benzimidazol-6-yloxy] phenyl)methanesulfonamide, (2-9) 1-(3-[2-[4-(2,4-dioxothiazolidin-5-ylmethyl) phenoxymethyl]-1-methyl-1H-benzimidazol-6-yloxy] phenyl)-3-phenylurea, (2-24) 1-(3-[2-[4-(2,4-dioxothiazolidin-5-ylmethyl) phenoxymethyl]-1-methyl-1H-benzimidazol-6-yloxy] phenyl)-3-[2-(trifluoromethyl)phenyl]urea, (2-26) 1-(3-[2-[4-(2,4-dioxothiazolidin-5-ylmethyl)phenoxymethyl]-1-methyl-1H-benzimidazol-6-yloxy]phenyl)-3-[4-(trifluoromethyl)phenyl]urea, (2-29) 1-(3-[2-[4-(2,4-dioxothiazolidin-5-ylmethyl)phenoxymethyl]-1-methyl-1H-benzimidazol-6-yloxy]phenyl)-3-(4-fluorophenyl)urea, (2-82) 1-(3-[2-[4-(2,4-dioxothiazolidin-5-ylmethyl)phenoxymethyl]-1-methyl-1H-benzimidazol-6-yloxy]phenyl)-3-[4-(trifluoromethyl)benzyl]urea, (6-1) N-[4-[2-[4-(2,4-dioxothiazolidin-5-ylmethyl)phenoxymethyl]-1-methyl-1H-benzimidazol-6-yloxy]phenyl]acetamide, (6-4) N-[4-[2-[4-(2,4-dioxothiazolidin-5-ylmethyl)phenoxymethyl]-1-methyl-1H-benzimidazol-6-yloxy]phenyl]-N-n-hexylacetamide, (6-7) N-[4-[2-[4-(2,4-dioxothiazolidin-5-ylmethyl)phenoxymethyl]-1-methyl-1H-benzimidazol-6-yloxy]phenyl]cyclopentanecarboxylic acid amide, (6-10) N-[4-[2-[4-(2,4-dioxothiazolidin-5-ylmethyl)phenoxymethyl]-1-methyl-1H-benzimidazol-6-yloxy]phenyl]benzamide, (6-11) N-[4-[2-[4-(2,4-dioxothiazolidin-5-ylmethyl)phenoxymethyl]-1-methyl-1H-benzimidazol-6-yloxy]phenyl]naphthalene-2-carboxylic acid amide, (6-19) 2,4-difluoro-N-[4-[2-[4-(2,4-dioxothiazolidin-5-ylmethyl)phenoxymethyl]-1-methyl-1H-benzimidazol-6-yloxy]phenyl]benzamide, (6-21) 3-chloro-N-[4-[2-[4-(2,4-dioxothiazolidin-5-ylmethyl)phenoxymethyl]-1-methyl-1H-benzimidazol-6-yloxy]phenyl]benzamide, (6-36) N-[4-[2-[4-(2,4-dioxothiazolidin-5-ylmethyl)phenoxymethyl]-1-methyl-1H-benzimidazol-6-yloxy]phenyl]nicotinamide, (6-37) N-[4-[2-[4-(2,4-dioxothiazolidin-5-ylmethyl)phenoxymethyl]-1-methyl-1H-benzimidazol-6-yloxy]phenyl]isonicotinamide, (6-51) 3,5-di-t-butyl-N-[2-(4-[2-[4-(2,4-dioxothiazolidin-5-ylmethyl)phenoxymethyl]-1-methyl-1H-benzimidazol-6-yloxy]phenyl)ethyl]-4-hydroxybenzamide, (6-56) 2-(3-chlorophenyl)-N-[2-[4-[2-[4-(2,4-dioxothiazolidin-5-ylmethyl)phenoxymethyl]-1-methyl-1H-benzimidazol-6-yloxy]phenyl]ethyl]acetamide, and (6-59) N-[2-[4-[2-[4-(2,4-dioxothiazolidin-5-ylmethyl)phenoxymethyl]-1-methyl-1H-benzimidazol-6-yloxy]phenyl]ethyl]nicotinamide, or pharmacologically acceptable salts thereof.

Most preferably, they include those of exemplification compound Nos.:

(1-2) 1-(4-[2-[4-(2,4-dioxothiazolidin-5-ylmethyl)phenoxymethyl]-1-methyl-1H-benzimidazol-6-yloxy]phenyl)-3-ethylurea, (1-8) 1-(adamant-1-yl)-3-(4-[2-[4-(2,4-dioxothiazolidin-5-ylmethyl)phenoxymethyl]-1-methyl-1H-benzimidazol-6-yloxy]phenyl)urea, (1-174) 1-(2,4-difluorophenyl)-3-[2-[4-[2-[4-(2,4-dioxothiazolidin-5-ylmethyl)phenoxymethyl]-1-methyl-1H-benzimidazol-6-yloxy]phenyl]ethyl]urea, (1-223) 1-benzyl-3-(7-[2-[4-(2,4-dioxothiazolidin-5-ylmethyl)phenoxymethyl]-1-methyl-1H-benzimidazol-6-yloxy]naphthalen-1-yl)urea, (1-284) 1-(4-[2-[4-(2,4-dioxothiazolidin-5-ylmethyl)phenoxymethyl]-1-methyl-1H-benzimidazol-6-yloxy]phenyl)-3-(cyclohexyl)thiourea, (1-316) N-(4-[2-[4-(2,4-dioxothiazolidin-5-ylmethyl)phenoxymethyl]-1-methyl-1H-benzimidazol-6-yloxy]phenyl)methanesulfonamide, (2-9) 1-(3-[2-[4-(2,4-dioxothiazolidin-5-ylmethyl)phenoxymethyl]-1-methyl-1H-benzimidazol-6-yloxy]phenyl)-3-phenylurea, (2-24) 1-(3-[2-[4-(2,4-dioxothiazolidin-5-ylmethyl)phenoxymethyl]-1-methyl-1H-benzimidazol-6-yloxy]phenyl)-3-[2-(trifluoromethyl)phenyl]urea, (2-26) 1-(3-[2-[4-(2,4-dioxothiazolidin-5-ylmethyl)phenoxymethyl]-1-methyl-1H-benzimidazol-6-yloxy]phenyl)-3-[4-(trifluoromethyl)phenyl]urea, (2-29) 1-(3-[2-[4-(2,4-dioxothiazolidin-5-ylmethyl)phenoxymethyl]-1-methyl-1H-benzimidazol-6-yloxy]phenyl)-3-(4-fluorophenyl)urea, (6-1) N-[4-[2-[4-(2,4-dioxothiazolidin-5-ylmethyl)phenoxymethyl]-1-methyl-1H-benzimidazol-6-yloxy]phenyl]acetamide, (6-7) N-[4-[2-[4-(2,4-dioxothiazolidin-5-ylmethyl)phenoxymethyl]-1-methyl-1H-benzimidazol-6-yloxy]phenyl]cyclopentanecarboxylic acid amide, (6-10) N-[4-[2-[4-(2,4-dioxothiazolidin-5-ylmethyl)phenoxymethyl]-1-methyl-1H-benzimidazol-6-yloxy]phenyl]benzamide, (6-19) 2,4-difluoro-N-[4-[2-[4-(2,4-dioxothiazolidin-5-ylmethyl)phenoxymethyl]-1-methyl-1H-benzimidazol-6-yloxy]phenyl]benzamide, (6-36) N-[4-[2-[4-(2,4dioxothiazolidin-5-ylmethyl)phenoxymethyl]-1-methyl-1H-benzimidazol-6-yloxy]phenyl]nicotinamide, (6-37) N-[4-[2-[4-(2,4dioxothiazolidin-5-ylmethyl)phenoxymethyl]-1-methyl-1H-benzimidazol-6-yloxy]phenyl]isonicotinamide, and (6-59) N-[2-[4-[2-[4-(2,4dioxothiazolidin-5-ylmethyl)phenoxymethyl]-1-methyl-1H-benzimidazol-6-yloxy]phenyl]ethyl]nicotinamide, or pharmacologically acceptable salts thereof.

The compound of the formula (I) of the present invention can be prepared according to the following processes.

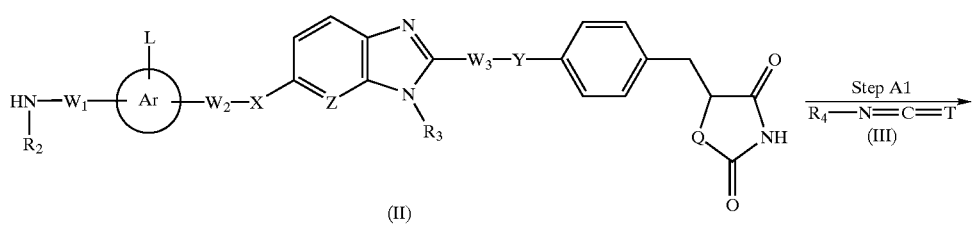

Process A

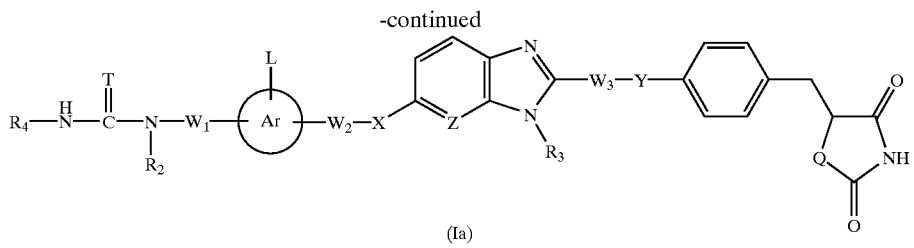

(Ia)

In the above formulae, $R_2$, $R_3$, $W_1$, $W_2$, $W_3$, X, Y, Q, Z, Ar and L have the same meanings as defined above, $R_4$ represents a group selected from the substituents a included in the definition of the group $R_1$, and T represents an oxygen atom or a sulfur atom.

Process A is a process for preparing a compound of formula (Ia) in which $R_1$ represents a carbamoyl group or a thiocarbamoyl group which may be substituted in the compound of formula (I).

Step A1 is a step for preparing a compound of formula (Ia) and is carried out by reacting a compound of formula (II) with an isocyanic acid or isothiocyanic acid of formula (III) in the presence or absence of a base in an inert solvent.

The solvent employable in the above reaction is not particularly limited so long as it is inactive in the present reaction and may include aliphatic hydrocarbons such as hexane, heptane, ligroin and petroleum ether; aromatic hydrocarbons such as benzene, toluene and xylene; halogenated hydrocarbons such as chloroform, dichloromethane, 1,2-dichloroethane and carbon tetrachloride; ethers such as diethyl ether, diisopropyl ether, tetrahydrofuran, dioxane, dimethoxyethane and di(ethylene glycol)dimethyl ether; amides such as N,N-dimethylformamide, dimethylacetamide and hexamethylphosphoric triamide; or a mixture of the above solvents, preferably an aliphatic hydrocarbon, an aromatic hydrocarbon, a halogenated hydrocarbon, an ether, an amide or a mixture of the above solvents (more preferably an aromatic hydrocarbon, an ether or an amide, particularly preferably toluene, tetrahydrofuran or N,N-dimethylformamide).

The base employable in the above reaction is not particularly limited so long as it does not affect the reaction and may preferably include alkali metal carbonates such as lithium carbonate, sodium carbonate and potassium carbonate; alkali metal hydroxides such as lithium hydroxide, sodium hydroxide and potassium hydroxide; alkali metal alkoxides such as lithium methoxide, sodium methoxide, sodium ethoxide and potassium t-butoxide; and ammonia solutions such as aqueous ammonia and concentrated ammonia in methanol.

The reaction temperature varies depending on the starting material, the solvent, etc., but it is usually from −20° C. to 150° C. (preferably from 0° C. to 60° C.).

The reaction time varies depending on the starting material, the solvent, the reaction temperature, etc., but it is usually from 30 minutes to 5 days (preferably from 5 hours to 72 hours).

After the reaction, the desired compound of formula (Ia) of the present reaction is collected from the reaction mixture according to a conventional method. For example, in the case where the desired compound of formula (Ia) is an insoluble precipitate, the compound is obtained by collecting by filtration and washing with a solvent. In cases other than the above, the compound is obtained by adding an organic solvent immiscible with water such as ethyl acetate, separating the organic layer containing the desired compound, washing with water, drying over anhydrous magnesium sulfate, anhydrous sodium sulfate, anhydrous sodium hydrogencarbonate, etc. and distilling off the solvent. The desired compound thus obtained can be separated and purified, if necessary, by a conventional method in appropriate combination, for example, a method usually used for separation and purification of organic compounds such as recrystallization, reprecipitation, etc., or chromatography using an appropriate eluant.

Process B

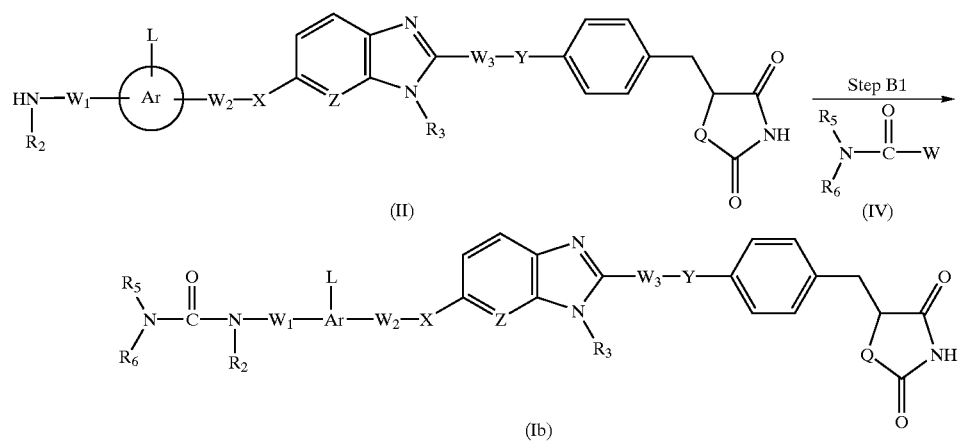

In the above formulae, $R_2$, $R_3$, $W_1$, $W_2$, $W_3$, X, Y, Q, Z, Ar and L have the same meanings as defined above, $R_5$ and $R_6$ each represent a group selected from the substituents α included in the definition of the group $R_1$, and W represents an alkoxy group, a nitrogen-substituted imidazole group or a p-nitrophenyloxy group.

Process B is a process for preparing a compound of formula (Ib) in which $R_1$ represents a carbamoyl group which may be substituted in the compound of formula (I).

Step B1 is a step for preparing a compound of formula (Ib) and is carried out by reacting a compound of formula (II) with a compound of formula (IV) in the presence or absence of a base in an inert solvent.

The inert solvent employable in the above reaction is not particularly limited so long as it is inactive in the present reaction and may include aliphatic hydrocarbons such as hexane, heptane, ligroin and petroleum ether, aromatic hydrocarbons such as benzene, toluene and xylene; ethers such as diethyl ether, diisopropyl ether, tetrahydrofuran, dioxane, dimethoxyethane and di(ethylene glycol)dimethyl ether; amides such as N,N-dimethylformamide, dimethylacetamide and hexamethylphosphoric triamide; or a mixture of the above solvents, preferably an amide (particularly preferably N,N-dimethylformamide).

The base employable in the above reaction may include alkali metal carbonates such as lithium carbonate, sodium carbonate and potassium carbonate; alkali metal hydrogencarbonates such as lithium hydrogencarbonate, sodium hydrogencarbonate and potassium hydrogencarbonate; alkali metal hydrides such as lithium hydride, sodium hydride and potassium hydride; alkali metal hydroxides such as lithium hydroxide, sodium hydroxide and potassium hydroxide; alkali metal alkoxides such as lithium methoxide, sodium methoxide, sodium ethoxide and potassium t-butoxide; and organic amines such as triethylamine, tributylamine, diisopropylethylamine, N-methylmorpholine, pyridine, 4-(N,N-dimethylamino)pyridine, N,N-dimethylaniline, N-N-diethylaniline, 1,5-diazabicyclo[4.3.0]non-5-ene, 1,4-diazabicylo[2.2.2]octane (DABCO) and 1,8-diazabicyclo[5.4.0]undec-7-ene (DBU); preferably an organic amine (particularly preferably triethylamine).

The reaction temperature varies depending on the starting material, the solvent, etc., but it is usually from −20° C. to 150° C. (preferably from 0° C. to 60° C.).

The reaction time varies depending on the starting material, the solvent, the reaction temperature, etc., but it is usually from 30 minutes to 5 days (preferably from 5 hours to 72 hours).

After the reaction, the desired compound of formula (Ib) of the present reaction is collected from the reaction mixture according to a conventional method. For example, in the case where the desired compound of formula (Ib) is an insoluble precipitate, the compound is obtained by appropriately neutralizing the reaction mixture, collecting by filtration and washing with a solvent. In other cases than the above, the compound is obtained by adding the organic solvent immiscible with water such as ethyl acetate, separating the organic layer containing the desired compound, washing with water, etc., drying over anhydrous magnesium sulfate, anhydrous sodium sulfate, anhydrous sodium hydrogencarbonate, etc. and distilling off the solvent. The desired compound thus obtained can be separated and purified, if necessary, by a conventional method in appropriate combination, for example, a method usually used for separation and purification of organic compounds such as recrystallization, reprecipitation, etc., or chromatography using an appropriate eluant.

The compound of formula (IV) can be obtained by reacting chlorocarbonates or 1,1'-carbonyldiimidazole with amines.

The compound of formula (II) is very useful as a synthetic intermediate of a compound including the compound of the present invention and having an insulin tolerance ameliorating effect, a blood sugar-lowering effect, etc. or a compound having other effects. Preferably, the compound of formula (II) is a compound of the following formula (II'); more preferably, a compound of the following formula (II").

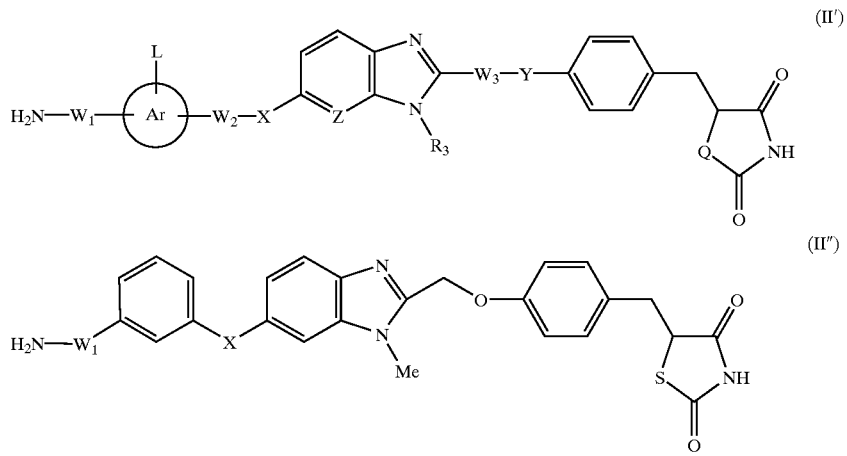

In the above formulae, $R_3$, $W_1$, $W_2$, $W_3$, X, Y, Q, Z, Ar and L have the same meanings as defined above.

Process C

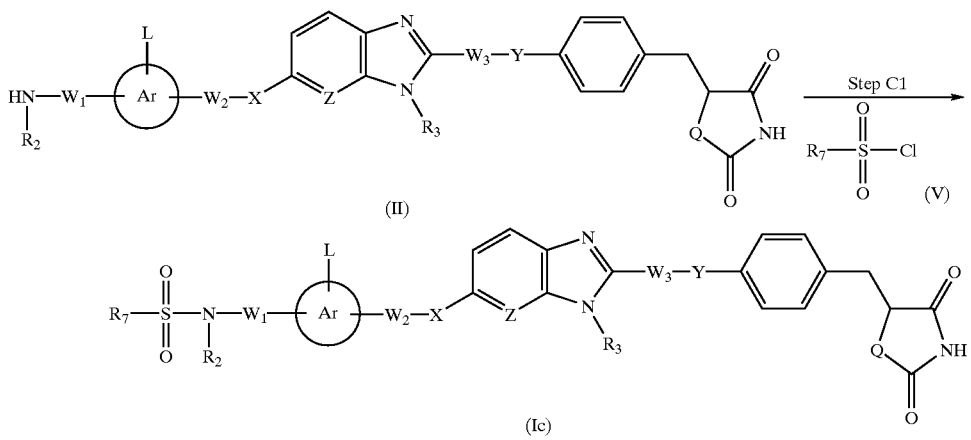

In the above formulae, $R_2$, $R_3$, $W_1$, $W_2$, $W_3$, X, Y, Q, Z, Ar and L have the same meanings as defined above and $R_7$ represents a group selected from the substituents α included in the definition of the group $R_1$.

Process C is a process for preparing a compound of formula (Ic) in which $R_1$ is a substituted sulfonyl group in the compound of formula (I).

Step C1 is a step for preparing a compound of the formula (Ic) and is carried out by reacting the compound of formula (II) with a sulfonyl chloride having the formula (V) in the presence or absence of a base in an inert solvent.

The inert solvent employable in the above reaction is not particularly limited so long as it is inactive in the present reaction and may include aliphatic hydrocarbons such as hexane, heptane, ligroin and petroleum ether; aromatic hydrocarbons such as benzene, toluene and xylene; ethers such as diethyl ether, diisopropyl ether, tetrahydrofuran, dioxane, dimethoxyethane and di(ethylene glycol)dimethyl ether; amides such as N,N-dimethylformamide, dimethylacetamide and hexamethylphosphoric triamide; or a mixture of the above solvents, preferably an amide (particularly preferably N,N-dimethylformamide).

The base employable in the above reaction may include alkali metal carbonates such as lithium carbonate, sodium carbonate and potassium carbonate; alkali metal hydrogencarbonates such as lithium hydrogencarbonate, sodium hydrogencarbonate and potassium hydrogencarbonate; alkali metal hydrides such as lithium hydride, sodium hydride and potassium hydride; alkali metal hydroxides such as lithium hydroxide, sodium hydroxide and potassium hydroxide; alkali metal alkoxides such as lithium methoxide, sodium methoxide, sodium ethoxide and potassium t-butoxide; and organic amines such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicylo[2.2.2]octane (DABCO) and 1,8-diazabicyclo[5.4.0]undec-7-ene (DBU), preferably an organic amine (particularly preferably triethylamine).

The reaction temperature varies depending on the starting material, the solvent, etc., but it is usually from −20° C. to 150° C. (preferably from 0° C. to 60° C.).

The reaction time varies depending on the starting material, the solvent, the reaction temperature, etc., but it is usually from 30 minutes to 5 days (preferably from 5 hours to 72 hours).

After the reaction, the desired compound (Ic) of the present reaction is collected from the reaction mixture according to a conventional method. For example, in the case where the desired compound of formula (Ic) is an insoluble precipitate, the compound of formula (Ic) is obtained by appropriately neutralizing the reaction mixture, collecting by filtration and washing with a solvent. In cases other than the above, the compound is obtained by adding an organic solvent immiscible with water such as ethyl acetate, separating the organic layer containing the desired compound, washing with water, etc., drying over anhydrous magnesium sulfate, anhydrous sodium sulfate, anhydrous sodium hydrogencarbonate, etc. and distilling off the solvent. The desired compound thus obtained can be separated and purified, if necessary, by a conventional method in appropriate combination, for example, a method usually used for separation and purification of organic compounds such as recrystallization, reprecipitation, etc., or chromatography using an appropriate eluant.

Process C'

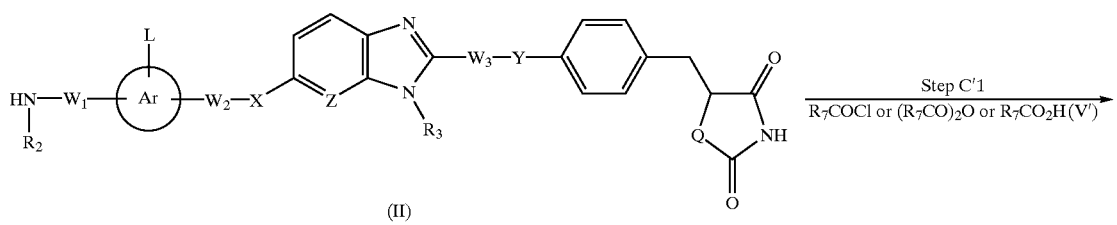

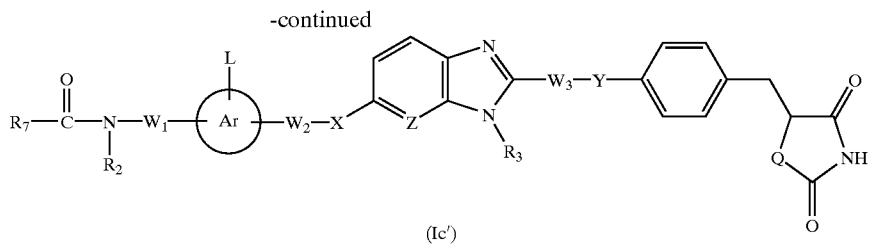

(Ic')

In the above formulae, $R_2$, $R_3$, $W_1$, $W_2$, $W_3$, X, Y, Q, Z, Ar, L and $R_7$ have the same meanings as defined above.

Process C' is a process for preparing a compound of formula (Ic') in which $R_1$ is a substituted carbonyl group in the compound of formula (I). Step C'1, which is a step for preparing a compound of the formula (Ic'), is carried out by reacting the compound of formula (II) with a compound of formula (V') in an inert solvent (a) in the presence of a base according to (b) an active ester method or (c) a mixed acid anhydride method.

(a)

In the case where the compound of formula (V') is an acid chloride or an acid anhydride, (a) is a reaction for condensing the compound of formula (II) and the compound of formula (V') in the presence of a base.

The inert solvent employable in the above reaction is not particularly limited so long as it is inactive in the present reaction and may include aliphatic hydrocarbons such as hexane, heptane, ligroin and petroleum ether; aromatic hydrocarbons such as benzene, toluene and xylene; ethers such as diethyl ether, diisopropyl ether, tetrahydrofuran, dioxane, dimethoxyethane and di(ethylene glycol)dimethyl ether; amides such as N,N-dimethylformamide, dimethylacetamide and hexamethylphosphoric triamide; and a mixture of the above solvents; preferably an amides (particularly preferably N,N-dimethylformamide).

The base employable in the above reaction may include alkali metal carbonates such as lithium carbonate, sodium carbonate and potassium carbonate; alkali metal hydrogencarbonates such as lithium hydrogencarbonate, sodium hydrogencarbonate and potassium hydrogencarbonate; alkali metal hydrides such as lithium hydride, sodium hydride and potassium hydride; alkali metal hydroxides such as lithium hydroxide, sodium hydroxide and potassium hydroxide; alkali metal alkoxides such as lithium methoxide, sodium methoxide, sodium ethoxide and potassium t-butoxide; and organic amines such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicylo[2.2.2]octane (DABCO) and 1,8-diazabicyclo[5.4.0]undec-7-ene (DBU), preferably organic amines (particularly preferably triethylamine).

The reaction temperature varies depending on the starting material, the solvent, etc., but it is usually from −20° C. to 150° C. (preferably from 0° C. to 60° C.).

The reaction time varies depending on the starting material, the solvent, the reaction temperature, etc., but it is usually from 30 minutes to 5 days (preferably from 5 hours to 72 hours).

(b) Active Ester Method

The active ester method is carried out by reacting the compound of formula (II) with the compound of formula (V') in the presence or absence (preferably in the presence) of a condensing agent and a base in an inert solvent.

The active esterifyng agent is preferably used in the presence of a condensing agent, which may include N-hydroxy compounds such as N-hydroxysuccinimide, 1-hydroxybenzotriazole and N-hydroxy-5-norbornen-2,3-dicarboximide; disulfide compounds such as dipyridyldisulfide; carbodiimides such as 1-ethyl-3-(3'-dimethylaminopropyl)carbodiimide and dicyclohexylcarbodiimide; carbonyldiimidazole; or triphenylphosphine.

The inert solvent employable in the present reaction may include similar inert solvents to those used in the above reaction (a).

The base employable in the present reaction may include the similar bases to those used in the above reaction (a).

The reaction temperature in the active esterification method varies depending on the starting material, the reagent, etc., but it is usually from −70° C. to 150° C. (preferably from −10° C. to 100° C.).

The reaction time varies depending on the starting material, the reagent, the reaction temperature, etc., but it is usually from 30 minutes to 80 hours (preferably from 1 hour to 48 hours).

(c) Mixed Acid Anhydride Method

In the case where the compound of formula (V') is a carboxylic acid, this method is carried out by preparing a mixed acid anhydride by reacting the compound of formula (V') with an agent for forming a mixed acid anhydride in the presence or absence (preferably in the presence) of a base in an inert solvent, and then reacting the mixed acid anhydride with the compound of formula (II) in an inert solvent.

The reagent for forming a mixed acid anhydride employable in the present reaction may include $C_1$–$C_4$ alkyl halocarbonates such as ethyl chloroformate, ethyl chlorocarbonate and isobutyl chlorocarbonate; $C_1$–$C_5$ alkanoyl halides such as pivaloyl chloride; di-($C_1$–$C_4$ alkyl) or di-($C_6$–$C_{14}$ aryl)cyanophosphonic acid derivatives such as diethyl cyanophosphonate and diphenyl cyanophosphonate, preferably a di-($C_1$–$C_4$ alkyl) or di-($C_6$–$C_{14}$ aryl) cyanophosphonate (particularly preferably diethyl cyanophosphonate).

The inert solvent and the base employable in the present reaction are not particularly limited so long as they do not inhibit the reaction and the inert solvent dissolves the starting material to some extent and may include similar inert solvents and bases to those used in the above reaction (a).

The reaction temperature varies depending on the starting material, the reagent, etc., but it is usually from −50° C. to 100° C. (preferably from 0° C. to 60° C.).

The reaction time varies depending on the starting material, the reagent, the reaction temperature, etc., but it is usually from 30 minutes to 72 hours (preferably from 1 hour to 24 hours).

In Process C', after the reaction, the desired compound of formula (Ic') of the present reaction is collected from the reaction mixture according to a conventional method. For example, in the case where the desired compound of formula (Ic) is an insoluble precipitate, the compound of formula (Ic)

is obtained by appropriately neutralizing the reaction mixture, collecting by filtration and washing with a solvent. In other cases than the above, the compound is obtained by adding an organic solvent immiscible with water such as ethyl acetate, separating the organic layer containing the desired compound, washing with water, etc., drying over anhydrous magnesium sulfate, anhydrous sodium sulfate, anhydrous sodium hydrogencarbonate, etc. and distilling off the solvent. The desired compound thus obtained can be separated and purified, if necessary, by a conventional method in appropriate combination, for example, a method usually used for separation and purification of organic compounds such as recrystallization, reprecipitation, etc., or chromatography using an appropriate eluant.

(a) Acid Halide Method

The acid halide method is carried out by preparing an acid halide by reacting the compound of formula (VII) with a halogenating agent (for example: thionyl chloride, thionyl bromide, oxalic chloride, oxalic dichloride, phosphorus oxychloride, phosphorus trichloride or phosphorus pentachloride) in an inert solvent and reacting the acid halide with the compound of formula (VI) in the presence or absence (preferably in the presence) of the base in an inert solvent.

The base employable in the above reaction may include alkali metal carbonates such as lithium carbonate, sodium carbonate and potassium carbonate; alkali metal hydrogencarbonates such as lithium hydrogencarbonate, sodium

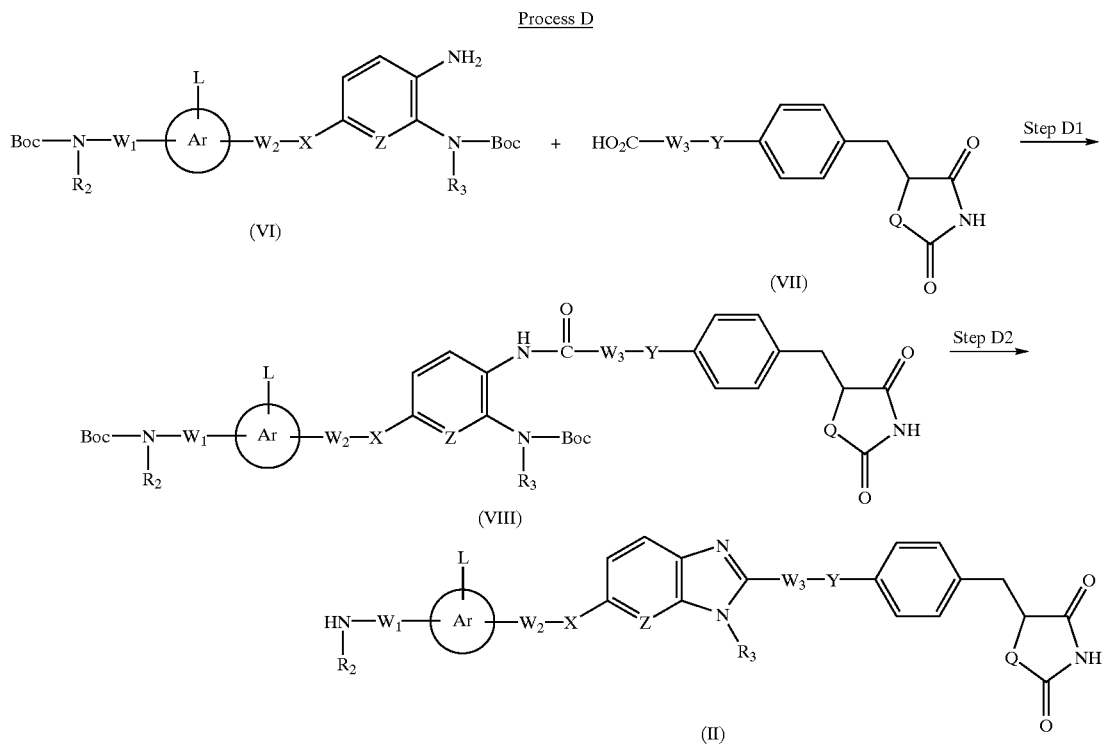

In the above formulae, $R_2$, $R_3$, $W_1$, $W_2$, $W_3$, X, Y, Q, Z, Ar and L have the same meanings as defined above and Boc represents a t-butoxycarbonyl group.

Process D is a process for preparing the compound of formula (II).

Step D1 is a step for preparing a compound of formula (VIII) and is carried out by reacting a reactive derivative (an acid halide, active ester or mixed acid anhydride) of the compound of formula (VII) with the compound of formula (VI) in an inert solvent.

The inert solvent employable in the above reaction is not particularly limited so long as it is inactive in the present reaction and may include aliphatic hydrocarbons such as hexane, heptane, ligroin and petroleum ether; aromatic hydrocarbons such as benzene, toluene and xylene; ethers such as diethyl ether, diisopropyl ether, tetrahydrofuran, dioxane, dimethoxyethane and di(ethylene glycol)dimethyl ether; amides such as formamide, N,N-dimethylformamide, dimethylacetamide and hexamethylphosphoric triamide; sulfoxides such as dimethyl sulfoxide; and sulfolane; and a mixture of the above solvents, preferably an ether (particularly preferably tetrahydrofuran).

hydrogencarbonate and potassium hydrogencarbonate; alkali metal hydrides such as lithium hydride, sodium hydride and potassium hydride; alkali metal hydroxides such as lithium hydroxide, sodium hydroxide and potassium hydroxide; alkali metal alkoxides such as lithium methoxide, sodium methoxide, sodium ethoxide and potassium t-butoxide; and organic amines such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicylo[4.3.0] non-5-ene, 1,4-diazabicylo[2.2.2]octane (DABCO) and 1,8-diazabicyclo[5.4.0]undec-7-ene (DBU), preferably an organic amine (particularly preferably triethylamine).

The inert solvent employable in the above reaction is not particularly limited so long as it is inactive in the present reaction and may include aliphatic hydrocarbons such as hexane, heptane, ligroin and petroleum ether; aromatic hydrocarbons such as benzene, toluene and xylene; halogenated hydrocarbons such as dichloromethane, chloroform, 1,2-dichloroethane and carbon tetrachloride; ethers such as diethyl ether, diisopropyl ether, tetrahydrofuran, dioxane, dimethoxyethane and di(ethylene glycol)dimethyl ether;

ketones such as acetone; amides such as formamide, N,N-dimethylformamide, dimethylacetamide and hexamethylphosphoric triamide; sulfoxides such as dimethyl sulfoxide; and sulfolane, preferably a halogenated hydrocarbon, an ether or an amide (particularly preferably dichloromethane, chloroform, tetrahydrofuran or N,N-dimethylformamide).

The reaction temperature varies depending on the starting material, the reagent, etc., but it is usually from −20° C. to 150° C. in both the reaction of the halogenating agent with the compound of formula (VII) and the acid halide with the compound of formula (VI), and is preferably from −10° C. to 100° C. in the reaction of the halogenating agent with the compound of formula (VII) and from −20° C. to 100° C. in the reaction of the acid halide with the compound of formula (VI).

The reaction time varies depending on the starting material, the reagent, the reaction temperature, etc., but it is usually from 30 minutes to 80 hours (preferably from 1 hour to 48 hours) in both the reaction of the halogenating agent with the compound of formula (VII) and of the acid halide with the compound of formula (VI).

(b) Active Ester Method

The active ester method is carried out by preparing an active ester by reacting the compound of formula (VII) with an active esterifying agent in an inert solvent and reacting the active ester with the compound of formula (VI) in the presence or absence (preferably in the presence) of a base in an inert solvent.

The active esterifying agent is preferably used in the presence of a condensing agent, which may include N-hydroxy compounds such as N-hydroxysuccinimide, 1-hydroxybenzotriazole and N-hydroxy-5-norbornene-2,3-dicarboximide; disulfide compounds such as dipyridyldisulfide; carbodiimides such as dicyclohexylcarbodiimide; carbonyldiimidazole; and triphenylphosphine.

The inert solvent employable in the above reaction is not particularly limited so long as it is inactive in the present reaction and may include aliphatic hydrocarbons such as hexane, heptane, ligroin and petroleum ether; aromatic hydrocarbons such as benzene, toluene and xylene; halogenated hydrocarbons such as dichloromethane, 1,2-dichloroethane and carbon tetrachloride; ethers such as diethyl ether, diisopropyl ether, tetrahydrofuran, dioxane, dimethoxyethane and di(ethylene glycol)dimethyl ether; ketones such as acetone; amides such as formamide, N,N-dimethylformamide, dimethylacetamide and hexamethylphosphoric triamide; sulfoxides such as dimethyl sulfoxide; and sulfolane, preferably an ether or an amide (particularly preferably dioxane, tetrahydrofuran or N,N-dimethylformamide).

The base employable in the above reaction may include similar bases to those used in the above acid halide method.

The reaction temperature varies depending on the starting material, the reagent, etc., but it is usually from −70° C. to 150° C. (preferably from −10° C. to 100° C.) in the active esterification reaction and from −20° C. to 100° C. (preferably from 0° C. to 50° C.) in the reaction of the active ester with the compound of formula (VI).

The reaction time varies depending on the starting material, the reagent, the reaction temperature, etc., but it is usually from 30 minutes to 80 hours (preferably from 1 hour to 48 hours) in both the active esterification reaction and the reaction of the active ester with the compound of formula (VI).

(c) Mixed Acid Anhydride Method

The mixed acid anhydride method is carried out by preparing a mixed acid anhydride by reacting the compound of formula (VII) with an agent for forming a mixed acid anhydride in the presence or absence (preferably in the presence) of a base in an inert solvent and reacting the mixed acid anhydride with the compound of formula (VI) in an inert solvent.

The base employable in the above reaction may include alkali metal carbonates such as lithium carbonate, sodium carbonate and potassium carbonate; alkali metal hydrogencarbonates such as lithium hydrogencarbonate, sodium hydrogencarbonate and potassium hydrogencarbonate; alkali metal hydrides such as lithium hydride, sodium hydride and potassium hydride; alkali metal hydroxides such as lithium hydroxide, sodium hydroxide and potassium hydroxide; alkali metal alkoxides such as lithium methoxide, sodium methoxide, sodium ethoxide and potassium t-butoxide; and organic amines such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicylo[2.2.2]octane (DABCO) and 1,8-diazabicyclo[5.4.0]undec-7-ene (DBU), preferably an organic amine (particularly preferably triethylamine).

The mixed acid anhydride agent employable in the above reaction may include $C_1-C_4$ alkyl halocarbonates such as ethyl chlorocarbonate and isobutyl chlorocarbonate; $C_1-C_5$ alkanoyl halides such as pivaloyl chloride; di($C_1-C_4$ alkyl) or di($C_6-C_{14}$ aryl)cyanophosphonic acid derivatives such as diethyl cyanophosphonate and diphenyl cyanophosphonate, preferably a di($C_1-C_4$ alkyl) or di($C_6-C_{14}$ aryl) cyanophosphoric acid derivative (particularly preferably diethyl cyanophosphonate).

The inert solvent employable in the case of preparing the mixed acid anhydride is not particularly limited so long as it does not inhibit the reaction and dissolves the starting material to some extent and may include aliphatic hydrocarbons such as hexane, heptane, ligroin and petroleum ether; aromatic hydrocarbons such as benzene, toluene and xylene; halogenated hydrocarbons such as dichloromethane, 1,2-dichloroethane and carbon tetrachloride; ethers such as diethyl ether, diisopropyl ether, tetrahydrofuran, dioxane, dimethoxyethane and di(ethylene glycol)dimethyl ether; ketones such as acetone; amides such as formamide, N,N-dimethylformamide, dimethylacetamide and hexamethylphosphoric triamide; sulfoxides such as dimethyl sulfoxide; and sulfolane, preferably an ether or an amide (particularly preferably tetrahydrofuran or N,N-dimethylformamide).

The reaction temperature in the reaction for preparing the mixed acid anhydride varies depending on the starting material, the reagent, etc., but it is usually from −50° C. to 100° C. (preferably from 0° C. to 60° C.).

The reaction time in the reaction for preparing the mixed acid anhydride varies depending on the starting material, the reagent, the reaction temperature, etc., but it is usually from 30 minutes to 72 hours (preferably from 1 hour to 24 hours).

The reaction of the mixed acid anhydride and the compound of formula (VI) is carried out in the presence or absence (preferably in the presence) of a base in an inert solvent. The base and the inert solvent employable here are similar to those used in the reaction for preparing the mixed acid anhydride described above.

The reaction temperature in the reaction of the mixed acid anhydride with the compound of formula (VI) varies depending on the starting material, the reagent, etc., but it is usually from −30° C. to 100° C. (preferably from 0° C. to 80° C.).

The reaction time in the reaction of the mixed acid anhydride and the compound of formula (VI) varies depending on the starting material, the reagent, the reaction temperature, etc., but it is usually from 5 minutes to 24 hours (preferably from 30 minutes to 16 hours).

In the present reaction, in the case where a di($C_1$–$C_4$ alkyl)cyanophosphoric acid derivative or di($C_6$–$C_{14}$ aryl) cyanophosphoric acid derivative is used, the compound of formula (VI) and the compound of formula (VII) can be directly reacted in the presence of a base.

After the reaction, the desired compound of formula (VIII) of the present reaction is collected from the reaction mixture according to a conventional method. For example, the compound of formula (VIII) is obtained by appropriately neutralizing the reaction mixture, removing insolubles by filtration in the case where insoluble substances are present, adding an organic solvent immiscible with water such as ethyl acetate, separating the organic layer containing the desired compound, washing with water, etc., drying over anhydrous magnesium sulfate, anhydrous sodium sulfate, anhydrous sodium hydrogencarbonate, etc. and distilling off the solvent. The desired compound thus obtained can be separated and purified, if necessary, by a conventional method in appropriate combination, for example, a method usually used for separation and purification of organic compounds such as recrystallization, reprecipitation, etc., or chromatography using an appropriate eluant.

Step D2 is a step for preparing the compound of formula (II) and is carried out by reacting the compound of formula (VIII) with an acid in the presence or absence of an inert solvent.

The acid employable in the above reaction is not particularly limited so long as it is used in a usual reaction as an acid catalyst and may include a Brønsted acid such as an inorganic acid, e.g., hydrochloric acid, hydrobromic acid, sulfuric acid, perchloric acid or phosphoric acid; an organic acid, e.g., acetic acid, formic acid, oxalic acid, methanesulfonic acid, p-toluenesulfonic acid, camphorsulfonic acid, trifluoroacetic acid or trifluoromethanesulfonic acid; or a Lewis acid such as zinc chloride, tin tetrachloride, boron trichloride or bromine trichloride; or an acidic ion exchange resin, preferably an inorganic acid or an organic acid (particularly preferably hydrochloric acid, acetic acid or trifluoroacetic acid).

The inert solvent employable in the above reaction is not particularly limited so long as it is inactive in the present reaction and may include aliphatic hydrocarbons such as hexane, heptane, ligroin and petroleum ether; aromatic hydrocarbons such as benzene, toluene and xylene; halogenated hydrocarbons such as chloroform, dichloromethane, 1,2-dichloroethane and carbon tetrachloride; esters such as methyl acetate, ethyl acetate, propyl acetate, butyl acetate and diethyl carbonate; ethers such as diethyl ether, diisopropyl ether, tetrahydrofuran, dioxane, dimethoxyethane and di(ethylene glycol)dimethyl ether; alcohols such as methanol, ethanol, n-propanol, isopropanol, n-butanol, isobutanol, t-butanol, isoamyl alcohol, di(ethylene glycol), glycerine, octanol, cyclohexanol and methyl cellosolve; amides such as formamide, N,N-dimethylformamide, dimethylacetamide and hexamethylphosphoric triamide; water; or a mixture of water and the above solvents, preferably a halogenated hydrocarbon, an ether, an alcohol or water (particularly preferably dichloromethane, 1,4-dioxane, ethanol or water).

The reaction temperature varies depending on the starting material, the acid used, the solvent, etc., but it is usually from −20° C. to the boiling point of the solvent (preferably from 0° C. to 50° C.).

The reaction time varies depending on the starting material, the acid used, the solvent, the reaction temperature, etc., but it is usually from 15 minutes to 48 hours (preferably from 30 minutes to 20 hours).

After the reaction, the desired compound of formula (II) of the present reaction is collected from the reaction mixture according to a conventional method. For example, the compound of formula (II) is obtained by appropriately neutralizing the reaction mixture, removing insolubles by filtration in the case where insoluble substances are present, adding an organic solvent immiscible with water such as ethyl acetate, separating the organic layer containing the desired compound, washing with water, etc., drying over anhydrous sodium sulfate and distilling off the solvent. The desired compound thus obtained can be separated and purified, if necessary, by a conventional method in appropriate combination, for example, a method usually used for separation and purification of organic compounds such as recrystallization, reprecipitation, etc., or chromatography using an appropriate eluant.

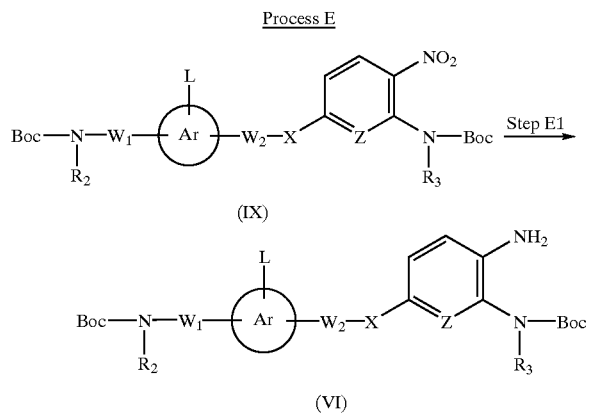

In the above formulae, $R_2$, $R_3$, $W_1$, $W_2$, X, Z, Ar, L and Boc have the same meanings as defined above.

Process E is a process for preparing the compound of formula (VI).

Step E1 is a step for preparing the compound of formula (VI) and is carried out by reducing a compound of formula (IX). The present reaction is carried out in an inert solvent using a catalytic reduction reaction or the general method for reduction of a nitro group, i.e., a zinc-acetic acid method, a tin-alcohol method or a tin-hydrochloric acid method, or using sodium dithionite as a reducing agent.

The inert solvent employable in the above reaction is not particularly limited so long as it is inactive in the present reaction and may include aliphatic hydrocarbons such as hexane, heptane, ligroin and petroleum ether; aromatic hydrocarbons such as benzene, toluene and xylene; halogenated hydrocarbons such as chloroform, dichloromethane, 1,2-dichloroethane and carbon tetrachloride; esters such as methyl acetate, ethyl acetate, propyl acetate, butyl acetate and diethyl carbonate; ethers such as diethyl ether, diisopropyl ether, tetrahydrofuran, dioxane, dimethoxyethane and di(ethylene glycol)dimethyl ether; alcohols such as methanol, ethanol, n-propanol, isopropanol, n-butanol, isobutanol, t-butanol, isoamyl alcohol, di(ethylene glycol), glycerine, octanol, cyclohexanol and methyl cellosolve; amides such as formamide, N,N-dimethylformamide, dimethylacetamide and hexamethylphosphoric triamide; water; or a mixed solvent of water and/or any of the above solvents; preferably a halogenated hydrocarbon, an ether, an alcohol or water (particularly preferably dichloromethane, 1,4-dioxane, ethanol or water).

The reaction temperature varies depending on the starting material, the acid used, the solvent, etc., but it is usually from −20° C. to the boiling point of the solvent (preferably from 0° C. to 50° C.).

The reaction time varies depending on the starting material, the acid used, the solvent, the reaction temperature, etc., but it is usually from 15 minutes to 48 hours (preferably from 30 minutes to 20 hours).

After the reaction, the desired compound of formula (VI) of the present reaction is collected from the reaction mixture according to a conventional method. For example, in the case of the catalytic reduction reaction, the compound of formula (VI) is obtained by removing the catalyst by filtration from the reaction mixture and distilling off the solvent. In the cases other than the above, the compound of formula (VI) is obtained by appropriately neutralizing the reaction mixture, removing insolubles by filtration in the case where insoluble substances are present, adding an organic solvent immiscible with water such as ethyl acetate, separating the organic layer containing the desired compound, washing with water, etc., drying over anhydrous magnesium sulfate, anhydrous sodium sulfate, anhydrous sodium hydrogencarbonate, etc. and distilling off the solvent. The desired compound thus obtained can be separated and purified, if necessary, by a conventional method in appropriate combination, for example, a method usually used for separation and purification of organic compounds such as recrystallization, reprecipitation, etc., or chromatography using an appropriate eluant.

Process F

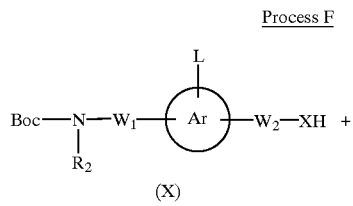
(X)

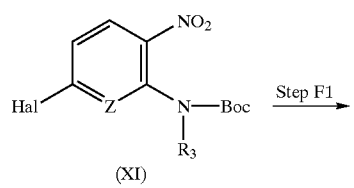
(XI)

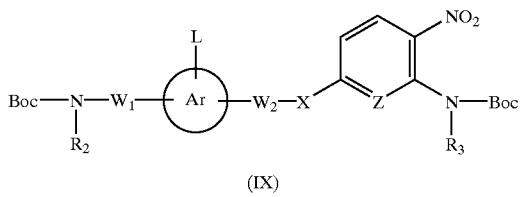
(IX)

In the above formulae, $R_2$, $R_3$, $W_1$, $W_2$, X, Z, Ar, L and Boc have the same meanings as defined above and Hal represents a halogen atom.

Process F is a process for preparing the compound of formula (IX).

Step F1 is a step for preparing the compound of formula (IX) and is carried out by reacting a compound of formula (X) with a compound of formula (XI) in the presence of a base in an inert solvent.

The base employable in the above reaction may include alkali metal carbonates such as lithium carbonate, sodium carbonate and potassium carbonate; alkali metal hydrogencarbonates such as lithium hydrogencarbonate, sodium hydrogencarbonate and potassium hydrogencarbonate; alkali metal hydrides such as lithium hydride, sodium hydride and potassium hydride; alkali metal hydroxides such as lithium hydroxide, sodium hydroxide and potassium hydroxide; alkali metal alkoxides such as lithium methoxide, sodium methoxide, sodium ethoxide and potassium t-butoxide; and organic amines such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicylo[2.2.2]octane (DABCO) and 1,8-diazabicyclo[5.4.0]undec-7-ene (DBU), preferably an alkali metal hydride (particularly preferably sodium hydride).

The inert solvent employable in the above reaction is not particularly limited so long as it is inactive in the present reaction and may include aliphatic hydrocarbons such as hexane, heptane, ligroin and petroleum ether; aromatic hydrocarbons such as benzene, toluene and xylene; ethers such as diethyl ether, diisopropyl ether, tetrahydrofuran, dioxane, dimethoxyethane and di(ethylene glycol)dimethyl ether; amides such as N,N-dimethylformamide, dimethylacetamide and hexamethylphosphoric triamide; and a mixture of the above solvents, preferably amide (particularly preferably N,N-dimethylformamide).

The reaction temperature varies depending on the starting material, the base used, the solvent, etc., but it is usually from −50° C. to 200° C. (preferably from 0° C. to 120° C.).

The reaction time varies depending on the starting material, the base, the solvent, the reaction temperature employed, etc., but it is usually from 30 minutes to 24 hours (preferably from 1 hour to 10 hours).

After the reaction, the desired compound of formula (IX) of the present reaction is collected from the reaction mixture according to a conventional method. For example, the compound of formula (IX) is obtained by appropriately neutralizing the reaction mixture, removing insolubles by filtration in the case where insoluble substances are present, adding an organic solvent immiscible with water such as ethyl acetate, separating the organic layer containing the desired compound, washing with water, etc., drying over anhydrous magnesium sulfate, anhydrous sodium sulfate, anhydrous sodium hydrogencarbonate, etc. and distilling off the solvent. The desired compound thus obtained can be separated and purified, if necessary, by appropriately combining a conventional method, for example, a method usually used for separation and purification of organic compounds such as recrystallization, reprecipitation, etc., or chromatography using an appropriate eluant.

Process G

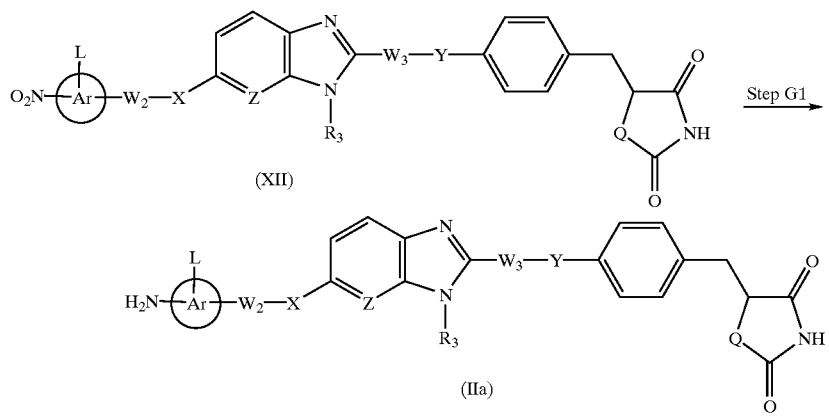

In the above formulae, $R_3$, $W_2$, $W_3$, X, Y, Q, Z, Ar and L have the same meanings as defined above.

Process G is a process for preparing the compound of formula (IIa) in the compound of formula (II) in which $W_1$ is a single bond and both $R_1$ and $R_2$ are hydrogen atoms different from Process D.

Step G1 is a step for preparing a compound of formula (IIa) and is carried out by reducing a compound of formula (XII). The present step is carried out in a similar manner to the above Step E1.

After the reaction, the desired compound of formula (IIa) of the present reaction is collected from the reaction mixture according to a conventional method. For example, after catalytic reduction, the compound of formula (IIa) is obtained by removing the catalyst by filtration from the reaction mixture and distilling off the solvent. In the cases other than the above, the compound of formula (IIa) is obtained by appropriately neutralizing the reaction mixture, removing insolubles by filtration in the case where insoluble substances are present, adding an organic solvent immiscible with water such as ethyl acetate, separating the organic layer containing the desired compound, washing with water, etc., drying over anhydrous magnesium sulfate, anhydrous sodium sulfate, anhydrous sodium hydrogencarbonate, etc. and distilling off the solvent. The desired compound thus obtained can be separated and purified, if necessary, by appropriately combining a conventional method, for example, a method usually used for separation and purification of organic compounds such as recrystallization, reprecipitation, etc., or chromatography using an appropriate eluant.

Process H

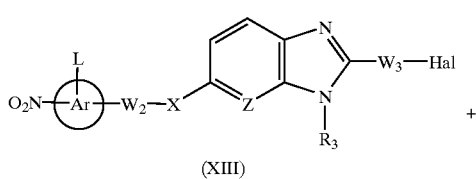

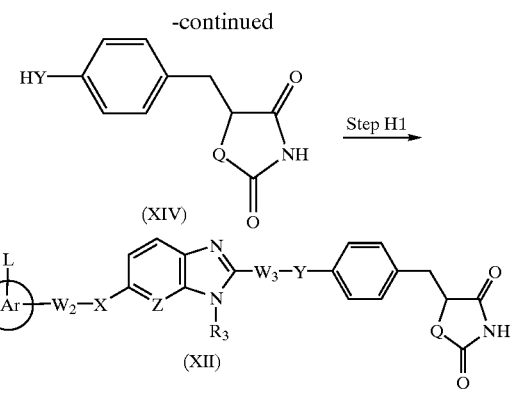

In the above formulae, $R_3$, $W_2$, $W_3$, X, Y, Q, Z, Ar, L and Hal have the same meanings as defined above.

Process H is a process for preparing the compound of formula (XII).

Step H1 is a step for preparing the compound of formula (XII) and is carried out by reacting a compound of formula (XIII) with a compound of formula (XIV) in the presence of a base in an inert solvent. This step is carried out in a similar manner to the above Step F1.

After the reaction, the desired compound of formula (XII) of the present reaction is collected from the reaction mixture according to a conventional method. For example, the compound of formula (XII) is obtained by appropriately neutralizing the reaction mixture, removing insolubles by filtration in the case where insoluble substances are present, adding an organic solvent immiscible with water such as ethyl acetate, separating an organic layer containing the desired compound, washing with water, etc., drying over anhydrous magnesium sulfate, anhydrous sodium sulfate, anhydrous sodium hydrogencarbonate, etc. and distilling off the solvent. The desired compound thus obtained can be separated and purified, if necessary, by appropriately combining a conventional method, for example, a method usually used for separation and a purification of organic compounds such as recrystallization, reprecipitation, etc., or chromatography using an appropriate eluant.

Process I

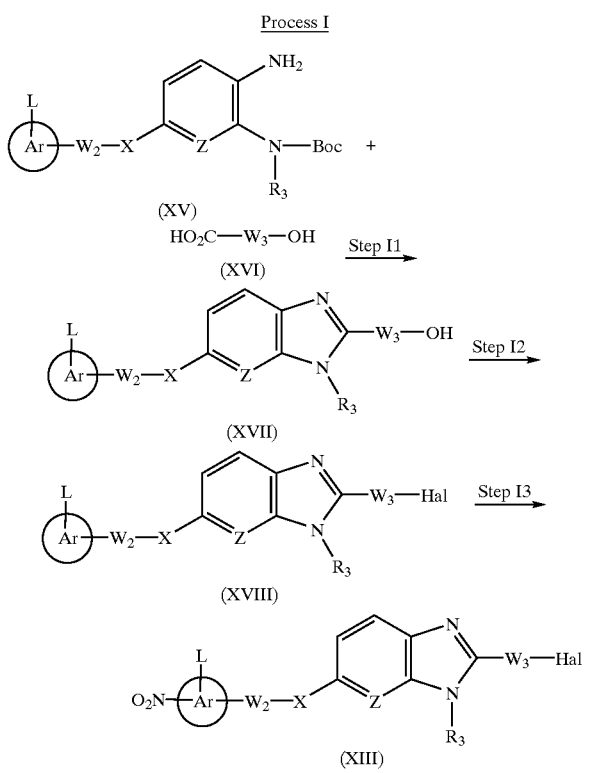

In the above formulae, $R_3$, $W_2$, $W_3$, X, Z, Ar, L and Hal have the same meanings as defined above.

Process I is a process for preparing a compound of formula (XIII).

Step I1 is a step for preparing the compound of formula (XVII) and is carried out by reacting a compound of formula (XV) with a compound of formula (XVI) in the presence or absence of an inert solvent in the presence or absence of a base.

The inert solvent employable in the reaction between the compound of formula (XV) and the compound of formula (XVI) is not particularly limited so long as it is inactive in the reaction and may include aliphatic hydrocarbons such as hexane, heptane, ligroin and petroleum ether; aromatic hydrocarbons such as benzene, toluene and xylene; ethers such as diethyl ether, diisopropyl ether, tetrahydrofuran, dioxane, dimethoxyethane and di(ethylene glycol)dimethyl ether; alcohols such as methanol, ethanol, n-propanol, isopropanol, n-butanol, isobutanol, t-butanol, isoamyl alcohol, di(ethylene glycol), glycerine, octanol, cyclohexanol and methyl cellosolve; amides such as formamide, N,N-dimethylformamide, dimethylacetamide and hexamethylphosphoric triamide; organic acids such as acetic acid and propionic acid; sulfoxides such as dimethyl sulfoxide; and sulfolane; and a mixture of the above solvents.

The temperature for the reaction between the compound of formula (XV) and the compound of formula (XVI) varies depending on the starting material, the base, the solvent used, etc., but it is usually from 0° C. to 200° C. (preferably from 50° C. to 150° C.).

The time for the reaction between the compound of formula (XV) and the compound of formula (XVI) varies depending on the starting material, the base, the solvent, the reaction temperature employed, etc., but it is usually from 1 hour to 50 hours (preferably from 5 hours to 24 hours).

After the reaction, the desired compound of formula (XVII) is collected from the reaction mixture according to a conventional method. For example, the compound of formula (XVII) is obtained by appropriately neutralizing the reaction mixture, removing insolubles by filtration in the case where insoluble substances are present, adding the organic solvent immiscible with water such as ethyl acetate, separating an organic layer containing the desired compound, washing with water, etc., drying over anhydrous magnesium sulfate, anhydrous sodium sulfate, anhydrous sodium hydrogencarbonate, etc. and distilling off the solvent. The desired compound thus obtained can be separated and purified, if necessary, by appropriately combining a conventional method, for example, a method usually used for separation and purification of organic compounds such as recrystallization, reprecipitation, etc., or chromatography using an appropriate eluant.

Step I2 is a step for preparing the compound of formula (XVIII) and is carried out by reacting a compound of formula (XVII) with a halogenating agent (for example, thionyl chloride, thionyl bromide, oxalic chloride, oxalic dichloride, phosphorus oxychloride, phosphorus trichloride, phosphorus pentachloride, etc.) in the presence or absence of an inert solvent.

The inert solvent employable for the reaction between the compound of formula (XVII) and the halogenating agent is not particularly limited so long as it is inactive in the reaction and may include aliphatic hydrocarbons such as hexane, heptane, ligroin and petroleum ether; aromatic hydrocarbons such as benzene, toluene and xylene; halogenated hydrocarbons such as chloroform, dichloromethane, 1,2-dichloroethane and carbon tetrachloride; and a mixture of the above solvents.

The temperature for the reaction between the compound of formula (XVII) and the halogenating agent varies depending on the starting material, the solvent used, etc., but it is usually from −20° C. to 150° C. (preferably from −10° C. to 100° C.).

The time for the reaction between the compound of formula (XVII) and the halogenating agent varies depending on the starting material compound, the solvent, the reaction temperature employed, etc., but it is usually from 30 minutes to 80 hours (preferably from 1 hour to 48 hours).

After the reaction, the desired compound of formula (XVIII) of the present reaction is collected from the reaction mixture according to a conventional method. For example, the compound of formula (XVIII) is obtained by appropriately neutralizing the reaction mixture, removing insolubles by filtration in the case where insoluble substances are present, adding an organic solvent immiscible with water such as ethyl acetate, separating the organic layer containing the desired compound, washing with water, etc., drying over anhydrous magnesium sulfate, anhydrous sodium sulfate, anhydrous sodium hydrogencarbonate, etc. and distilling off the solvent. The desired compound thus obtained can be separated and purified, if necessary, by appropriately combining a conventional method, for example, a method usually used for separation and purification of organic compounds such as recrystallization, reprecipitation, etc., or chromatography using an appropriate eluant.

Step I3 is a step for preparing a compound of formula (XIX) and is carried out by reacting a compound of formula (XVIII) with a nitrating agent (for example, mixed acid, nitric acid, nitronium tetrafluoroborate etc.) in the presence or absence of an inert solvent.

The inert solvent employable for the reaction between the compound of formula (XVIII) and the nitrating agent is not particularly limited so long as it is inactive in the reaction and may include aliphatic hydrocarbons such as hexane, heptane, ligroin and petroleum ether; halogenated hydrocarbons such as chloroform, dichloromethane, 1,2-dichloroethane and carbon tetrachloride; ethers such as diethyl ether, diisopropyl ether, tetrahydrofuran, dioxane, dimethoxyethane and di(ethylene glycol)dimethyl ether, alcohols such as methanol, ethanol, n-propanol, isopropanol, n-butanol, isobutanol, t-butanol, isoamyl alcohol, di(ethylene glycol), glycerine, octanol, cyclohexanol and methyl cellosolve; amides such as formamide, N,N-dimethylformamide, dimethylacetamide and hexamethylphosphoric triamide; organic acids such as acetic and and propionic acid; sulfoxides such as dimethyl sulfoxide; sulfolane; acetonitrile; and a mixture of the above solvents.

The temperature for the reaction between the compound of formula (XVIII) and the nitrating agent varies depending on the starting material, the solvent used, etc., but it is usually from −20° C. to 100° C. (preferably from −10° C. to 50° C.).

The time for the reaction between the compound of formula (XVIII) and the nitrating agent varies depending on the starting material, the solvent used, the reaction temperature, etc., but it is usually from 15 minutes to 48 hours (preferably from 30 minutes to 24 hours).

After the reaction, the desired compound of formula (XIX) of the present reaction is collected from the reaction mixture according to a conventional method. For example, the compound of formula (XIX) is obtained by appropriately neutralizing the reaction mixture, removing insolubles by filtration in the case where insoluble substances are present, adding an organic solvent immiscible with water such as ethyl acetate, separating an organic layer containing the desired compound, washing with water, etc., drying over anhydrous magnesium sulfate, anhydrous sodium sulfate, anhydrous sodium hydrogencarbonate, etc. and distilling off the solvent. The desired compound thus obtained can be separated and purified, if necessary, by appropriately combining a conventional method, for example, a method usually used for separation and purification of organic compounds such as recrystallization, reprecipitation, etc., or chromatography using an appropriate eluant.

The compounds of the formula (I) and their pharmacologically acceptable salts of the present invention have superior PPAR γ-activation effects, insulin tolerance ameliorating effects, blood sugar lowering effects, anti-inflammatory effects, immunoregulatory effects, aldose reductase inhibitory effects, 5-lipoxygenase inhibitory effects, lipid peroxide formation inhibitory effects, PPAR activation effects, antiosteoporosis effects, leukotriene antagonistic effects, fat cell promotion effects, cancer cell proliferation inhibitor effects and calcium antagonistic effects. The present invention provides treatment and/or prophylaxis for diseases such as diabetes, hyperlipemia, obesity, impaired glucose tolerance, hypertension, fatty liver, diabetic complications (including retinopathy, nephropathy, neuropathy, cataracts and coronary diseases), arteriosclerosis, pregnancy diabetes, polycystic ovary syndrome, cardiovascular diseases (such as ischemic heart diseases), cell injury induced by non-atherosclerotic or ischemic heart disease (such as brain injury induced by stroke), gout, inflammatory diseases (including arthritis, pain, pyrexia, rheumatoid arthritis, inflammatory enteritis, acne, sunburn, psoriasis, eczema, allergic diseases, asthma, GI ulcer, cachexia, autoimmune diseases and pancreatitis), cancer, osteoporosis and cataracts by administering to an animal (including a human) in need thereof, an effective amount of a compound of the formula (I).

Moreover, pharmaceutical compositions comprising a combination of the compound of the above formula (I) or their pharmacologically acceptable salts of the present invention and at least one kind of RXR activator (RXR agonist), α-glucosidase inhibitory agent, aldose reductase inhibitory agent, biguanide drug, statin compound, squalene synthesis inhibitory agent, fibrate compound, LDL disassimilation promoter, angiotensin converting enzyme inhibitory agent and FBPase inhibitory agent (particularly preferable are compositions for prevention and/or treatment of diabetes or diabetic complications), are also useful.

The compounds of the formula (I) according to the present invention or pharmacologically acceptable salts thereof can be used for treatment or prevention of the above-described diseases by administering the compound alone or in combination with a suitable pharmacologically acceptable carrier in a suitable dosage form, such as tablets, capsules, granules, powders or syrups for oral administration, or injections or suppositories for parenteral administration. Other usage dosage forms, e.g., ointments and sprays, may be used for alternate administration routes.

These preparations are prepared by a well-known method using carriers such as excipients (which may include organic excipients such as sugar derivatives, e.g., lactose, sucrose, glucose, mannitol and sorbitol; starch derivatives, e.g., corn starch, potato starch, α-starch and dextrin; cellulose derivatives, e.g., crystalline cellulose; gum arabic; dextran; and pullulan; and inorganic excipients such as silicate derivatives, e.g., light silicic anhydride, synthetic aluminum silicate, calcium silicate and magnesium aluminate metasilicate; phosphates, e.g., calcium hydrogenphosphate; carbonates, e.g., calcium carbonate; and sulfates, e.g., calcium sulfate), lubricants (for example, stearic acid, stearic acid metal salts such as calcium stearate and magnesium stearate; talc; colloidal silica; waxes such as bee gum and spermaceti; boric acid; adipic acid; sulfates such as sodium sulfate; glycol; fumaric acid; sodium benzoate; DL-leusine; fatty acid sodium salts; lauryl sulfates such as sodium lauryl sulfate and magnesium lauryl sulfate; silicic acids such as silicic anhydride and silicic acid hydrate; and the above starch derivatives), binders (for example, hydroxypropyl cellulose, hydroxypropyl methyl cellulose, polyvinylpyrrolidone, Macrogol (trade mark) and compounds similar to the above excipients), disintegrants (for example, cellulose derivatives such as low-substituted hydroxypropyl cellulose, carboxymethyl cellulose, calcium carboxymethyl cellulose and internally bridged sodium carboxymethyl cellulose; and chemically modified starch/cellulose such as carboxymethyl starch, sodium carboxymethyl starch and bridged polyvinylpyrrolidone), stabilizers (which may include para-oxy benzoates such as methyl paraben and propyl paraben; alcohols such as chlorobutanol, benzyl alcohol and phenylethyl alcohol; benzalkonium chloride; phenols such as phenol and cresol; thimerosal; dehydroacetic acid; and sorbic acid), corrigents (which may include sweeteners, souring agents, flavors, etc. usually used), diluents, etc.

The dose will vary depending on the disease state, age of the patient, e.g. human, the chosen route of administration, etc. In the case of oral administration, a desirable single unit dose contains the compound of the present invention in an amount of 0.001 to 500 mg/kg of body weight and preferably from 0.01 to 50 mg/kg of body weight. In the case of intravenous administration, a desirable single unit dose contains the compound of the present invention in an amount of 0.005 to 50 mg/kg of body weight and preferably 0.05 to 5 mg/kg of body weight. It is desirable to administer the single unit dose one time or several times throughout the day depending on the conditions of the patient. Other dosage forms for other administration routes will also be within the aforesaid ranges and preferably in an amount of 0.01 to 50 mg/kg of body weight. Dosage for treatment or prevention of a specific patient in need thereof is determined by those skilled in the art by applying usual techniques.

The following Examples, Reference Examples and Test Examples are intended to further illustrate the present invention and are not intended to limit the scope of this invention.

EXAMPLE 1

1-(4-[2-[4-(2,4-Dioxothiazolidin-5-ylmethyl) phenoxymethyl]-1-methyl-1H-benzimidazol-6-yloxy]-2,6-dimethylphenyl)-3-[4-(trifluoromethyl) phenyl]urea (exemplification compound number 1-187)

A mixture of 5-[4-[6-(4-amino-3,5-dimethylphenoxy)-1-methyl-1H-benzimidazol-2-ylmethoxy]benzyl]thiazolidine-2,4-dione dihydrochloride (288 mg), α,α,α-trifluoro-p-tolyl isocyanate (112 mg), triethylamine (121 mg) and anhydrous tetrahydrofuran (10 ml) was stirred at room temperature for 40 hours. The reaction mixture was concentrated and diluted with water. The precipitate was isolated by filtration and washed with water and ethyl acetate to afford the title compound (257 mg, mp 206–208° C.).

EXAMPLE 2

1-(4-Chlorophenyl)-3-(4-[2-[4-(2,4-dioxothiazolidin-5-ylmethyl)phenoxymethyl]-1-methyl-1H-benzimidazol-6-yloxy]-2,6-dimethylphenyl)thiourea (exemplification compound number 1-312)

A mixture of 5-[4-[6-(4-amino-3,5-dimethylphenoxy)-1-methyl-1H-benzimidazol-2-ylmethoxy]benzyl]thiazolidine-2,4-dione dihydrochloride (288 mg), 4-chlorophenyl isothiocyanate (102 mg), triethylamine (121 mg) and anhydrous tetrahydrofuran (10 ml) was stirred at room temperature for 23 hours. The reaction mixture was concentrated and diluted with water. The precipitate was isolated by filtration and then chromatographed on a silica gel column using ethyl acetate:n-hexane=3:1 as the eluant to afford the title compound (215 mg, mp 160–162° C.).

EXAMPLE 3

1-(4-[2-[4-(2,4-Dioxothiazolidin-5-ylmethyl) phenoxymethyl]-1-methyl-1H-benzimidazol-6-yloxy]-2,6-dimethylphenyl)-3-(4-nitrophenyl)urea (exemplification compound number 1-192)

A mixture of 5-[4-[6-(4-amino-3,5-dimethylphenoxy)-1-methyl-1H-benzimidazol-2-ylmethoxy]benzyl]thiazolidine-2,4-dione dihydrochloride (288 mg), 4-nitrophenyl isocyanate (98 mg), triethylamine (121 mg), anhydrous tetrahydrofuran (10 ml) and anhydrous N,N-dimethylformamide (10 ml) was stirred at room temperature for 23 hours. The reaction mixture was concentrated and diluted with water. The precipitate was isolated by filtration and then chromatographed on a silica gel column using ethyl acetate as the eluant to afford the title compound (182 mg, mp 178–180° C.).

EXAMPLE 4

1-(4-[2-[4-(2,4-Dioxothiazolidin-5-ylmethyl) phenoxymethyl]-1-methyl-1H-benzimidazol-6-yloxy]phenyl)-3-phenylurea (exemplification compound number 1-9)

The title compound (326 mg, mp 164.5–168.3° C.) was obtained by a similar procedure to that described in Example 1 using 5-[4-[6-(4-aminophenoxy)-1-methyl-1H-benzimidazol-2-ylmethoxy]benzyl]thiazolidine-2,4-dione dihydrochloride (400 mg), phenyl isocyanate (99 mg), triethylamine (153 mg) and anhydrous N,N-dimethylformamide (8 ml).

EXAMPLE 5

1-(2,4-Difluorophenyl)-3-(4-[2-[4-(2,4-dioxothiazolidin-5-ylmethyl)phenoxymethyl]-1-methyl-1H-benzimidazol-6-yloxy]phenyl)urea (exemplification compound number 1-59)

The title compound (394 mg, mp 203° C. (dec)) was obtained by a similar procedure to that described in Example 1 using 5-[4-[6-(4-aminophenoxy)-1-methyl-1H-benzimidazol-2-ylmethoxy]benzyl]thiazolidine-2,4-dione dihydrochloride (400 mg), 2,4-difluorophenyl isocyanate (94 mg), triethylamine (153 mg) and anhydrous N,N-dimethylformamide (8 ml).

EXAMPLE 6

1-(4-[2-[4-(2,4-Dioxothiazolidin-5-ylmethyl) phenoxymethyl]-1-methyl-1H-benzimidazol-6-yloxy]phenyl)-3-(phenyl)thiourea (exemplification compound number 1-286)

A mixture of 5-[4-[6-(4-aminophenoxy)-1-methyl-1H-benzimidazol-2-ylmethoxy]benzyl]thiazolidine-2,4-dione dihydrochloride (400 mg), phenyl isothiocyanate (113 mg), triethylamine (153 mg) and anhydrous N,N-dimethylformamide (8 ml) was stirred at room temperature for 4 hours. The reaction mixture was concentrated and partitioned between ethyl acetate and water. The extract was washed with saturated aqueous sodium chloride solution, dried over anhydrous sodium sulfate and then concentrated. The residue was recrystallized from a mixture of ethanol and ethyl acetate (5:1) to afford the title compound (347 mg, mp 129.6–130.9° C.).

EXAMPLE 7

1-(4-[2-[4-(2,4-Dioxothiazolidin-5-ylmethyl) phenoxymethyl]-1-methyl-1H-benzimidazol-6-yloxy]phenyl)-3-(naphthalen-1-yl)thiourea (exemplification compound number 1-298)

A mixture of 5-[4-[6-(4-aminophenoxy)-1-methyl-1H-benzimidazol-2-ylmethoxy]benzyl]thiazolidine-2,4-dione dihydrochloride (400 mg), 1-naphthyl isothiocyanate (148 mg), triethylamine (153 mg) and anhydrous N,N-dimethylformamide (8 ml) was stirred at room temperature for 1 hour and then allowed to stand overnight. The reaction mixture was concentrated and partitioned between ethyl acetate and water. The extract was washed with saturated aqueous sodium chloride solution, dried over anhydrous sodium sulfate and then concentrated. The residue was chromatographed on a silica gel column using ethyl acetate:n-hexane=3:2→2:1→4:1→1:0 as the eluant to afford the title compound (301 mg, mp 185.8–188.1° C.).

EXAMPLE 8

1-(4-[2-[4-(2,4-Dioxothiazolidin-5-ylmethyl) phenoxymethyl]-1-methyl-1H-benzimidazol-6-yloxy]phenyl)-3-(naphthalen-1-yl)urea (exemplification compound number 1-103)

The title compound (392 mg, mp 210.7–214.4° C.) was obtained by a similar procedure to that described in Example 1 using 5-[4-[6-(4-aminophenoxy)-1-methyl-1H-benzimidazol-2-ylmethoxy]benzyl]thiazolidine-2,4-dione dihydrochloride (400 mg), 1-naphthyl isocyanate (129 mg), triethylamine (153 mg) and anhydrous N,N-dimethylformamide (8 ml).

EXAMPLE 9

1-(4-[2-[4-(2,4-Dioxothiazolidin-5-ylmethyl) phenoxymethyl]-1-methyl-1H-benzimidazol-6-yloxy]phenyl)-3-(cyclohexyl)thiourea (exemplification compound number 1-284)

The title compound (265 mg, mp 173.1–174.0° C.) was obtained by a similar procedure to that described in Example 1 using 5-[4-[6-(4-aminophenoxy)-1-methyl-1H-benzimidazol-2-ylmethoxy]benzyl]thiazolidine-2,4-dione dihydrochloride (400 mg), cyclohexyl isocyanate (329 mg), triethylamine (153 mg) and anhydrous N,N-dimethylformamide (8 ml).

EXAMPLE 10

1-(4-[2-[4-(2,4-Dioxothiazolidin-5-ylmethyl) phenoxymethyl]-1-methyl-1H-benzimidazol-6-yloxy]phenyl)-3-[4-(trifluoromethyl)phenyl]urea (exemplification compound number 1-26)

The title compound (230 mg, mp 178.6–180.2° C.) was obtained by a similar procedure to that described in Example 1 using 5-[4-[6-(4-aminophenoxy)-1-methyl-1H-benzimidazol-2-ylmethoxy]benzyl]thiazolidine-2,4-dione dihydrochloride (400 mg), α,α,α-trifluoro-p-tolyl isocyanate (144 mg), triethylamine (153 mg) and anhydrous N,N-dimethylformamide (8 ml).

EXAMPLE 11

1-Benzyl-3-(4-[2-[4-(2,4-dioxothiazolidin-5-ylmethyl)phenoxymethyl]-1-methyl-1H-benzimidazol-6-yloxy]phenyl)thiourea (exemplification compound number 1-299)

A mixture of 5-[4-[6-(4-aminophenoxy)-1-methyl-1H-benzimidazol-2-ylmethoxy]benzyl]thiazolidine-2,4-dione dihydrochloride (400 mg), benzyl isothiocyanate (248 mg), triethylamine (153 mg) and anhydrous N,N-dimethylformamide (8 ml) was stirred at room temperature for 3.5 hours. The reaction mixture was concentrated and partitioned between ethyl acetate and water. The extract was washed with saturated aqueous sodium chloride solution, dried over anhydrous sodium sulfate and then concentrated. The residue was chromatographed on a silica gel column using ethyl acetate:n-hexane=2:1→3:1→4:1 as the eluant to afford the title compound (291 mg, mp 174.8–177.2° C.).

EXAMPLE 12

1-(4-[2-[4-(2,4-Dioxothiazolidin-5-ylmethyl) phenoxymethyl]-1-methyl-1H-benzimidazol-6-yloxy]phenyl)-3-ethylurea (exemplification compound number 1-2)

The title compound (327 mg, mp 226.7–230.2° C.) was obtained by a similar procedure to that described in Example 1 using 5-[4-[6-(4aminophenoxy)-1-methyl-1H-benzimidazol-2-ylmethoxy]benzyl]thiazolidine-2,4-dione dihydrochloride (400 mg), ethyl isocyanate (108 mg), triethylamine (153 mg) and anhydrous N,N-dimethylformamide (8 ml).

EXAMPLE 13

1-(4-[2-[4-(2,4-Dioxothiazolidin-5-ylmethyl) phenoxymethyl]-1-methyl-1H-benzimidazol-6-yloxy]phenyl)-3-(2,6-diisopropylphenyl)urea (exemplification compound number 1-17)

The title compound (474 mg, mp 221.5–224.9° C.) was obtained by a similar procedure to that described in Example 1 using 5-[4-[6-(4-aminophenoxy)-1-methyl-1H-benzimidazol-2-ylmethoxy]benzyl]thiazolidine-2,4-dione dihydrochloride (400 mg), 2,6-diisopropylphenyl isocyanate (247 mg), triethylamine (153 mg) and anhydrous N,N-dimethylformamide (8 ml).

EXAMPLE 14

1-(Adamant-1-yl)-3-(4-[2-[4-(2,4-dioxothiazolidin-5-ylmethyl)phenoxymethyl]-1-methyl-1H-benzimidazol-6-yloxy]phenyl)urea (exemplification compound number 1-8)

A mixture of 5-[4-[6-(4-aminophenoxy)-1-methyl-1H-benzimidazol-2-ylmethoxy]benzyl]thiazolidine-2,4-dione dihydrochloride (400 mg), 1-adamantyl isothiocyanate (284 mg), triethylamine (153 mg) and anhydrous N,N-dimethylformamide (8 ml) was stirred at room temperature for 4.5 hours, at 50° C. for 2.5 hours and then at 80° C. for 4.5 hours. The reaction mixture was concentrated and partitioned between ethyl acetate and water. The extract was washed with saturated aqueous sodium chloride solution, dried over anhydrous sodium sulfate and then concentrated. The residue was chromatographed on a silica gel column using ethyl acetate:n-hexane=1:1→2:1→3:1 as the eluant and the product was recrystallized from ethyl acetate to afford the title compound (192 mg, mp 164.0–166.6° C.).

EXAMPLE 15

1-(4-[2-[4-(2,4-Dioxothiazolidin-5-ylmethyl) phenoxymethyl]-1-methyl-1H-benzimidazol-6-yloxy]phenyl)-1-n-hexyl-3-{4-(trifluoromethyl) phenyl]urea (exemplification compound number 1-202)

A mixture of 5-[4-[6-(4-n-hexylaminophenoxy)-1-methyl-1H-benzimidazol-2-ylmethoxy]benzyl]thiazolidine-2,4-dione (0.39 g), α,α,α-trifluoro-p-tolyl isocyanate (0.15 g) and anhydrous tetrahydrofuran (20 ml) was allowed to stand at room temperature for 2 days. The reaction mixture was concentrated and partitioned between ethyl acetate and water. The extract was dried over anhydrous sodium sulfate and then concentrated. The residue was reprecipitated from a mixture of ether and diisopropyl ether to afford the title compound (0.37 g, $R_f$=0.49: thin layer chromatography on a silica gel plate using ethyl acetate:n-hexane=2:1 as the eluant).

EXAMPLE 16

1-(4-[2-[4-(2,4-Dioxothiazolidin-5-ylmethyl) phenoxymethyl]-1-methyl-1H-benzimidazol-6-yloxy]phenyl)-1-n-hexyl-3-(4-fluorophenyl)urea (exemplification compound number 1-203)

A mixture of 5-[4-[6-(4-n-hexylaminophenoxy)-1-methyl-1H-benzimidazol-2-ylmethoxy]benzyl]thiazolidine-2,4-dione (0.39 g), 4-fluorophenyl isocyanate (0.11 g) and anhydrous tetrahydrofuran (20 ml) was allowed to stand at room temperature for 2 days. The reaction mixture was concentrated and partitioned between ethyl acetate and water. The extract was dried over anhydrous sodium sulfate and then concentrated. The residue was chromatographed on a silica gel column using ethyl acetate:n-hexane=3:2 as the eluant and the product was reprecipitated from a mixture of ethyl acetate and diisopropyl ether to afford the title compound (0.32 g, $R_f$=0.45: thin layer chromatography on a silica gel plate using ethyl acetate:n-hexane=2:1 as the eluant).

EXAMPLE 17

1-(4-[2-[4-(2,4-Dioxothiazolidin-5-ylmethyl) phenoxymethyl]-1-methyl-1H-benzimidazol-6-yloxy]phenyl)-1-n-hexyl-3-phenylurea (exemplification compound number 1-196)

A mixture of 5-[4-[6-(4-n-hexylaminophenoxy)-1-methyl-1H-benzimidazol-2-ylmethoxy]benzyl]thiazolidine-2,4-dione (0.39 g), phenyl isocyanate (95 mg) and anhydrous tetrahydrofuran (20 ml) was allowed to stand at room temperature for 2 days. The reaction mixture was concentrated and partitioned between ethyl acetate and water. The extract was dried over anhydrous sodium sulfate and then concentrated. The residue was chromatographed on a silica gel column using ethyl acetate:n-hexane=3:2 as the eluant and the product was reprecipitated from a mixture of n-hexane and diethyl ether to afford the title compound (0.30 g, $R_f$=0.56: thin layer chromatography on a silica gel plate using ethyl acetate:n-hexane=2:1 as the eluant).

EXAMPLE 18

N-(4-[2-[4-(2,4-Dioxothiazolidin-5-ylmethyl) phenoxymethyl]-1-methyl-1H-benzimidazol-6-yloxy]phenyl)methanesulfonamide (exemplification compound number 1-316)

A mixture of 5-[4-[6-(4-aminophenoxy)-1-methyl-1H-benzimidazol-2-ylmethoxy]benzyl]thiazolidine-2,4-dione dihydrochloride (400 mg), methanesulfonyl chloride (88 mg), triethylamine (234 mg) and anhydrous N,N-dimethylformamide (8 ml) was stirred at room temperature for 3.5 hours. The reaction mixture was concentrated and partitioned between ethyl acetate and water. The extract was washed with saturated aqueous sodium chloride solution, dried over anhydrous sodium sulfate and then concentrated. The residue was chromatographed on a silica gel column using ethyl acetate:n-hexane=3:1→4:1→1:0 as the eluant and the product was recrystallized from ethyl acetate to afford the title compound (159 mg, mp 224.8–226.5° C.).

EXAMPLE 19

N-(4-[2-[4-(2,4-Dioxothiazolidin-5-ylmethyl) phenoxymethyl]-1-methyl-1H-benzimidazol-6-yloxy]phenyl)-p-toluenesulfonamide (exemplification compound number 1-319)

A mixture of 5-[4-[6-(4-aminophenoxy)-1-methyl-1H-benzimidazol-2-ylmethoxy]benzyl]thiazolidine-2,4-dione dihydrochloride (400 mg), p-toluenesulfonyl chloride (153 mg), triethylamine (234 mg) and anhydrous N,N-dimethylformamide (8 ml) was stirred at room temperature for 2.5 hours. The reaction mixture was concentrated and partitioned between ethyl acetate. and water. The extract was washed with saturated aqueous sodium chloride solution, dried over anhydrous sodium sulfate and then concentrated. The residue was chromatographed on a silica gel column using ethyl acetate:n-hexane=2:1→4:1 as the eluant and the product was recrystallized from a mixture of ethyl acetate and diisopropyl ether to afford the title compound (237 mg, mp 132.0–135.6° C.).

EXAMPLE 20

1-(3-[2-[4-(2,4Dioxothiazolidin-5-ylmethyl) phenoxymethyl]-1-methyl-1H-benzimidazol-6-yloxy]phenyl)-3-phenylurea (exemplification compound number 2-9)

The title compound (319 mg, mp 165.3–166.8° C.) was obtained by a similar procedure to that described in Example 1 using 5-[4-[6-(3-aminophenoxy)-1-methyl-1H-benzimidazol-2-ylmethoxy]benzyl]thiazolidine-2,4-dione dihydrochloride (400 mg), phenyl isocyanate (99 mg), triethylamine (153 mg) and anhydrous N,N-dimethylformamide (8 ml).

EXAMPLE 21

1-(3-[2-[4-(2,4-Dioxothiazolidin-5-ylmethyl) phenoxymethyl]-1-methyl-1H-benzimidazol-6-yloxy]phenyl)-3-[4-(trifluoromethyl)phenyl]urea (exemplification compound number 2-26)

The title compound (362 mg, mp 192.5–194.1° C.) was obtained by a similar procedure to that described in Example 1 using 5-[4-[6-(3-aminophenoxy)-1-methyl-1H-benzimidazol-2-ylmethoxy]benzyl]thiazolidine-2,4-dione dihydrochloride (400 mg), α,α,α-trifluoro-p-tolyl isocyanate (144 mg), triethylamine (153 mg) and anhydrous N,N-dimethylformamide (8 ml).

EXAMPLE 22

1-(3-[2-[4-(2,4-Dioxothiazolidin-5-ylmethyl) phenoxymethyl]-1-methyl-1H-benzimidazol-6-yloxy]phenyl)-3-[3-(trifluoromethyl)phenyl]urea (exemplification compound number 2-25)

A mixture of 5-[4-[6-(3-aminophenoxy)-1-methyl-1H-benzimidazol-2-ylmethoxy]benzyl]thiazolidine-2,4-dione dihydrochloride (400 mg), α,α,α-trifluoro-m-tolyl isocyanate (149 mg), triethylamine (153 mg) and anhydrous N,N-dimethylformamide (4 ml) was stirred at room temperature for 2 hours. The reaction mixture was concentrated and partitioned between ethyl acetate and water. The extract was washed with saturated aqueous sodium chloride solution, dried over anhydrous sodium sulfate and then concentrated. The residue was chromatographed on a silica gel column using ethyl acetate:n-hexane=2:1→ethyl acetate as the eluant and the product was recrystallized from a mixture of methanol and diisopropyl ether (1:3) to afford the title compound (239 mg, mp 161.8–163.4° C.).

EXAMPLE 23

1-(3-[2-[4-(2,4-Dioxothiazolidin-5-ylmethyl) phenoxymethyl]-1-methyl-1H-benzimidazol-6-yloxy]phenyl)-3-(4-fluorophenyl)urea (exemplification compound number 2-29)

The title compound (211 mg, mp 168.7–170.9° C.) was obtained by a similar procedure to that described in Example 1 using 5-[4-[6-(3-aminophenoxy)-1-methyl-1H-benzimidazol-2-ylmethoxy]benzyl]thiazolidine-2,4-dione dihydrochloride (400 mg), 4fluorophenyl isocyanate (109 mg), triethylamine (153 mg) and anhydrous N,N-dimethylformamide (4 ml).

EXAMPLE 24

1-(3-[2-[4-(2,4-Dioxothiazolidin-5-ylmethyl)
phenoxymethyl]-1-methyl-1H-benzimidazol-6-
yloxy]phenyl)-3-[2-(trifluoromethyl)phenyl]urea
(exemplification compound number 2-24)

The title compound (452 mg, mp 160.7–164.4° C.) was obtained by a similar procedure to that described in Example 1 using 5-[4-[6-(3-aminophenoxy)-1-methyl-1H-benzimidazol-2-ylmethoxy]benzyl]thiazolidine-2,4-dione dihydrochloride (400 mg), α,α,α-trifluoro-o-tolyl isocyanate (210 mg), triethylamine (153 mg) and anhydrous N,N-dimethylformamide (8 ml).

EXAMPLE 25

1-(3-[2-[4-(2,4-Dioxothiazolidin-5-ylmethyl)
phenoxymethyl]-1-methyl-1H-benzimidazol-6-
yloxy]phenyl)-3-n-hexylurea (exemplification
compound number 2-5)

A mixture of 5-[4-[6-(3-aminophenoxy)-1-methyl-1H-benzimidazol-2-ylmethoxy]benzyl]thiazolidine-2,4-dione dihydrochloride (400 mg), n-hexyl isocyanate (280 mg), triethylamine (153 mg) and anhydrous N,N-dimethylformamide (8 ml) was stirred at room temperature for 7 hours and then allowed to stand overnight. The reaction mixture was concentrated and partitioned between ethyl acetate and water. The extract was washed with saturated aqueous sodium chloride solution, dried over anhydrous sodium sulfate and then concentrated. The residue was chromatographed on a silica gel column using ethyl acetate/n-hexane=3:1→4:1→ethyl acetate→ethyl acetate:methanol=15:1 as the eluant. The product was recrystallized from ethyl acetate to afford the title compound (298 mg, mp 143.7–146.9° C.).

EXAMPLE 26

1-(3-Cyanophenyl)-3-(3-[2-[4-(2,4-dioxothiazolidin-
5-ylmethyl)phenoxymethyl]-1-methyl-1H-
benzimidazol-6-yloxy]phenyl)urea (exemplification
compound number 2-41)

A mixture of 5-[4-[6-(3-aminophenoxy)-1-methyl-1H-benzimidazol-2-ylmethoxy]benzyl]thiazolidine-2,4-dione dihydrochloride (400 mg), 3-cyanophenyl isocyanate (260 mg), triethylamine (153 mg) and anhydrous N,N-dimethylformamide (8 ml) was stirred at room temperature for 4 hours and then at 50° C. for 2.5 hours. The reaction mixture was concentrated and partitioned between ethyl acetate and water. The extract was washed with saturated aqueous sodium chloride solution, dried over anhydrous sodium sulfate and then concentrated. The residue was chromatographed on a silica gel column using ethyl acetate:n-hexane=3:1→ethyl acetate as the eluant. The product was recrystallized from methanol to afford the title compound (260 mg, mp 148.4–154.0° C.).

EXAMPLE 27

1-(3-[2-[4-(2,4-Dioxothiazolidin-5-ylmethyl)
phenoxymethyl]-1-methyl-1H-benzimidazol-6-
yloxy]phenyl)-3-p-tolylurea (exemplification
compound number 2-12)

A mixture of p-toluic acid (109 mg), diphenylphosphoryl azide (209 mg), triethylamine (314 mg) and anhydrous toluene (8 ml) was stirred at 80° C. for 1 hour. To the reaction mixture was added 5-[4-[6-(3-aminophenoxy)-1-methyl-1H-benzimidazol-2-ylmethoxy]benzyl]thiazolidine-2,4-dione dihydrochloride (400 mg) and anhydrous N,N-dimethylformamide (4 ml) at room temperature and the mixture was stirred at the same temperature for 2.5 hours. The reaction mixture was concentrated and partitioned between ethyl acetate and water. The extract was washed with saturated aqueous sodium chloride solution, dried over anhydrous sodium sulfate and then concentrated. The residue was chromatographed on a silica gel column using ethyl acetate:n-hexane=3/2→3/1→ethyl acetate as the eluant. The product insoluble in methanol was isolated by filtration and further purified by preparative reverse phase high performance liquid chromatography using acetonitrile:water= 50:50→55:45→60:40 as the eluant to afford the title compound (27 mg, mp 173.0–175.2° C.).

EXAMPLE 28

1-(Adamant-1-yl)-3-(3-[2-[4-(2,4-dioxothiazolidin-
5-ylmethyl)phenoxymethyl]-1-methyl-1H-
benzimidazol-6-yloxy]phenyl)urea (exemplification
compound number 2-8)

A mixture of 5-[4-[6-(3-aminophenoxy)-1-methyl-1H-benzimidazol-2-ylmethoxy]benzyl]thiazolidine-2,4-dione dihydrochloride (400 mg), 1-adamantyl isocyanate (142 mg), triethylamine (153 mg) and anhydrous N,N-dimethylformamide (4 ml) was stirred at room temperature for 3 hours. The reaction mixture was concentrated and partitioned between ethyl acetate and water. The extract was washed with saturated aqueous sodium chloride solution, dried over anhydrous sodium sulfate and then concentrated. The residue was chromatographed on a silica gel column using ethyl acetate:n-hexane=3:1→4:1→ethyl acetate as the eluant. The product insoluble in methanol was isolated by filtration and further purified by preparative reverse phase high performance liquid chromatography using acetonitrile:water=50:50→60:40→65:35→70:30 as the eluant to afford the title compound (66 mg, mp 227.1–231.4° C.).

EXAMPLE 29

1-(Benzo[1,3]dioxol-5-yl)-3-(3-[2-[4-(2,4-
dioxothiazolidin-5-ylmethyl)phenoxymethyl]-1-
methyl-1H-benzimidazol-6-yloxy]phenyl)urea
(exemplification compound number 2-72)

A mixture of piperonylic acid (133 mg), diphenylphosphoryl azide (217 mg), triethylamine (314 mg) and anhydrous toluene (8 ml) was stirred at 80° C. for 1 hour. To the reaction mixture was added 5-[4-[6-(3-aminophenoxy)-1-methyl-1H-benzimidazol-2-ylmethoxy]benzyl]thiazolidine-2,4-dione dihydrochloride (400 mg) and anhydrous N,N-dimethylformamide (4 ml) at room temperature and the mixture was stirred at the same temperature for 1 hour and then allowed to stand overnight. The reaction mixture was concentrated and partitioned between ethyl acetate and water. The extract was washed with saturated aqueous sodium chloride solution, dried over anhydrous sodium sulfate and then concentrated. The residue was chromatographed on a silica gel column using ethyl acetate:n-hexane=3:1→1:0 as the eluant. The product insoluble in a mixture of methanol and diisopropyl ether (5:1) was isolated by filtration and was further purified by preparative reverse phase high performance liquid chromatography using acetonitrile/water=50:50 as the eluant to afford the title compound (26 mg, mp 179.2–182.4° C.).

EXAMPLE 30

1-(3-[2-[4-(2,4-Dioxothiazolidin-5-ylmethyl)
phenoxymethyl]-1-methyl-1H-benzimidazol-6-
yloxy]phenyl)-3-[4-(trifluoromethyl)benzyl]urea
(exemplification compound number 2-82)

To a solution of 1,1'-carbonyldiimidazole (130 mg) in anhydrous N,N-dimethylformamide (8 ml) was added 4-(trifluoromethyl)benzylamine (135 mg) and the mixture was stirred at room temperature for 2 hours. To the reaction mixture was added 5-[4-[6-(3-aminophenoxy)-1-methyl-1H-benzimidazol-2-ylmethoxy]benzyl]thiazolidine-2,4-dione dihydrochloride (400 mg) and triethylamine (153 mg) and the mixture was stirred at 60° C. for 1 hour and then allowed to stand at room temperature overnight. The reaction mixture was concentrated and partitioned between ethyl acetate and water. The extract was washed with saturated aqueous sodium chloride solution, dried over anhydrous sodium sulfate and then concentrated. The residue was chromatographed on a silica gel column using ethyl acetate as the eluant. The product insoluble in methanol was isolated by filtration and further purified by preparative reverse phase high performance liquid chromatography using acetonitrile:water=50:50→60:40 as the eluant to afford the title compound (102 mg, mp 127.9–132.4° C.).

EXAMPLE 31

1-(2,4-Difluorophenyl)-3-[2-(4-[2-[4-(2,4-
dioxothiazolidin-5-ylmethyl)phenoxymethyl]-1-
methyl-1H-benzimidazol-6-yloxy]phenyl)ethyl]urea
(exemplification compound number 1-174)

To a mixture of 5-[4-[6-[4-(2-aminoethyl)phenoxy]-1-methyl-1H-benzimidazol-2-ylmethoxy]benzyl]thiazolidine-2,4-dione dihydrochloride (0.3 g), triethylamine (65 mg) and anhydrous N,N-dimethylformamide (5 ml) was added 2,4-difluorophenyl isocyanate (81 mg) and the mixture was stirred at room temperature for 4.5 hours and then allowed to stand for 2 days. The reaction mixture was concentrated and diluted with water and tetrahydrofuran and then extracted with ethyl acetate. The extract was washed with saturated aqueous sodium chloride solution, dried over anhydrous sodium sulfate and then concentrated. To the residue was added ethyl acetate and the precipitate was isolated by filtration and washed with ethyl acetate to afford the title compound (0.2 g, mp 161–164° C.).

EXAMPLE 32

1-(2,6-Diisopropylphenyl)-3-[2-(4-[2-[4-(2,4-
dioxothiazolidin-5-ylmethyl)phenoxymethyl]-1-
methyl-1H-benzimidazol-6-yloxy]phenyl)ethyl]urea
hydrochloride (hydrochloride of exemplification
compound number 1-168)

1-(2,6-Diisopropylphenyl)-3-[2-(4-[2-[4-(2,4-dioxothiazolidin-5-ylmethyl)phenoxymethyl]-1-methyl-1H-benzimidazol-6-yloxy]phenyl)ethyl]urea was obtained by a similar procedure to that described in Example 31 using 5-[4-[6-[4-(2-aminoethyl)phenoxy]-1-methyl-1H-benzimidazol-2-ylmethoxy]benzyl]thiazolidine-2,4-dione dihydrochloride (0.4 g), 2,6-diisopropylphenyl isocyanate (0.14 g), N,N-diisopropylethylamine (0.18 g) and anhydrous N,N-dimethylformamide (15 ml). To a solution of the product in tetrahydrofuran (10 ml) was added 4N hydrogen chloride in ethyl acetate (5 ml) and the mixture was stirred at room temperature for 1.5 hours. To the reaction mixture was added diethyl ether (15 ml) and this mixture was stirred for 1 hour. The precipitate was isolated by filtration and washed with ethyl acetate and n-hexane to afford the title compound (0.4 g, mp 153–155° C.).

EXAMPLE 33

1-(Adamant-1-yl)-3-[2-(4-[2-[4-(2,4-
dioxothiazolidin-5-ylmethyl)phenoxymethyl]-1-
methyl-1H-benzimidazol-6-yloxy]phenyl)ethyl]urea
dihydrochloride (dihydrochloride of exemplification
compound number 1-165)

1-(Adamant-1-yl)-3-[2-(4-[2-[4-(2,4-dioxothiazolidin-5-ylmethyl)phenoxymethyl]-1-methyl-1H-benzimidazol-6-yloxy]phenyl)ethyl]urea was obtained by a similar procedure to that described in Example 31 using 5-[4-[6-[4-(2-aminoethyl)phenoxy]-1-methyl-1H-benzimidazol-2-ylmethoxy]benzyl]thiazolidine-2,4-dione dihydrochloride (0.3 g), 1-adamantyl isocyanate (94 mg), triethylamine (65 mg) and anhydrous N,N-dimethylformamide (15 ml). To a solution of the product in tetrahydrofuran (10 ml) was added 4N hydrogen chloride in dioxane (10 ml) and the mixture was stirred at room temperature for 3 hours. The precipitate was isolated by filtration and washed with tetrahydrofuran and n-hexane to afford the title compound (0.3 g, mp 174–176° C.).

EXAMPLE 34

1-[2-(4-[2-[4-(2,4-Dioxothiazolidin-5-ylmethyl)
phenoxymethyl]-1-methyl-1H-benzimidazol-6-
yloxy]phenyl)ethyl]-3-[4-(trifluoromethyl)phenyl]
urea hydrochloride (hydrochloride of
exemplification compound number 1-172)

1-[2-(4-[2-[4-(2,4-Dioxothiazolidin-5-ylmethyl)phenoxymethyl]-1-methyl-1H-benzimidazol-6-yloxy]phenyl)ethyl]-3-(4-trifluoromethylphenyl)urea hydrochloride was obtained by a similar procedure to that described in Example 31 using 5-[4-[6-[4-(2-aminoethyl)phenoxy]-1-methyl-1H-benzimidazol-2-ylmethoxy]benzyl]thiazolidine-2,4-dione dihydrochloride (0.3 g), α,α,α-trifluoro-p-tolyl isocyanate (97 mg), triethylamine (65 mg) and anhydrous N,N-dimethylformamide (5 ml). To a solution of the product in tetrahydrofuran (10 ml) was added 4N hydrogen chloride in 1,4-dioxane (10 ml) and the mixture was stirred at room temperature for 3 hours. To the reaction mixture was added diethyl ether (50 ml) and this mixture was further stirred for 30 minutes. The precipitate was isolated by filtration and washed with ethyl acetate to afford the title compound (0.3 g, mp 153–156° C.).

EXAMPLE 35

4-Chloro-N-[2-(4-[2-[4-(2,4-dioxothiazolidin-5-
ylmethyl)phenoxymethyl]-1-methyl-1H-
benzimidazol-6-yloxy]phenyl)ethyl]
benzenesulfonamide hydrochloride (hydrochloride
of exemplification compound number 1-342)

To a mixture of 5-[4-[6-[4-(2-aminoethyl)phenoxy]-1-methyl-1H-benzimidazol-2-ylmethoxy]benzyl]thiazolidine-2,4-dione dihydrochloride (0.4 g), N,N-diisopropylethylamine (0.27 g) and anhydrous N,N-dimethylformamide (15 ml) was added 4-chlorobenzenesulfonyl chloride (0.15 g) and the mixture was stirred at room temperature for 3.5 hours. The reaction mixture was concentrated and diluted with water and tetrahydrofuran and then extracted with ethyl acetate. The extract was washed with saturated aqueous sodium chloride solution, dried over anhydrous sodium sulfate and then concentrated. To a solution of the residue in tetrahydrofuran (10 ml) was added 4N hydrogen chloride in ethyl acetate (5 ml) and the mixture was stirred at room temperature for 1.5 hours. To the reaction mixture was added diethyl ether (10 ml) and this mixture was stirred at room temperature for 30 minutes and then was irradiated with ultrasound for 30 minutes. The precipitate was isolated by filtration and washed with acetone, ethyl acetate and n-hexane to afford the title compound (0.3 g, mp 155–160° C.).

EXAMPLE 36

N-[2-(4-[2-[4(2,4-Dioxothiazolidin-5-ylmethyl) phenoxymethyl]-1-methyl-1H-benzimidazol-6-yloxy]phenyl)ethyl]-2,4,6-triisopropylbenzenesulfonamide hydrochloride (hydrochloride of exemplification compound number 1-336)

To a mixture of 5-[4-[6-[4-(2-aminoethyl)phenoxy]-1-methyl-1H-benzimidazol-2-ylmethoxy]benzyl]thiazolidine-2,4-dione dihydrochloride (0.3 g), triethylamine (0.17 g) and anhydrous N,N-dimethylformamide (10 ml) was added 2,4,6-triisopropylbenzenesulfonyl chloride (0.17 g) and the mixture was stirred at room temperature for 4.5 hours. The reaction mixture was concentrated and partitioned between ethyl acetate and water. The extract was washed with saturated aqueous sodium chloride solution, dried over anhydrous sodium sulfate and then concentrated. The residue was chromatographed on a silica gel column using ethyl acetate:n-hexane=2:1 as the eluant. To a solution of the product in ethyl acetate (15 ml) was added 4N hydrogen chloride in 1,4-dioxane (2 ml) and the mixture was stirred at room temperature for 20 minutes. The precipitate was isolated by filtration and washed with ethyl acetate to afford the title compound (0.28 g, mp 134–136° C.).

EXAMPLE 37

1-[4-(2-[2-[4-(2,4-Dioxothiazolidin-5-ylmethyl) phenoxymethyl]-1-methyl-1H-benzimidazol-6-yloxy]ethyl)phenyl]-3-[4-(trifluoromethyl)phenyl] urea (exemplification compound number 1-232)

To a mixture of 5-[4-[6-[2-(4-aminophenyl)ethoxy]-1-methyl-1H-benzimidazol-2-ylmethoxy]benzyl]thiazolidine-2,4-dione (0.4 g) and N,N-dimethylformamide (10 ml) was added α,α,α-trifluoro-p-tolyl isocyanate (0.17 g) and the mixture was stirred at room temperature for 2 hours and allowed to stand overnight. The reaction mixture was partitioned between ethyl acetate and water. The extract was washed with saturated aqueous sodium chloride solution, dried over anhydrous sodium sulfate and then concentrated. To the residue was added a mixture of ethyl acetate and diethyl ether (1:1). The precipitate was isolated by filtration and washed with diethyl ether to afford the title compound (0.4 g, mp 145–147° C.).

EXAMPLE 38

1-(4-Chlorophenyl)-3-[4-(2-[2-[4-(2,4-dioxothiazolidin-5-ylmethyl)phenoxymethyl]-1-methyl-1H-benzimidazol-6-yloxy]ethyl)phenyl]urea (exemplification compound number 1-235)

To a mixture of 5-[4-[6-[2-(4-aminophenyl)ethoxy]-1-methyl-1H-benzimidazol-2-ylmethoxy]benzyl]thiazolidine-2,4-dione (0.4 g) and N,N-dimethylformamide (10 ml) was added 4-chlorophenyl isocyanate (0.15 g) and the mixture was stirred at room temperature for 1 hour and allowed to stand overnight. The reaction mixture was partitioned between ethyl acetate and water. The extract was washed with saturated aqueous sodium chloride solution, dried over anhydrous sodium sulfate and then concentrated. To the residue was added diethyl ether. The precipitate was isolated by filtration and recrystallized from a mixture of tetrahydrofuran and ethyl acetate to afford the title compound (0.37 g, mp 157–162° C.).

EXAMPLE 39

1-[4-(2-[2-[4-(2,4-Dioxothiazolidin-5-ylmethyl) phenoxymethyl]-1-methyl-1H-benzimidazol-6-yloxy]ethyl)phenyl]-3-(4-nitrophenyl)urea hydrochloride (hydrochloride of exemplification compound number 1-237)

To a mixture of 5-[4-[6-[2-(4-aminophenyl)ethoxy]-1-methyl-1H-benzimidazol-2-ylmethoxy]benzyl]thiazolidine-2,4-dione (4 g) and N,N-dimethylformamide (10 ml) was added 4-nitrophenyl isocyanate (0.16 g) and the mixture was stirred at room temperature for 1 hour and allowed to stand overnight. The reaction mixture was partitioned between ethyl acetate and water. The extract was washed with saturated aqueous sodium chloride solution, dried over anhydrous sodium sulfate and then concentrated. To the residue was added ethyl acetate. The precipitate was isolated by filtration and purified by preparative normal phase medium pressure liquid chromatography using ethyl acetate:tetrahydrofuran=4:1 as the eluant to give 1-[4-(2-[2-[4-(2,4-dioxothiazolidin-5-ylmethyl)phenoxymethyl]-1-methyl-1H-benzimidazol-6-yloxy]ethyl)phenyl]-3-(4-nitrophenyl)urea. To a solution of the product in a mixture of tetrahydrofuran and methanol (1:1, 10 ml) was added 4N hydrogen chloride in 1,4-dioxane (2 ml) and the mixture was stirred at room temperature for 15 minutes. The reaction mixture was concentrated and the residue was recrystallized from a mixture of methanol and tetrahydrofuran to afford the title compound (0.16 g, mp 170° C.(dec)).

EXAMPLE 40

1-(2,6-Diisopropylphenyl)-3-[7-[2-[4-(2,4-dioxothiazolidin-5-ylmethyl)phenoxymethyl]-1-methyl-1H-benzimidazol-6yloxy]naphthalen-1-yl) urea (exemplification compound number 1-213)

To a mixture of 5-[4-[6-(8-aminonaphthalen-2-yloxy)-1-methyl-1H-benzimidazol-2-ylmethoxy]benzyl]thiazolidine-2,4-dione (0.5 g) and N,N-dimethylformamide (10 ml) was added 2,6-diisopropylphenyl isocyanate (0.20 g) and the mixture was allowed to stand at room temperature for 5 days. The reaction mixture was partitioned between ethyl acetate and water. The extract was washed with saturated aqueous sodium chloride solution, dried over anhydrous sodium sulfate and then concentrated. The residue was chromatographed on a silica gel column using ethyl acetate:n-hexane=3/2→3/1 as the eluant. The product was recrystallized from methanol to afford the title compound (0.24 g, mp 164–169° C.).

EXAMPLE 41

1-(2,4-Difluorophenyl)-3-(7-[2-[4-(2,4-dioxothiazolidin-5-ylmethyl)phenoxymethyl]-1-methyl-1H-benzimidazol-6-yloxy]naphthalen-1-yl) urea (exemplification compound number 1-219)

The title compound (0.25 g, mp 222–224° C.) was obtained by a similar procedure to that described in Example 1 using 5-[4-[6-(8-aminonaphthalen-2-yloxy)-1-methyl-1H-benzimidazol-2-ylmethoxy]benzyl]thiazolidine-2,4-dione (0.50 g), 2,4-difluorophenyl isocyanate (0.16 g) and anhydrous N,N-dimethylformamide (10 ml).

EXAMPLE 42

1-(7-[2-[4-(2,4-Dioxothiazolidin-5-ylmethyl) phenoxymethyl]-1-methyl-1H-benzimidazol-6-yloxy]naphthalen-1-yl)-3-[4-(trifluoromethyl) phenyl]urea (exemplification compound number 1-217)

The title compound (0.27 g, mp 250–254° C.) was obtained by a similar procedure to that described in Example 1 using 5-[4-[6-(8-aminonaphthalen-2-yloxy)-1-methyl-1H-benzimidazol-2-ylmethoxy]benzyl]thiazolidine-2,4-dione (0.5 g), α,α,α-trifluoro-p-tolyl isocyanate (0.19 g) and anhydrous N,N-dimethylformamide (10 ml).

EXAMPLE 43

1-(Adamant-1-yl)-3-(7-[2-[4-(2,4-dioxothiazolidin-5-ylmethyl)phenoxymethyl]-1-methyl-1H-benzimidazol-6-yloxy]naphthalen-1-yl)urea (exemplification compound number 1-210)

To a solution of 5-[4-[6-(8-aminonaphthalen-2-yloxy)-1-methyl-1H-benzimidazol-2-ylmethoxy]benzyl]thiazolidine-2,4-dione (0.5 g) in anhydrous N,N-dimethylformamide (10 ml) was added 1-adamantyl isocyanate (0.18 g) and the mixture was stirred at room temperature for 5 days. The reaction mixture was concentrated. The residue was purified by preparative reverse phase high performance liquid chromatography using acetonitrile:water=50:50→60:40→70:30 as the eluant to afford the title compound (0.45 g, mp 250° C. (dec)).

EXAMPLE 44

1-Benzyl-3-(7-[2-[4-(2,4-dioxothiazolidin-5-ylmethyl)phenoxymethyl]-1-methyl-1H-benzimidazol-6-yloxy]naphthalen-1-yl)thiourea (exemplification compound number 1-300)

To a solution of 5-[4-[6-(8-aminonaphthalen-2-yloxy)-1-methyl-1H-benzimidazol-2-ylmethoxy]benzyl]thiazolidine-2,4-dione (0.4 g) in anhydrous tetrahydrofuran (10 ml) was added benzyl isothiocyanate (0.24 g) and the mixture was stirred at room temperature for 5.5 hours and then at 50° C. for 9 hours. The reaction mixture was concentrated. The residue was chromatographed on a silica gel column using ethyl acetate:n-hexane=1:1→3:1 as the eluant to afford the title compound (0.36 g, $R_f$=0.53: thin layer chromatography on a silica gel plate using ethyl acetate:n-hexane=3:1).

EXAMPLE 45

1-Benzyl-3-(7-[2-[4-(2,4-dioxothiazolidin-5-ylmethyl)phenoxymethyl]-1-methyl-1H-benzimidazol-6-yloxy]naphthalen-1-yl)urea (exemplification compound number 1-223)

The title compound (0.32 g, mp 220–222° C.) was obtained by a similar procedure to that described in Example 1 using 5-[4-[6-(8-aminonaphthalen-2-yloxy)-1-methyl-1H-benzimidazol-2-ylmethoxy]benzyl]thiazolidine-2,4-dione (0.3 g), benzyl isocyanate (0.08 g) and anhydrous tetrahydrofuran (6 ml).

EXAMPLE 46

1-Benzenesulfonyl-3-(7-[2-[4-(2,4-dioxothiazolidin-5-ylmethyl)phenoxymethyl]-1-methyl-1H-benzimidazol-6-yloxy]naphthalen-1-yl)urea (exemplification compound number 1-256)

To a solution of 5-[4-[6-(8-aminonaphthalen-2-yloxy)-1-methyl-1H-benzimidazol-2-ylmethoxy]benzyl]thiazolidine-2,4-dione (0.4 g) in anhydrous tetrahydrofuran (8 ml) was added benzenesulfonyl isocyanate (0.22 g) and the mixture was stirred at room temperature for 3 hours. The reaction mixture was concentrated. The residue was chromatographed on a silica gel column using ethyl acetate:n-hexane=3:1 as the eluant. The product was recrystallized from n-hexane to afford the title compound (55 mg, mp 199–205° C.).

EXAMPLE 47

N-(7-[2-[4-(2,4-dioxothiazolidin-5-ylmethyl) phenoxymethyl]-1-methyl-1H-benzimidazol-6-yloxy]naphthalen-1-yl)-4-methylbenzenesulfonamide (exemplification compound number 1-349)

A mixture of 5-[4-[6-(8-aminonaphthalen-2-yloxy)-1-methyl-1H-benzimidazol-2-ylmethoxy]benzyl]thiazolidine-2,4-dione (0.4 g), p-toluenesulfonyl chloride (0.30 g), triethylamine (0.16 g) and anhydrous tetrahydrofuran (8 ml) was stirred at 50° C. for 5 hours and then at 70° C. for 2 hours. The reaction mixture was concentrated. To the residue was added water and the precipitate was washed with water and tetrahydrofuran to afford the title compound (0.14 g, mp 137–144° C.).

EXAMPLE 48

1-(2-t-Butyl-5-[2-[4-(2,4-dioxothiazolidin-5-ylmethyl)phenoxymethyl]-1-methyl-1H-benzimidazol-6-yloxymethyl]phenyl)-3-[4-(trifluoromethyl)phenyl]urea (exemplification compound number 2-190)

A mixture of 5-[4-[6-(3-amino-4-t-butyl)benzyloxy)-1-methyl-1H-benzimidazol-2-ylmethoxy]benzyl]thiazolidine-2,4-dione dihydrochloride (0.5 g), α,α,α-trifluoro-p-tolyl isocyanate (0.17 g), triethylamine (0.16 g) and anhydrous N,N-dimethylformamide (10 ml) was stirred at room temperature for 19 hours and then at 60° C. for 5 hours. The reaction mixture was concentrated and partitioned between ethyl acetate and water. The extract was washed with saturated aqueous sodium chloride solution, dried over anhydrous sodium sulfate and then concentrated. The residue was purified by preparative reverse phase high performance liquid chromatography using acetonitrile:water= 55:45 as the eluant. The product was recrystallized from a mixture of ethyl acetate and n-hexane to afford the title compound (0.18 g, mp 200–202° C.).

EXAMPLE 49

1-[2-t-Butyl-5-(2-[2-[4-(2,4-dioxothiazolidin-5-ylmethyl)phenoxymethyl]-1-methyl-1H-benzimidazol-6-yloxy]ethyl)phenyl]-3-[4-(trifluoromethyl)phenyl]urea (exemplification compound number 2-205)

A mixture of 5-[4-[6-[2-(3-amino-4-t-butylphenyl) ethoxy]-1-methyl-1H-benzimidazol-2-ylmethoxy]benzyl] thiazolidine-2,4-dione dihydrochloride (0.40 g), α,α,α-trifluoro-p-tolyl isocyanate (0.13 g), triethylamine (0.13 g) and anhydrous N,N-dimethylformamide (8 ml) was stirred at room temperature for 24 hours and then at 60° C. for 2.5 hours. The reaction mixture was concentrated and partitioned between ethyl acetate and water. The extract was washed with saturated aqueous sodium chloride solution, dried over anhydrous sodium sulfate and then concentrated.

The residue was purified by preparative reverse phase high performance liquid chromatography using acetonitrile:water=57:43 containing triethylamine (2%) and acetic acid (2%) as the eluant to afford the title compound (0.24 g, mp 165–167° C.).

EXAMPLE 50

1-(4-[2-[4-(2,4-Dioxothiazolidin-5-ylmethyl) phenoxymethyl]-3-methyl-3H-imidazo[4,5-b] pyridin-5-ylthio]-2,6-dimethylphenyl)-3-[4- (trifluoromethyl)phenyl]urea (exemplification compound number 3-70)

A mixture of 5-[4-[5-(3,5-dimethyl4-nitrophenylthio)-3-methyl-3H-imidazo[4,5-b]pyridin-2-ylmethoxy]benzyl] thiazolidine-2,4-dione (0.37 g), 10% palladium on carbon (0.44 g), ethanol (10 ml) and 1,4-dioxane (10 ml) was vigorously stirred under a hydrogen atmosphere at room temperature for 7 hours. The reaction mixture was filtered in order to remove the catalyst and concentrated. To a solution of the residue in a mixture of anhydrous tetrahydrofuran and anhydrous N,N-dimethylformamide (2:1, 15 ml) was added α,α,α-trifluoro-p-tolyl isocyanate (0.38 g) and the mixture was stirred at room temperature for 5 hours and then at 60° C. for 4 hours. The reaction mixture was concentrated and partitioned between ethyl acetate and water. The extract was dried over anhydrous sodium sulfate and concentrated. To the residue was added n-hexane and the precipitate was isolated by filtration and reprecipitated from a mixture of ethanol and diethyl ether to afford the title compound (0.12 g, mp 193–195° C.).

EXAMPLE 51

1-(4-[2-[4-(2,4-Dioxothiazolidin-5-ylmethyl) phenoxymethyl]-1-methyl-1H-benzimidazol-6- yloxy]-2,6-dimethylphenyl)-3-(4-methoxyphenyl) urea (exemplification compound number 1-189)

The title compound (201 mg, mp 229–231° C.) was obtained by a similar procedure to that described in Example 1 using 5-[4-[6-(4-amino-3,5-dimethylphenoxy)-1-methyl-1H-benzimidazol-2-ylmethoxy]benzyl]thiazolidine-2,4-dione (251 mg), 4-methoxyphenyl isocyanate (89 mg), triethylamine (61 mg) and anhydrous tetrahydrofuran (10 ml).

EXAMPLE 52

N-[4-[2-[4-(2,4-Dioxothiazolidin-5-ylmethyl) phenoxymethyl]-1-methyl-1H-benzimidazol-6- yloxy]phenyl]acetamide (exemplification compound number 6-1)

Triethylamine (0.36 ml) and acetyl chloride (0.06 ml) were added to a solution of 5-[4-[6-(4-aminophenoxy)-1-methyl-1H-benzimidazol-2-ylmethoxy]benzyl]thiazolidine-2,4-dione dihydrochloride (400 mg) in anhydrous N,N-dimethylformamide (8 ml) and the mixture was stirred at room temperature for 1 hour. The reaction mixture was concentrated under reduced pressure. The residue was partitioned between ethyl acetate and water. The extract was washed with saturated aqueous sodium chloride solution, dried over anhydrous sodium sulfate and then concentrated. The residue was chromatographed on a silica gel column using ethyl acetate:n-hexane=4:1→1:0→ethyl acetate:methanol=10:1 as the eluant to afford the title compound (320 mg, white amorphous, mp 92–95° C.).

EXAMPLE 53

N-[4-[2-[4-(2,4-Dioxothiazolidin-5-ylmethyl) phenoxymethyl]-1-methyl-1H-benzimidazol-6- yloxy]phenyl]benzamide (exemplification compound number 6-10)

A reaction was conducted by a similar procedure to that described in Example 52 using triethylamine (0.36 ml), benzoyl chloride (0.10 ml), 5-[4-[6-(4-aminophenoxy)-1-methyl-1H-benzimidazol-2-ylmethoxy]benzyl]thiazolidine-2,4-dione dihydrochloride (400 mg) and anhydrous N,N-dimethylformamide (8 ml). The reaction mixture was concentrated under reduced pressure. The residue was partitioned between ethyl acetate and water. The extract was washed with saturated aqueous sodium chloride solution, dried over anhydrous sodium sulfate and then concentrated. The residue was chromatographed on a silica gel column using ethyl acetate:n-hexane=1:1→2:1→3:1→4:1 as the eluant to afford the title compound (247 mg, white powder, mp 200–204° C.).

EXAMPLE 54

3-Chloro-N-[4-[2-[4-(2,4-dioxothiazolidin-5- ylmethyl)phenoxymethyl]-1-methyl-1H- benzimidazol-6-yloxy]phenyl]benzamide (exemplification compound number 6-21)

A reaction was conducted by a similar procedure to that described in Example 52 using triethylamine (0.32 ml), 3-chlorobenzoyl chloride (0.09 ml), 5-[4-[6-(4-aminophenoxy)-1-methyl-1H-benzimidazol-2-ylmethoxy] benzyl]thiazolidine-2,4-dione dihydrochloride (400 mg) and anhydrous N,N-dimethylformamide (8 ml). The reaction mixture was concentrated under reduced pressure. The residue was partitioned between ethyl acetate and water. The extract was washed with saturated aqueous sodium chloride solution, dried over anhydrous sodium sulfate and then concentrated. The residue was chromatographed on a silica gel column using ethyl acetate:n-hexane=3:2→5:2 as the eluant to afford the title compound (232 mg, white powder, mp 238–239° C.).

EXAMPLE 55

N-[4-[2-[4-(2,4-Dioxothiazolidin-5-ylmethyl) phenoxymethyl]-1-methyl-1H-benzimidazol-6- yloxy]phenyl]isonicotinamide (exemplification compound number 6-37)

A reaction was conducted by a similar procedure to that described in Example 52 using triethylamine (0.54 ml), isonicotinoyl chloride hydrochloride (284 mg), 5-[4-[6-(4-aminophenoxy)-1-methyl-1H-benzimidazol-2-ylmethoxy] benzyl]thiazolidine-2,4-dione dihydrochloride (400 mg) and anhydrous N,N-dimethylformamide (8 ml). The reaction mixture was concentrated under reduced pressure. To the residue was added ethyl acetate and water. The precipitate was isolated by filtration to afford the title compound (306 mg, pale yellow powder, mp 222° C. (dec)).

EXAMPLE 56

N-[4-[2-[4-(2,4-Dioxothiazolidin-5-ylmethyl) phenoxymethyl]-1-methyl-1H-benzimidazol-6- yloxy]phenyl]nicotinamide (exemplification compound number 6-36)

A reaction was conducted by a similar procedure to that described in Example 52 using triethylamine (0.49 ml), nicotinoyl chloride hydrochloride (195 mg), 5-[4-[6-(4-aminophenoxy)-1-methyl-1H-benzimidazol-2-ylmethoxy] benzyl]thiazolidine-2,4-dione dihydrochloride (400 mg) and anhydrous N,N-dimethylformamide (8 ml). The reaction mixture was concentrated under reduced pressure. To the residue was added ethyl acetate and water. The precipitate was isolated by filtration to afford the title compound (297 mg, pale yellow powder, mp 213–215° C.).

EXAMPLE 57

2,4-Difluoro-N-[4-[2-[4-(2,4-dioxothiazolidin-5-ylmethyl)phenoxymethyl]-1-methyl-1H-benzimidazol-6-yloxy]phenyl]benzamide
(exemplification compound number 6-19)

A reaction was conducted by a similar procedure to that described in Example 52 using triethylamine (0.32 ml), 2,4-difluorobenzoyl chloride (0.10 ml), 5-[4-[6-(4-aminophenoxy)-1-methyl-1H-benzimidazol-2-ylmethoxy]benzyl]thiazolidine-2,4-dione dihydrochloride (400 mg) and anhydrous N,N-dimethylformamide (8 ml). The reaction mixture was concentrated under reduced pressure and partitioned between ethyl acetate and water. The extract was washed with saturated aqueous sodium chloride solution, dried over anhydrous sodium sulfate and concentrated. The residue was chromatographed on a silica gel column using ethyl acetate:n-hexane=3:1 to afford the title compound (251 mg, white powder, mp 172–174° C.).

EXAMPLE 58

N-[4-[2-[4-(2,4-dioxothiazolidin-5-ylmethyl)phenoxymethyl]-1-methyl-1H-benzimidazol-6-yloxy]phenyl]cyclohexanecarboxamide
(exemplification compound number 6-8)

Triethylamine (0.32 ml) and ethyl chloroformate (0.08 ml) were added dropwise to a solution of cyclohexanecarboxylic acid (0.09 ml) in anhydrous N,N-dimethylformamide (8 ml). After stirring the mixture for 90 minutes, 5-[4-[6-(4-aminophenoxy)-1-methyl-1H-benzimidazol-2-ylmethoxy]benzyl]thiazolidine-2,4-dione dihydrochloride (400 mg) was added and this mixture was stirred at room temperature for 2 hours and then for 90 minutes in an oil bath at 50° C. The reaction mixture was concentrated under reduced pressure. The residue was partitioned between ethyl acetate and water. The extract was washed with saturated aqueous sodium chloride solution, dried over anhydrous sodium sulfate and concentrated. The residue was recrystallized from ethyl acetate to afford the title compound (262 mg, pale orange powder, mp 182–184° C.).

EXAMPLE 59

N-[4-[2-[4(2,4-dioxothiazolidin-5-ylmethyl)phenoxymethyl]-1-methyl-1H-benzimidazol-6-yloxy]phenyl]cyclopentanecarboxamide
(exemplification compound number 6-7)

A reaction was conducted by a similar procedure to that described in Example 58 using triethylamine (0.32 ml), ethyl chloroformate (0.08 ml), cyclopentanecarboxylic acid (0.09 ml), anhydrous N,N-dimethylformamide (8 ml) and 5-[4-[6-(4-aminophenoxy)-1-methyl-1H-benzimidazol-2-ylmethoxy]benzyl]thiazolidine-2,4-dione dihydrochloride (400 mg). The reaction mixture was concentrated under reduced pressure. The residue was partitioned between ethyl acetate and water. The extract was washed with saturated aqueous sodium chloride solution, dried over anhydrous sodium sulfate and concentrated. To the residue was added water and ethyl acetate and the insoluble material was isolated by filtration to afford the title compound (236 mg, white powder, mp 227–228° C.).

EXAMPLE 60

N-[4-[2-[4-(2,4-Dioxothiazolidin-5-ylmethyl)phenoxymethyl]-1-methyl-1H-benzimidazol-6-yloxy]phenyl]naphthalene-2-carboxamide
(exemplification compound number 6-11)

A reaction was conducted by a similar procedure to that described in Example 52 using triethylamine (0.32 ml), 2-naphthoyl chloride (153 mg), 5-[4-[6-(4-aminophenoxy)-1-methyl-1H-benzimidazol-2-ylmethoxy]benzyl]thiazolidine-2,4-dione dihydrochloride (400 mg) and anhydrous N,N-dimethylformamide (8 ml). The reaction mixture was concentrated under reduced pressure. To the residue was added ethyl acetate and water. The precipitate was isolated by filtration to afford the title compound (337 mg, white powder, mp 221–223° C.).

EXAMPLE 61

N-[4-[2-[4-(2,4-Dioxothiazolidin-5-ylmethyl)phenoxymethyl]-1-methyl-1H-benzimidazol-6-yloxy]phenyl]-N-n-hexylacetamide hydrochloride
(hydrochloride of exemplification compound number 6-4)

A mixture of pyridine (356 mg), 4-dimethylaminopyridine (37 mg), acetic anhydride (112 mg), 5-[4-[6-(4-n-hexylaminophenoxy)-1-methyl-1H-benzimidazol-2-ylmethoxy]benzyl]thiazolidine-2,4-dione (502 mg) and anhydrous tetrahydrofuran (30 ml) was stirred at room temperature for 14 hours. The reaction mixture was concentrated and partitioned between ethyl acetate and water. The extract was dried over anhydrous sodium sulfate and concentrated. The residue was chromatographed on a silica gel column using ethyl acetate:n-hexane=3:1 as the eluant. The product was treated with 4N hydrogen chloride in ethyl acetate (20 ml) to afford the title compound (410 mg, mp 125–128° C.).

EXAMPLE 62

3,5-Di-t-butyl-N-[4-[2-[4-(2,4-dioxothiazolidin-5-ylmethyl)phenoxymethyl]-1-methyl-1H-benzimidazol-6-yloxy]phenyl]4-hydroxybenzamide
(exemplification compound number 6-25)

To a mixture of 5-[4-[6-(4-aminophenoxy)-1-methyl-1H-benzimidazol-2-ylmethoxy]benzyl]thiazolidine-2,4-dione dihydrochloride (400 mg) and 3,5-di-t-butyl-4-hydroxybenzoic acid (204 mg) in anhydrous N,N-dimethylformamide (8 ml) were added triethylamine (0.32 ml) and 1-ethyl-3-(3'-dimethylaminopropyl)carbodiimide hydrochloride (153 mg). The mixture was stirred at room temperature for 1 hour and then allowed to stand at room temperature overnight. To the reaction mixture was further added triethylamine (0.10 ml) and 1-ethyl-3-(3'-dimethylaminopropyl)carbodiimide hydrochloride (134 mg) and this mixture was stirred at room temperature for 8 hours and allowed to stand at room temperature overnight. The reaction mixture was concentrated under reduced pressure and partitioned between ethyl acetate and water. The extract was washed with saturated aqueous sodium chloride solution, dried over anhydrous sodium sulfate and concentrated. The residue was chromatographed on a silica gel column using ethyl acetate:n-hexane=2:1→3:1 as the eluant to afford the title compound (176 mg, mp 160–162° C.).

EXAMPLE 63

N-[2-[4-[2-[4-(2,4-Dioxothiazolidin-5-ylmethyl)phenoxymethyl]-1-methyl-1H-benzimidazol-6-yloxy]phenyl]ethyl]nicotinamide dihydrochloride
(dihydrochloride of exemplification compound number 6-59)

A mixture of 5-[4-[6-[4-(2-aminoethyl)phenoxy]-1-methyl-1H-benzimidazol-2-ylmethoxy]benzyl]thiazolidine- 2,4-dione dihydrochloride (0.3 g), triethylamine (0.17 g) and anhydrous N,N-dimethylformamide (15 ml) was stirred at room temperature for 30 minutes. To the mixture was added nicotinamide hydrochloride (0.1 g) and this mixture was irradiated with ultrasound for 30 minutes, stirred at room temperature for 6 hours and then allowed to stand overnight. The reaction mixture was concentrated and partitioned between a mixture of ethyl acetate:tetrahydrofuran (1:1) and water. The extract was washed with saturated aqueous sodium chloride solution, dried over anhydrous magnesium sulfate and concentrated. The residue was purified by liquid chromatography (LiChroprepDIOL (MERCK)) using ethyl acetate:tetrahydrofuran=3:1 as the eluant. To a solution of the glassy product in tetrahydrofuran (5 ml) was added 4N hydrogen chloride in 1,4-dioxane (5 ml) and the mixture was irradiated with ultrasound for 30 minutes. The precipitate was isolated by filtration to afford the title compound (0.15 g, pale yellow powder, mp 176–180° C. (dec)).

EXAMPLE 64

2-(3-Chlorophenyl)-N-[2-[4-[2-[4-(2,4-dioxothiazolidin-5-ylmethyl)phenoxymethyl]-1-methyl-1H-benzimidazol-6-yloxy]phenyl]ethyl]acetamide hydrochloride (hydrochloride of exemplification compound number 6-56)

The title compound (0.17 g, milk-white powder, mp 131–134° C.) was obtained by similar procedures to those described in Example 62 and 63 using anhydrous triethylamine (0.106 g), 5-[4-[6-[4-(2-aminoethyl)phenoxy]-1-methyl-1H-benzimidazol-2-ylmethoxy]benzyl]thiazolidine-2,4-dione dihydrochloride (0.3 g), (3-chlorophenyl)acetic acid (0.09 g), 1-ethyl-3-[(3'-dimethylamino)propyl]carbodiimide hydrochloride (WSC.HCl, 0.13 g), 1-hydroxybenzotriazole (0.11 g), anhydrous N,N-dimethylformamide (10 ml), methanol (2 ml), 1,4-dioxane (5 ml) and 4N hydrogen chloride in 1,4-dioxane (2 ml).

EXAMPLE 65

3,5-Di-t-butyl-N-[2-[4-[2-[4-(2,4-dioxothiazolidin-5-ylmethyl)phenoxymethyl]-1-methyl-1H-benzimidazol-6-yloxy]phenyl]ethyl]-4-hydroxybenzamide hydrochloride (hydrochloride of exemplification compound number 6-51)

A mixture of anhydrous triethylamine (0.106 g), 5-[4-[6-[4-(2-aminoethyl)phenoxy]-1-methyl-1H-benzimidazol-2-ylmethoxy]benzyl]thiazolidine-2,4-dione dihydrochloride (0.3 g), anhydrous N,N-dimethylformamide (10 ml), 3,5-di-t-butyl-4-hydroxybenzoic acid (0.13 g) and 1-ethyl-3-[(3'-dimethylamino)propyl]carbodiimide hydrochloride (WSC.HCl, 0.13 g) was stirred at room temperature for 4.5 hours. The reaction mixture was concentrated and partitioned between ethyl acetate and water. The extract was washed with saturated aqueous sodium chloride solution, dried over anhydrous magnesium sulfate and concentrated. The residue was purified by liquid chromatography on a silica gel column using ethyl acetate:n-hexane=4:1 as the eluant. To a solution of the glassy product in ethyl acetate (15 ml) was added 4N hydrogen chloride in 1,4-dioxane (2 ml) and the mixture was stirred at room temperature for 30 minutes. The reaction mixture was concentrated and the residue was crystallized in acetone to afford the title compound (0.17 g, pale yellow powder, mp 164–168° C.).

Reference Example 1 t-Butyl N-[5-(4-amino-3,5-dimethylphenoxy)-2-nitrophenyl]-N-methylcarbamate

To a suspension of anhydrous N,N-dimethylformaide (30 ml) containing sodium hydride (0.35 g, 55% (w/w)) was added 4-amino-3,5-dimethylphenol (1.10 g) and the mixture was stirred at room temperature for 15 minutes. To the mixture was added in limited amounts t-butyl N-(5-chloro-2-nitrophenyl)-N-methylcarbamate (2.29 g) and the mixture was stirred at 120° C. for 1 hour. The reaction mixture was concentrated and partitioned between ethyl acetate and water. The extract was dried over anhydrous sodium sulfate and concentrated. The residue was chromatographed on a silica gel column using ethyl acetate:n-hexane=1:3 as the eluant to afford the desired compound (2.27 g, $R_f$=0.24: thin layer chromatography on a silica gel plate using ethyl acetate:n-hexane=1:3 as the eluant).

Reference Example 2 t-Butyl N-[5-(4-t-butoxycarbonylamino-3,5-dimethylphenoxy)-2-nitrophenyl]-N-methylcarbamate A mixture of t-butyl N-[5-(4-amino-3,5-dimethylphenoxy)-2-nitrophenyl]-N-methylcarbamate (2.27 g), di-t-butyl dicarbonate (0.59 g), triethylamine (0.59 g) and anhydrous tetrahydrofuran (20 ml) was heated at reflux for 6 hours. The reaction mixture was concentrated and partitioned between ethyl acetate and water. The extract was dried over anhydrous sodium sulfate and concentrated. The residue was chromatographed on a silica gel column using ethyl acetate:n-hexane=1:10 as the eluant to afford the desired compound (1.74 g, mp 154–156° C.).

Reference Example 3 t-Butyl N-[2-amino-5-(4-t-butoxycarbonylamino-3,5-dimethylphenoxy)phenyl]-N-methylcarbamate To a solution of t-butyl N-[5-(4-t-butoxycarbonylamino-3,5-dimethylphenoxy)-2-nitrophenyl]-N-methylcarbamate (1.71 g) in methanol (100 ml) was added 10% palladium on carbon (0.2 g). The mixture was vigorously stirred under a hydrogen atmosphere at room temperature for 11 hours. The catalyst was filtered off and the solvent of the filtrate was evaporated to afford the desired compound (1.56 g, $R_f$=0.14: thin layer chromatography on a silica gel plate using ethyl acetate:n-hexane=1:3 as the eluant).

Reference Example 4 t-Butyl N-[5-(4-t-butoxycarbonylamino-3,5-dimethylphenoxy)-2-[4-(2,4-dioxothiazolidin-5-ylmethyl)phenoxyacetylamino]phenyl]-N-methylcarbamate A mixture of t-butyl N-[2-amino-5-(4-t-butoxycarbonylamino-3,5-dimethylphenoxy)phenyl]-N-methylcarbamate (1.56 g), 4-(2,4-dioxothiazolidin-5-ylmethyl)phenoxyacetic acid (1.05 g), diethyl cyanophosphonate (0.61 g), triethylamine (0.38 g) and anhydrous tetrahydrofuran (30 ml) was stirred at room temperature for 19 hours. The reaction mixture was concentrated and partitioned between ethyl acetate and water. The extract was dried over anhydrous sodium sulfate and concentrated. The residue was chromatographed on a silica gel column using ethyl acetate:n-hexane=1:1 as the eluant to afford the desired compound (1.89 g, $R_f$=0.19: thin layer chromatography on a silica gel plate using ethyl acetate:n-hexane=2:3 as the eluant).

Reference Example 5

5-[4-[6-(4-Amino-3,5-dimethylphenoxy)-1-methyl-1H-benzimidazol-2-ylmethoxy]benzyl]thiazolidine-2,4-dione A mixture of t-butyl N-[5-(4-t-butoxycarbonylamino-3,5-dimethylphenoxy)-2-[4-(2,4dioxothiazolidin-5-ylmethyl)

phenoxyacetylamino]phenyl]-N-methylcarbamate (1.88 g) and 4N hydrogen chloride in 1,4-dioxane (20 ml) was stirred at room temperature for 23 hours. The reaction mixture was concentrated and water added to the residue. The mixture was neutralized with sodium bicarbonate and extracted with ethyl acetate. The extract was dried over anhydrous sodium sulfate and concentrated. The residue was chromatographed on a silica gel column using ethyl acetate:n-hexane=2:1 as the eluant to afford the desired compound (0.26 g, mp 209–211° C.).

Reference Example 6

5-[4-[6-(4-Amino-3,5-dimethylphenoxy)-1-methyl-1H-benzimidazol-2-ylmethoxy]benzyl]thiazolidine-2,4-dione dihydrochloride A mixture of 5-[4-[6-(4-amino-3,5-dimethylphenoxy)-1-methyl-1H-benzimidazol-2-ylmethoxy]benzyl]thiazolidine-2,4-dione (0.25 g) and 4N hydrogen chloride in ethyl acetate (50 ml) was stirred at room temperature for 24 hours. The insoluble product was filtered and washed with ethyl acetate to afford the desired product (0.25 g, mp 165–175° C.).

Reference Example 7 t-Butyl N-[5-(4-t-butoxycarbonylaminophenoxy)-2-nitrophenyl]-N-methylcarbamate

The desired compound (7.7 g, $R_f$=0.33: thin layer chromatography on a silica gel plate using toluene:diisopropyl ether=10:1 as the eluant) was obtained by a similar procedure to that described in Reference Example 1 using t-butyl (4-hydroxyphenyl)carbamate (15.6 g), t-butyl N-(5-chloro-2-nitrophenyl)-N-methylcarbamate (21 g), sodium hydride (3.22 g, 55% w/w) and anhydrous N,N-dimethylformamide (130 ml).

Reference Example 8 t-Butyl N-[2-amino-5-(4-t-butoxycarbonylaminophenoxy)phenyl]-N-methylcarbamate

The desired compound (26.2 g, $R_f$=0.37: thin layer chromatography on a silica gel plate using c-hexane:tetrahydrofuran=2:1 as the eluant) was obtained by a similar procedure to that described in Reference Example 2 using t-butyl N-[5-(4-t-butoxycarbonylaminophenoxy)-2-nitrophenyl]-N-methylcarbamate (27.7 g), 10% palladium on carbon (1.07 g) and a mixture of tetrahydrofuran and ethyl acetate (9:8, 170 ml).

Reference Example 9 t-Butyl N-[5-(4-t-butoxycarbonylaminophenoxy)-2-[4-(2,4-dioxothiazolidin 5-ylmethyl)phenoxyacetylamino]phenyl]-N-methylcarbamate The desired compound (395 mg, $R_f$=0.51: thin layer chromatography on a silica gel plate using n-hexane:ethyl acetate=2:3 as the eluant) was obtained by a similar procedure to that described in Reference Example 4 using t-butyl N-[2-amino-5-(4-t-butoxycarbonylaminophenoxy)phenyl]-N-methylcarbamate (500 mg), 4-(2,4-dioxothiazolidin-5-ylmethyl)phenoxyacetic acid (366 mg), diethyl cyanophosphonate (212 mg), triethylamine (132 mg) and anhydrous tetrahydrofuran (10 ml).

Reference Example 10

5-[4-6-(4-Aminophenoxy)-1-methyl-1H-benzimidazol-2-ylmethoxy]benzyl]thiazolidine-2,4-dione dihydrochloride To a solution of t-butyl N-[5-(4-t-butoxycarbonylaminophenoxy)-2-[4-(2,4-dioxothiazolidin-5-ylmethyl)phenoxyacetylamino]phenyl]-N-methylcarbamate (27.08 g) in 1,4-dioxane was added 4N hydrogen chloride in 1,4-dioxane (150 ml). The mixture was stirred at room temperature for 2 days. The insoluble product was filtered an d washed with ethyl acetate to afford the desired compound (14.43 g, mp 195° C. (dec)).

Reference Example 11 t-Butyl N-[5-[4-(t-butoxycarbonyl-n-hexylamino)phenoxy]-2-nitrophenyl]-N-methylcarbamate To a suspension of sodium hydride (1.26 g 55% w/w) in anhydrous N,N-dimethylformamide (100 ml) was added t-butyl N-[5-(4-t-butoxycarbonylaminophenoxy)-2-nitrophenyl]-N-methylcarbamate (12.1 g). The mixture was stirred at room temperature for several minutes. To this mixture was added hexyl bromide (6.5 g) in an ice bath and the mixture was stirred for 30 minutes and then at room temperature for 1 hour. The reaction mixture was concentrated and partitioned between ethyl acetate and water. The extract was dried over anhydrous sodium sulfate and concentrated. The residue was chromatographed on a silica gel column using toluene:diisopropyl ether=100:7 as the eluant to afford the desired compound (13.8 g). $R_f$=0.32: thin layer chromatography on a silica gel plate using toluene/diisopropyl ether=100:7 as the eluant.

Reference Example 12 t-Butyl N-[2-amino-5-[4-(t-butoxycarbonyl-n-hexylamino)phenoxy]phenyl]-N-methylcarbamate The title compound (13.1 g, $R_f$=0.44: thin layer chromatography on a silica gel plate using toluene:ethyl acetate=3:1 as the eluant) was obtained by a similar procedure to that described in Reference Example 3 using t-butyl N-[5-[4-(t-butoxycarbonyl-n-hexylamino)phenoxy]-2-nitrophenyl]-N-methylcarbamate (13.2 g), 10% palladium on carbon (1.0 g) and a mixture of toluene:ethyl acetate (140 ml 1:1).

Reference Example 13

5-[4-[6-(4-n-Hexylaminophenoxy)-1-methyl-1H-benzimidazol-2-ylmethoxy]benzyl]thiazolidine-2,4-dione A mixture of t-butyl N-[2-amino-5-(4-t-butoxycarbonyl-n-hexylaminophenoxy)phenyl]-N-methylcarbamate (4.10 g), 4-(2,4-dioxothiazolidin-5-ylmethyl)phenoxyacetic acid (2.81 g), diethyl cyanophosphonate (1.63 g), triethylamine (1.01 g) and anhydrous tetrahydrofuran (100 ml) was stirred at room temperature for 28 hours. The reaction mixture was concentrated and partitioned between ethyl acetate and water. The extract was dried over anhydrous sodium sulfate and concentrated. To the residue was added 4N hydrogen chloride in 1,4-dioxane (50 ml) and the mixture was stirred at room temperature for 66 hours. To the reaction mixture was added water and this mixture was neutralized with sodium bicarbonate and extracted with ethyl acetate. The extract was dried over sodium sulfate and concentrated. The residue was chromatographed on a silica gel column using ethyl acetate:n-hexane=3:2 as the eluant to afford the desired compound (2.89 g, mp 177–179° C.).

Reference Example 14 t-Butyl N-[5-(3-t-butoxycarbonylaminophenoxy)-2-nitrophenyl]-N-methylcarbamate

The desired compound (20.1 g, $R_f$=0.25: thin layer chromatography on a silica gel plate using toluene:diisopropyl ether=10:1 as the eluant) was obtained by a similar procedure to that described in Reference Example 1 using t-butyl (3-hydroxyphenyl)carbamate (15.8 g), t-butyl N-(5-chloro-2-nitrophenyl)-N-methylcarbamate (18.1 g), sodium hydride (3.3 g, 55% w/w) and anhydrous N,N-dimethylformamide (130 ml).

Reference Example 15 t-Butyl N-[2-amino-5-(3-t-butoxycarbonylaminophenoxy)phenyl]-N-methylcarbamate

The desired compound (11.7 g, $R_f$=0.30: thin layer chromatography on a silica gel plate using n-hexane:tetrahydrofuran=2:1 as the eluant) was obtained by a similar procedure to that described in Reference Example 2 using t-butyl N-[5-(3-t-butoxycarbonylaminophenoxy)-2-nitrophenyl]-N-methylcarbamate (12.6 g), 10% palladium on carbon (1.07 g) and a mixture of tetrahydrofuran, ethyl acetate and toluene (1:1:1, 120 ml).

Reference Example 16

5-[4-[6-(3-Aminophenoxy)-1-methyl-1H-benzimidazol-2-ylmethoxy]benzyl]thiazolidine-2,4-dione dihydrochloride t-Butyl N-[5-(3-t-butoxycarbonylaminophenoxy)-2-[4-(2,4-dioxothiazolidin-5-ylmethyl)phenoxyacetylamino]phenyl]-N-methylcarbamate (16.39 g) was obtained by a similar procedure to that described in Reference Example 4 using t-butyl N-[2-amino-5-(3-t-butoxycarbonylaminophenoxy)phenyl]-N-methylcarbamate (9.83 g), 4-(2,4-dioxothiazolidin-5-ylmethyl)phenoxyacetic acid (8.44 g), diethyl cyanophosphonate (4.95 g), triethylamine (3.07 g) and anhydrous tetrahydrofuran (200 ml).

To a solution of this product in 1,4-dioxane (40 ml) was added 4N hydrogen chloride in 1,4-dioxane (70 ml) and the mixture was stirred at room temperature for 2 hours and allowed to stand overnight. The precipitate was collected by filtration and washed with ethyl acetate to afford the desired compound (9.31 g, mp 146.5–150.8° C.).

Reference Example 17 t-Butyl N-[5-[4-(2-t-butoxycarbonylaminoethyl)phenoxy]-2-nitrophenyl]-N-methylcarbamate The desired compound (12.37 g, $R_f$=0.10: thin layer chromatography on a silica gel plate using ethyl acetate:n-hexane=1:8 as the eluant) was obtained by a similar procedure to that described in Reference Example 1 using t-butyl 2-(4-hydroxyphenyl)ethylcarbamate (10 g), t-butyl N-(5-chloro-2-nitrophenyl)-N-methylcarbamate (9.3 g), sodium hydride (2.0 g, 55% w/w) and anhydrous N,N-dimethylformamide (200 ml).

Reference Example 18 t-Butyl N-[2-amino-5-[4-(2-t-butoxycarbonylaminoethyl)phenoxy]phenyl]-N-methylcarbamate The desired compound (12.05 g, $R_f$=0.74: thin layer chromatography on a silica gel plate using n-hexane:ethyl acetate=1:1 as the eluant) was obtained by a similar procedure to that described in Reference Example 2 using t-butyl N-[5-[4-(2-t-butoxycarbonylaminoethyl)phenoxy]-2-nitrophenyl]-N-methylcarbamate (12.35 g), 10% palladium on carbon (1.5 g) and a mixture of toluene and methanol (2:1, 120 ml).

Reference Example 19 t-Butyl N-[5-[4-(2-t-butoxycarbonylaminoethyl)phenoxy]-2-[4-(2,4-dioxothiazolidin-5-ylmethyl)phenoxyacetylamino]phenyl]-N-methylcarbamate The desired compound (16.2 g, $R_f$=0.11: thin layer chromatography on a silica gel plate using n-hexane:ethyl acetate=2:1 as the eluant) was obtained by a similar procedure to that described in Reference Example 4 using t-butyl N-[2-amino-5-[4-(2-t-butoxycarbonylaminoethyl)phenoxy]phenyl]-N-methylcarbamate (12 g), 4-(2,4-dioxothiazolidin-5-ylmethyl)phenoxyacetic acid (6.52 g), diethyl cyanophosphonate (6.52 g), triethylamine (4.04 g) and anhydrous tetrahydrofuran (150 ml).

Reference Example 20

5-(4-[6-[4-(2-Aminoethyl)phenoxy]-1-methyl-1H-benzimidazol-2-ylmethoxy]benzyl)thiazolidine-2,4-dione dihydrochloride A solution of t-butyl N-[5-[4-(2-t-butoxycarbonylaminoethyl)phenoxy]-2-[4-(2,4-dioxothiazolidin-5-ylmethyl)phenoxyacetylamino]phenyl]-N-methylcarbamate (16.1 g) in trifluoroacetic acid (150 ml) was stirred at 50° C. for 7.5 hours. The trifluoroacetic acid was evaporated and to the residue was added 4N hydrogen chloride in ethyl acetate (150 ml) and 1,4-dioxane (300 ml). The mixture was irradiated with ultrasound at room temperature for 4 hours and allowed to stand overnight. The precipitate was collected by filtration and washed with ethyl acetate to afford the desired compound (11.85 g, mp 244–247° C.).

Reference Example 21 t-Butyl 4-(2-hydroxyethyl)phenylcarbamate

Di-t-butyl dicarbonate (30.6 g) was added to a mixture of 2-(4-aminophenyl)ethanol (15 g), triethylamine (15 g), water (100 ml) and 1,4-dioxane (250 ml). The mixture was stirred at room temperature for 2 hours and then allowed to stand for 4 days. The reaction mixture was partitioned between ethyl acetate and water. The organic layer was washed with saturated aqueous sodium chloride solution, dried over anhydrous sodium sulfate and concentrated. The precipitate was collected by filtration to afford the desired compound (50.2 g, mp 104–105° C.).

Reference Example 22 t-Butyl N-[5-[2-(4-t-butoxycarbonylaminophenyl)ethoxy]-2-nitrophenyl]-N-methylcarbamate The desired compound (16.4 g, $R_f$=0.46: thin layer chromatography on a silica gel plate using ethyl acetate:n-hexane=1:3 as the eluant) was obtained by a similar procedure to that described in Reference Example 1 using t-butyl 4-(2-hydroxyethyl) phenylcarbamate (10 g), t-butyl N-(5-chloro-2-nitrophenyl)-N-methylcarbamate (10 g), sodium hydride (3.9 g, 55% w/w) and anhydrous N,N-dimethylformamide (200 ml).

Reference Example 23 t-Butyl N-[2-amino-5-[2-(4-t-butoxycarbonylaminophenyl)ethoxy]phenyl]-N-methylcarbamate The desired compound (11.7 g, $R_f$=0.35: thin layer chromatography on a silica gel plate using n-hexane:ethyl acetate=2:1 as the eluant) was obtained by a similar procedure to that described in Reference Example 2 using t-butyl N-[5-[2-(4-t-butoxycarbonylaminophenyl)ethoxy]-2-nitrophenyl]-N-methylcarbamate (16.3 g), 10% palladium on carbon (2.0 g) and a mixture of toluene and methanol (3:1, 200 ml).

Reference Example 24 t-Butyl N-[5-[2-(4-t-butoxycarbonylaminophenyl)ethoxy]-2-[4-(2,4-dioxothiazolidin-5-ylmethyl)phenoxyacetylamino]phenyl]-N-methylcarbamate The desired compound (18.3 g, $R_f$=0.25: thin layer chromatography on a silica gel plate using n-hexane:ethyl acetate=3:2 as the eluant) was obtained by a similar procedure to that described in Reference Example 4 using t-butyl N-[2-amino-5-[2-(4-t-butoxycarbonylaminophenyl)ethoxy]phenyl]-N-methylcarbamate (11.5 g), 4-(2,4-dioxothiazolidin-5-ylmethyl)phenoxyacetic acid (9.8 g), diethyl cyanophosphonate (5.7 g), triethylamine (3.54 g) and anhydrous tetrahydrofuran (150 ml).

Reference Example 25

5-(4-[6-[2-(4-Aminophenyl)ethoxy]-1-methyl-1H-benzimidazol-2-ylmethoxy]benzyl)thiazolidine-2,4-dione A solution of t-butyl N-[5-[2-(4-t-butoxycarbonylaminophenyl)ethoxy]-2-[4-(2,4-dioxothiazolidin-5-ylmethyl)phenoxyacetylamino]phenyl]-N-methylcarbamate (18.2 g) in trifluoroacetic acid (100 ml) was stirred at 70° C. for 3.5 hours. The reaction mixture was concentrated, diluted with water, neutralized with sodium bicarbonate and extracted with ethyl acetate. The extract was washed with saturated aqueous sodium chloride solution, dried over anhydrous sodium sulfate and concentrated. The residue was chromatographed on a silica gel column using ethyl acetate as the eluant to afford the desired compound (9.2 g, mp 184–188° C.).

Reference Example 26 t-Butyl (7-hydroxynaphthalen-1-yl)carbamate

Di-t-butyl dicarbonate (65.8 g) was added dropwise to a mixture of 1-amino-7-naphthol (24.0 g), triethylamine (61.0 g), 1,4-dioxane (100 ml) and water (100 ml). The mixture was stirred at room temperature for 23 hours. The reaction mixture was concentrated and partitioned between ethyl acetate and water. The extract was washed with saturated aqueous sodium chloride solution, dried over anhydrous sodium sulfate and concentrated. To a solution of the residue in methanol (370 ml) was added sodium methoxide (7.02 g) in an ice bath. The mixture was stirred at room temperature overnight. The reaction mixture was concentrated and to the residue was added water. The mixture was neutralized with 2N hydrochloric acid and then extracted with ethyl acetate. The extract was washed with saturated aqueous sodium chloride solution, dried over anhydrous sodium sulfate and concentrated. The residue was chromatographed on a silica gel column using ethyl acetate:n-hexane=1:2 as the eluant to afford the desired compound (32.5 g, $R_f$=0.26: thin layer chromatography on a silica gel plate using n-hexane:ethyl acetate=3:1 as the eluant).

Reference Example 27 t-Butyl (7-[3-(t-butoxycarbonylmethylamino-4-nitrophenoxy]naphthalen-1-yl)carbamate The desired compound (28.8 g, $R_f$=0.59: thin layer chromatography on a silica gel plate using ethyl acetate:n-hexane=1:3 as the eluant) was obtained by a similar procedure to that described in Reference Example 1 using t-butyl (7-hydroxynaphthalen-1-yl)carbamate (30.0 g), t-butyl N-(5-chloro-2-nitrophenyl)-N-methylcarbamate (33.1 g), sodium hydride (10.1 g, 55% w/w) and anhydrous N,N-dimethylformamide (400 ml).

Reference Example 28 t-Butyl [7-[4-amino-3-(t-butoxycarbonylmethylamino)phenoxy]naphthalen-1-yl]carbamate The desired compound (14.2 g, $R_f$=0.31: thin layer chromatography on a silica gel plate using n-hexane:ethyl acetate=2:1 as the eluant) was obtained by a similar procedure to that described in Reference Example 2 using t-butyl [7-[3-(t-butoxycarbonylmethylamino)-4-nitrophenoxy]naphthalen-1-yl]carbamate (15.0 g), 10% palladium on carbon (1.5 g) and a mixture of toluene and ethyl acetate (1:1, 160 ml).

Reference Example 29 t-Butyl (7-[3-(t-butoxycarbonylmethylamino)-4-[4-(2,4-dioxothiazolidin-5-ylmethyl)phenoxyacetylamino]phenoxy]naphthalen-1-yl)carbamate The desired compound (20.7 g, $R_f$=0.31: thin layer chromatography on a silica gel plate using n-hexane:ethyl acetate=1:1 as the eluant) was obtained by a similar procedure to that described in Reference Example 4 using t-butyl [7-[4-amino-3-(t-butoxycarbonylmethylamino)phenoxy]naphthalen-1-yl]carbamate (14.2 g), 4-(2,4-dioxothiazolidin-5-ylmethyl)phenoxyacetic acid (9.16 g), diethyl cyanophosphonate (5.31 g), triethylamine (3.30 g) and anhydrous tetrahydrofuran (280 ml).

Reference Example 30

5-[4-[6-(8-Aminonaphthalen-2-yloxy)-1-methyl-1H-benzimidazol-2-ylmethoxy]benzyl]thiazolidine-2,4-dione To a solution of t-butyl (7-[3-(t-butoxycarbonylmethylamino)-4-[4-(2,4-dioxothiazolidin-5-ylmethyl)phenoxyacetylamino]phenoxy]naphthalen-1-yl)carbamate (20.7 g) in anhydrous tetrahydrofuran (200 ml) was added 4N hydrogen chloride in 1,4-dioxane (150 ml). The mixture was stirred at room temperature for 2.5 hours and then allowed to stand overnight. The precipitate was collected by filtration, washed with diethyl ether and then dried under reduced pressure. A solution of the precipitate in trifluoroacetic acid (150 ml) was stirred at 70° C. for 2.5 hours and then allowed to stand at room temperature overnight. The reaction mixture was concentrated, diluted with water, neutralized with sodium bicarbonate and then extracted with ethyl acetate. The extract was washed with saturated aqueous sodium chloride solution, dried over anhydrous sodium sulfate and concentrated. The residue was chromatographed on a silica gel column using ethyl acetate:n-hexane=2:1 as the eluant to afford the desired compound (8.78 g, $R_f$=0.30: thin layer chromatography on a silica gel plate using n-hexane/ethyl acetate=1/2 as the eluant).

Reference Example 31

3-Amino-4-t-butylbenzyl alcohol

A solution of 3-amino-4-t-butylbenzoic acid (10 g) in anhydrous tetrahydrofuran (150 ml) was added dropwise to a suspension of lithium aluminium hydride (4.0 g) in anhydrous tetrahydrofuran (150 ml) over a period of 45 minutes. The mixture was stirred at room temperature for 3 hours. The reaction mixture was diluted with tetrahydrofuran (150 ml) and aqueous sodium hydroxide solution (15%) was added to the mixture while cooling in an ice bath in order to decompose the excess lithium aluminium hydride. The insoluble material was filtered off through Celite (trademark) and the solvent of the filtrate was evaporated under reduced pressure to afford the desired compound (8.41 g, $R_f$=0.55: thin layer chromatography on a silica gel plate using n-hexane:ethyl acetate=1:3 as the eluant).

Reference Example 32

2-(3-amino-4-t-butylphenyl)ethanol

A solution of methyl 2-(3-amino-4-t-butylphenyl)acetate (11.1 g) in anhydrous tetrahydrofuran (70 ml) was added dropwise to a suspension of lithium aluminium hydride (4.0 g) in anhydrous tetrahydrofuran (150 ml) over a period of 15 minutes. The mixture was stirred at room temperature for 1 hour. The reaction mixture was diluted with tetrahydrofuran (150 ml) and aqueous sodium hydroxide solution (15%) was added to the mixture while cooling in an ice bath in order to decompose the excess lithium aluminium hydride. The insoluble material was filtered off through Celite (trademark) and the solvent of the filtrate was evaporated under reduced pressure to afford the desired compound 10.2 g, $R_f$=0.49: thin layer chromatography on a silica gel plate using n-hexane:ethyl acetate=1:3 as the eluant).

Reference Example 33 t-Butyl N-[5-(3-amino-4-t-butyl)benzyloxy-2-nitrophenyl]-N-methylcarbamate

The desired compound (2.01 g, $R_f$=0.43: thin layer chromatography on a silica gel plate using ethyl acetate:n-hexane=1:2 as the eluant) was obtained by a similar procedure to that described in Reference Example 1 using 3-amino-4-t-butylbenzyl alcohol (5.09 g), t-butyl N-(5-chloro-2-nitrophenyl)-N-methylcarbamate (7.40 g), sodium hydride (1.24 g, 55% w/w) and anhydrous N,N-dimethylformamide (120 ml).

Reference Example 34 t-Butyl N-[5-(3-amino-4-t-butylphenyl)ethoxy-2-nitrophenyl]-N-methylcarbamate

The desired compound (2.61 g, $R_f$=0.53: thin layer chromatography on a silica gel plate using ethyl acetate:n-hexane=1:2 as the eluant) was obtained by a similar procedure to that described in Reference Example 1 using 2-(3-amino-4-t-butylphenyl)ethanol (5.03 g), t-butyl N-(5-chloro-2-nitrophenyl)-N-methylcarbamate (6.78 g), sodium hydride (1.14 g, 55% w/w) and anhydrous N,N-dimethylformamide (120 ml).

Reference Example 35 t-Butyl N-[2-amino-5-(3-amino-4-t-butyl)benzyloxy phenyl]-N-methylcarbamate

A mixture of t-butyl N-[5-(3-amino-4-t-butyl) benzyloxyphenyl]-2-nitrophenyl]-N-methylcarbamate (3.02 g), sodium dithionite (4.90 g), sodium bicarbonate (5.91 g), 1,4-dioxane (75 ml) and water (15 ml) was heated at reflux for 30 minutes. The reaction mixture was cooled to room temperature and partitioned between ethyl acetate and water. The extract was washed with saturated aqueous sodium chloride solution, dried over anhydrous sodium sulfate and concentrated. The residue was chromatographed on a silica gel column using ethyl acetate:n-hexane=1:1 as the eluant to afford the desired compound (1.30 g, $R_f$=0.35: thin layer chromatography on a silica gel plate using n-hexane:ethyl acetate=1:1 as the eluant).

Reference Example 36 t-Butyl N-[2-amino-5-(3-amino-4-t-butylphenyl) ethoxyphenyl]-N-methylcarbamate

The desired compound (2.42 g, $R_f$=0.14: thin layer chromatography on a silica gel plate using n-hexane:ethyl acetate=2:1 as the eluant) was obtained by a similar procedure to that described in Reference Example 2 using t-butyl N-[5-(3-amino-4-t-butylphenyl)ethoxy-2-nitrophenyl]-N-methylcarbamate (2.50 g), 10% palladium on carbon (0.25 g) and a mixture of toluene and ethyl acetate (1:1, 50 ml).

Reference Example 37 t-Butyl N-[5-(3-amino-4-t-butyl)benzyloxy-2-[4-(2,4-dioxothiazolidin-5-ylmethyl)phenoxyacetylamino] phenyl]-N-methylcarbamate The desired compound (1.66 g, $R_f$=0.53: thin layer chromatography on a silica gel plate using n-hexane:ethyl acetate=1:2 as the eluant) was obtained by a similar procedure to that described in Reference Example 4 using t-butyl N-[2-amino-5-(3-amino-4-t-butyl)benzyloxyphenyl]-N-methylcarbamate (1.86 g), 4-(2,4-dioxothiazolidin-5-ylmethyl)phenoxyacetic acid (1.44 g), diethyl cyanophosphonate (0.84 g), triethylamine (0.52 g) and anhydrous tetrahydrofuran (40 ml).

Reference Example 38 t-Butyl N-[5-[2-(3-amino-4-t-butylphenyl)ethoxy-2-[4-(2,4-dioxothiazolidin-5-ylmethyl) phenoxyacetylamino]phenyl]-N-methylcarbamate The desired compound (3.20 g, $R_f$=0.40: thin layer chromatography on a silica gel plate using n-hexane:ethyl acetate=1:2 as the eluant) was obtained by a similar procedure to that described in Reference Example 4 using t-butyl N-[2-amino-5-(3-amino-4-t-butylphenyl)ethoxyphenyl]-N-methylcarbamate (2.33 g), 4-(2,4-dioxothiazolidin-5-ylmethyl)phenoxyacetic acid (2.36 g), diethyl cyanophosphonate (1.37 g), triethylamine (0.85 g) and anhydrous tetrahydrofuran (45 ml).

Reference Example 39

5-[4-[6-(3-Amino-4-t-butyl)benzyloxy-1-methyl-1H-benzimidazol-2-ylmethoxy]benzyl]thiazolidine-2,4-dione dihydrochloride To a solution of t-butyl N-[5-(3-amino-4-t-butyl) benzyloxy-2-[4-(2,4-dioxothiazolidin-5-ylmethyl) phenoxyacetylamino]phenyl]-N-methylcarbamate (1.60 g) in a mixture of 1,4-dioxane and ethanol (1:1, 20 ml) was added 4N hydrogen chloride in 1,4-dioxane (10 ml). The mixture was stirred at room temperature for 4 hours and then allowed to stand overnight. The precipitate was collected by filtration and washed with ethyl acetate to afford the desired compound (1.28 g, mp 152–157° C.).

Reference Example 40

5-[4-[6-[2-(3-Amino-4-t-butylphenyl)ethoxy-1-methyl-1H-benzimidazol-2-ylmethoxy]benzyl] thiazolidine-2,4-dione dihydrochloride To a solution of t-butyl N-[5-[2-(3-amino-4-t-butylphenyl)ethoxy-2-[4-(2,4-dioxothiazolidin-5-ylmethyl)

phenoxyacetylamino]phenyl]-N-methylcarbamate (3.08 g) in 1,4-dioxane (30 ml) was added 4N hydrogen chloride in 1,4-dioxane (30 ml). The mixture was allowed to stand at room temperature overnight. To this mixture was added further ethanol (40 ml) and the solution was allowed to stand for 6 days. The precipitate was collected by filtration and washed with ethyl acetate to afford the desired compound (2.48 g, mp 163–167° C.).

Reference Example 41

2-Chloromethyl-5-(3,5-dimethylphenylthio)-3-methyl-3H-imidazo[4,5-b]pyridine

A mixture of 3,5-dimethylbenzenethiol (41.3 g), 6-chloro-2-methylamino-3-nitropyridine (56.1 g), potassium carbonate (207 g) and anhydrous N,N-dimethylformamide (300 ml) was stirred at 80° C. for 1.5 hours. The reaction mixture was concentrated and partitioned between ethyl acetate and water. The extract was dried over anhydrous sodium sulfate and concentrated. To a solution of the residue in a mixture of ethanol and toluene (1:1, 600 ml) was added 10% palladium on carbon (41.1 g) and the mixture was vigorously stirred under a hydrogen atmosphere at room temperature for 4 hours. The catalyst was removed by filtration and the filtrate was concentrated. To the residue was added glycolic acid (68.4 g) and the mixture was heated at 150° C. for 1.5 hours, 3N hydrochloric acid (200 ml) was added, and the mixture was then heated at reflux for 1 hour. The reaction mixture was neutralized with aqueous sodium bicarbonate solution (10%). The precipitate was isolated by filtration, washed with water and ethyl acetate and then dried under reduced pressure to give 5-(3,5-dimethylphenylthio)-2-hydroxymethyl-3-methyl-3H-imidazo[4,5-b]pyridine. A solution of the product in thionyl chloride (150 ml) was stirred in a bath at 80° C. for 30 minutes. The reaction mixture was concentrated, diluted with water, neutralized with sodium bicarbonate and then extracted with ethyl acetate. The extract was dried over anhydrous sodium sulfate and concentrated. The residue was chromatographed on a silica gel column using ethyl acetate:n-hexane=1:1 as the eluant to afford the desired compound (54.3 g, mp 87–90° C.).

Reference Example 42

2-Chloromethyl-5-(3,5-dimethyl-4-nitrophenylthio)-3-methyl-3H-imidazo[4,5-b]pyridine To a mixture of 2-chloromethyl-5-(3,5-dimethylphenylthio)-3-methyl-3H-imidazo[4,5-b]pyridine (2.54 g), sulfuric acid (5 ml) and acetic acid (45 ml) was added nitric acid (0.52 ml) in an ice bath. The mixture was allowed to stand at room temperature for 64 hours. The reaction mixture was concentrated, diluted with water, neutralized with sodium bicarbonate and then extracted with ethyl acetate. The extract was concentrated. The residue was chromatographed on a silica gel column using ethyl acetate:n-hexane=1:1 as the eluant to afford the desired compound (0.53 g, mp 133–135° C.).

Reference Example 43

5-[4-[5-(3,5-Dimethyl-4-nitrophenylthio)-3-methyl-3H-imidazo[4,5-b]pyridin-2-ylmethoxy]benzyl]thiazolidine-2,4-dione To a suspension of sodium hydride (0.12 g, 55% w/w) in N,N-dimethylformamide (6 ml) was added 5-(4-hydroxybenzyl)thiazolidine-2,4-dione (0.31 g). The mixture was stirred at room temperature for 20 minutes. To the reaction mixture was added dropwise a solution of 2-chloromethyl-5-(3,5-dimethyl-4-nitrophenylthio)-3-methyl-3H-imidazo[4,5-b]pyridine (0.51 g) in anyhdrous N,N-dimethylformamide (14 ml). The mixture was stirred at room temperature for 15 hours. The reaction mixture was concentrated and neutralized with 3N hydrochloric acid and sodium bicarbonate and then extracted with ethyl acetate. The extract was dried over anhydrous sodium sulfate and concentrated. The residue was chromatographed on a silica gel column using ethyl acetate as the eluant to afford the desired compound (0.39 g, $R_f$=0.60: thin layer chromatography on a silica gel plate using ethyl acetate as the eluant).

[Test Example] Blood Sugar Lowering Effect

Blood samples were collected from the caudal vein of KK mice (age 4–5 months) with diabetes followed by measurement of their blood sugar levels. Next, after assigning the mice to groups (of 4 mice each) so that the mean blood sugar levels of each group were the same, mouse laboratory powder diet (F-1, Funabashi Farms), prepared so as to contain 0.01% of the test compound, was given to the mice for 3 days. The groups of mice that were given test compound were designated as the drug dose groups. It should be noted that a group that was given laboratory diet not containing the test compound was designated as the control group. Blood samples were collected from the caudal vein of the mice 3 days later and the glucose concentration of the plasma obtained by centrifugal separation was measured with a glucose analyzer (Glucoloader, A & T Corp.). The mean decrease of blood sugar rate (%) was determined according to the following equation.

Blood sugar decrease rate (%)=(mean blood sugar value of control group−mean blood sugar value decrease of drug dose group)×100/(blood sugar value of control group)

TABLE 7

| Test compound | Blood sugar decrease rate (%) |
|---|---|
| Compound of example | |
| 2 | 48.9 |
| 3 | 49.9 |
| 4 | 48.6 |
| 5 | 36.2 |
| 9 | 47.1 |
| 11 | 32.9 |
| 12 | 56.1 |
| 14 | 63.2 |
| 16 | 42.9 |
| 18 | 61.0 |
| 31 | 50.5 |
| 33 | 30.4 |
| 34 | 32.8 |
| 37 | 35.2 |
| 40 | 59.3 |
| 44 | 47.2 |
| 45 | 54.1 |
| 52 | 58.5 |
| 53 | 59.6 |
| 54 | 43.4 |
| 55 | 53.8 |
| 56 | 63.6 |
| 57 | 57.3 |
| 59 | 56.8 |
| 60 | 49.8 |
| 61 | 54.2 |

TABLE 7-continued

| Test compound | Blood sugar decrease rate (%) |
|---|---|
| 63 | 55.7 |
| 64 | 43.5 |

The above results show superior blood sugar lowering effects.

Formulation Examples (1) Capsule

| Compound of Example 2 | 10 mg |
|---|---|
| Lactose | 110 mg |
| Corn starch | 58 mg |
| Magnesium stearate | 2 mg |
| | 180 mg |

Powders of each component indicated above were mixed well and passed through a 60 mesh sieve (mesh standards are in accordance with the Tyler standards). The resulting powder is filled into a gelatin capsule (No. 3) to prepare the capsule.

(2) Tablet

| Compound of Example 2 | 10 mg |
|---|---|
| Lactose | 85 mg |
| Corn starch | 34 mg |
| Microcrystalline cellulose | 20 mg |
| Magnesium stearate | 1 mg |
| | 150 mg |

Powders of each component indicated above are mixed well and compressed into a tablet. The capsule may be coated with sugar or a film if necessary.

(3) Granule

| Compound of Example 2 | 10 mg |
|---|---|
| Lactose | 839 mg |
| Corn starch | 150 mg |
| Hydroxypropyl cellulose | 1 mg |
| | 1000 mg |

Powders of each component indicated above are mixed well, moistened with pure water and then granulated with a basket granulating machine followed by drying to obtain a granule.

The compounds of the above-mentioned formula (I) of the present invention or their pharmacologically acceptable salts have superior insulin tolerance ameliorating effects, blood sugar lowering effects, anti-inflammatory effects, immunoregulatory effects, aldose reductase inhibitory effects, 5-lipoxygenase inhibitory effects, lipid peroxide formation inhibitory effects, PPAR activation effects, antiosteoporosis effects, leukotriene antagonistic effects, fat cell promotion effects, cancer cell proliferation inhibitory effects and calcium antagonistic effects, and are useful for treatment and/or prophylaxis of diseases such as diabetes, hyperlipemia, obesity, impaired glucose tolerance, hypertension, fatty liver, diabetic complications (including retinopathy, nephropathy, neuropathy, cataracts and coronary disease), arteriosclerosis, pregnancy diabetes, polycystic ovary syndrome, cardiovascular diseases (such as ischemic heart diseases), cell injury induced by non-atherosclerosis or ischemic heart disease (such as brain injury induced by stroke), gout, inflammatory diseases (including arthritis, pain, pyrexia, rheumatoid arthritis, inflammatory enteritis, acne, sunburn, psoriasis, eczema, allergic diseases, asthma, GI ulcer, cachexia, autoimmune diseases and pancreatitis), cancer, osteoporosis and cataracts. Further, the combination of (i) at least one compound of the formula (I) or a pharmacologically acceptable salt thereof and (ii) at least one selected from an α-glucosidase inhibitory agent, aldose reductase inhibitory agent, biguanide agent, statin compound, squalene synthesis inhibitory agent, fibrate compound, LDL disassimilation promoter, angiotensin converting enzyme inhibitory agent and FBPase inhibitory agent are also useful for the treatment and/or prophylaxis of said diseases, and particularly for the treatment and/or prevention of diabetes and diabetic complications.

What is claimed is:

1. An amine compound of the formula (I):

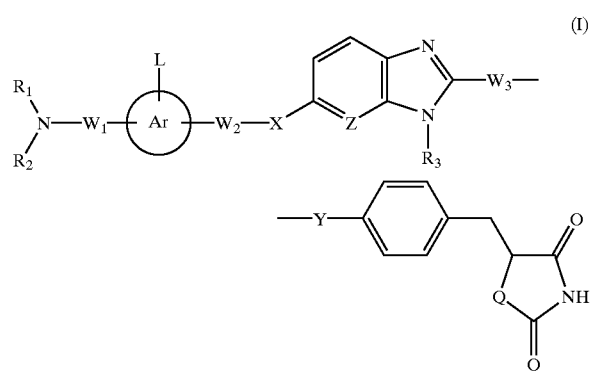

wherein:
  $R_1$ represents a carbamoyl group (which may have one or two substituents α described later), a thiocarbamoyl group (which may have one or two substituents α described later), a sulfonyl group (which has one substituent α described later) or a carbonyl group (which has one substituent α described later);
  $R_2$ and $R_3$ each represent a hydrogen atom, a $C_1$–$C_{10}$ alkyl group, a $C_6$–$C_{10}$ aryl group (which may have from 1 to 3 substituents β described later) or a $C_7$–$C_{16}$ aralkyl group (which may have from 1 to 3 substituents β described later on the aryl portion);
  $W_1$, $W_2$ and $W_3$ each represent a single bond or a $C_1$–$C_8$ alkylene group;
  X, Y and Q each represent an oxygen atom or a sulfur atom;
  Z represents a =CH— group or a nitrogen atom;
  Ar represents a benzene ring or a naphthalene ring;
  L represents from 1 to 4 substituents on the Ar ring and the or each substituent is a hydrogen atom, a $C_1$–$C_6$ alkyl group, a $C_6$–$C_{10}$ aryl group (which may have from 1 to 3 substituents β described later) or a $C_7$–$C_{16}$ aralkyl group (which may have from 1 to 3 substituents β described later on the aryl portion);
  the substituent α represents (i) a $C_1$–$C_{10}$ alkyl group, (ii) a $C_1$–$C_6$ halogenoalkyl group, (iii) a $C_3$–$C_{10}$ cycloalkyl group, (iv) a $C_6$–$C_{10}$ aryl group (which may have from 1 to 3 substituents γ described later), (v) a $C_7$-$C_{16}$ aralkyl group (which may have from 1 to 3 substituents γ described later on the aryl portion), (vi) a $C_4$-$C_{11}$ cycloalkylcarbonyl group, (vii) a $C_7$–$C_{11}$ arylcarbonyl group (which may have from 1 to 3 substituents γ described later on the aryl portion), (viii) a $C_8$–$C_{17}$ aralkylcarbonyl group (which may have from 1 to 3 substituents γ described later on the aryl portion), (ix) an aromatic heterocyclic group (which may have from 1 to 3 substituents γ described later), (x) an aromatic heterocyclic carbonyl group (which may have from 1 to 3 substituents γ described later), (xi) a $C_1$–$C_6$ alkylsulfonyl group, (xii) a $C_1$–$C_6$ halogenoalkylsulfonyl group, (xiii) a $C_6$–$C_{10}$ arylsulfonyl group (which may have from 1 to 3 substituents γ described later on the aryl portion), or (xiv) a $C_7$-$C_{16}$ aralkylsulfonyl group (which may have from 1 to 3 substituents γ described later on the aryl portion);

the substituent β represents (i) a $C_1$–$C_6$ alkyl group, (ii) a $C_1$–$C_6$ halogenoalkyl group, (iii) a $C_1$–$C_6$ alkoxy group, (iv) a halogen atom, (v) a hydroxyl group, (vi) a $C_6$–$C_{10}$ aryl group (which may have from 1 to 3 substituents δ described later), (vii) a $C_7$–$C_{16}$ aralkyl group (which may have from 1 to 3 substituents δ described later on the aryl portion), (viii) a cyano group, (ix) a nitro group, or (x) an amino group (which may have one or two substituents δ described later);

the substituent γ represents (i) a $C_1$–$C_6$ alkyl group, (ii) a $C_1$–$C_6$ halogenoalkyl group, (iii) a $C_1$–$C_6$ alkoxy group, (iv) a halogen atom, (v) a hydroxyl group, (vi) a cyano group, (vii) a nitro group, (viii) a $C_3$–$C_{10}$ cycloalkyl group, (ix) a $C_6$–$C_{10}$ aryl group (which may have from 1 to 3 $C_1$–$C_6$ alkyl groups, $C_1$–$C_6$ halogenoalkyl groups, $C_1$–$C_6$ alkoxy groups or halogen atoms as the substituents), (x) a $C_7$–$C_{16}$ aralkyl group (which may have from 1 to 3 $C_1$–$C_6$ alkyl groups, $C_1$–$C_6$ halogenoalkyl groups, $C_1$–$C_6$ alkoxy groups or halogen atoms as the substituents on the aryl portion), (xi) a $C_1$–$C_7$ aliphatic acyl group, (xii) a $C_1$–$C_7$ aliphatic acyloxy group, (xiii) an amino group, (xiv) a di-($C_1$–$C_6$ alkyl)amino group or (xv) a $C_1$–$C_4$ alkylenedioxy group;

the substituent δ represents (i) a $C_1$–$C_{10}$ alkyl group, (ii) a $C_6$–$C_{10}$ aryl group (which may have from 1 to 3 $C_1$–$C_6$ alkyl groups, $C_1$–$C_6$ halogenoalkyl groups, $C_1$–$C_6$ alkoxy groups or halogen atoms as the substituents), (iii) a $C_7$–$C_{16}$ aralkyl group (which may have from 1 to 3 $C_1$–$C_6$ alkyl groups, $C_1$–$C_6$ halogenoalkyl groups, $C_1$–$C_6$ alkoxy groups or halogen atoms as the substituents on the aryl portion), (iv) a $C_1$–$C_7$ aliphatic acyl group, (v) a $C_4$–$C_{11}$ cycloalkylcarbonyl group, (vi) a $C_7$–$C_{11}$ arylcarbonyl group (which may have from 1 to 3 $C_1$–$C_6$ alkyl groups, $C_1$–$C_6$ halogenoalkyl groups, $C_1$–$C_6$ alkoxy groups or halogen atoms as the substituents), (vii) a $C_8$–$C_{17}$ aralkylcarbonyl group (which may have from 1 to 3 $C_1$–$C_6$ alkyl groups, $C_1$–$C_6$ halogenoalkyl groups, $C_1$–$C_6$ alkoxy groups or halogen atoms as the substituents on the aryl portion), (viii) an aromatic heterocyclic carbonyl group (which may have from 1 to 3 $C_1$–$C_6$ alkyl groups, $C_1$–$C_6$ halogenoalkyl groups, $C_1$–$C_6$ alkoxy groups or halogen atoms as the substituents);

or a pharmacologically acceptable salt thereof.

2. The amine compound or pharmacologically acceptable salt thereof according to claim 1, wherein $R_1$ represents a carbamoyl group (which may have one substituent α), a thiocarbamoyl group (which may have one substituent α), a sulfonyl group (which has one substituent α) or a carbonyl group (which has one substituent α).

3. The amine compound or pharmacologically acceptable salt thereof according to claim 1, wherein $R_1$ represents a carbamoyl group (which has one substituent α), a thiocarbamoyl group (which has one substituent α), a sulfonyl group (which has one substituent α) or a carbonyl group (which has one substituent α).

4. The amine compound or pharmacologically acceptable salt thereof according to claim 1, wherein $R_1$ represents a carbamoyl group (which has one substituent α).

5. The amine compound or pharmacologically acceptable salt thereof according to claim 1, wherein $R_1$ represents a carbonyl group (which has one substituent α).

6. The amine compound or pharmacologically acceptable salt thereof according to claim 1, wherein $R_2$ represents a hydrogen atom, a $C_1$–$C_{10}$ alkyl group, a phenyl group (which may have one substituent β) or a benzyl group (which may have one substituent β on the phenyl portion).

7. The amine compound or pharmacologically acceptable salt thereof according to claim 1, wherein $R_2$ represents a hydrogen atom or a $C_1$–$C_{10}$ alkyl group.

8. The amine compound or pharmacologically acceptable salt thereof according to claims 1, wherein $R_2$ represents a hydrogen atom.

9. The amine compound or pharmacologically acceptable salt thereof according to claim 1, wherein $R_2$ represents a $C_1$–$C_6$ alkyl group.

10. The amine compound or pharmacologically acceptable salt thereof according to claim 1, wherein $R_3$ represents a hydrogen atom, a $C_1$–$C_6$ alkyl group, a phenyl group (which may have one substituent β) or a benzyl group (which may have one substituent β on the phenyl portion).

11. The amine compound or pharmacologically acceptable salt thereof according to claim 1, wherein $R_3$ represents a hydrogen atom or a $C_1$–$C_4$ alkyl group.

12. The amine compound or pharmacologically acceptable salt thereof according to claim 1, wherein $R_3$ represents a $C_1$–$C_2$ alkyl group.

13. The amine compound or pharmacologically acceptable salt thereof according to claim 1, wherein $W_1$, $W_2$ and $W_3$ each represent a single bond or a $C_1$–$C_4$ alkylene group.

14. The amine compound or pharmacologically acceptable salt thereof according to claim 1, wherein $W_1$ and $W_2$ each represent a single bond or a $C_1$–$C_4$ alkylene group, and $W_3$ represents a $C_1$–$C_2$ alkylene group.

15. The amine compound or pharmacologically acceptable salt thereof according to claim 1, wherein $W_1$ and $W_2$ each represent a single bond or a $C_1$–$C_2$ alkylene group, and $W_3$ represents a methylene group.

16. The amine compound or pharmacologically acceptable salt thereof according to claim 1, wherein X represents an oxygen atom or a sulfur atom, Y represents an oxygen atom and Q represents a sulfur atom.

17. The amine compound or pharmacologically acceptable salt thereof according to claim 1, wherein X represents an oxygen atom, Y represents an oxygen atom and Q represents a sulfur atom.

18. The amine compound or pharmacologically acceptable salt thereof according to claim 1, wherein Z represents a =CH— group.

19. The amine compound or pharmacologically acceptable salt thereof according to claim 1, wherein Z represents a nitrogen atom.

20. The amine compound or the pharmacologically acceptable salt thereof according claim 1, wherein Ar represents a naphthalene ring.

21. The amine compound or pharmacologically acceptable salt thereof according to claim 1, wherein Ar represents a benzene ring.

22. The amine compound or pharmacologically acceptable salt thereof according to claim 1, wherein L represents from 1 to 4 substituents on the Ar ring and the or each substituent is a hydrogen atom, a $C_1$–$C_6$ alkyl group, a phenyl group (which may have from 1 to 3 substituents β) or a benzyl group (which may have from 1 to 3 substituents β on the phenyl portion).

23. The amine compound or pharmacologically acceptable salt thereof according to claim 1, wherein L represents from 1 to 4 substituents on the Ar ring and the or each substituent is a hydrogen atom or a $C_1$–$C_6$ alkyl group.

24. The amine compound or pharmacologically acceptable salt thereof according to claim 1, wherein L represents a hydrogen atom.

25. The amine compound or pharmacologically acceptable salt thereof according to claim 1, wherein substituent α represents (i) a $C_1$–$C_8$ alkyl group, (ii) a $C_5$–$C_{10}$ cycloalkyl group, (iii) a $C_6$–$C_{10}$ aryl group (which may have from 1 to 3 substituents γ), (iv) a phenyl-$C_1$–$C_4$ alkyl group (which may have from 1 to 3 substituents γ on the phenyl portion), (v) a pyridyl group or (vi) a phenylsulfonyl group (which may have from 1 to 3 substituents γ on the phenyl portion).

26. The amine compound or pharmacologically acceptable salt thereof according to claim 1, wherein substituent α represents (i) a $C_1$–$C_4$ alkyl group, (ii) a $C_5$–$C_{10}$ cycloalkyl group, (iii) a $C_6$–$C_{10}$ aryl group (which may have from 1 to 3 substituents γ), (iv) a benzyl group (which may have from 1 to 3 substituents γ on the phenyl portion) or (v) a pyridyl group.

27. The amine compound or pharmacologically acceptable salt thereof according to claim 1, wherein substituent α represents (i) a $C_1$–$C_4$ alkyl group, (ii) a $C_5$–$C_{10}$ cycloalkyl group, (iii) a $C_6$–$C_{10}$ aryl group (which may have from 1 to 3 substituents γ), (iv) a benzyl group (which may have from 1 to 3 substituents γ on the phenyl portion) or (v) a pyridyl group.

28. The amine compound or pharmacologically acceptable salt thereof according to claim 1, wherein substituent a represents a phenyl group (which may have from 1 to 3 substituents γ).

29. The amine compound or pharmacologically acceptable salt thereof according to claim 1, wherein substituent β represents (i) a $C_1$–$C_4$ alkyl group, (ii) a trifluoromethyl group, (iii) a $C_1$–$C_2$ alkoxy group, (iv) a halogen atom, (v) a hydroxyl group or (vi) an amino group.

30. The amine compound or pharmacologically acceptable salt thereof according to claim 1, wherein substituent β represents (i) a $C_1$–$C_4$ alkyl group, (ii) a halogen atom or (iii) a hydroxyl group.

31. The amine compound or pharmacologically acceptable salt thereof according to claim 1, wherein substituent γ represents (i) a $C_1$–$C_6$ alkyl group, (ii) a $C_1$–$C_2$ halogenoalkyl group, (iii) a $C_1$–$C_4$ alkoxy group, (iv) a halogen atom, (v) a hydroxyl group, (vi) a cyano group, (vii) a nitro group, (viii) a $C_1$–$C_2$ aliphatic acyl group or (ix) a $C_1$–$C_4$ alkylenedioxy group.

32. The amine compound or pharmacologically acceptable salt thereof according to claim 1, wherein substituent γ represents (i) a $C_1$–$C_6$ alkyl group, (ii) a trifluoromethyl group, (iii) a $C_1$–$C_4$ alkoxy group, (iv) a halogen atom, (v) a hydroxyl group, (vi) a cyano group, (vii) a nitro group, (viii) a $C_1$–$C_2$ aliphatic acyl group or (ix) a $C_1$–$C_4$ alkylenedioxy group.

33. The amine compound or pharmacologically acceptable salt thereof according to claim 1, wherein the substituent γ represents (i) a $C_1$–$C_4$ alkyl group, (ii) a trifluoromethyl group, (iii) a halogen atom or (iv) a nitro group.

34. The amine compound or pharmacologically acceptable salt thereof according to claim 1, wherein substituent δ represents (i) a $C_1$–$C_4$ alkyl group, (ii) a phenyl group, (iii) a benzyl group, (iv) a $C_1$–$C_5$ aliphatic acyl group or (v) a benzoyl group.

35. The amine compound or pharmacologically acceptable salt thereof according to claim 1, wherein substituent δ represents a $C_1$–$C_4$ alkyl group or a $C_1$–$C_2$ aliphatic acyl group.

36. The amine compound or pharmacologically acceptable salt thereof according to claim 1, wherein:

$R_1$ represents a carbamoyl group (which may have one substituent α), a thiocarbamoyl group (which may have one substituent α), a sulfonyl group (which has one substituent α) or a carbonyl group (which has one substituent α);

$R_2$ represents a hydrogen atom, a $C_1$–$C_{10}$ alkyl group, a phenyl group (which may have one substituent β) or a benzyl group (which may have one substituent β on the phenyl portion);

$R_3$ represents a hydrogen atom, a $C_1$–$C_6$ alkyl group, a phenyl group (which may have one substituent β) or a benzyl group (which may have one substituent β on the phenyl portion);

$W_1$, $W_2$ and $W_3$ each represent a single bond or a $C_1$–$C_4$ alkylene group;

X represents an oxygen atom or a sulfur atom, Y represents an oxygen atom and Q represents a sulfur atom;

Z represents a =CH— group;

Ar represents a benzene ring;

L represents from 1 to 4 substituents on the Ar ring and the or each substituent is a hydrogen atom, a $C_1$–$C_6$ alkyl group, a phenyl group (which may have from 1 to 3 substituents β) or a benzyl group (which may have from 1 to 3 substituents β on the phenyl portion);

substituent a represents (i) a $C_1$–$C_8$ alkyl group, (ii) a $C_5$–$C_{10}$ cycloalkyl group, (iii) a $C_6$–$C_{10}$ aryl group (which may have from 1 to 3 substituents γ), (iv) a phenyl-$C_1$–$C_4$ alkyl group (which may have from 1 to 3 substituents γ on the phenyl portion), (v) a pyridyl group, (vi) a methanesulfonyl group, (vii) a trifluoromethanesulfonyl group or (viii) a phenylsulfonyl group (which may have from 1 to 3 substituents γ on the phenyl portion);

substituent β represents (i) a $C_1$–$C_4$ alkyl group, (ii) a trifluoromethyl group, (iii) a $C_1$–$C_2$ alkoxy group, (iv) a halogen atom, (v) a hydroxyl group or (vi) an amino group; and substituent γ represents (i) a $C_1$–$C_6$ alkyl group, (ii) a $C_1$–$C_4$ halogenoalkyl group, (iii) a $C_1$–$C_6$ alkoxy group, (iv) a halogen atom, (v) a hydroxyl group, (vi) a cyano group, (vii) a nitro group, (viii) a phenyl group, (ix) a benzyl group, (x) a $C_1$–$C_5$ aliphatic acyl group, (xi) an amino group or (xii) a $C_1$–$C_4$ alkylenedioxy group.

37. The amine compound or pharmacologically acceptable salt thereof according to claim 1, wherein:

$R_1$ represents a carbamoyl group (which has one substituent α), a thiocarbamoyl group (which has one substituent α), a sulfonyl group (which has one substituent α) or a carbonyl group (which has one substituent α);

$R_2$ represents a hydrogen atom or a $C_1$–$C_{10}$ alkyl group;

$R_3$ represents a hydrogen atom or a $C_1$–$C_4$ alkyl group;

129

W₁ and W₂ each represent a single bond or a $C_1$–$C_4$ alkylene group and W₃ represents a $C_1$–$C_2$ alkylene group;

X represents an oxygen atom or a sulfur atom, Y represents an oxygen atom and Q represents a sulfur atom;

Z represents a =CH— group;

Ar represents a benzene ring;

L represents from 1 to 4 substituents on the Ar ring and the or each substituent is a hydrogen atom or a $C_1$–$C_4$ alkyl group;

substituent α represents (i) a $C_1$–$C_8$ alkyl group, (ii) a $C_5$–$C_{10}$ cycloalkyl group, (iii) a $C_6$–$C_{10}$ aryl group (which may have from 1 to 3 substituents γ), (iv) a phenyl-$C_1$–$C_4$ alkyl group (which may have from 1 to 3 substituents γ on the phenyl portion), (v) a pyridyl group or (vi) a phenylsulfonyl group (which may have from 1 to 3 substituents γ on the phenyl portion); and substituent γ represents (i) a $C_1$–$C_6$ alkyl group, (ii) a trifluoromethyl group, (iii) a $C_1$–$C_4$ alkoxy group, (iv) a halogen atom, (v) a hydroxyl group, (vi) a cyano group, (vii) a nitro group, (viii) a $C_1$–$C_2$ aliphatic acyl group or (ix) a $C_1$–$C_4$ alkylenedioxy group.

38. The amine compound or pharmacologically acceptable salt thereof according to claim 1, wherein:

R₁ represents a carbamoyl group (which may have one or two substituents α), a thiocarbamoyl group (which may have one or two substituents α) or a sulfonyl group (which has one substituent α);

R₂ and R₃ represent a hydrogen atom, a $C_1$–$C_{10}$ alkyl group, a $C_6$–$C_{10}$ aryl group (which may have from 1 to 3 substituents β) or a $C_7$–$C_{16}$ aralkyl group (which may have from 1 to 3 substituents β on the aryl portion) respectively;

W₁, W₂ and W₃ each represent a single bond or a $C_1$–$C_8$ alkylene group;

X, Y and Q each represent an oxygen atom or a sulfur atom;

Z represents a =CH— group or a nitrogen atom;

Ar represents a benzene ring or a naphthalene ring;

L represents from 1 to 4 substituents on the Ar ring and the or each substituent is a hydrogen atom, a $C_1$–$C_6$ alkyl group, a $C_6$–$C_{10}$ aryl group (which may have from 1 to 3 substituents β) or a $C_7$–$C_{16}$ aralkyl group (which may have from 1 to 3 substituents β on the aryl portion);

substituent α represents (i) a $C_1$–$C_{10}$ alkyl group, (ii) a $C_1$–$C_6$ halogenoalkyl group, (iii) a $C_3$–$C_{10}$ cycloalkyl group, (iv) a $C_6$–$C_{10}$ aryl group (which may have from 1 to 3 substituents γ), (v) a $C_7$–$C_{16}$ aralkyl group (which may have from 1 to 3 substituents γ on the aryl portion), (vi) a $C_4$–$C_{11}$ cycloalkylcarbonyl group, (vii) a $C_7$–$C_{11}$ arylcarbonyl group (which may have from 1 to 3 substituents γ on the aryl portion), (viii) a $C_8$–$C_{17}$ aralkylcarbonyl group (which may have from 1 to 3 substituents γ on the aryl portion), (ix) an aromatic heterocyclic group (which may have from 1 to 3 substituents γ), (x) a aromatic heterocyclic carbonyl group (which may have from 1 to 3 substituents γ), (xi) a $C_1$–$C_6$ alkylsulfonyl group, (xii) a $C_1$–$C_6$ halogenoalkylsulfonyl group, (xiii) a $C_6$–$C_{10}$ arylsulfonyl group (which may have from 1 to 3 substituents γ on the aryl portion) or (xiv) a $C_7$–$C_{16}$ aralkylsulfonyl group (which may have from 1 to 3 substituents γ on the aryl portion);

substituent β represents (i) a $C_1$–$C_6$ alkyl group, (ii) a $C_1$–$C_6$ halogenoalkyl group, (iii) a $C_1$–$C_6$ alkoxy group, (iv) a halogen atom, (v) a hydroxyl group, (vi) a $C_6$–$C_{10}$ aryl group (which may have from 1 to 3 substituents δ), (vii) a $C_7$–$C_{16}$ aralkyl group (which may have from 1 to 3 substituents δ on the aryl portion), (viii) a cyano group, (ix) a nitro group or (x) an amino group (which may have one or two substituents δ);

substituent γ represents (i) a $C_1$–$C_6$ alkyl group, (ii) a $C_1$–$C_6$ halogenoalkyl group, (iii) a $C_1$–$C_6$ alkoxy group, (iv) a halogen atom, (v) a hydroxyl group, (vi) a cyano group, (vii) a nitro group, (viii) a $C_3$–$C_{10}$ cycloalkyl group, (ix) a $C_6$–$C_{10}$ aryl group (which may have from 1 to 3 $C_1$–$C_6$ alkyl groups, $C_1$–$C_6$ halogenoalkyl groups, $C_1$–$C_6$ alkoxy groups or halogen atoms as the substituents), (x) a $C_7$–$C_{16}$ aralkyl group (which may have from 1 to 3 $C_1$–$C_6$ alkyl groups, $C_1$–$C_6$ halogenoalkyl groups, $C_1$–$C_6$ alkoxy groups or halogen atoms on the aryl moiety), (xi) a $C_1$–$C_7$ aliphatic acyl group, (xii) a $C_1$–$C_7$ aliphatic acyloxy group, (xiii) an amino group, (xiv) a di-($C_1$–$C_6$ alkyl) amino group or (xv) a $C_1$–$C_4$ alkylenedioxy group;

substituent δ represents (i) a $C_1$–$C_{10}$ alkyl group, (ii) a $C_6$–$C_{10}$ aryl group (which may have from 1 to 3 $C_1$–$C_6$ alkyl groups, $C_1$–$C_6$ halogenoalkyl groups, $C_1$–$C_6$ alkoxy groups or halogen atoms as the substituents), (iii) a $C_7$–$C_{16}$ aralkyl group (which may have from 1 to 3 $C_1$–$C_6$ alkyl groups, $C_1$–$C_6$ halogenoalkyl groups, $C_1$–$C_6$ alkoxy groups or halogen atoms as the substituents on the aryl moiety), (iv) a $C_1$–$C_7$ aliphatic acyl group, (v) a $C_4$–$C_{11}$ cycloalkylcarbonyl group, (vi) a $C_7$–$C_{11}$ arylcarbonyl group (which may have from 1 to 3 $C_1$–$C_6$ alkyl groups, $C_1$–$C_6$ halogenoalkyl groups, $C_1$–$C_6$ alkoxy groups or halogen atoms as the substituents), (vii) a $C_8$–$C_{17}$ aralkylcarbonyl group (which may have from 1 to 3 $C_1$–$C_6$ alkyl groups, $C_1$–$C_6$ halogenoalkyl groups, $C_1$–$C_6$ alkoxy groups or halogen atoms as a substituent on the aryl moiety) or (viii) an aromatic heterocyclic carbonyl group (which may have from 1 to 3 $C_1$–$C_6$ alkyl groups, $C_1$–$C_6$ halogenoalkyl groups, $C_1$–$C_6$ alkoxy groups or halogen atoms as the substituents).

39. The amine compound of claim 1 selected from the group consisting of 1-(4-[2-[4-(2,4-Dioxothiazolidin-5-ylmethyl) phenoxymethyl]-1-methyl-1H-benzimidazol-6-yloxy] phenyl)-3-ethylurea, 1-(adamant-1-yl)-3-(4-[2-[4-(2,4-dioxothiazolidin-5-ylmethyl)phenoxymethyl]-1-methyl-1H-benzimidazol-6-yloxy]phenyl)urea, 1-(4-[2-[4-(2,4-dioxothiazolidin-5-ylmethyl) phenoxymethyl]-1-methyl-1H-benzimidazol-6-yloxy] phenyl)-3-phenylurea, 1-(2,4-difluorophenyl)-3-[2-(4-[2-[4-(2,4-dioxothiazolidin-5-ylmethyl)phenoxymethyl]-1-methyl-1H-benzimidazol-6-yloxy]phenyl)ethyl]urea, 1-(4-[2-[4-(2,4-dioxothiazolidin-5-ylmethyl) phenoxymethyl]-1-methyl-1H-benzimidazol-6-yloxy]-2,6-dimethylphenyl)-3-(4-nitrophenyl)urea, 1-(4-[2-[4-(2,4-dioxothiazolidin-5-ylmethyl) phenoxymethyl]-1-methyl-1H-benzimidazol-6-yloxy] phenyl-1-n-hexyl-3-(4-fluorophenyl)urea, 1-(2,6-diisopropylphenyl)-3-(7-[2-[4-(2,4-dioxothiazolidin-5-ylmethyl)phenoxymethyl]-1-methyl-1H-benzimidazol-6-yloxy]naphthalen-1-yl)urea, 1-benzyl-3-(7-[2-[4-(2,4-dioxothiazolidin-5-ylmethyl) phenoxymethyl]-1-methyl-1H-benzimidazol-6-yloxy] naphthalen-1-yl)urea, 1-(4-[2-[4-(2,4-dioxothiazolidin-5-ylmethyl) phenoxymethyl]-1-methyl-1H-benzimidazol-6-yloxy] phenyl)-3-(cyclohexyl)thiourea, 1-benzyl-3-(7-[2-[4-(2,4-dioxothiazolidin-5-ylmethyl)
   phenoxymethyl]-1-methyl-1H-benzimidazol-6-yloxy]
   naphthalen-1-yl)thiourea,
1-(4-chlorophenyl)-3-(4-[2-[4-(2,4-dioxothiazolidin-5-
   ylmethyl)phenoxymethyl]-1-methyl-1H-benzimidazol-6-
   yloxy]-2,6-dimethylphenyl)thiourea,
N-(4-[2-[4-(2,4-dioxothiazolidin-5-ylmethyl)
   phenoxymethyl]-1-methyl-1H-benzimidazol-6-yloxy]
   phenyl)methanesulfonamide,
1-(3-[2-[4-(2,4-dioxothiazolidin-5-ylmethyl)
   phenoxymethyl]-1-methyl-1H-benzimidazol-6-yloxy]
   phenyl)-3-phenylurea,
1-(3-[2-[4-(2,4-dioxothiazolidin-5-ylmethyl)
   phenoxymethyl]-1-methyl-1H-benzimidazol-6-yloxy]
   phenyl)-3-[2-(trifluoromethyl)phenyl]urea,
1-(3-[2-[4-(2,4-dioxothiazolidin-5-ylmethyl)
   phenoxymethyl]-1-methyl-1H-benzimidazol-6-yloxy]
   phenyl)-3-[4-(trifluoromethyl)phenyl]urea,
1-(3-[2-[4-(2,4-dioxothiazolidin-5-ylmethyl)
   phenoxymethyl]-1-methyl-1H-benzimidazol-6-yloxy]
   phenyl)-3-(4-fluorophenyl)urea,
1-(3-[2-[4-(2,4-dioxothiazolidin-5-ylmethyl)
   phenoxymethyl]-1-methyl-1H-benzimidazol-6-yloxy]
   phenyl)-3-[4-(trifluoromethyl)benzyl]urea,
N-[4-[2-[4-(2,4-dioxothiazolidin-5-ylmethyl)
   phenoxymethyl]-1-methyl-1H-benzimidazol-6-yloxy]
   phenyl]acetamide,
N-[4-[2-[4-(2,4-dioxothiazolidin-5-ylmethyl)
   phenoxymethyl]-1-methyl-1H-benzimidazol-6-yloxy]
   phenyl]-N-n-hexylacetamide,
N-[4-[2-[4-(2,4-dioxothiazolidin-5-ylmethyl)
   phenoxymethyl]-1-methyl-1H-benzimidazol-6-yloxy]
   phenyl]cyclopentanecarboxylic acid amide,
N-[4-[2-[4-(2,4-dioxothiazolidin-5-ylmethyl)
   phenoxymethyl]-1-methyl-1H-benzimidazol-6-yloxy]
   phenyl]benzamide,
N-[4-[2-[4-(2,4-dioxothiazolidin-5-ylmethyl)
   phenoxymethyl]-1-methyl-1H-benzimidazol-6-yloxy]
   phenyl]naphthalene-2-carboxylic acid amide,
2,4-difluoro-N-[4-[2-[4-(2,4-dioxothiazolidin-5-ylmethyl)
   phenoxymethyl]-1-methyl-1H-benzimidazol-6-yloxy]
   phenyl]benzamide,
3-chloro-N-[4-[2-[4-(2,4-dioxothiazolidin-5-ylmethyl)
   phenoxymethyl]-1-methyl-1H-benzimidazol-6-yloxy]
   phenyl]benzamide,
N-[4-[2-[4-(2,4-dioxothiazolidin-5-ylmethyl)
   phenoxymethyl]-1-methyl-1H-benzimidazol-6-yloxy]
   phenyl]nicotinamide,
N-[4-[2-[4-(2,4-dioxothiazolidin-5-ylmethyl)
   phenoxymethyl]-1-methyl-1H-benzimidazol-6-yloxy]
   phenyl]isonicotinamide,
3,5-di-t-butyl-N-[2-(4-[2-[4-(2,4-dioxothiazolidin-5-
   ylmethyl)phenoxymethyl]-1-methyl-1H-benzimidazol-6-
   yloxy]phenyl)ethyl]-4-hydroxybenzamide,
2-(3-chlorophenyl)-N-[2-[4-[2-[4-(2,4-dioxothiazolidin-5-
   ylmethyl)phenoxymethyl]-1-methyl-1H-benzimidazol-6-
   yloxy]phenyl]ethyl]acetamide, and
N-[2-[4-[2-[4-(2,4-dioxothiazolidin-5-ylmethyl)
   phenoxymethyl]-1-methyl-1H-benzimidazol-6-yloxy]
   phenyl]ethyl]nicotinamide,
or a pharmacologically acceptable salt thereof.

40. The amine compound of claim 1 which is 1-(4-[2-[4-(2,4-dioxothiazolidin-5-ylmethyl)phenoxymethyl]-1-methyl-1H-benzimidazol-6-yloxy]phenyl)-3-ethylurea.

41. The amine compound of claim 1 which is 1-(adamant-1-yl)-3-(4-[2-[4-(2,4-dioxothiazolidin-5-ylmethyl) phenoxymethyl]-1-methyl-1H-benzimidazol-6-yloxy] phenyl)urea.

42. The amine compound of claim 1 which is 1-(2,4-difluorophenyl)-3-[2-(4-[2-[4-(2,4-dioxothiazolidin-5-ylmethyl)phenoxymethyl]-1-methyl-1H-benzimidazol-6-yloxy]phenyl)ethyl]urea.

43. The amine compound of claim 1 which is 1-benzyl-3-(7-[2-[4-(2,4-dioxothiazolidin-5-ylmethyl) phenoxymethyl]-1-methyl-1H-benzimidazol-6-yloxy] naphthalen-1-yl)urea.

44. The amine compound of claim 1 which is 1-(4-[2-[4-(2,4-dioxothiazolidin-5-ylmethyl)phenoxymethyl]-1-methyl-1H-benzimidazol-6-yloxy]phenyl)-3-(cyclohexyl) thiourea.

45. The amine compound of claim 1 which is N-(4-[2-[4-(2,4-dioxothiazolidin-5-ylmethyl)phenoxymethyl]-1-methyl-1H-benzimidazol-6-yloxy]phenyl) methanesulfonamide.

46. The amine compound of claim 1 which is 1-(3-[2-[4-(2,4-dioxothiazolidin-5-ylmethyl)phenoxymethyl]-1-methyl-1H-benzimidazol-6-yloxy]phenyl)-3-phenylurea.

47. The amine compound of claim 1 which is 1-(3-[2-[4-(2,4-dioxothiazolidin-5-ylmethyl)phenoxymethyl]-1-methyl-1H-benzimidazol-6-yloxy]phenyl)-3-[2-(trifluoromethyl)phenyl]urea.

48. The amine compound of claim 1 which is 1-(3-[2-[4-(2,4-dioxothiazolidin-5-ylmethyl)phenoxymethyl]-1-methyl-1H-benzimidazol-6-yloxy]phenyl)-3-[4-(trifluoromethyl)phenyl]urea.

49. The amine compound of claim 1 which is 1-(3-[2-[4-(2,4-dioxothiazolidin-5-ylmethyl)phenoxymethyl]-1-methyl-1H-benzimidazol-6-yloxy]phenyl)-3-(4-fluorophenyl)urea.

50. The amine compound of claim 1 which is N-[4-[2-[4-(2,4-dioxothiazolidin-5-ylmethyl)phenoxymethyl]-1-methyl-1H-benzimidazol-6-yloxy]phenyl]acetamide.

51. The amine compound of claim 1 which is N-[4-[2-[4-(2,4-dioxothiazolidin-5-ylmethyl)phenoxymethyl]-1-methyl-1H-benzimidazol-6-yloxy]phenyl] cyclopentanecarboxylic acid amide.

52. The amine compound of claim 1 which is N-[4-[2-[4-(2,4-dioxothiazolidin-5-ylmethyl)phenoxymethyl]-1-methyl-1H-benzimidazol-6-yloxy]phenyl]benzamide.

53. The amine compound of claim 1 which is 2,4-difluoro-N-[4-[2-[4-(2,4-dioxothiazolidin-5-ylmethyl) phenoxymethyl]-1-methyl-1H-benzimidazol-6-yloxy] phenyl]benzamide.

54. The amine compound of claim 1 which is N-[4-[2-[4-(2,4-dioxothiazolidin-5-ylmethyl)phenoxymethyl]-1-methyl-1H-benzimidazol-6-yloxy]phenyl]nicotinamide.

55. The amine compound of claim 1 which is N-[4-[2-[4-(2,4-dioxothiazolidin-5-ylmethyl)phenoxymethyl]-1-methyl-1H-benzimidazol-6-yloxy]phenyl]isonicotinamide.

56. The amine compound of claim 1 which is N-[2-[4-[2-[4-(2,4-dioxothiazolidin-5-ylmethyl)phenoxymethyl]-1-methyl-1H-benzimidazol-6-yloxy]phenyl]ethyl] nicotinamide.

57. A pharmaceutical composition comprising an effective amount of a pharmacologically active compound together with a carrier therefor, wherein said pharmacologically active compound is a compound according to any one of claims 1 and 36 to 56 or a pharmaceutically acceptable salt thereof.

58. A method of treating an animal in need of treatment with an active agent selected from the group consisting of insulin resistance improving agents, hypoglycemic agents, 5-lipoxygenase inhibitors, lipid peroxide production inhibitors, PPAR activators and adipose cell formation promoters comprising administering an effective amount of said active agent to said animal, wherein said active agent is an amine compound of the formula (I) or a pharmacologically acceptable salt thereof according to any one of claims 1 to 39.

59. A method according to claim 58 wherein said active agent is an insulin resistance improving agent.

60. A method of treating a human in need of treatment with an active agent selected from the group consisting of insulin resistance improving agents, hypoglycemic agents, 5-lipoxygenase inhibitors, lipid peroxide production inhibitors, PPAR activators and adipose cell formation promoters comprising administering an effective amount of said active agent to said human, wherein said active agent is an amine compound of the formula (I) or a pharmacologically acceptable salt thereof according to any one of claims 36 to 56.

61. A method according to claim 60 wherein said active agent is a hypoglycemic agent.

62. A method of treatment or prophylaxis of a disease selected from the group consisting of diabetes mellitus, impaired glucose tolerance, gestational diabetes mellitus, and cancer comprising administering to a human in need thereof, an effective amount of an active agent, wherein said active agent is an amine compound of the formula (I) or a pharmacologically acceptable salt thereof according to any one of claims 1 to 56.

63. A method of treatment or prophylaxis of diabetes mellitus comprising administering to a human in need thereof an effective amount of an active agent, wherein said active agent is an amine compound of the formula (I) or a pharmacologically acceptable salt thereof according to any one of claims 36 to 56.

64. A method of treatment or prophylaxis of impaired glucose tolerance comprising administering to a human in need thereof an effective amount of an active agent, wherein said pharmacologically acceptable salt thereof according to any one of claims 36 to 56.

65. A pharmaceutical composition comprising a compound according to claim 1 or a pharmacologically acceptable salt thereof in combination with an RXR activator.

66. A method of treating a patient in need of antitumor treatment or treatment for diabetes or diabetic complications, comprising administering to said patient an effective amount of a (i) compound according to claim 1 or a pharmacologically acceptable salt thereof (ii) in combination with an RXR activator.

\* \* \* \* \*

UNITED STATES PATENT AND TRADEMARK OFFICE
CERTIFICATE OF CORRECTION

PATENT NO. : 6,562,849 B1
DATED : May 13, 2003
INVENTOR(S) : Fujita et al.

It is certified that error appears in the above-identified patent and that said Letters Patent is hereby corrected as shown below:

<u>Title page,</u>
Item [56], References Cited, U.S. PATENT DOCUMENTS, after "5,965,470 A 10/1999", delete "Bening" and insert -- Bening et al --.

<u>Column 124,</u>
Line 66, after "substituent" delete "a" and insert -- α --.

<u>Column 127,</u>
Line 40, after "substituent" delete "a" and insert -- α --.

<u>Column 128,</u>
Line 39, after "substituent" delete "a" and insert -- α --.

Signed and Sealed this

Twenty-eighth Day of December, 2004

JON W. DUDAS
*Director of the United States Patent and Trademark Office*